US011479516B2

(12) United States Patent
Voigt et al.

(10) Patent No.: US 11,479,516 B2
(45) Date of Patent: Oct. 25, 2022

(54) NITROGEN FIXATION USING REFACTORED NIF CLUSTERS

(71) Applicant: Massachusetts Institute of Technology, Cambridge, MA (US)

(72) Inventors: Christopher A. Voigt, Belmont, MA (US); Min-Hyung Ryu, Cambridge, MA (US); Mi Ryoung Song, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 113 days.

(21) Appl. No.: 15/766,122

(22) PCT Filed: Oct. 5, 2016

(86) PCT No.: PCT/US2016/055429
§ 371 (c)(1),
(2) Date: Apr. 5, 2018

(87) PCT Pub. No.: WO2017/062412
PCT Pub. Date: Apr. 13, 2017

(65) Prior Publication Data
US 2018/0290942 A1    Oct. 11, 2018

Related U.S. Application Data

(60) Provisional application No. 62/237,426, filed on Oct. 5, 2015.

(51) Int. Cl.
| | | |
|---|---|---|
| *C12N 15/82* | (2006.01) | |
| *C05F 11/08* | (2006.01) | |
| *C12N 15/70* | (2006.01) | |
| *C12N 15/52* | (2006.01) | |

(52) U.S. Cl.
CPC .............. *C05F 11/08* (2013.01); *C12N 15/52* (2013.01); *C12N 15/70* (2013.01)

(58) Field of Classification Search
None
See application file for complete search history.

(56) References Cited

U.S. PATENT DOCUMENTS

| | | |
|---|---|---|
| 1,520,545 A | 12/1924 | Murphy |
| 4,782,022 A | 11/1988 | Puhler et al. |
| 4,832,728 A | 5/1989 | Allan et al. |
| 5,071,743 A | 12/1991 | Slilaty et al. |
| 5,116,506 A | 5/1992 | Williamson et al. |
| 5,188,960 A | 2/1993 | Payne et al. |
| 5,229,291 A | 7/1993 | Nielsen et al. |
| 5,354,670 A | 10/1994 | Nickoloff et al. |
| 5,427,785 A | 6/1995 | Ronson et al. |
| 5,610,044 A | 3/1997 | Lam et al. |
| 5,780,270 A | 7/1998 | Lesley |
| 5,789,166 A | 8/1998 | Bauer et al. |
| 5,877,012 A | 3/1999 | Estruch et al. |
| 5,880,275 A | 3/1999 | Fischhoff et al. |
| 5,916,029 A | 6/1999 | Smith et al. |
| 6,033,861 A | 3/2000 | Schafer et al. |
| 6,033,874 A | 3/2000 | Baum et al. |
| 6,083,499 A | 7/2000 | Narva et al. |
| 6,107,279 A | 8/2000 | Estruch et al. |
| 6,114,148 A | 9/2000 | Seed et al. |
| 6,127,180 A | 10/2000 | Narva et al. |
| 6,137,033 A | 10/2000 | Estruch et al. |
| 6,218,188 B1 | 4/2001 | Cardineau et al. |
| 6,248,535 B1 | 6/2001 | Danenberg et al. |
| 6,326,351 B1 | 12/2001 | Donovan et al. |
| 6,340,593 B1 | 1/2002 | Cardineau et al. |
| 6,391,548 B1 | 5/2002 | Bauer et al. |
| 6,399,330 B1 | 6/2002 | Donovan et al. |
| 6,548,289 B1 | 4/2003 | Beynon et al. |
| 6,548,291 B1 | 4/2003 | Narva et al. |
| 6,596,509 B1 * | 7/2003 | Bauer .................... C07K 14/21 |
| | | 435/252.3 |
| 6,624,145 B1 | 9/2003 | Narva et al. |
| 6,673,610 B2 | 1/2004 | Miyawaki et al. |
| 6,713,063 B1 | 3/2004 | Malvar et al. |
| 6,713,285 B2 | 3/2004 | Bauer et al. |
| 6,773,900 B2 | 8/2004 | Short et al. |
| 6,841,358 B1 | 1/2005 | Locht et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,084,331 B2 | 8/2006 | Isawa et al. |
| 7,105,332 B2 | 9/2006 | Abad et al. |

(Continued)

FOREIGN PATENT DOCUMENTS

| | | |
|---|---|---|
| AU | 636565 B2 | 5/1993 |
| CA | 2051071 A1 | 3/1993 |

(Continued)

OTHER PUBLICATIONS

US 8,476,226 B2, 07/2013, Lira (withdrawn)
Zhang et al. (World J Microbiol Biotechnol (2015) 31:921-927). (Year: 2015).*
Temme, et al. (Proceedings of the National Academy of Sciences 109.18 (2012): 7085-7090). (Year: 2012).*
Lee et al. (Planta (2009) 229:747-755). (Year: 2009).*
Cornelis (Nature Reviews Microbiology 4.11 (2006): 811). (Year: 2006).*
Kent et al. (Appl. Environ. Microbiol. 64.5 (1998): 1657-1662). (Year: 1998).*
Extended European Search Report dated Feb. 20, 2019 for Application No. EP 16854192.8.

(Continued)

*Primary Examiner* — Charles Logsdon
(74) *Attorney, Agent, or Firm* — Wolf, Greenfield & Sacks, P.C.

(57) ABSTRACT

The invention relates to methods for promoting fixed nitrogen from atmospheric nitrogen, and related products. Endophytic bacteria having an exogenous nif cluster promote fixed nitrogen for cereal plants.

15 Claims, 3 Drawing Sheets

Figure 1:
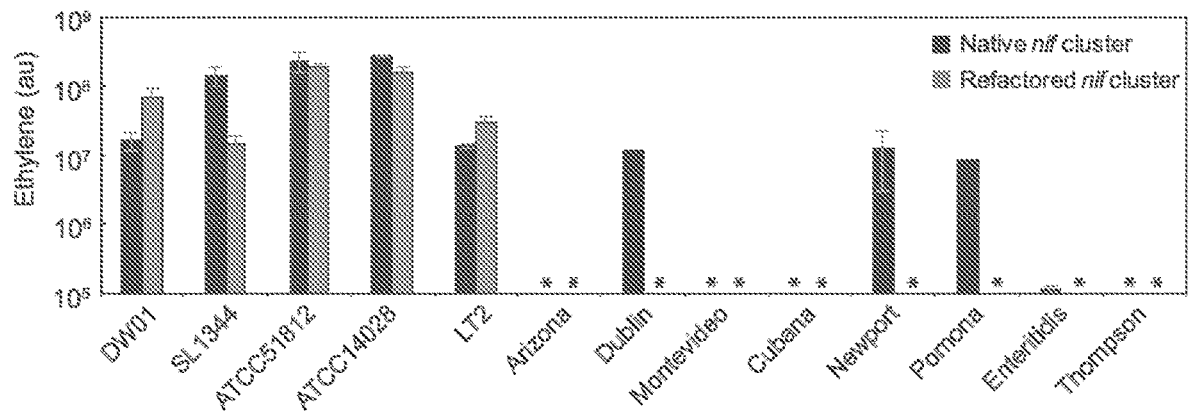
Figure 2:
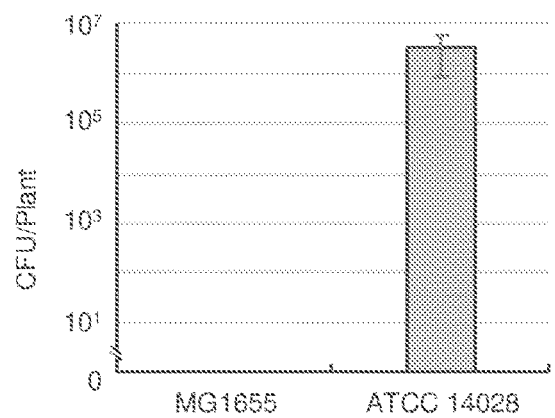
Figure 3:
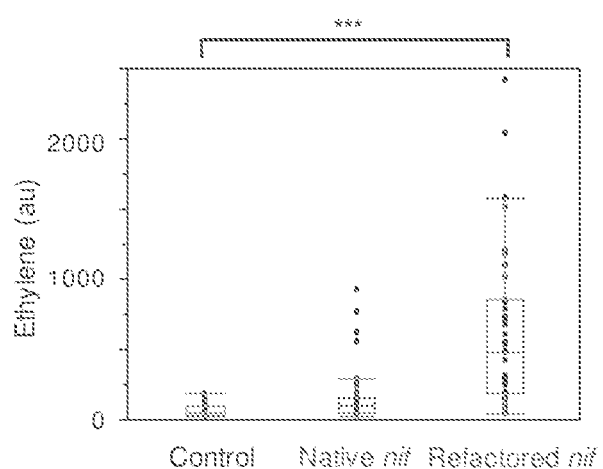

Specification includes a Sequence Listing.

(56) References Cited

U.S. PATENT DOCUMENTS

| | | |
|---|---|---|
| 7,132,265 B2 | 11/2006 | Bauer et al. |
| 7,244,820 B2 | 7/2007 | Miles et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |
| 7,470,427 B2 | 12/2008 | Cocking |
| 7,476,781 B2 | 1/2009 | Abad et al. |
| 7,485,451 B2 | 2/2009 | Vandergheynst et al. |
| 7,491,698 B2 | 2/2009 | Hey et al. |
| 7,491,869 B2 | 2/2009 | Abad et al. |
| 7,504,229 B2 | 3/2009 | Donovan et al. |
| 7,615,686 B2 | 11/2009 | Miles et al. |
| 7,803,943 B2 | 9/2010 | Mao et al. |
| 7,858,849 B2 | 12/2010 | Cerf et al. |
| 7,923,602 B2 | 4/2011 | Carozzi et al. |
| 8,076,142 B2 | 12/2011 | Huang et al. |
| 8,084,416 B2 | 12/2011 | Sampson et al. |
| 8,084,418 B2 | 12/2011 | Hey et al. |
| 8,137,665 B2 | 3/2012 | Cocking |
| 8,236,757 B2 | 8/2012 | Carozzi et al. |
| 8,237,020 B2 | 8/2012 | Miles et al. |
| 8,268,584 B1 | 9/2012 | Harwood et al. |
| 8,304,604 B2 | 11/2012 | Lira et al. |
| 8,304,605 B2 | 11/2012 | Lira et al. |
| 8,319,019 B2 | 11/2012 | Abad et al. |
| 8,334,366 B1 | 12/2012 | Hughes et al. |
| 8,334,431 B2 | 12/2012 | Sampson et al. |
| 8,377,671 B2 | 2/2013 | Cournac et al. |
| 8,481,026 B1 | 7/2013 | Woodruff et al. |
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,795,965 B2 | 8/2014 | Zhang |
| 8,802,933 B2 | 8/2014 | Abad et al. |
| 8,802,934 B2 | 8/2014 | Abad et al. |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto, Sr. et al. |
| 9,796,957 B2 | 10/2017 | Barney et al. |
| 9,957,509 B2 | 5/2018 | Mirsky et al. |
| 9,975,817 B2 | 5/2018 | Temme et al. |
| 9,994,557 B2 | 6/2018 | Davidson et al. |
| 10,384,983 B2 | 8/2019 | Temme et al. |
| 10,525,318 B2 | 1/2020 | Dougherty |
| 10,556,839 B2 | 2/2020 | Temme et al. |
| 10,662,432 B2 | 5/2020 | Mirsky et al. |
| 10,919,814 B2 | 2/2021 | Temme et al. |
| 10,934,226 B2 | 3/2021 | Temme et al. |
| 10,968,446 B2 | 4/2021 | Zhao et al. |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0235663 A1 | 11/2004 | Cocking |
| 2004/0241847 A1 | 12/2004 | Okuyama et al. |
| 2004/0250311 A1 | 12/2004 | Carozzi et al. |
| 2005/0081262 A1 | 4/2005 | Cook et al. |
| 2005/0266541 A1 | 12/2005 | Dillon |
| 2006/0033867 A1 | 2/2006 | Krisko et al. |
| 2006/0096918 A1 | 5/2006 | Semmens |
| 2006/0112447 A1 | 5/2006 | Bogdanova et al. |
| 2006/0127988 A1 | 6/2006 | Wood et al. |
| 2006/0191034 A1 | 8/2006 | Baum |
| 2006/0243011 A1 | 11/2006 | Someus |
| 2007/0249018 A1 | 10/2007 | Vemuri et al. |
| 2008/0295207 A1 | 11/2008 | Baum et al. |
| 2008/0311632 A1 | 12/2008 | Figge et al. |
| 2009/0105076 A1 | 4/2009 | Stewart et al. |
| 2009/0137390 A1 | 5/2009 | Triplett |
| 2009/0144852 A1 | 6/2009 | Tomso et al. |
| 2009/0152195 A1 | 6/2009 | Rodgers et al. |
| 2009/0162477 A1 | 6/2009 | Nadel |
| 2009/0258404 A1 | 10/2009 | Mikkelsen et al. |
| 2009/0308121 A1 | 12/2009 | Reddy et al. |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015806 A1 | 1/2012 | Paikray et al. |
| 2012/0107889 A1 | 5/2012 | Doty et al. |
| 2012/0192605 A1 | 8/2012 | McSpadden |
| 2012/0266332 A1 | 10/2012 | Kuykendall |
| 2012/0278954 A1 | 11/2012 | Bowen et al. |
| 2012/0284813 A1 | 11/2012 | Olivier et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0155283 A1 | 6/2014 | Venkateswaran |
| 2014/0182018 A1 | 6/2014 | Lang et al. |
| 2014/0223598 A1 | 8/2014 | Sampson et al. |
| 2014/0223599 A1 | 8/2014 | Sampson et al. |
| 2014/0230504 A1 | 8/2014 | Finlayson et al. |
| 2014/0273226 A1 | 9/2014 | Wu |
| 2014/0301990 A1 | 10/2014 | Gregory et al. |
| 2014/0329326 A1* | 11/2014 | Mirsky ........... C12N 15/67 435/471 |
| 2014/0336050 A1* | 11/2014 | Soto, Sr. ........... C07K 14/21 504/117 |
| 2015/0080261 A1 | 3/2015 | Wigley et al. |
| 2015/0101373 A1* | 4/2015 | Munusamy ........ A01N 63/00 71/7 |
| 2015/0128670 A1 | 5/2015 | Das |
| 2015/0237807 A1 | 8/2015 | Valiquette |
| 2015/0239789 A1 | 8/2015 | Kang et al. |
| 2015/0315570 A1 | 11/2015 | Zhao et al. |
| 2016/0174570 A1 | 6/2016 | Vujanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2017/0086402 A1 | 3/2017 | Meadows-Smith et al. |
| 2017/0119690 A1 | 5/2017 | Hansen et al. |
| 2017/0152519 A1 | 6/2017 | Mirsky |
| 2017/0267997 A1 | 9/2017 | Nicol et al. |
| 2017/0367349 A1 | 12/2017 | Gruver et al. |
| 2018/0002243 A1* | 1/2018 | Temme ............. C12N 1/20 |
| 2018/0020671 A1 | 1/2018 | Bioconsortia |
| 2018/0065896 A1 | 3/2018 | Ibema et al. |
| 2018/0073028 A1 | 3/2018 | Mirsky |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1 | 2/2019 | Temme et al. |
| 2019/0144352 A1 | 5/2019 | Temme et al. |
| 2020/0087221 A1 | 3/2020 | Temme et al. |
| 2020/0115715 A1 | 4/2020 | Mirsky et al. |
| 2020/0299637 A1 | 9/2020 | Voigt et al. |
| 2020/0308594 A1 | 10/2020 | Tamsir et al. |
| 2020/0331820 A1 | 10/2020 | Tamsir et al. |
| 2021/0009483 A1 | 1/2021 | Temme et al. |

(56) References Cited

U.S. PATENT DOCUMENTS

| | | | |
|---|---|---|---|
| 2021/0163374 A1 | 6/2021 | Bioch et al. |
| 2021/0214282 A1 | 7/2021 | Temme et al. |
| 2021/0315212 A1 | 10/2021 | Rezaei et al. |
| 2022/0017911 A1 | 1/2022 | Temme et al. |
| 2022/0079163 A1 | 3/2022 | Reisinger et al. |

FOREIGN PATENT DOCUMENTS

| | | |
|---|---|---|
| CN | 1289852 A | 4/2001 |
| CN | 1500801 A | 6/2004 |
| CN | 1552846 A | 12/2004 |
| CN | 1746304 A | 3/2006 |
| CN | 101880676 | 11/2010 |
| CN | 102041241 | 5/2011 |
| CN | 102417882 | 4/2012 |
| CN | 102690808 A | 9/2012 |
| CN | 103451130 A | 12/2013 |
| CN | 104136599 A | 11/2014 |
| CN | 104204211 | 12/2014 |
| EP | 0256889 B1 | 2/1988 |
| EP | 0292984 A2 | 11/1988 |
| EP | 339830 B1 | 11/1989 |
| EP | 1535913 B1 | 6/2005 |
| EP | 2186890 A1 | 5/2010 |
| EP | 3322679 A1 | 5/2018 |
| FR | 2910230 A1 | 6/2008 |
| JP | S63-501924 A | 8/1988 |
| JP | H01225483 A | 9/1989 |
| JP | H02-131581 A | 5/1990 |
| JP | 2009-232721 | 10/2009 |
| JP | 2014096996 A | 5/2014 |
| JP | 2015037385 A | 2/2015 |
| JP | 2015042633 A | 3/2015 |
| JP | 2015-518023 A | 6/2015 |
| JP | 2015113274 A | 6/2015 |
| JP | 2015-519352 A | 7/2015 |
| WO | WO 1987/004182 A1 | 7/1987 |
| WO | WO 93/05154 A1 | 3/1993 |
| WO | WO 98/10088 A1 | 3/1998 |
| WO | WO 99/09834 A2 | 3/1999 |
| WO | WO 00/57183 A1 | 9/2000 |
| WO | WO 01/07567 A1 | 2/2001 |
| WO | WO 2004/074462 A2 | 9/2004 |
| WO | WO 2005/021585 A2 | 3/2005 |
| WO | WO 2005/038032 A1 | 4/2005 |
| WO | WO 2006/005100 A1 | 1/2006 |
| WO | WO 2006/083891 A2 | 8/2006 |
| WO | WO 2006/098225 A1 | 9/2006 |
| WO | WO 2006/119457 A2 | 11/2006 |
| WO | WO 2007/027776 A2 | 3/2007 |
| WO | WO 2009/060012 A2 | 5/2009 |
| WO | WO 2009/091557 A1 | 7/2009 |
| WO | WO 2010/080184 A1 | 7/2010 |
| WO | WO 2011/099019 A1 | 8/2011 |
| WO | WO 2011/099024 A1 | 8/2011 |
| WO | WO 2011/103247 A1 | 8/2011 |
| WO | WO 2011/103248 A2 | 8/2011 |
| WO | WO 2011/154960 A1 | 12/2011 |
| WO | WO 2012/139004 A1 | 10/2012 |
| WO | WO 2012/154651 A2 | 11/2012 |
| WO | WO 2012/174271 A2 | 12/2012 |
| WO | WO 2013/076687 A2 | 5/2013 |
| WO | WO 2013/132518 A1 | 9/2013 |
| WO | WO 2014/042517 A2 | 3/2014 |
| WO | WO 2014/071182 A1 | 5/2014 |
| WO | WO 2014/201044 A2 | 12/2014 |
| WO | WO 2016/016629 A1 | 2/2016 |
| WO | WO 2016/016630 A1 | 2/2016 |
| WO | WO 2016/100727 A1 | 6/2016 |
| WO | WO 2016/146955 A1 | 9/2016 |
| WO | WO 2016/178580 A2 | 11/2016 |
| WO | WO 2016/179046 A1 | 11/2016 |
| WO | WO 2016/181228 A2 | 11/2016 |
| WO | WO 2016/191828 A1 | 12/2016 |
| WO | WO 2017/011602 A1 | 1/2017 |
| WO | WO 2017/042833 A1 | 3/2017 |
| WO | WO 2017/062412 A1 | 4/2017 |
| WO | WO 2017/069717 A1 | 4/2017 |
| WO | WO 2017/112827 A1 | 6/2017 |
| WO | WO 2017/203440 A1 | 11/2017 |
| WO | WO 2018/081543 A1 | 5/2018 |
| WO | WO 2018/132774 A1 | 7/2018 |
| WO | WO 2018/133774 A1 | 7/2018 |
| WO | WO 2019/032926 A1 | 2/2019 |
| WO | WO 2019/084342 A1 | 5/2019 |
| WO | WO 2019/140125 A1 | 7/2019 |
| WO | WO 2020/006064 A2 | 1/2020 |
| WO | WO 2020/006246 A1 | 1/2020 |
| WO | WO 2020/014498 A1 | 1/2020 |
| WO | WO 2020/023630 A1 | 1/2020 |
| WO | WO 2020/061363 A1 | 3/2020 |
| WO | WO 2020/092940 A1 | 5/2020 |
| WO | WO 2020/118111 A1 | 6/2020 |
| WO | WO 2020/146372 A1 | 7/2020 |
| WO | WO 2020/163251 A1 | 8/2020 |
| WO | WO 2020/190363 A1 | 9/2020 |
| WO | WO 2020/191201 A1 | 9/2020 |
| WO | WO 2020/219893 A1 | 10/2020 |
| WO | WO 2020/219932 A1 | 10/2020 |
| WO | WO 2021/113352 A1 | 6/2021 |
| WO | WO 2021/146209 A1 | 7/2021 |

OTHER PUBLICATIONS

International Search Report and Written Opinion mailed Dec. 30, 2016 for Application No. PCT/US2016/055429.

International Preliminary Report on Patentability dated Apr. 19, 2018 for Application No. PCT/US2016/055429.

[No. Author Listed], 40 CFR 725.3 U.S. Government Publishing Office. Jul. 1, 2010. Retrieved from https://www.gpo.gov/fdsys/pkg/CFR-2010-title40-vol30/pdf/CFR-2010-title40-vol30-sec725-3.pdf 3 pages.

[No. Author Listed], T7 RNA Polymerase Expression System for Bacillus megaterium; T7 RNAP Expression System Handbook, Jan. 2010, © MoBiTec GmbH. 18 pages.

[No. Author Listed], BLAST. Basic local alignment search tool. Available at http://blast.ncbi.nlm.nih.gov/Blast.cgi. Accessed on Oct. 10, 2016. 2 pages.

[No. Author Listed], EMBOSS. EMBOSS Needle: Pairwise Sequence Alignment (Nucleotide). Available at http://www.ebi.ac.uk/Tools/psa/emboss_needle/nucleotide.html. Accessed on Oct. 10, 2016. 2 pages.

[No. Author Listed], EMBOSS. EMBOSS Water: Pairwise Sequence Alignment (Nucleotide). Available at http://www.ebi.ac.uk/Tools/psa/emboss_water/nucleotide.html. Accessed on Oct. 10, 2016. 2 pages.

Alper et al., Tuning genetic control through promoter engineering. Proc Natl Acad Sci U S A. Sep. 6, 2005; 102(36):12678-83. Epub Aug. 25, 2005. Erratum in: Proc Natl Acad Sci U S A. Feb. 21, 2006;103(8):3006.

Altschul et al. Basic local alignment search tool. J Mol Biol 215(3):403-410 (1990).

Altschul, et al. Gapped BLAST and PSI-BLAST: a new generation of protein database search programs. Nucleic Acids Res 25:3389-3402 (1977).

An et al. Constitutive expression of the nifA gene activates associative nitrogen fixation of Enterobacter gergoviae 57-7, an opportunistic endophytic diazotroph. Journal of Applied Microbiology 103(3):613-620 (Sep. 1, 2007). First published Feb. 7, 2007.

Andersen, et al. Herpesvirus-mediated gene delivery into the rat brain: specificity and efficiency of the neuron-specific enolase promoter. Cell Mol Neurobiol. Oct. 1993;13(5):503-15.

Andersen, et al. Energetics of biological nitrogen fixation: determination of the ratio of formation of H2 to NH4+ catalysed by nitrogenase of Klebsiella pneumoniae in vivo. J Gen Microbial. Nov. 1977; 103(1):107-22.

Andrews et al. Use of Nitrogen Fixing Bacteria Inoculants as a Substitute for Nitrogen Fertiliser for Dryland Graminaceous Crops: Progress Made, Mechanisms of Action and Future Potential. Symbiosis. 2003;34:1-21.

(56) References Cited

OTHER PUBLICATIONS

Arbuthnot, et al. In vitro and in vivo hepatoma cell-specific expression of a gene transferred with an adenoviral vector. Hum Gene Ther. Aug. 20, 1996;7(13): 1503-14.
Arsene, et al., Modulation of NifA activity by PII in Azospirillum brasilense: Evidence for a Regulatory role of the NifA N-Terminal Domain. J Biotechnol. Aug. 1996;178(16):4830-8.
Austin, et al. Characterisation of the Klebsiella pneumoniae nitrogen-fixation regulatory proteins NIFA and NIFL in vitro. Eur J Biochem. Jan. 26, 1990;187(2):353-60.
Bageshwar, et al. An Environmentally Friendly Engineered Azotobacter Strain That Replaces a Substantial Amount of Urea Fertilizer while Sustaining the Same Wheat Yield. Appl Environ Microbiol. Aug. 1, 2017; 83(15):e00590-17, 14 pages.
Bali, et al., Excretion of Ammonium by a nifL Mutant of Azotobacter vine landii fixing Nitrogen. Appl Environ Microbiol. May 1992;58(5):1711-8.
Barney, et al., Gene deletions resulting in increased nitrogen release by azotobacter vinelandii: application of a novel nitrogen biosensor. Appl. Environ. Microbiol. 2015; 81 (13):4316-4328. Published online Apr. 17, 2015.
Barney, et al., Transcriptional analysis of an Ammonium-excreting stain of azotobacter vinelandii deregulated for nitrogen fixation. Appl. Environ. Microbial. 2017; 83(20): 1-22.
Barrango et al., Exploiting CRISPR-Cas immune systems for genome editing in bacteria. Curr Opin Biotechnol. 2016;37:61-8.
Beringer, et al., Genetic engineering and nitrogen fixation. Biotech Gen Eng Rev. 1984; 1(1):65-88.
Bikard et al., The synthetic integron: an in vivo genetic shuffling device. Nucleic Acids Res. Aug. 2010;38(15):e153. doi:10.1093/nar/gkq511. Epub Jun. 9, 2010.
Bilitchenko et al., Eugene-a domain specific language for specifying and constraining synthetic biological parts, devices, and systems. PLoS One. Apr. 29, 2011;6(4):e18882. doi: 10.1371/journal.pone.0018882. 12 pages.
Blanco, et al. Sequence and molecular analysis of the nifL gene of Azotobacter vinelandii. Mol Microbial. Aug. 1993;9(4):869-79.
Boshart, et al. A very strong enhancer is located upstream of an immediate early gene of human cytomegalovirus. Cell. Jun. 1985;41(2):521-30.
Bosworth, et al. Alfalfa yield response to inoculation with recombinant strains of Rhizobium meliloti with an extra copy of dctABD and/or modified nifA expression. Appl Environ Microbial. Oct. 1994;60(10):3815-32.
Brandl, et al. Salmonella interactions with plants and their associated microbiota. Phytopathology. 2013;103:316-25.
Brewin, et al., The Basis of Ammonium release in nifL Mutants of Azotobacter vinelandii. J Bacteriol. Dec. 1999;181(23):7356-62.
Buchanan-Wollaston, et al. Role of the nifA gene product in the regulation of nif expression in Klebsiella pneumoniae. Nature. Dec. 2, 19814;294(5843):776-8.
Buddrus-Schiemann, et al. Root colonization by Pseudomonas sp. DSMZ 13134 and impact on the indigenous rhizosphere bacterial community of barley. Microb Ecol. Aug. 2010;60(2):381-93. doi: 10.1007/s00248-010-9720-8. Epub Jul. 20, 2010.
Chan et al., Refactoring bacteriophage T7. Mol Sys Biol. Sep. 13, 2005;1(1): E1-10. oi:10.1038/msb4100025.
Chen, et al. Expression of rat bone sialoprotein promoter in transgenic mice. J Bone Miner Res. May 1996;11(5):654-64.
Chen, et al., Complete genome sequence of Kosakonia sacchari type strain SP1T. Stand Genomic Sci. Jun. 15, 2014; 9(3): 1311-1318.
Chiang, et al., Mutagenic Oligonucleotide-directed PCR Amplification (Mod-PCR): An Efficient Method for Generating Random Base Substitution Mutations in a DNA sequence element. PCR Method Appl. 1993; 2:210-217.
Choi, et al. A Tn7-based broad-range bacterial cloning and expression system. Nat Methods. Jun. 2005;2(6):443-8.
Choudhary, et al. Interactions of *Bacillus* spp. and Plants—With Special Reference to Induced Systemic Resistance (ISR). Microbiol Res. 2009;164(5):493-513. doi: 10.1016/j.micres.2008.08.007.

Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012.
Cohen, J.D., In vitro Tomato Fruit Cultures Demonstrate a Role for lndole-3-acetic Acid in Regulating Fruit Ripening. J Amer Soc Hort Sci. 1996;121(3):520-4.
Colnaghi et al., Lethality of glnD null mutations in Azotobacter vinelandii is suppressible by prevention of glutamine synthetase adenylylation. Microbiology. May 2001;147(5):1267-76.
Colnaghi et al., Strategies for increased ammonium production in free-living or plant associated nitrogen fixing bacteria. Plant and Soil, 1997;194:145-54.
Conniff, R., Microbes help grow better crops. Sci Amer. Sep. 1, 2013. 7 pages.
Contreras, et al. The product of the nitrogen fixation regulatory gene nfrX of Azotobacter vinelandii is functionally and structurally homologous to the uridylyltransferase encoded by glnD in enteric bacteria. J Bacterial. Dec. 1991;173(24):7741-9.
Curatti, et al., Genes required for rapid expression of nitrogenase activity in Azotobacter vinelandii. PNAS. 2005;102(18):6291-6.
Datsenko et al., One-step inactivation of chromosomal genes in *Escherichia coli* K-12 using PCR products. PNAS. Jun. 6, 2000;97(12):6640-5.
Debruijn et al., The Cloning and characterization of the glnF (ntrA) Gene of Klebsiella pneumoniae: Role of glnF (ntrA) in the Regulation of Nitrogen Fixation (nif) and other Nitrogen assimilation genes. Mol Genet. 1983;192:342-53.
Delaux et al., Tracing the evolutionary path to nitrogen-fixing crops. Curr Opin Plant Biol. 2015;26:95-9.
Dent et al., Establishing symbiotic nitrogen fixation in cereals and other non-legume crops: The greener nitrogen revolution. Agric & Food Secur. 2017;6(7):1-9.
Desnoues et al., Nitrogen fixation genetics and regulation in a Pseudomonas stutzeri strain associated with rice. Microbiology. 2003;149:2251-62. doi: 10.1099/mic.0.26270-0.
Dixon et al., Genetic regulation of biological nitrogen fixation. Nat Rev. 2004;2:621-31.
Dong et al., Kinetics and Strain Specificity of Rhizosphere and Endophytic Colonization by Enteric Bacteria on Seedlings of Medicago sativa and Medicago truncatula. Appl Environ Microbiol. Mar. 2003;69(3):1783-90. doi: 10.1128/AEM.69.3.1783-1790.2003.
Dos Santos et al., Distribution of nitrogen fixation and nitrogenase-like sequences amongst microbial genomes. BMC Genomics. 2012;13:162, 12 pages.
Du et al., Customized optimization of metabolic pathways by combinatorial transcriptional engineering. Nucl Acids Res. Oct. 2012;40(18):e142. doi: 10.1093/nar/pks549. Epub Jun. 19, 2012. 10 pages.
Easter et al., Role of the parCBA Operon of the Broad-Host-Range Plasmid RK2 in Stable Plasmid Maintenance. J Bacteriol. Nov. 1998;180(22):6023-30.
Egener et al., Identification of NifL-like protein in a diazotroph of the b-subgroup of the proteobacteria, *Azoarcus* sp. strain BH72. Microbiol. 2002;148:3203-12.
Engler, et al. A one pot, one step, precision cloning method with high throughput capability. PLoS One. 2008;3(11):e3647. doi: 10.1371/journal.pone.0003647. Epub Nov. 5, 2008. 7 pages.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009. 9 pages.
Ferrieres, et al. The yjbEFGH locus in *Escherichia coli* K-12 is an operon encoding proteins involved in exopolysaccharide production. Microbiology. Apr. 2007;153(4):1070-80.
Fischbach et al., Prokaryotic gene clusters: A rich toolbox for synthetic biology. Biotechnol J. 2010;15(12):1277-96.
Fox et al., Major cereal crops benefit from biological nitrogen fixation when inoculated with the nitrogen-fixing bacterium Pseudomonas protegens Pf-5 X940. Environ Microbiol. 2016;18(10):3522-34.

(56) References Cited

OTHER PUBLICATIONS

Frasch et al., Design-based re-engineering of biosynthetic gene clusters: plug-and-play in practice. Curr Opin Biotechnol. Dec. 2013;24(6): 1144-50. doi: 10.1016/j.copbio.2013.03.006. Epub Mar. 27, 2013.
Gebeyehu et al., Novel biotinylated nucleotide-analogs for labeling and colorimetric detection of DNA. Nucl Acids Res. 1987;15:4513-34.
Geddes et al., Use of plant colonizing bacteria as chassis for transfer of N2-fixation to cereals. Curr Opin Biotechnol. 2015;32:216-22.
Gibson, Physical Environment and Symbiotic Nitrogen Fixation. Aust J Biol Sci. 1963; 16:28-42.
Gossen et al. Tight control of gene expression in mammalian cells by tetracycline-responsive promoters. PNAS USA. Jun. 1992;89:5547-51.
Gossen et al. Transcriptional activation by tetracyclines in mammalian cells. Sci. Jun. 23, 1995;268(5218):1766-9.
Govantes et al., Mechanism of coordinated synthesis of the antagonistic regulatory proteins NifL and NifA of Klebsiella pneumoniae. J Bacteriol. Dec. 1996;178(23):6817-23.
Guo et al., Discovery of Reactive Microbiota-Derived Metabolites that Inhibit Host Proteases. Cell. Jan. 26, 2017;168(3):517-26. doi:10.1016/j.cell.2016.12.021. Epub Jan. 19, 2017.
Haapalainen et al., Soluble plant cell signals induce the expression of the type III secretion system of Pseudomonas syringae and upregulate the production of pilus protein HrpA. Mol Plant Microbe Interact. 2009;22:282-90.
Hale et al., An efficient stress-free strategy to displace stable bacterial plasmids. BioTechniques 2010;48:223-8.
Hansal et al., Induction of antigen-specific hyporesponsiveness by transplantation of hemopoietic cells containing an MHC class I transgene regulated by a lymphocyte-specific promoter. J Immunol. Aug. 1, 1998; 161(3):1063-8.
Harvey et al., Inducible control of gene expression: prospects for gene therapy. Curr Opin Chem Biol. Aug. 1998;2(4):512-8.
Herlache et al., Characterization of the Agrobacterium vitis pehA gene and comparison of the encoded polygalacturonase with the homologous enzymes from Erwinia carotovora and Ralstonia solanacearum. Appl Environ Microbiol. Jan. 1997;63(1):338-46.
Hidaka et al., Promotion of the Growth of Rice by Inoculation of Nitrogen-Fixing-Activity-Enhanced Bacteria to the Rhizosphere. Curr Plant Sci Biotechnol Agri. 1999;38:445.
Holden et al., Colonization outwith the colon: plants as an alternative environmental reservoir for human pathogenic enterobacteria. FEMS Microbiol Rev. 2009;33:689-703.
Hunter, "Genetically Modified Lite" placates public but not activists. EMBO Reports. 2014;15(2):138-41.
Iniguez et al., Nitrogen Fixation in Wheat Provided by Klebsiella pneumoniae 342. MPMI. 2004; 17(10):1078-85.
Jaschke et al., A fully decompressed synthetic bacteriophage øX174 genome assembled and archived in yeast. Virology. 2012;434:278-84.
Kant et al., Understanding plant response to nitrogen limitation for the improvement of crop nitrogen use efficiency. J Exper Botany. 2011;62(4):1499-509.
Karlin et al., Applications and statistics for multiple high-scoring segments in molecular sequences. PNAS USA. Jun. 15, 1993;90(12):5873-7.
Karlin et al., Methods for assessing the statistical significance of molecular sequence features by using general scoring schemes. PNAS USA. Mar. 1990;87(6):2264-8.
Kerby et al., Photoproduction of ammonium by immobilized mutant strains of Anabaena variabilis. Applied Microbiology and Biotechnology. Apr. 1986, vol. 24, Issue 1, pp. 42-46.
Kim, et al. Constitutive expression of nitrogenase system in Klebsiella oxytoca by gene targeting mutation to the chromosomal nifLA operon. J Biotechnol. Jun. 1989;10(3-4):293-301.
Kornberg, DNA Replication. Stanford University. 1980. pp. 75-77. 5 pages.

Kurzweil, Plant Bacteria breakthrough enables crops worldwide to take nitrogen from the air. Plant Bacteria Breakthrough Enables Crops Worldwide Take Nitrogen From Air. Aug. 1, 2013. 4 pages.
Kutter et al., Colonization of barley (*Hordeum vulgare*) with *Salmonella enterica* and *Listeria* spp. FEMS Microbiol Ecol. 2006;56:262-71.
Lauritsen et al., A versatile one-step CRISPR-Cas9 based approach to plasmid-curing. Microb Cell Fact. 2017;16(135):1-10.
Leang et al., Genome-wide analysis of the RpoN regulon in Geobacter sulfurreducens. BMC Genomics. Jul. 22, 2009;10:331. doi: 10.1186/1471-2164-10-331.
Liang et al., Minimal effect of gene clustering on expression in *Escherichia coli*. Genetics. Feb. 2013;193(2):453-65. doi: 10.1534/genetics.112.147199. Epub Dec. 5, 2012.
Lim et al., Fundamental relationship between operon organization and gene expression. PNAS USA. Jun. 28, 2011; 108(26):10626-31. doi: 10.1073/pnas.1105692108. Epub Jun. 13, 2011.
Liu et al., Whole genome analysis of halotolerant and alkalotolerant plant growth-promoting rhizobacterium *Klebsiella* sp. D5A. Sci Rep. May 24, 2016;6:1-10.
MacNeil et al., Fine-structure mapping and complementation analysis of nif (nitrogen fixation) genes in Klebsiella pneumoniae. J Bacteriol. Oct. 1978;136(1):253-66.
MacNeil et al., Mutations in nif genes that cause Klebsiella pneumoniae to be derepressed for nitrogenase synthesis in the presence of ammonium. J Bacteriol. Nov. 1980;144(2):744-51.
Magari et al., Pharmacologic control of a humanized gene therapy system implanted into nude mice. J Clin Invest. Dec. 1, 1997;100(11):2865-72.
Marroqui et al., Enhanced Symbiotic Performance by Rhizobium tropici Glycogen Synthase Mutants. J Bacteriol. Feb. 2001;183(3):854-64.
Martinez-Noel et al., NifB and NifEN protein levels are regulated by ClpX2 under nitrogen fixation conditions in Azotobacter vinelandii. Mol Microbiol. Mar. 2011;79(5):1182-93. doi: 10.1111/j.1365-2958. 2011.07540.x. Epub Jan. 25, 2011.
Marx et al., Broad-host-range cre-lox system for antibiotic marker recycling in gram-negative bacteria. Biotechniques. Nov. 2002;33(5):1062-7.
Masepohl et al., Organization and regulation of genes encoding the molybdenum nitrogenase and the alternative nitrogenase in Rhodobacter capsulatus. Arch Microbial. 1996;165:80-90.
Matsubayashi et al., Peptide hormones in plants. Annu Rev Plant Biol. 2006;57:649-74.
Medema et al., Computational tools for the synthetic design of biochemical pathways. Nat Rev Microbiol. Jan. 2, 20123;10(3):191-202. doi: 10.1038/nrmicro2717.
Mengel, Roots, growth and nutrient uptake. Purdue Univ. Dept of Agronomy. May 1995. Publication No. AGRY-95-08. 8 pages.
Mirsky, Refactoring the Salmonella Type III Secretion System. University of California, San Francisco Dissertation. Doctor of Philosophy in Biophysics. Apr. 12, 2012. 59 pages.
Mitra, Regulation of nifLA operon in Azotobacter vinelandii. Jawaharlal Nehru University Thesis. Doctor of Philosophy in Biotechnology. 2000. 163 pages.
Moon et al., Genetic programs constructed from layered logic gates in single cells. Nature. Nov. 8, 2012;491(7423):249-53. doi: 10.1038/naturell516. Epub Oct. 7, 2012.
Mueller et al., Closing yield gaps through nutrient and water management. Nature. 2012;490:254-57.
Mus et al., Symbiotic Nitrogen Fixation and the Challenges to Its Extension to Nonlegumes. Appl Environ Microbial. Jul. 1, 2016; 82(13): 3698-710. doi: 10.1128/AEM.01055-16. Epub Jun. 13, 2016. Pre-Epub Apr. 15, 2016.
Nassar et al., Promotion of plant growth by an auxin-producing isolate of the yeast *Williopsis saturnus* endophytic in maize (*Zea mays* L.) roots. Biol Fertil Soils. 2005;42:97-108.
Nelissen et al., Translational research: from pot to plot. Plant Biotechnol J. 2014;12:277-85.
Nestmann, Mutagenesis by nitrosoguanidine, ethyl methanesulfonate, and mutator gene mutH in continuous cultures of *Escherichia coli*. Sci Direct. Jun. 1975;28(3):323-30.

(56) References Cited

OTHER PUBLICATIONS

Nichkawade, Studies on upstream regulatory sequence of the nifLA promoter of Klebsiella pnuemoniae. Jawaharlal Nehru University Thesis. Doctor of Philosophy in Biotechnology. 1996. 166 pages.
Nielsen, Transgenic organisms—time for conceptual diversification? Nat Biotechnol. 2003;21:227-8.
No et al., Ecdysone-inducible gene expression in mammalian cells and transgenic mice. PNAS USA. Apr. 1996;93(8):3346-51.
Okubo et al., Effects of Elevated Carbon Dioxide, Elevated Temperature, and Rice Growth Stage on the Community Structure of Rice Root-Associated Bacteria. Microbes Environ. Jun. 2014; 29(2):184-90. doi: 10.1264/jsme2.ME14011. Epub May 31, 2014.
Ortiz-Marquez et al., Association with an Ammonium-excreting bacterium allows diazotrophic culture of oil-rich Eukaryotic microalagae. Appl Microbial. 2012;78(7):2345-52.
Pfleger, et al. Combinatorial engineering of intergenic regions in operons tunes expression of multiple genes. Nat Biotechnol. Aug. 2006;24(8):1027-32. Epub Jul. 16, 2006.
Piccioli et al., Neuroantibodies: ectopic expression of a recombinant anti-substance P antibody in the central nervous system of transgenic mice. Neuron. Aug. 1995;15(2):373-84.
Piccioli et al., Neuroantibodies: molecular cloning of a monoclonal antibody against substance P for expression in the central nervous system. PNAS USA. Jul. 1, 1991;88(13): 5611-5.
Plotnikova et al., Pathogenesis of the human opportunistic pathogen Pseudomonas aeruginosa PA14 in Arabidopsis. Plant Physiol. 2000;124:1766-74.
Qiu et al., Construction of genetically engineered strains of Enterobacter cloacae (nifl-(-) A-(c)). Acta Phytophysiologica Sinica. Jan. 1, 1999;25(3):269-73.
Ran et al., Genome erosion in a nitrogen-fixing vertically transmitted endosymbiotic multicellular cyanobacterium. PLoS One. Jul. 8, 2010;5(7):el1486, 11 pages, doi: 10.1371/journal.pone.0011486.
Roberts et al., Regulation and characterization of protein products coded by the nif (nitrogen fixation) genes of Klebsiella pneumoniae. J Bacterial. Oct. 1978;136(1):267-79.
Rogers et al., Synthetic biology approaches to engineering the nitrogen symbiosis in cereals. J Exper Botany. 2014;65(8):1939-46.
Rommens et al., Intergeneric transfer and functional expression of the tomato disease resistance gene Pto. Plant Cell. Oct. 1995;7(10):1537-44.
Roncato-Maccari et al., Endophytic Herbaspirillum seropedicae expresses nif genes in gramineous plants. FEMS Microbiology Ecology. 2003;45:39-47.
Rosenblueth et al., Bacterial Endophytes and Their Interaction with Hosts. Mol Plant Microbe Interact. Aug. 2006;19(8):827-37.
Rosenblueth et al., Nitrogen Fixation in Cereals. Frontiers in Microbiol. Aug. 9, 2018;9:1794, 13 pages.
Saikia et al., Biological nitrogen fixation with non-legumes: An achievable target or a dogma? Curr Sci. 2007;92(3):317-22.
Sandig et al., HBV-derived promoters direct liver-specific expression of an adenovirally transduced LDL receptor gene. Gene Ther. Nov. 1996;3(11):1002-9.
Santi et al., Biological nitrogen fixation in non-legume plants. Annals of Botany. 2013;111:743-67.
Schmitz et al., Iron is required to relieve inhibitory effects on NifL on transcriptional activation by NifA in Klebsiella pneumoniae. J Bacterial. Aug. 1996;178(15):4679-87.
Schouten et al., Do cisgenic plants warrant less stringent oversight? Nat Biotechnol. 2006;24:753.
Service, Genetically engineered microbes make their own fertilizer, could feed the world's poorest. Science. Apr. 2017. 2 pages. doi:I0.H26/science.aallOOO.
Setten et al., Engineering Pseudomonas protegens Pf-5 for Nitrogen Fixation and its application to improve plant growth under nitrogen-deficient conditions. PLOS One. 2013;8(5):e63666. 14 pages.
Shamseldin, The role of different genes involved in symbiotic nitrogen fixation—review. Global J Biotechnol Biochem. 2013;8(4):84-94.
Sibold et al., A nif mutant of Klebsiella pneumoniae fixing nitrogen in the presence of ammonia. FEMS Microbiol Lett. Jan. 1, 1981;10(1):37-41.
Siddavattam et al., Regulation of nif Gene expression in Enterobacter agglomerans: Nucleotide sequence of the nifLA operon and influence of temperature and ammonium on its transcription. Mol Gen Genet. Dec. 20, 1995;249(6):629-36.
Singh et al., An L-methionine-D,L-sulfoximine-resistant mutant of the cyanobacterium Nostoc muscorum showing inhibitor-resistant γ-glutamyl-transferase, defective glutamine synthetase and producing extracellular ammonia during N2 fixation. FEBS Letters. Apr. 5, 1983;154(1):10-4.
Sleight et al., Designing and engineering evolutionary robust genetic circuits. J Biol Engin. 2010;4(12):1-20.
Smanski et al., Synthetic biology to access and expand nature's chemical diversity. Nat Rev Microbiol. Mar. 2016;14(3):135-49. doi: 10.1038/nrmicro.2015.24.
Smanski, et al. Functional optimization of gene clusters by combinatorial design and assembly. Nat Biotechnol. Dec. 2014;32(12):1241-9. doi: 10.1038/nbt.3063. Epub Nov. 24, 2014, 12 pages.
Souza, et al., The N-Terminus of the NIFA protein of herbaspirillum seropedicae is probably involved in sensing of ammonia. Proceedings of the 10th International Congress on Nitrogen Fixation, St. Petersburg, Russia. 1995:260, 1 page.
Spiller et al., Isolation and characterization of nitrogenase-derepressed mutant strains of cyanobacterium Anabaena variabilis. J Bacteriol. Feb. 1986;165(2):412-9.
Steenhoudt et al., Azospirillum, a free-living nitrogen-fixing bacterium closely associated with grasses: genetic, biochemical and ecological aspects. FEMS Microbial Rev. 2000;24:487-506.
Stein et al., The osteocalcin gene: a model for multiple parameters of skeletal-specific transcriptional control. Mol Biol Rep. Aug. 1997;24(3):185-96.
Stemmer, DNA shuffling by random fragmentation and reassembly: In vitro recombination for molecular evolution. PNAS USA. Oct. 1994;91:10747-51.
Stemple, Tilling—a high-throughput harvest for functional genomics. Nat Rev Genet. Feb. 2004;5:145-50. doi:10.1038/nrg1273.
Stephanopoulos, Challenges in engineering microbes for biofuels production. Science. Feb. 9, 2007;315(5813):801-4.
Subtil et al., Secretion of Predicted Inc Proteins of Chlamydia pneumoniae by a Heterologous Type III Machinery. Mol Microbiol. Feb. 2001;39(3):792-800. doi: 10.1046/j.1365-2958.2001.02272.x.
Swain et al., Nitrogen fixation and its improvement through genetic engineering. J Global Biosciences. 2013;2(5):98-112.
Temme et al., Modular control of multiple pathways using engineered orthogonal T7 polymerases. Nucleic Acids Res. Sep. 1, 2012;40(17):8773-81. Epub Jun. 28, 2012.
Temme, et al., Refactoring the nitrogen fixation gene cluster from Klebsiella oxytoca. PNAS, May 1, 2012;109(18):7085-90.
Temme, Designing and Engineering Complex Behavior in Living Machines. University of California, San Francisco Dissertation. Doctor of Philosophy in Bioengineering. Oct. 1, 2011. 74 pages.
Thomas, et al. Ammonium Excretion by an 1-Methionine-dl-Sulfoximine-Resistant Mutant of the Rice Field Cyanobacterium Anabaena siamensis. Appl Environ Microbiol. Nov. 1990; 56(11):3499-504.
Tilman et al., Global food demand and the sustainable intensification of agriculture. PNAS. Oct. 12, 2011;108(50):20260-4.
Triplett, Diazotrophic endophytes: progress and prospects for nitrogen fixation in monocots. Plant and Soil. 1996;186:29-38.
Tritt et al., An Integrated Pipeline for de Novo Assembly of Microbial Genomes. PLOS one. Sep. 13, 2012;7(9):e42304. doi: 10.1371/journal.pone.0042304. 9 pages.
Ueda et al., Remarkable N2-Fixing Bacterial Diversity Detected in Rice Roots by Molecular Evolutionary Analysis of nifH Gene Sequences. J Bacteriol. Mar. 1995;177(5):1414-7.
Vernon et al., Analysis of 16S rRNA gene sequences and circulating cell-free DNA from plasma of chronic fatigue syndrome and non-fatigued subjects. BMC Microbiol. Dec. 23, 2002;2:39, 6 pages.

(56) References Cited

OTHER PUBLICATIONS

Villa et al., Azotobacter vinelandii siderophore can provide nitrogen to support the culture of the green algae neochloris oleoabundans and scenedesmus. FEMS Microbiol Lett. 2014;351(1):70-7.
Voigt et al., Genetic parts to program bacteria. Curr Opin Biotechnol. 2006;17(5):548-57.
Voigt, Gaining Access: Rebuilding Genetics from the Ground Up. MIT. Department of Biological Engineering. Mar. 14, 2011. 20 pages.
Wang et al., Positive and negative regulation of gene expression in eukaryotic cells with an inducible transcriptional regulator. Gene Ther. May 1997;4:432-41.
Wang et al., A minimal nitrogen fixation gene cluster from *Paenibacillus* sp. WLY78 enables expression of active nitrogenase in *Escheichia coli*. PLoS Genet. Oct. 17, 2013;9(10):e1003865. 11 pages. doi:10.1371/journal.pgen.1003865.
Wang et al., Using Synthetic biology to distinguish and overcome regulatory and functional barriers related to nitrogen fixation. PLoS One. 2013;8(7):e68677. 11 pages.
Watanabe et al., Chapter 15. Plasmid-borne gene cluster assemblage and heterologous biosynthesis of nonribosomal peptides in *Escherichia coli*. Methods Enzymol. 2009;458:379-99. doi: 10.1016/S0076-6879(09)04815-0.
Weber et al., A modular cloning system for standardized assembly of multigene constructs. PLoS One. Feb. 18, 2011;6(2):e16765, 11 pages, doi: 10.1371/journal.pone.0016765.
Welch et al., Design Parameters to Control Synthetic Gene Expression in *Escherichia coli*. PLoS One. Sep. 2009;4(9):e7002, 10 pages.
Werner et al., Fast track assembly of multigene constructs using Golden Gate cloning and the MoClo system. Bioeng Bugs. Jan. 1, 2012;3(1):38-43. doi: 10.1371/journal.pone.0016765. Epub Jan. 1, 2012.
Widmaier et al., Engineering the Salmonella type III secretion system to export spider silk monomers. Mol Syst Biol. 2009;5:309, 9 pages.
Wootton et al., Statistics of local complexity in amino acid sequences and sequence databases. Computers & Chemistry. Jun. 1993;17(2):149-63.
Yoshida et al., Atmospheric dinitrogen fixation in the flooded rice rhizosphere as determined by the N-15 isotope technique. Soil Sci Plant Nutr. 1980;26(4):551-9. doi: 10.1080/00380768.1980.10431242.
Young et al., Relationships between corn plants and nitrogen fixing bacteria on an organic farm. Ceres Trust. Dec. 31, 2012. 9 pages.
Zehr et al., New Nitrogen-Fixing Microorganisms Detected in Oligotrophic Oceans by Amplification of Nitrogenase (nifH) Genes. Appl Environ Microbial. Sep. 1998;64(9):3444-50.
Zhang et al., GlnD is Essential for NifA Activation, NtrB/NtrC-Regulated Gene Expression, and Posttranslational Regulation of Nitrogenase Activity in the Photosynthetic, Nitrogen-Fixing Bacterium Rhodospirillum rubrum. J Bacteriol. Feb. 2005;187(4):1254-65.
Zhang et al., Involvement of the ammonium transporter AmtB in nitrogenase regulation and ammonium excretion in Pseudomonas stutzeri A 1501. Res Microbial. 2012;163:332-9.
Brazilian Office Action dated Mar. 10, 2020 for Application No. BR112018006800-4.
European Office Action dated Oct. 16, 2019 for Application No. EP 16854192.8.
Clancy et al., The Domains Carrying the Opposing Activities in Adenylyltransferase are Separated by a Central Regulatory Domain. FEBS J. 2007;274(11):2865-77.
U.S. Appl. No. 14/440,183, filed May 1, 2015, Zhao et al.
U.S. Appl. No. 15/954,557, filed Apr. 16, 2018, Temme et al.
U.S. Appl. No. 15/954,558, filed Apr. 16, 2018, Temme et al.
EP 16854192.8, Feb. 20, 2019, Extended European Search Report.
PCT/US2016/055429, Dec. 30, 2016, International Search Report and Written Opinion.
PCT/US2016/055429, Apr. 19, 2018, International Preliminary Report on Patentability.
Andrianantoandro et al., Synthetic biology: new engineering rules for an emerging discipline. Mol Syst Biol. 2006;2:2006.0028. doi: 10.1038/msb4100073. Epub May 16, 2006.
Batista et al., Manipulating nitrogen regulation in diazotrophic bacteria for agronomic benefit. Biochem Soc Trans. Apr. 1, 2019;47(2):603-14.
Biggins et al., Metabolites from the induced expression of cryptic single operons found in the genome of Burkholderia pseudomallei. J Am Chem Soc. Feb. 16, 2011; 133(6):1638-41. doi: 10.1021/ja1087369. Epub Jan. 19, 2011.
Bonde et al., MODEST: a web-based design tool for oligonucleotide-mediated genome engineering and recombineering. Nucleic Acids Res. Jul. 2014;42(Web Server issue):W408-15. doi: 10.1093/nar/gku428. Epub May 16, 2014.
Brandl et al., Salmonella interactions with plants and their associated microbiota. Phytopathology. Apr. 2013;103(4):316-25. doi: 10.1094/PHYTO-11-12-0295-RVW.
Burris, Nitrogenases. J Biol Chem. May 25, 1991;266(15):9339-42.
Cardinale et al., Contextualizing context for synthetic biology identifying causes of failure of synthetic biological systems. Biotechnol. J. 7:856-866 (2012).
Carr et al., Enhanced multiplex genome engineering through co-operative oligonucleotide coselection. Nucleic Acids Res., 2012, 40(17):e132.
U.S. Appl. No. 17/204,219, filed Mar. 17, 2021, Zhao et al.
[No Author Listed] GM Crop Database. Center for Environmental Risk Assessment (CERA), 2010, retrieved from <http://ucbiotech.org/biotech_info/PDFs/Center_for_Environmental_Risk_Assessment_CERA_2011_GM_Crop_Database.pdf>, 1 page.
[No Author Listed] *Escherichia coli* as a Model Organism and Its Application in Biotechnology. IntechOpen, 2020, retrieved on Mar. 31, 2020, retrieved from https://www.intechopen.com/books/-i-escherichia-coli-i-recent-advances-on-physiology-pathogenesis-and-biotechnological-applications/-i-escherichi%E2%80%A6>, 15 pages.
[No Author Listed] Zehr Lab NifH database, retrieved from URL <https://wwwzehr.pmc.ucsc.edu/nifH_Database_Public/>, Apr. 4, 2014, 1 page.
Amalraj et al., Effect of Polymeric Additives, Adjuvants, Surfactants on Survival, Stability and Plant Growth Promoting Ability of Liquid Bioinoculants. J. Plant Physiol Pathol, 2013, 1:2, 6 pages.
Ambrosio et al., Metabolic engineering of a diazotrophic bacterium improves ammonium release and biofertilization of plants and microalgae, Metab Eng., Mar. 2017, 40:59-68.
Anderson et al., BglBricks: A flexible standard for biological part assembly, J Biological Engineering, 2010;4:1, 12 pages.
Arnold et al., Nucleotide sequence of a 24,206-base-pair DNA fragment carrying the entire nitrogen fixation gene cluster of Klebsiella pneumoniae. J Mol Biol. Oct. 5, 1988;203(3):715-38. doi: 10.1016/0022-2836(88)90205-7.
Arriel-Elias et al., Shelf life enhancement of plant growth promoting rhizobacteria using a simple formulation screening method. African J Microbiology Research, Feb. 2018, 12(5):115-126.
Ausubel et al., Glutamine Synthetase Mutations Which Affect Expression of Nitrogen Fixation Genes in Klebsiella pneumoniae, J Bacteriol, Nov. 1979, 140(2):597-606.
Batzer et al., Enhanced evolutionary PCR using oligonucleotides with inosine at the 3'-terminus. Nucleic Acids Res. Sep. 2, 19915;19(18):5081. doi: 10.1093/nar/19.18.5081.
Baum et al., Control of coleopteran insect pests through RNA interference, Nature Biotechnology, Nov. 2007, 25(11): 1322-1326.
Bayer et al., Synthesis of methyl halides from biomass using engineered microbes. J Am Chem Soc. May 1, 20093;131(18):6508-15. doi: 10.1021/ia809461u.
Bender et al., Regulatory mutations in the Klebsiella aerogenes structural gene for glutamine synthetase, J Bacteriol., Oct. 1977, 132(1):100-105.
Benyon et al., The nif promoters of Klebsiella pneumoniae have a characteristic primary structure. Cell. Sep. 1983;34(2):665-71. doi: 10.1016/0092-8674(83)90399-9.

(56) References Cited

OTHER PUBLICATIONS

Berninger et al., Maintenance and assessment of cell viability in formulation of non-sporulating bacterial inoculants. Microb. Biotechnol., Mar. 2018, 11(2):277-301 (2018); doi: 10.1111/1751-7915.12880.
Bittner et al., RpoS and RpoN are involved in the growth-dependent regulation of rfaH transcription and 0 antigen expression in *Salmonella enterica* serovar typhi, Microbial Pathogenesis, Jan. 2004;36(1): 19-24.
Bloch et al., Biological nitrogen fixation in maize: optimizing nitrogenase expression in a rootassociated diazotroph. J Experimental Botany, Jul. 2020, 71(15):4591-4603.
Bosmans et al., Sea anemone venom as a source of insecticidal peptides acting on voltage-gated Na+ channels, Toxicon, Mar. 2007, 49(4):550-560.
Boyle et al., Tools for genome-wide strain design and construction. Curr Opin Biotechnol. Oct. 2012;23(5):666-71.
Buck et al., Frameshifts close to the Klebsiella pneumoniae nifH promoter prevent multicopy inhibition by hybrid nifH plasmids. Mol Gen Genet. May 1987;207(2-3):492-8. doi: 10.1007/BF00331620.
Buckley et al., NifH Sequence Database. Retrieved from <https://blogs.cornell.edu/buckley/nifh-sequence-database/>. Buckley Lab. Available on or before Jan. 10, 2018. 2 pages.
Chakroun et al., Bacterial Vegetative Insecticidal Proteins (Vip) from Entomopathogenic Bacteria, Microbiol Mol Biol Rev., Mar. 2016, 80(2):329-50.
Chen et al., Characterization of 582 natural and synthetic terminators and quantification of their design constraints, Nat. Methods, 2013, 10:659-664.
Chin, Programming and engineering biological networks, Curr Opin Struct Biol 16:551-556 (2006).
Colby, Calculating Synergistic and Antagonistic Responses of Herbicide Combinations. Weeds, Jan. 1967, 15(1):20-22, 4 pages.
Colebatch et al., Symbiotic nitrogen fixation research in the postgenomics era, New Phytologist., 2002, 153(1):37-42.
Compant et al., A review on the plant microbiome: Ecology, functions, and emerging trends in microbial application, Journal of Advanced Research, Sep. 2019, 19:29-37.
Costerton et al., Microbial Biofilms. Annu. Rev. Microbial., Oct. 1995, 49:711-745.
Crameri et al., Molecular evolution of an arsenate detoxification pathway by DNA shuffling, Nat. Biotechnol., 1997, 15:436-438.
Crickmore et al., Revision of the Nomenclature for the Bacillus thuringiensis Pesticidal Crystal Proteins, Microbiol Mol Biol Rev., Sep. 1998, 62(3):807-813.
Crook et al., Re-engineering multicloning sites for function and convenience, Nucl. Acids Res., 2011, 39:e92, 10 pages.
Czar et al., Gene synthesis demystified, Trends Biotechnol, 2009, 27(2):63-72.
Da Silva et al., Survival of endophytic bacteria in polymer-based inoculants and efficiency of their aplication to sugarcane/Plant Soil, May 2012, 356:231-243.
Dandekar et al., Conservation of gene order: a fingerprint of proteins that physically interact, Trends Biochem. Sci., 1998, 23:324-328.
Das et al., Microbial assay of N2 fixation rate, a simple alternate for acetylene reduction assay, MethodsX, 2018, 5:909-914.
Davin-Regli et al., Enterobacter aerogenes and Enterobacter cloacae; versatile bacterial pathogens confronting antibiotic treatment, Front Microbiol, 2015, 6:392, 10 pages.
De Freitas, Yield and N assimilation of winter wheat (Triticum aestivum L., var. Norstar) inoculated with rhizobacteria, Pedobiologia, Jan. 2000, 44(2):97-104.
De Raad et al., A solid-phase platform for combinatorial and scarless multipart gene assembly, ACS Synth. Biol., 2013, 2:316-326.
Dykxhoorn et al., A set of compatible tac promoter expression vectors, Gene, 1996, 177(1-2):133-136.
Endy et al., Foundations for engineering biology, Nature, 2005, 438:449-453.
Enkh-Amgalan et al., Molecular evolution of the nif gene cluster carrying nifI1 and nifI2 genes in the Gram-positive phototrophic bacterium Heliobacterium chlorum, International Journal of Systematic and Evolutionary Microbiology, 2006, 56:65-74.
Estrem et al., Identification of an UP element consensus sequence for bacterial promoters, PNAS, 1998, 95(11):9761-9766.
Eyraud et al., Expression and Biological Activity of the Cystine Knot Bioinsecticide PA1b (Pea Albumin 1 Subunit b), PLOS One, Dec. 2013, 8(12):e81619, 9 pages.
Fani et al., Molecular evolution of nitrogen fixation: the evolutionary history of the nifD, nifK, nifE, and nifN gene, J Mol Evol., 2000;51(1):1-11.
Feher et al., In the fast lane: large-scale bacterial genome engineering, J Biotechnol., Jul. 2012, 160(1-2):72-9.
Fischbach et al., The evolution of gene collectives: how natural selection drives chemical innovation, Proc. Natl. Acad. Sci. USA, 2008, 105:4601-4608.
Fontana et al., RNA folding and combinatory landscapes, Phys. Rev. E., 1993, 47:2083-2099.
Forner et al., Treatment of hepatocellular carcinoma, Crit Rev Oncol Hematol., Nov. 2006, 60(2):89-98.
Gaby et al., A comprehensive aligned nifH gene database: a multipurpose tool for studies of nitrogen- fixing bacteria, Database, 2014, 2014:bau001, 8 pages.
Gamer et al., A T7 RNA polymerase-dependent gene expression system for *Bacillus megaterium*, Appl Micro Biol Biotechnol., Apr. 2009, 82(6): 1195-203.
GenBank Accession No. CP007215.3, Kosakonia sacchari SP1 chromosome, complete genome, Sep. 19, 2017, 729 pages.
GenBank Accession No. CP016337.1 Kosakonia sacchari strain BO-1 chromosome, complete Genome. Jul. 11, 2016, 1119 pages.
Georg et al., cis-antisense RNA, another level of gene regulation in bacteria, Microbiol Mol Biol Rev, 2011,75(2):286-300.
Gibson et al., Chemical synthesis of the mouse mitochondrial genome, Nat. Methods, 2010, 7:901-903.
Gibson et al., Enzymatic assembly of DNA molecules up to several hundred kilobases, Nat. Methods, 2009, 6(5):343-345.
Gosink et al., The product of the Klebsiella pneumoniae nifX gene is a negative regulator of the nitrogen fixation (nit) regulon, J Bacteriology, 1990, 172(3):1441-1447.
Gottelt et al., Deletion of a regulatory gene within the cpk gene cluster reveals novel antibacterial activity in Streptomyces coelicolor A3(2), Microbiology, 2010, 156:2343-2353.
Guell et al., Bacterial transcriptomics: what is beyond the RNA horiz-ome?, Nature reviews Microbiology, 2011, 9(9):658-669.
Guell et al., Transcriptome complexity in a genome-reduced bacterium, Science, 2009, 326:1268-1271.
Hernandez et al., Biochemical analysis of the recombinant Fur (ferric uptake regulator) protein from Anabaena PCC 7119: factors affecting its oligomerization state, Biochem J., 2002, 366:315-322.
Hoeschle-Zeledon et al., Regulatory challenges for biological control. The CGIAR Systemwide Program on Integrated Pest Management, Jan. 2013, SP-IPM Secretariat, International Institute Tropical Agriculture (IITA), Ibadan, Nigeria, 53 pages.
Hu et al., Assembly of nitrogenase MoFe protein, Biochemistry, 2008, 47(13):3973-3981.
Huynen et al., Smoothness within ruggedness: the role of neutrality in adaptation, Proc. Natl. Acad. Sci. USA, 1996, 93:397-401.
Iber, A quantitative study of the benefits of co-regulation using the spoIIA operon as an example, Mol. Sys. Biol., 2006, 2:1-6.
Idalia et al., *Escherichia coli* as a model organism and its application in biotechnology, Recent Advances on Physiology, Pathogenesis, and Biotechnological Applications, Chapter 13, 2017, pp. 253-274.
Ishihama, Prokaryotic genome regulation: multifactor promoters, multitarget regulators and hierarchic networks, FEMS Microbial Rev, 2010, 34(5):628-645.
Ivanova et al., Artificial Regulation of Genes, Of the coding proteins of the nitrogenase complex Rhizobial bacteria, Natural Sciences, 2014, 13(174):36-39.
Izquierdo et al., Distribution of Extensive nifH Gene Diversity Across Physical Soil Microenvironments, Microbial Ecology, 2006, 51(4):441-452.

(56) References Cited

OTHER PUBLICATIONS

Jacob et al., Solid-state NMR studies of Klebsiella pneumoniae grown under nitrogen-fixing conditions, J Biol Chem, 1987, 262(1):254-259.
Jacoby et al., The Role of Soil Microorganisms in Plant Mineral Nutrition-Current Knowledge and Future Directions, Frontiers in Plant Scients, 2017, 8(19):1-19.
Jahn et al., Extraction of Extracellular Polymeric Substances (EPS) from Biofilms Using a Cation Exchange Resin. Wat. Sci. Tech., 1995, 32(8):157-164.
Janczarek et al., Multiple copies of rosR and pssA genes enhance exopolysaccharide production, symbiotic competitiveness and clover nodulation in Rhizobium leguminosarum bv. trifolii, Antonie Van Leeuwenhoek, Nov. 2009, 96(4):471-86.
Jensen, The Escherichia coli K-12 wild types W3110 and MG1655 have an rph frameshift mutation that leads to pyrimidine starvation due to low pyre expression levels, J. Bacteriol., 1993, 175:3401-3407.
Johnson et al., Properties of overlapping genes are conserved across microbial genomes, Genome Res, 2004, 14(11):2268-2272.
Joseph et al., Recent developments of the synthetic biology toolkit for Clostridum, Frontiers in microbology, 2018, 9(154):1-13.
Kabaluk et al., The use and regulation of microbial pesticides in representative jurisdictions Worldwide. IOBC Global, 2010, 99 pages.
Kalir et al., Ordering genes in a flagella pathway by analysis of expression kinetics from living bacteria, Science, 2001, 292(5524):2080-2083.
Kaneko et al., Complete genomic structure of the cultivated rice endophyte Azospirillum sp. B510, DNA Res., 2010, 17:37-50.
Katsnelson, Engineered bacteria could boost corn yields: Gene-edited microbe offer continuous nitrogen fixation, Chemical & Engineering News, Dec. 28, 2021, retrieved from URL https://cen.acs.org/food/agriculture/Engineered-bacteria-boost-corn-yields/99/web/2021/12>, 3 pages.
Kececiglu et al., Of mice and men: Algorithms for evolutionary distances between genomes with translocation, SODA: Proceedings of the sixth annual ACM-SIAM symposium on Discrete algorithms, 1995, 10 pages.
Kelly et al., Measuring the activity of BioBrick promoters using an in vivo reference standard, J Biol Eng, 2009, 3:4, 13 pages.
Kim et al., "A 20 nucleotide upstream element is essential for the nopaline synthase (nos) promoter activity," Plant Mol Biol., Jan. 1994, 24(1): 105-17.
King et al., Spider-Venom Peptides: Structure, Pharmacology, and Potential for Control of Insect Pests, Annu. Rev. Entomol., 2013, 58:475-96.
Kingsford et al., Rapid, accurate, computational discovery of Rho-independent transcription terminators illuminates their relationship to DNA uptake, Genome Bio. 2007, 8(2):R22, 12 pages.
Kitano, Systems biology: a brief overview, Science, 2002, 295(5560): 1662-1664.
Klose et al., "Glutamate at the site of phosphorylation of nitrogen-regulatory protein NTRC mimics aspartyl-phosphate and activates the protein," J Mol Biol., Jul. 1993, 232(1):67-78.
Knight, Idempotent Vector Design for Standard Assembly of Biobricks, MIT Artificial Intelligence Laboratory, The TTL Data Book for Design Engineers, 2003, 11 pages.
Kovacs et al., Stochasticity in protein levels drives colinearity of gene order in metabolic operons of Escherichia coli, PLoS Biol, 2009, 7(5):e1000115, 9 pages.
Kranz et al., "Ammonia-constitutive nitrogen fixation mutants of Rhodobacter capsulatus," Gene, Nov. 1988, 71(1):65-74.
Kumar et al., Metabolic regulation of Escherichia coli and its gdhA, glnL, gltB, D mutants under different carbon and nitrogen limitations in the continuous culture, Microbial Cell Factories, Jan. 2010, 9(8): 1-17.
Lenski et al., Effects of Segregation and Selection on Instability of Plasmid pACYC184 in Escherichia coli B, Journal of Bacteriology, Nov. 1987, 169(11):5314-5316.
Levican et al., Comparative genomic analysis of carbon and nitrogen assimilation mechanisms in three indigenous bioleaching bacteria: predictions and validations, BMC Genomics, 2008, 9:581, 19 pages.
Levin-Karp et al., Quantifying translational coupling in E. coli synthetic operons using RBS modulation and fluorescent reporters, ACS Synth. Biol., 2013, 2:327-336.
Li et al., "Human Enhancers Are Fragile and Prone to Deactivating Mutations," Mol Biol Evol., Aug. 2015, 32(8):2161-80.
Lin et al., PC, a Novel Oral Insecticidal Toxin from Bacillus bombysepticus Involved in Host Lethality via APN and BtR-175, Scientific Reports, Jun. 2015, 5:11101, 14 pages.
Liu et al., Phenazine-1-carboxylic acid biosynthesis in Pseudomonas Chlororaphis GP72 is positively regulated by the sigma factor RpoN, World J Microbiology and Biotechnology, Jan. 2008, 24(9): 1961-1966.
Lombo et al., The mithramycin gene cluster of Streptomyces argillaceus contains a positive regulatory gene and two repeated DNA sequences that are located at both ends of the cluster, J. Bacterial., 1999, 181:642-647.
Lowman et al., Strategies for enhancement of switchgrass (Panicum virgatum L.) performance under limited nitrogen supply based on utilization of N-fixing bacterial endophytes. Plant and Soil, Aug. 2016, 405(1):47-63, 17 pages.
Lucks et al., Toward scalable parts families for predictable design of biological circuits, Curr. Opin. Microbiol., 2008, 11:567-573.
Ma et al., Effect of nicotine from tobacco root exudates on chemotaxis, growth, biocontrol efficiency, and colonization byPseudomonas aeruginosaNXHG29, Antonie van Leeuwenhoek, 2018, 111(7):1237-1257.
Mabrouk et al., Chapter 6: Potential of Rhizobia in Improving Nitrogen Fixation and Yields of Legumes, Symbiosis, May 30, 2018, IntechOpen, pp. 1-16, retrieved on Jan. 12, 2021, retrieved from URL<https://www.intechopen.com/books/symbiosis/potential-of-rhizobia-in-improving-B351nitrogen-fixation-and-yields-of-legumes> 2 pages, Abstract.
Magasanik, Genetic control of nitrogen assimilation in bacteria, Ann. Rev. Genet, 1982, 16:135-68.
Mandal et al., Gene regulation by riboswitches, Nat Rev Mol Cell Biol, 2004, 5(6):451-463.
Mao et al., Silencing a cotton bollworm P450 monooxygenase gene by plant-mediated RNAi impairs larval tolerance of gossypol. Nature Biotechnology, Nov. 2007, 25(11): 1307-1313.
Martinelli et al., Structure-function studies on jaburetox, a recombinant insecticidal peptide derived from jack bean (Canavalia ensiformis) urease, Biochimica et Biophysica Acta, Mar. 2014, 1840(3):935-44.
Mason et al., Cryptic Growth in Klebsiella-Pneumoniae, Appl Microbiol Biot, 1987, 25(6):577-584.
Medema et al., Exploiting plug-and-play synthetic biology for drug discovery and production in microorganisms, Nat. Rev. Microbiol., 2011, 9:131-137.
Mirzahoseini et al., Heterologous Proteins Production in Escherichia coli: An Investigation on the Effect of Codon Usage and Expression Host Optimization, Cell Journal (Yakhteh), Dec. 2011, 12(4):453, 7 pages.
Miyazaki, Creating random mutagenesis libraries by megaprimer PCR of whole plasmid (MEGA WHOP), Methods Mol Biol, 2003, 231:23-28.
Mus et al., "Diazotrophic Growth Allows Azotobacter vinelandii To Overcome the Deleterious Effects of a glnE Deletion," Appl Environ Microbiol., Jun. 2017, 83(13):e00808-17.
Muse et al., The nac (Nitrogen Assimilation Control) Gene from Escherichia coli, J Bacteriology, Mar. 1998, 180(5):1166-1173.
Mutalik et al., Quantitative estimation of activity and quality for collections of functional genetic elements, Nat. Methods, 2013, 10:347-353.
Nagy et al., Nanofibrous solid dosage form of living bacteria prepared by electrospinning. eXPRESS Polymer Letters, 2014, 8(5):352-361.

(56) References Cited

OTHER PUBLICATIONS

Naimov et al., Solubilization, Activation, and Insecticidal Activity of Bacillus thuringiensis Serovar thompsoni HD542 Crystal Proteins, Applied and Environmental Microbiology, Dec. 2008, 74(23):7145-7151.
Nielsen et al., Conceptual model for production and composition of exopolymers in biofilms. Wat. Sci. Tech., 1997, 36(1): 11-19.
Nielsen et al., Extraction of EPS. Wingender et al. (eds.), Microbial Extracellular Polymeric Substances, 1999, 24 pages.
Noskov et al., Assembly of large, high G+C bacterial DNA fragments in yeast, ACS Synth. Biol., 2012, 1:267-273.
Oh et al., Organization of nif gene cluster in *Frankia* sp. EuIK1 strain, a symbiont of Elaeagnus umbellata, Arch. Microbiol., 2012, 194:29-34.
Ohta et al., Associative N2-fixation of rice with soiol microorganisms. Soil and Microorganisms. 1985;27:17-27.
Ohtsuka et al., An alternative approach to deoxyoligonucleotides as hybridization probes by insertion of deoxyinosine at ambiguous codon positions, J. Biol. Chem., 1985, 260:2605-2608.
Orme-Johnson, Molecular basis of biological nitrogen fixation, Annu Rev Biophys Biophys Chem, 1985, 14:419-459.
Ortiz-Marquez et al., Association with an Ammonium-excreting bacterium allows diazotrophic culture of oil-rich Eukaryotic microalagae, Appl. Microbial., 2012, 78(7):2345-2352.
Pakula et al., "Genetic analysis of protein stability and function," Annu Rev Genet, 1989, 23:289-310.
Parker et al., Pore-forming protein toxins: from structure to function, Progress in Biophysics & Molecular Biology, 2005, 88:91-142.
Patil et al., Liquid formulations of Acetobacter diazotrophicus L 1 and Herbaspirillum seropedicae J24 and their field trials on wheat. International J Environmental Science, 2012, 3(3): 1116-1129, 4 pages (Abstract Only).
Philippe et al., Improvement of pCVD442, a suicide plasmid for gene allele exchange in bacteria, Plasmid, 2004, 51(3):246-255.
Pickens et al., Metabolic engineering for the production of natural products, Annu. Rev. Chem. Biomol. Eng., 2011, 2:211-236.
Poliner et al., Nontransgenic Marker-Free Gene Disruption by an Episomal CRISPR System in the Oleaginous Microalga, Nannochloropsis oceanica CCMP1779. Plant J. Jul. 2019; 99(1): 112-127.
Price et al., Operon formation is driven by coregulation and not by horizontal gene transfer, Genome Res., 2005, 15:809-819.
Price et al., The life-cycle of operons, PLoS Genet., 2006, 2:e96, 15 pages.
Purcell et al., Cholesterol oxidase: a potent insecticidal protein active against boll weevil larvae, Biochem Biophys Res Commun, Nov. 1993, 196(3): 1406-13.
Purnick et al., The second wave of synthetic biology: from modules to systems, Nat Rev Mol Cell Biol, 2009, 10(6):410-422.
Pyne et al., Coupling the CRISPR/Cas9 System with Lambda Red Recombineering Enables Simplified Chromosomal Gene Replacement in *Escherichia coli*, Applied and Environmental Microbioloy, Aug. 2015, 81(15):5103-5144.
Qaim et al., Yield Effects of Genetically Modified Crops in Developing Countries. Science, Feb. 2003, 299(5608):900-2.
Rakhee et al., Extracellular polymeric substances of the marine fouling diatom amphora rostrata Wm.Sm. Biofouling, 2001, 17(2):117-127, 12 pages.
Ramirez et al., Burkholderia and Paraburkholderia are Predominant Soybean Rhizobial Genera in Venezuelan Soils. Different Climatic and Topographical Regions, Microbes and Environments. Mar. 2019, 34(1):43-58.
Ramon et al., Single-step linker-based combinatorial assembly of promoter and gene cassettes for pathway engineering. Biotechnol. Lett., 2011, 33:549-555.
Resendis-Antonio et al., Systems biology of bacterial nitrogen fixation: High-throughput technology and its integrative description with constraint-based modeling. BMC Syst Biol., 2011,5:120, 15 pages.
Riedel et al., Nitrogen fixation by Klebsiella pneumoniae is inhibited by certain multicopy hybrid nif plasmids. J Bacterial, 1983, 153(1):45-56.
Robledo et al., Rhizobium cellulase CelC2 is essential for primary symbiotic infection of legume host roots. Proc Natl Acad Sci USA, May 2008, 105(19):7064-9.
Robledo et al., Role of Rhizobium endoglucanase CelC2 in cellulose biosynthesis and biofilm formation on plant roots and abiotic surfaces. Microb Cell Fact., Sep. 2012, 11:125, 12 pages.
Robson et al., Azotobacter Genomes: The Genome of Azotobacter chroococcum NCIMB 8003 (ATCC 4412). Plos One. 2015; 10(6): e0127997.
Rojas-Tapias et al., Preservation of Azotobacter chroococcum vegetative cells in dry polymers. Univ. Sci., 2015, 20(2):201-207.
Rong et al., Promoter specificity determinants of T7 RNA polymerase, Proc. Natl. Acad. Sci. USA, 1998;95(2):515-519.
Rossolini et al., Use of Deoxyinosine-Containing Primers vs Degenerate Primers for Polymerase Chain Reaction Based on Ambiguous Sequence Information, Mol. Cell. Probes, 1994, 8:91-98.
Rubio et al., Maturation of Nitrogenase: a Biochemical Puzzle. J. Bacteriology, 2005; 187(2):405-414.
Ryu et al., Control of nitrogen fixation in bacteria that associate with cereals. Nat. Microbiol., Feb. 2020, 5(2):314-330, 31 pages.
Saleh et al., Involvement of gacS and rpoS in enhancement of the plant growth-promoting capabilities of Enterobacter cloacae CAL2 and UW4, Canadian Journal of Microbiology, Aug. 2001, 47(8):698-705.
Salis et al., Automated design of synthetic ribosome binding sites to control protein expression. Nat Biotechnol, 2009, 27(10):946-950.
Sanahuja et al., Bacillus thuringiensis: a century of research, development and commercial applications. Plant Biotechnology J, Apr. 2011, 9(3):283-300.
Sandoval et al., Strategy for directing combinatorial genome engineering in *Escherichia coli*, Proc Natl Acad Sci USA, Jun. 2012, 109(26): 10540-5.
Sanjuan et al., Multicopy plasmids carrying the klebsiella pneumoniae nifA gene enhance rhizobium meliloti nodulation competitiveness on alfalfa. Mol Plant Microbe Int. 1991;4(4):365-9.
Sanyal et al., The etiology of hepatocellular carcinoma and consequences for treatment. Oncologist, 2010, 15(Suppl 4):14-22.
Schmidt-Dannert et al., Molecular breeding of carotenoid biosynthetic pathways. Nat. Biotechnol., 2000, 18:750-753.
Schuler et al., Insect-resistant transgenic plants, Trends in Biotechnology, Apr. 1998, 16(4):168-175.
Schuler et al., Potential side effects of insect-resistant transgenic plants on arthropod natural Enemies. Trends Biotechnol., May 1999, 17(5):210-216.
Shetty et al., Engineering BioBrick vectors from BioBrick parts. J Biol Eng, 2008, 2:5, 12 pages.
Sibold et al., Constitutive expression of nitrogen fixation (nif) genes of Klebsiella pneumoniae due to a DNA duplication. Embo J., 1982, 1(12):1551-8.
Simon et al., Perturbation of niff expression in Klebsiella pneumoniae has limited effect on nitrogen fixation, J Bacteriol, 1996, 178(10):2975-2977.
Singer et al., "Genes and Genomes," Moscow: Mir, 1998, 1:33, 4 pages (with machine translation).
Sivaraman et al., Codon choice in genes depends on flanking sequence information—implications for theoretical reverse translation, Nucleic Acids Res, 2008, 36(3):e16, 8 pages.
Sleight et al., Randomized BioBrick assembly: a novel DNA assembly method for randomizing and optimizing genetic circuits and metabolic pathways, ACS Synth. Biol., 2013, 2(9):506-518.
Smanski et al., Engineered Streptomyces platensis strains that overproduce antibiotics platensimycin and platencin, Antimicrob. Agents Chemother., 2009, 53:1299-12304.
Sorek et al., Prokaryotic transcriptomics: a new view on regulation, physiology, and pathogenicity, Nat. Rev. Genet., 2010, 11:9-16.
Staron et al., The Third Pillar of Bacterial Signal Transduction: Classification of the Extracytoplasmic Function (ECF) Sigma Factor Protein Family, Mol Microbiol, 2009, 14(3): 557-81.
Stewart et al., In situ studies on nitrogen fixation with the acetylene reduction technique, Science, 1967, 158(3800):536.

(56) References Cited

OTHER PUBLICATIONS

Stucken et al., The smallest known genomes of multicellular and toxic cyanobacteria: comparison, minimal gene sets for linked traits and the evolutionary implications, PLoS One, 2010, 5:e9235, 15 pages.
Suh et al., Functional expression of the FeMo-cofactor-specific biosynthetic genes nifEN as a NifE-N fusion protein synthesizing unit in Azotobacter vinelandii, Biochem. Biophys. Res. Comm., 2002, 299:233-240.
Suzuki et al., Immune-mediated motor polyneuropathy after hematopoietic stem cell transplantation, Bone Marrow Transplant., Aug. 2007, 40(3):289-91.
Tamsir et al., Robust multicellular computing using genetically encoded NOR gates and chemical 'wires', Nature, 2011, 469(7329):212-215.
Tan, A synthetic biology challenge: making cells compute, Mol Biosyst, 2007, 3:343-353.
Temme et al., Induction and relaxation dynamics of the regulatory network controlling the type III secretion system encoded within Salmonella pathogenicity island 1, J Mol Biol, 2008, 377(1):47-61.
Thiel et al., Characterization of genes for a second Modependent nitrogenase in the cyanobacterium Anabaena variabilis, J. Bact., 1997, 179:5222-5225.
Tijssen, Laboratory Techniques In Biochemistry And Molecular Biology, Elsevier, 1993, 24:65 pages.
Uozumi et al., Cloning and Expression of the nif A Gene of Klebsiella oxytoca in K. pneumoniae and Azospirillum lipoferum, Agricultural and Biological Chemistry, 1986, 50(6): 1539-1544.
Van Dongen, Performance criteria for graph clustering and Markov cluster experiments, CWI, 2000, 36 pages.
Van Heeswijk et al., Nitrogen Assimilation in Escherichia coli: Putting Molecular Data into a Systems Perspective, Microbiology and Molecular Biology Reviews, Dec. 2013, 77(4):628-695.
Villalobos et al., Gene Designer: a synthetic biology tool for constructing artificial ONA segments, BMC Bioinformatics, 2006, 7:285, 8 pages.
Wang et al., Biofilm formation enables free-living nitrogen-fixing rhizobacteria to fix nitrogen under aerobic conditions. ISME Journal, Jul. 2017, 11:1602-1613.
Wang et al., Ligand-inducible and liver-specific target gene expression in transgenic mice, Nat Biotechnol., Mar. 1997, 15(3):239-43.
Wang et al., Positive and negative regulation of gene expression in eukaryotic cells with an inducible transcriptional regulator, Gene Ther., May 1997, 4(5):432-441.
Wang et al., Programming cells by multiplex genome engineering and accelerated evolution, Nature, Aug. 2009, 460(7257):894-8.
Wang et al., Roles of poly-3-hydroxybutyrate (PHB) and glycogen in symbiosis of Sinorhizobium meliloti with Medicago sp. Microbiology, Feb. 2007, 153(2):388-398.
Watanabe et al., Total biosynthesis of antitumor nonribosomal peptides in *Escherichia coli*, Nature Chemical Biology, 2006, 2:423-428.
Wei et al., Endophytic nitrogen-fixing Klebsiella variicola strain DX120E promotes sugarcane growth, Biology and fertility of soils, 2014, 50:657-666.
Wells, Additivity of mutational effects in proteins, Biochemistry, 1990, 29:8509-8517.
Wen et al., Enabling Biological Nitrogen Fixation for Cereal Crops in Fertilized Fields. ACS Synth. Biol., Dec. 2021, 10(12):3264-3277.
Wenzel et al., Recent developments towards the heterologous expression of complex bacterial natural product biosynthetic pathways, Curr Opin Biotechnol, 2005, 16(6):594-606.
Wimpenny et al., Community structure and co-operation in biofilms. 59th Symposium of the Society for General Microbiology, Allison et al. (eds.), Sep. 2000, 23 pages.
Witkowski et al., Conversion of a β-Ketoacyl synthase to a malonyl decarboxylase by replacement of the active-site cysteine with glutamine. Biochemistry, Sep. 1999, 38(36):11643-50.
Woolbright et al., Novel insight into mechanisms of cholestatic liver injury, World J Gastroenterol., Sep. 2012, 18(36):4985-93.
Wu et al., Effects of biofertilizer containing N-fixer, P and K solubilizers and AM fungi on maize growth: a greenhouse trial. Geodernna, Mar. 2005, 125(1-2):155-166.
Wu et al., Multivariate modular metabolic engineering of *Escherichia coli* to produce resveratrol from L-tyrosine. J. Biotechnol., 2013, 167:404-411.
Wu et al., Root exudates from two tobacco cultivars affect colonization of Ralstonia solanacearum and the disease index. European J Plant Pathology. 2014;141(4):667-677.
Xie et al., Interaction between NifL and NifA in the nitrogen-fixing Pseudomonas stutzeri A1501. Microbiology (Reading), Dec. 2006, 152(Pt 12):3535-3542.
Xu et al., ePathBrick: a synthetic biology platform for engineering metabolic pathways in *E. coli.*, ACS Synth. Biol, 2012, 1:256-266.
Yan et al., Global transcriptional analysis of nitrogen fixation and ammonium repression in rootassociated Pseudomonas stutzeri A1501, BMC Genomics, Jan. 2010, 11(11):1-13.
Yao et al., Complementation analysis of heterologous nifA genes to nifA mutants of Sinorhizobium pallida. Chinese Science Bulletin, Oct. 2006, 51(19):2258-2264, 2 pages.
Yarza et al., Uniting the classification of cultured and uncultured bacteria and archaea using 16S rRNA gene sequences, Nature Rev. Micro., 2014, 12:635-345.
Ye et al., Primer-BLAST: a tool to design target-specific primers for polymerase chain reaction, BMC Bioinformatics., Jun. 2012, 13(134): 1-11.
Yokobayashi et al., Directed evolution of a genetic circuit, Proc Natl Acad Sci USA, 2002, 99(26):16587-16591.
Yu et al., Recombineering Pseudomonas protegens CHA0: An innovative approach that improves nitrogen fixation with impressive bactericidal potency.Microbiological Research, Jan. 2019,218:58-65.
Zaslaver et al., Optimal gene partition into operons correlates with gene functional order, Phys Biol, 2006, 3(3):183-189.
Zazopoulos et al., A genomics-guided approach for discovering and expressing cryptic metabolic pathways, Nat Biotechnol, 2003, 21(2):187-190.
Zhang et al., Mutagenesis and functional characterization of the four domains of GlnD, a bifunctional nitrogen sensor protein. J Bacteriology, Jun. 2010, 192(11):2711-2721.
Zhang et al., Mutagenesis and Functional Characterization of the glnB, glnA, and nifA Genes from the Photosynthetic Bacterium Rhodospirillum rubrum, Journal of Bacteriology, Feb. 2000, 182(4):983-992.
Zhao et al., Evidence for nifU and nifS participation in the biosynthesis of the iron-molybdenum cofactor of nitrogenase, J. Biol. Chem., 2007, 282(51):37016-37025.
Zomer et al., PPP: Perform Promoter Prediction, retrieved from URL <http://bioinformatics.biol.rug.nl/websoftware/ppp/ppp_start.php>, 2011, 2 pages.

\* cited by examiner

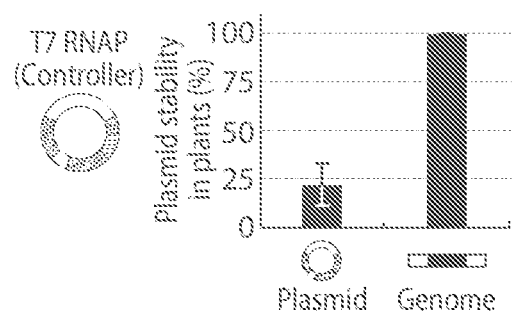 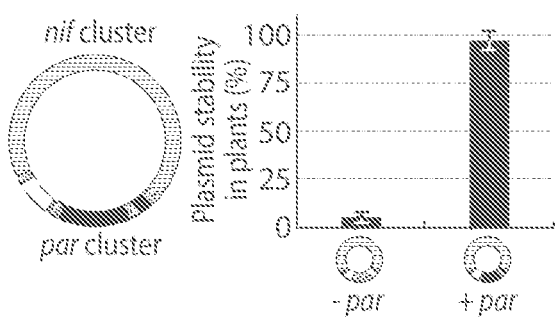
Fig. 4A  Fig. 4B
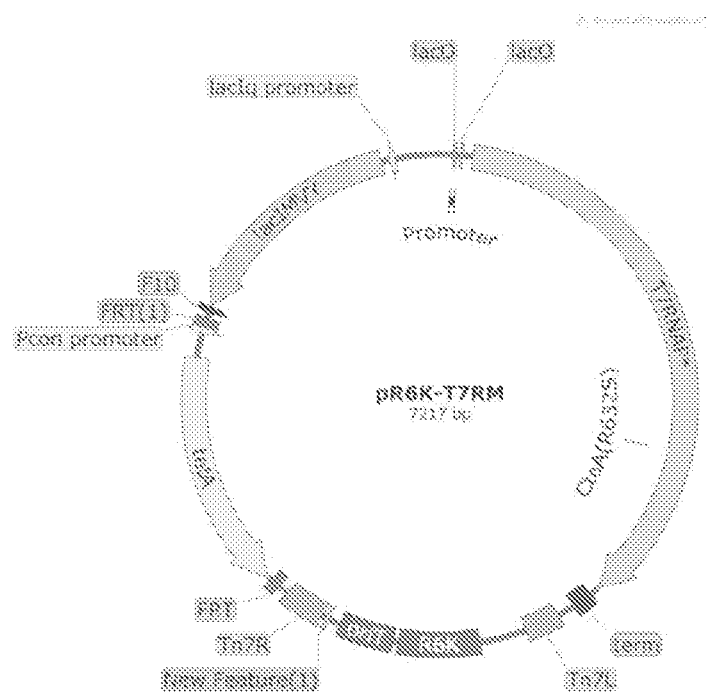
Fig. 5

```
SEQUENCE LISTING

<160> NUMBER OF SEQ ID NOS: 6

<210> SEQ ID NO 1
<211> LENGTH: 19311
<212> TYPE: DNA
<213> ORGANISM: Artificial Sequence
<220> FEATURE:
<223> OTHER INFORMATION: Synthetic Polynucleotide

<400> SEQUENCE: 1
taatacgact cactataggg agaacaataa actaacataa ggaggataaa tatgaccatg      60
cgtcagtgcg cgatttatgg caaaggtggt attggcaaaa gcacgacgac ccagaacttg     120
gtggcggccc tggccgagat gggtaaaaag gttatgattg tgggttgcga cccgaaggcc     180
gacagcacgc gcctgattct gcacgcgaaa gcacaaaaca cgattatgga gatggctgcc     240
gaggttggta gcgtggagga tctggagctg gaggacgttc tgcaaattgg ttacggtgat     300
```

```
gttcgttgcg cagagagcgg tggtccggaa ccaggtgtcg gctgtgcggg tcgtggtgta    360
attaccgcta tcaatttcct ggaagaagag ggtgcgtacg aagatgatct ggatttcgtt    420
ttctacgatg tgctgggtga tgtcgtgtgc ggtggttttg caatgccgat tcgcgagaat    480
aaggcacaag aaatttacat tgtctgtagc ggcgagatga tggcaatgta cgctgctaac    540
aacatcagca agggtattgt taaatacgca aaaagcggta aggttcgctt gggtggtttg    600
atttgcaaca gccgtcagac cgaccgtgag gacgaactga tcatcgccct ggctgagaaa    660
ctgggcaccc aaatgatcca cttcgtgcca cgcgataata ttgttcaacg tgcagaaatc    720
cgccgtatga ccgtcattga gtatgacccg gcatgcaagc aagcgaacga gtaccgcacc    780
ttggcacaga aaatcgtgaa caacaccatg aaggttgttc cgacgccgtg tacgatggac    840
gagctggaga gcctgctgat ggagttcggc attatggagg aggaggacac cagcattatc    900
ggtaagaccg cagcggagga gaatgcggca taagcgtgcg tacaccttaa tcaccgcttc    960
atgctaaggt cctggctgca tgcaaaaatt cacatcccta tctagcggag gagccggatg   1020
atgactaatg ctactggcga acgtaacctg gcactgattc aagaagtact ggaagtgttc   1080
ccggaaaccg cgcgcaaaga gcgccgtaaa cacatgatgg tttctgaccc ggaaatggaa   1140
tctgtgggta aatgcatcat ctctaatcgc aaatctcagc cgggtgtcat gactgttcgt   1200
ggctgtgcgt acgcaggttc taaaggtgtc gtattcggcc cgatcaaaga tatggcgcat   1260
atctctcatg gcccggtagg ctgtggccag tactctcgcg cgggacgtcg taactactac   1320
acgggcgttt ctggcgttga ctctttcggc acgctgaact tcacctctga cttccaggaa   1380
cgtgacatcg ttttcggtgg cgataaaaag ctgtccaaac tgatcgaaga aatggaactg   1440
ctgttcccgc tgactaaagg cattactatc caaagcgaat gtccggtggg tctgatcggt   1500
gatgacatca gcgcggtcgc aaacgcatct tccaaagccc tggataagcc ggtgatcccg   1560
gttcgttgcg agggcttccg cggcgtttct cagtctctgg gtcatcacat cgcaaacgat   1620
gttgtgcgtg actggattct gaacaaccgt gaaggtcagc cttttgaaac cacccccttat   1680
gacgttgcga ttattggcga ctataacatc ggcggcgacg cctgggcatc ccgcatcctg   1740
ctggaggaga tgggtctgcg tgttgtcgca cagtggtctg gcgatggcac cctggttgaa   1800
atggaaaaca ccccgtttgt taaactgaac ctggttcact gctaccgctc catgaactac   1860
attgcccgtc acatggaaga aaaacatcag atcccttgga tggaatacaa cttcttcggt   1920
ccgactaaaa tcgcagaatc cctgcgtaaa atcgccgatc agtttgatga taccattcgc   1980
gcgaacgctg aagcagtaat tgcgcgctac gaaggccaga tggcagcaat cattgctaag   2040
taccgtccgc gcctggaagg tcgtaaagtg ctgctgtaca tgggtggtct gcgtccacgt   2100
catgtgatcg gtgcctacga ggacctgggc atggagatca tcgcagcggg ttacgaattt   2160
gcacacaacg acgactatga tcgtacgctg ccagacctga agaaggtac gctgctgttt   2220
gacgacgcca gctcttatga actggaagcc ttcgtgaaag cgctgaaacc agacctgatc   2280
ggctccggca tcaaggaaaa atacattttc cagaaaatgg cgtgccgtt ccgccagatg   2340
cactcctggg actactccgg tccgtaccac ggctacgacg gtttcgctat cttcgctcgt   2400
gacatggata tgaccctgaa taacccagcg tggaatgaac tgaccgcacc gtggctgaaa   2460
tctgcataac aaacacccca tgtcgatact gaacgaatcg acgcacactc ccttccttgc   2520
aatctcatac tctcaaaaat taggcgaggt aacatgtctc aaactatcga taaaatcaac   2580
tcttgttacc cgctgttcga gcaggacgaa tatcaggaac tgttccgtaa caacgtcag   2640
ctggaagaag cgcacgacgc acagcgcgtg caggaagtgt tcgcatggac caccaccgcg   2700
```

```
gaatacgaag ctctgaactt ccagcgcgaa gccctgacgg ttgatccggc gaaagcgtgc   2760
cagcctctgg gtgcggttct gtgcagcctg ggttttgcca acaccctgcc gtatgtccac   2820
ggttcccagg gctgcgtagc ctacttccgt acctatttca accgccactt taaagaacca   2880
atcgcgtgcg tgtccgacag catgacggag gacgcggcag ttttcggtgg taacaacaac   2940
atgaacctgg gcctgcaaaa tgcttccgca ctgtacaaac cggaaatcat cgcagtgtct   3000
accacctgca tggcagaggt tattggtgat gatctgcaag catttattgc caacgcaaag   3060
aaagacggtt tcgttgacag ctctatcgcg gttccgcacg ctcataccCC gtccttcatc   3120
ggttctcacg taactggttg ggacaacatg ttcgaaggct tcgcaaaaac ttttaccgca   3180
gactatcaag gccaaccggg taaactgccg aagctgaacc tggtgaccgg ctttgaaacc   3240
tacctgggca ctttcgtgt cctgaagcgc atgatggagc agatggcggt tccgtgttct   3300
ctgctgtctg acccgtctga ggttctggac actccagcgg acggccacta cgcatgtat   3360 tctggtggca ccactcagca ggaaatgaaa gaggccccag acgcgattga caccctgctg   3420
ctgcaaccgt ggcagctgct gaaaagcaag aaagttgttc aggaaatgtg gaaccagccg   3480
gcaacggaag ttgcaatccc gctgggtctg gcagctactg acgaactgct gatgaccgtg   3540
tcccaactga gcggcaaacc aatcgcggat gctctgaccc tggaacgcgg tcgcctggtg   3600
gacatgatgc tggacagcca cacgtggctg catggcaaga atttggcct gtacggtgac   3660 ccggacttcg taatgggcct gacccgtttc ctgctggaac tgggctgcga gccgactgtt   3720
atcctgtctc acaacgctaa caaacgttgg cagaaggcca tgaacaaaat gctggatgcg   3780
agcccatacg gccgtgatag cgaagtgttc atcaactgcg acctgtggca tttccgctct   3840
ctgatgttta cgcgtcagcc ggatttcatg atcggtaact cttacggcaa attcatccag   3900
cgtgacactc tggccaaagg caaagcgttt gaagtgccgc tgattcgtct gggctttccg   3960
ctgttcgacc gtcaccacct gcaccgccag accactgggg gttacgaagg cgcgatgaac   4020
atcgtaacta ctctggtaaa cgcagtactg gaaaagctgg acagcgatac ttcccagctg   4080
ggcaaaaccg actattcttt cgatctggtt cgttaacctg attgtatccg catctgatgc   4140
taccgtggtt gagttaccat actcactccc ggaggtactt ctatgtctga caatgatacc   4200
ctgttttggc gcatgctggc gctgtttcag tcgctgccgg atttgcagcc ggctcaaatc   4260
gtcgattggc tggcgcagga atccggcgaa accctgacgc cggagcgcct tgccaccctg   4320
acccaaccgc aactcgcggc gtcgttccca tccgcgacgg cagtgatgag cccggctcgc   4380
tggagccgcg ttatggcttc tctgcaaggc gccctcccag cccacttgcg catcgtacgt   4440
ccggcgcagc gtaccccgca actgctcgcc gcgttttgca gccaagacgg ccttgttatc   4500
aatggtcatt tcggccaggg tcgtctgttc ttcatttacg cctttgacga gcagggcggc   4560
tggctgtatg acttgcgccg ctatccgagc gcaccgcacc agcaggaagc gaatgaggtg   4620
cgtgctcgtc tgattgaaga ttgccagctg ctgttctgcc aggagattgg cggtccggca   4680
gcagcgcgtc tgatccgcca ccgcatccat ccgatgaagg cgcagccggg tactacgatt   4740
caggcgcagt gtgaagctat caacacCCtg ctggccggtc gcctgccgcc gtggctcgcc   4800
aaacgtttga accgtgataa cccgctggaa gagcgtgtgt tttaacattt ttgccttgcg   4860
acagacctcc tacttagatt gccacactat tcaatacatc actggaggtt attacaaatg   4920
aagggtaacg agattcttgc tctgctggac gaaccggcct gtgaacacaa ccataaacag   4980
aaatccggct gtagcgcccc aaagccgggt gcgacggcgg ctggctgcgc tttcgatggt   5040
```

| | |
|---|---|
| gcgcagatca ccctgctccc gattgcggac gttgcccacc tcgtgcatgg cccaatcggt | 5100 |
| tgcgcaggta gctcttggga caaccgtggc agcgcctcca gcggtccgac cctgaatcgt | 5160 |
| ttgggctttta ccactgactt gaatgaacaa gatgtgatca tgggtcgcgg cgagcgtcgc | 5220 |
| ctgttccacg ctgtgcgcca tattgtcacc cgttaccacc cagcggcagt attcatctac | 5280 |
| aatacgtgcg tgccggctat ggaaggcgat gacctggagg ccgtgtgtca ggcagcccag | 5340 |
| actgcgaccg cgtcccggt aatcgcaatt gatgcggctg gcttctacgg ttcgaagaac | 5400 |
| ctgggcaacc gtccggcagg cgatgtcatg gttaaacgcg tcattggcca acgtgagcca | 5460 |
| gcgccgtggc cggagagcac cctgtttgcc ccggagcaac gtcatgacat tggcttgatc | 5520 |
| ggtgagttca acattgcggg cgagttttgg cacattcagc cgctgcttga tgagctgggt | 5580 |
| atccgcgttt tgggttcgct cagcggcgat ggtcgtttcg ccgagattca aaccatgcac | 5640 |
| cgtgcccagg cgaacatgct ggtgtgcagc cgtgctctga tcaatgttgc gcgtgctctg | 5700 |
| gaacagcgct atggcacccc gtggtttgaa ggctcgttct atggtatccg cgcgaccagc | 5760 |
| gacgccctgc gccagttagc ggcgctgctg ggcgatgacg acctccgtca gcgcaccgag | 5820 |
| gcgctgatcg cgcgtgaaga acaggcggct gagctggccc tgcaaccgtg gcgtgaacag | 5880 |
| ctgcgtggcc gcaaggccct gctctacacg ggtggtgtca aaagctggtc tgtggtgtcc | 5940 |
| gcgcttcagg atctgggtat gaccgtggtt gccacgggca cgcgtaagag cacggaagag | 6000 |
| gataaacagc gcatccgcga attgatgggc gaagaggccg tgatgcttga agaaggcaac | 6060 |
| gcacgtacct tattggatgt agtttatcgc tatcaagcag acctgatgat tgccggtggc | 6120 |
| cgcaacatgt ataccgccta caaagcgcgc ttgccgttcc tggacatcaa ccaggaacgc | 6180 |
| gagcacgcgt ttgcgggcta ccaaggcatc gtgaccttag cgcgccagct gtgccaaacg | 6240 |
| attaacagcc cgatctggcc gcagactcat tcccgcgcac cgtggcgcta atgtcacgct | 6300 |
| aggaggcaat tctataagaa tgcacactgc acctaaacct accacacctg gaagaagtaa | 6360 |
| ttatggcaga catttttccgc actgataagc cgttggctgt gtcgccgatc aagaccggcc | 6420 |
| agccgctggg tgcgatcctg gcgtccctgg gtatcgagca ctcgattccg ctggtacatg | 6480 |
| gcgcgcaggg ctgttcggct tttgccaagg tttttctttat ccagcacttc cacgatccgg | 6540 |
| tcccgctgca aagcacggca atggacccga ccagcaccat catgggcgct gatggtaaca | 6600 |
| tcttcaccgc gctggacact ctctgccaac gcaataaccc gcaagcaatt gtgctgctga | 6660 |
| gcaccggcct ctccgaggcg cagggcagcg acatttcccg tgtagtgcgt cagttccgtg | 6720 |
| aagaatatcc gcgtcataaa ggcgtggcga ttctgactgt taacaccccg gacttttacg | 6780 |
| gtagcatgga gaacggcttt tccgctgtcc tggagtctgt gattgaacag tgggttccgc | 6840 |
| cagccccacg tccggcgcag cgcaatcgtc gcgtcaatct tttggtgagc catctctgta | 6900 |
| gcccaggcga tattgagtgg ctgcgccgtt gcgtcgaggc cttcggtctg caaccgatca | 6960 |
| ttctgccgga tctggctcag agcatggacg gccaccttgc tcagggtgac ttttcgccgc | 7020 |
| tgacgcaggg cggcacgccg ttgcgccaaa tcgagcagat gggccagagc ctttgctctt | 7080 |
| ttgcgattgg cgtcagcctg caccgtgcga gcagcctgct ggctccgcgt tgtcgtggcg | 7140 |
| aagtcatcgc cttgccgcac ctcatgacct tggaacgctg cgacgccttt atccatcagt | 7200 |
| tggcgaaaat cagcggtcgc gccgttccgg agtggctgga acgccagcgc ggtcagctgc | 7260 |
| aagacgccat gatcgattgc cacatgtggc tgcaaggcca gcgcatggcg attgccgccg | 7320 |
| aaggcgacct gctggcagcg tggtgcgatt tcgcgaactc tcaaggtatg cagcggtc | 7380 |
| cactggttgc tccgacgggt catccgagcc tgcgtcagtt gccggtggag cgcgtggtgc | 7440 |

```
cgggtgatct ggaggatctt cagaccctct tatgcgcaca tccggccgac ttactggtgg   7500
cgaactccca cgcccgtgat ttagcagagc aattcgccct gccgctggtg cgcgcaggct   7560
tcccgctgtt tgacaaactg ggcgaatttc gtcgtgttcg ccagggttat agcggtatgc   7620
gtgataccct gttcgagttg gcgaacctga tccgtgaacg ccatcatcat ctggctcatt   7680
atcgcagccc gctgcgccag aacccagaat cctcgttgtc tacgggtggc gcgtacgcag   7740
cggattaact agagattaaa gaggagaaat taagcatgaa aactatggac ggtaacgctg   7800
cggctgcatg gattagctac gcctttaccg aagtggctgc gatctacccg attacgccga   7860
gcaccccgat ggcggaaaat gtggacgaat gggctgcgca gggcaagaag aacctcttcg   7920
gccagccggt gcgcctgatg gagatgcagt cggaagcggg tgcagcaggt gctgtgcatg   7980
gcgccttgca agctggcgca ctgacgacca cctacaccgc gtcgcagggc ctgttgctga   8040
tgatcccaaa catgtacaaa atcgcgggtg aactgctgcc gggtgtcttt catgtttcgg   8100
cacgcgcact ggccaccaat agcctcaaca tctttggcga tcatcaggat gtaatggcgg   8160
tgcgccaaac gggctgcgcg atgttggccg agaataacgt ccagcaagtt atggatttgt   8220
ccgcggtagc ccacttggca gcgatcaaag gtcgcattcc gttcgtgaac ttcttcgatg   8280
gctttcgcac cagccacgaa atccagaaga tcgaggttct ggaatatgaa cagctggcca   8340
ccttgttgga tcgtccggcc ctggacagct tccgccgtaa cgcccttcac ccggaccacc   8400
cggtcatccg tggcaccgcc cagaacccgg acatctactt ccaggaacgt gaggccggta   8460 accgttttcta tcaggcgctc ccggatattg tggaatctta catgacccag atttctgccc   8520
tgactggtcg cgagtatcac ctgtttaact acactggtgc tgcggatgcg gagcgcgtga   8580
tcatcgcgat gggctctgtc tgtgacaccg tccaagaggt ggttgacacg ctgaatgcag   8640
cgggtgagaa agttggtctg ctctccgttc atcttttccg cccgttttcg ttagcgcact   8700
tcttcgccca actgccgaaa actgtacagc gtatcgcagt attggaccgt acgaaagagc   8760
caggtgctca agcagagccg ctgtgcctcg atgtgaagaa tgccttttac caccatgacg   8820 atgcccgtt gattgtgggt ggtcgctatg ccttgggcgg taaggacgtg ttgccgaacg   8880
atattgcggc cgtgtttgat aacctgaaca aaccgctgcc gatggacggc ttcacgctgg   8940
gtatcgtgga cgatgttacc ttcacctctc tcccgccagc gcagcagacc ctggcggttt   9000
ctcacgacgg catcacggca tgtaagtttt ggggcatggg ctccgacggc acggttggtg   9060
cgaacaagtc cgcgatcaag attatcggcg acaaaacgcc actgtatgcg caagcgtact   9120
tttcctacga ctcgaagaag agcggtggta ttaccgtcag ccatctgcgt tttggtgatc   9180
gcccgatcaa ctccccgtat ttgatccatc gcgcggattt catctcgtgc agccagcaaa   9240
gctatgttga acgctacgat ctgctggatg gccttaaacc gggtggcacc tttctgctga   9300
actgctcctg gagcgatgcc gaactggagc aacatctgcc ggtcggtttc aaacgttatc   9360
tggcacgcga gaatatccac ttctacactc tcaacgctgt ggacatcgcc cgtgagcttg   9420
gtttgggtgg ccgtttcaac atgctgatgc aggctgcctt cttcaaactg gccgcgatca   9480
ttgacccgca gactgctgcg gactatctga gcaggctgt tgagaaaagc tatggcagca   9540
aaggtgcggc ggtcatcgag atgaaccagc gtgccatcga gcttggcatg ccagcctgc   9600 accaggtgac gatcccggca cattgggcca ccctggatga gccagcggcg caggcgtccg   9660
cgatgatgcc ggactttatc cgcgacatcc tgcaaccgat gaaccgtcag tgcggcgacc   9720
agcttccggt gtcggctttt gtcggcatgg aagatggcac cttcccgtcc ggcacggccg   9780
```

```
catgggagaa acgtggcatc gcccttgagg tgccagtctg gcagccggaa ggctgcacgc    9840
agtgcaacca gtgcgccttc atttgtccgc acgccgcgat tcgtccggcg ttgttgaatg    9900
gcgaagagca tgatgctgcc ccggttggcc tgctgagcaa accggcacaa ggcgctaaag    9960
aatatcacta tcatctggcg attagcccgc tggactgctc cggctgtggc aactgcgttg   10020
acatttgtcc agctcgtggc aaagcgttga agatgcagtc tctggatagc caacgccaga   10080
tggctccggt gtgggattat gcgctggcgc tgaccccgaa gtctaacccg tttcgtaaaa   10140
ccaccgtcaa aggctcgcag ttcgaaaccc gctgctgga gtttagcggt gcgtgcgctg    10200
gttgtggcga aacgccgtat gcgcgcctca ttacccagct gttttggcgac cgcatgctga   10260 ttgccaatgc caccggctgt tccagcatct ggggcgcatc tgcgccgagc atcccgtata   10320
ccaccaatca tcgtggtcat ggtccggcct gggcgaatag cctgtttgag acaatgccg    10380 aatttggttt aggtatgatg ctgggcggtc aagctgtgcg tcaacagatc gcggacgata   10440
tgacggctgc gttagcgctc ccggtttccg atgagctgag cgacgcgatg cgccagtggt   10500
tggcgaaaca ggacgagggt gaaggcacgc gtgagcgtgc ggaccgtctg agcgagcgct   10560
tagccgcgga gaaagagggc gttccgctgt tagagcagct gtggcaaaat cgtgattact   10620
ttgtgcgtcg cagccagtgg attttcggcg gtgacgctg gcctatgat attggcttcg    10680 gtggcctgga ccacgtcctc gccagcggtg aggatgtgaa cattctggta tttgacaccg   10740
aagtctactc gaacaccggc ggtcaaagca gcaaatcgac cccggtcgcg gccatcgcca   10800
agttcgcggc tcagggcaag cgcacccgca agaaagacct gggtatgatg gcgatgagct   10860
acggcaacgt ctatgtagcc caggtggcga tgggtgcgga taaagatcaa actctgcgcg   10920
ccattgcgga agctgaagcg tggccaggcc cgtcgctggt gattgcgtat gcggcctgca   10980
tcaatcatgg cctgaaggcc ggtatgcgtt gcagccaacg tgaggcgaag cgcgctgttg   11040
aggcgggcta ctggcacctg tggcgttatc acccgcagcg cgaagcggaa ggcaagacgc   11100
cgtttatgtt agatagcgaa gaaccggaag agtcgttccg tgactttctg ttgggtgagg   11160
tgcgctacgc atccctgcac aagaccaccc cgcacctcgc cgatgcccctt ttcagccgta   11220 ccgaagaaga tgcgcgtgcg cgcttttgcgc aataccgtcg cctggctggc gaagagtaat   11280
aatactctaa ccccatcggc cgtcttaggg gtttttttgtc cgtggttgag tcagcgtcga   11340
gcacgcggct aatacgactc actagagaga gacgcgactt ccagagaaga agactactga   11400
cttgagcgtt ccctctctgt aatacatcaa atcaatcata ggagggctaa aatgacctct   11460
tgttcgtcgt tttctggcgg taaagcgtgc cgtccggccg atgactccgc gctgactccg   11520
ctggtggccg acaaggcagc tgcgcacccg tgctatagcc gccacggcca tcaccgcttc   11580
gcgcgtatgc acctgccagt cgctccggcc tgcaacttac aatgcaacta ctgcaaccgc   11640
aagttcgatt gcagcaatga aagccgtccg ggcgtgtcct ctaccctgct gacgccggaa   11700
caggctgtgg tgaaggtgcg ccaggtcgcc caagctatcc cgcagctgtc ggtggtcggt   11760
attgctggtc cgggcgatcc gcttgcgaat atcgcccgca ccttccgtac cttggagctt   11820
attcgcgaac agttgccgga cctgaaactg tgcctgagca ccaacggctt ggtgctgcca   11880
gatgccgttg atcgtctgct cgatgtgggc gtggatcacg ttaccgtcac cattaacacc   11940
ctggacgcag aaatcgcagc gcaaatctac gcgtggttgt ggctggatgg cgaacgctac   12000
tccggtcgcg aagccggcga aattctcatt gcccgccagc tggaaggcgt acgtcgcctg   12060
accgcgaaag gtgtgctcgt caagatcaac agcgtattga ttccgggcat caatgacagc   12120
ggcatggcgg gtgttagccg tgcgctgcgc gcgtctggtg cgttcatcca caacatcatg   12180
```

```
ccactgattg cgcgtccgga gcatggcact gttttcggtc tgaacggcca gccggaaccg   12240
gacgcggaaa ccctggcggc gacgcgctcc cgctgcggcg aggttatgcc acaaatgacc   12300
cactgccacc agtgccgtgc cgacgcgatt ggcatgcttg gtgaggatcg ctcgcaacag   12360
tttacgcaat taccggctcc ggagtccctc ccggcctggc tgccgatcct gcatcagcgt   12420
gctcagttgc atgcgagcat cgccacgcgc ggtgagagcg aagccgatga cgcctgcctg   12480
gtggccgttg cgtcgagccg tggcgatgta attgactgcc atttcggcca tgccgaccgt   12540
ttctatatct atagcctgtc tgcggctggt atggttctgg ttaacgaacg tttcacccccg   12600 aaatactgcc agggtcgcga tgactgcgag ccgcaggaca atgccgcacg ctttgctgcc   12660
atccttgagt tgctggcgga cgtcaaagcg gtgttttgtg tgcgtatcgg ccatacccccg   12720 tggcaacagc tggagcagga aggcatcgaa ccgtgcgtgg atggcgcctg cgtccggta   12780 tccgaggtcc tgccggcatg gtggcagcag cgccgtggta gctggccggc tgcattgccg   12840
cacaaaggcg ttgcgtaaac tacgagattt gaggtaaacc aaataagcac gtagtggcat   12900
taaagaggag aaattaagca tgccgccatt ggactggttg cgtcgtttgt ggttactcta   12960
tcacgccggc aaaggcagct ttccgcttcg tatgggcttg tcgccgcgtg actggcaagc   13020
tctgcgccgt cgcctgggcg aggtggaaac gccgctggat ggcgaaaccc tgaccgtcg   13080 ccgtctgatg gcggagctga atgcgacccg cgaagaagaa cgccagcagc tgggtgcctg   13140
gctggccggt tggatgcaac aggatgccgg tccgatggcg cagattatcg cagaggtgag   13200
cctggcgttc aaccatctct ggcaggacct tggcctcgcg agccgcgctg aactgcgtct   13260
gctgatgtct gactgcttcc cgcagctggt tgttatgaac gagcacaaca tgcgctggaa   13320
gaaattcttt taccgccagc gttgcctgct gcaacagggc gaagtcatct gtcgcagccc   13380
gtcttgcgat gaatgctggg aacgttctgc gtgctttgag taatacatat cggggggta   13440 ggggttttttt gtgtctgtag cacgtgcatc taatacgact cactaatggg agagacaaga   13500
gtctcaatta taaggaggct ttactacatg gcgaacatcg gcatcttctt tggtacggat   13560
accggcaaaa cccgcaagat tgcgaagatg attcacaaac agctgggcga gctggccgat   13620
gccccggtta acatcaatcg taccactttg gatgactttta tggcttaccc agtcctgttg   13680
ctcggcacgc cgacgcttgg tgatggtcaa ctgccgggct tagaggcggg ctgcgagagc   13740
gaaagctggt ctgagtttat ctccggtctg gatgacgctt ccctgaaggg caaaaccgtg   13800
gcgctgtttg gcctgggcga ccagcgtggt taccccggaca acttcgtgtc gggtatgcgt   13860
ccgctgttcg acgcgctgag cgcccgtggc gcccagatga ttggtagctg gccgaacgaa   13920
ggttatgagt ttagcgcatc gtccgcgctg gaaggcgacc gcttcgtcgg cttggtgctg   13980
gatcaagaca atcagttcga ccagaccgaa gcgcgcctgg cgtcttggct tgaagagatc   14040
aaacgcaccg ttctgtaata atacatatcg gggggtagg ggttttttgt ggtcattaca   14100
acggttatta atacgactca ctagagagag aaacatagcg ttccatgagg ctagaatta   14160 cctaccggcc tcagatactg acaaataaac cagcgaagga ggttcctaat gtggaactac   14220
agcgagaaag tcaaggacca tttcttcaat ccgcgcaacg cgcgtgttgt ggataacgca   14280
aatgcggtgg gcgacgtcgg cagcttatct tgtggcgatg ctctccgctt gatgctgcgc   14340
gtggacccgc agagcgaaat catcgaagaa gcgggctttc agaccttcgg ctgcggcagc   14400
gcgattgcgt cgtccagcgc actgacggag ctgatcatcg gtcacaccct ggcggaagcg   14460
ggtcagatca ccaaccagca gatcgccgac tatctggacg gcttaccgcc ggaaaagatg   14520
```

```
cactgctctg taatgggcca ggaagctctt cgtgcggcca ttgctaactt tcgcggtgaa   14580
tcgctggaag aggagcatga cgagggtaag ctgatctgca agtgcttcgg cgtcgatgaa   14640
ggccatattc gccgtgctgt ccagaacaac ggtcttacga ctctggccga ggtgatcaat   14700
tacaccaagg caggtggcgg ttgtaccagc tgccatgaga aaatcgagct ggccctggcc   14760
gagattctcg cccaacagcc gcaaaccacc ccggcagttg cgtccggtaa agatccgcac   14820
tggcagagcg tcgtggatac catcgctgaa ctgcgtccac atatccaagc ggacggtggt   14880
gacatggcgc tgttgtccgt gacgaaccac caagtgactg tttcgctgtc gggcagctgt   14940
tctggctgca tgatgaccga catgaccctg cgtggctgc aacagaaatt gatggagcgt    15000
accggctgct atatggaagt tgttgccgcc taacattgta atagccacca aaagagtgat   15060
gatagtcatg ggtgataccc gtagaccatt ctgaaatcga aggaggtttt ccatgaaaca   15120
agtgtacctg gacaacaacg cgaccacccg cctggacccg atggttctgg aagcgatgat   15180
gccgtttctc acggatttct atggcaatcg tccagcatc catgacttcg gcatcccggc    15240
acaagcggcg ctggaacgtg cgcaccagca agctgcggca ctgctgggcg cagagtaccc   15300
gtctgaaatc attttcacga gctgtgcgac cgaggccact gcaaccgcca ttgcgtcggc   15360
catcgcgtta ttgccggaac gccgcgaaat catcacctcg gtagtggagc acccggctac   15420
gctggcggcg tgcgagcacc tggaacgcca aggctatcgc atccatcgca ttgcggtgga   15480
tagcgaaggt gcgctggaca tggcccagtt ccgtgcagcg ctctcgccgc gtgtcgcgtt   15540
ggtgagcgtg atgtgggcca caacgaaac cggcgtgctg ttcccgattg gcgaaatggc    15600
cgagcttgcc cacgagcagg gcgctctgtt ccactgcgat gccgtcagg tcgttggcaa    15660 aatcccaatt gctgttggcc agacgcgcat cgacatgctg tcttgctccg cgcacaagtt   15720
tcatggtccg aagggtgttg gttgcttgta cttacgtcgt ggcacgcgct ttcgtccgct   15780
gcttcgcggt ggccatcaag aatatggtcg ccgtgccggc actgagaata tctgtggcat   15840
cgtcggcatg ggcgctgcgt gcgaactggc gaacatccat ctgccgggta tgacccatat   15900
tggccagtta cgcaatcgcc tggagcaccg tctgctcgcc agcgtgccgt ccgtgatggt   15960
tatgggcggt ggtcagccgc gtgtaccggg tactgtcaac ctggcgttcg agtttatcga   16020
aggtgaagcg atcctgctct tgctgaacca ggctggcatt gccgcaagct ccggctccgc   16080
gtgtacctct ggcagcttgg agccgagcca tgtgatgcgc gccatgaaca ttccatacac   16140
cgcggctcac ggcaccattc gttttagcct gagccgttat acgcgcgaga aagagatcga   16200
ctacgtcgtt gcgaccctcc cgccaatcat tgatcgtctg cgtgccttgt ccccgtattg   16260
gcagaatggt aagccgcgtc cggcagatgc agtctttacc ccggtttacg gttaagagtt   16320
actggccctg atttctccgc ttctaatacc gcacagcgac taggagccta actcgccaca   16380
aggaaacata tggagcgcgt cttgatcaac gatactaccc tgcgtgatgg cgaacaatct   16440
ccgggcgtag cgtttcgtac ctccgagaaa gttgccatcg cggaggcact gtacgctgcg   16500
ggtatcaccg cgatggaagt cggcactccg gcgatgggtg atgaagagat cgcccgcatt   16560
cagctggtgc gtcgtcaact gccggacgcg acgcttatga cctggtgccg tatgaacgct   16620
ctggaaatcc gtcagagcgc ggatctgggt attgactggg tggatatctc gatcccagca   16680
tccgacaagc tgcgtcagta caagctgcgt gagccgctgg ccgtgctgct ggagcgcctt   16740
gcgatgttta ccatctggcc ccacacgtta ggcctcaaag tatgtattgg ttgcgaggat   16800
gcgagccgtg cgtctggtca gaccctgcgc gccattgccg aggtggccca gcaatgcgcg   16860
gctgcgcgct tgcgttacgc tgacaccgtg ggcctgctgg acccgttcac caccgcagcc   16920
```

```
cagatcagcg ccctgcgtga cgtttggtcg ggcgagatcg agatgcatgc tcacaatgat   16980
ctgggcatgg ctaccgcgaa cacgctggcg gcagtttcgg ctggcgccac gtcggtgaac   17040
actaccgtcc tcggtctggg tgaacgtgca ggcaacgcag ccctggaaac cgttgcgctg   17100
ggcctggaac gctgcctggg cgtggaaacc ggcgtccatt tcagcgcgct cccagcgctc   17160
tgtcagcgcg tcgcggaggc tgcacagcgc gcaatcgacc cgcaacagcc gctggtgggt   17220
gaattggttt tcacccacga gtctggtgtt cacgttgcgg cgctgctgcg cgacagcgaa   17280
tcctatcaat ctattgcccc aagcctcatg ggccgtagct accgtctggt gctcggcaag   17340
cattcgggtc gtcaggctgt caacggtgtt ttcgaccaga tgggttacca cctgaatgcg   17400
gcgcagatca atcagttgct gccggccatt cgccgcttcg ccgagaattg gaaacgctct   17460
ccgaaagact acgaactggt tgcgatctat gacgaattgt gcggtgaatc cgcccttcgt   17520
gctcgcggct aagactcaac acgctaggga cgtgaagtcg attccttcga tgcagaaggc   17580
gagaactaga tttaagggcc attatagatg gagtggtttt accagattcc gggtgtagac   17640
gaattgcgca gcgctgaatc cttctttcag ttcttcgcgg ttccatacca gccggaactg   17700
ctgggccgct gctcgcttcc ggtgttagcg acgttccacc gtaaactgcg tgcggaggtc   17760
ccgctgcaaa accgtctgga ggacaatgat cgtgcgccgt ggctcttggc gcgccgcctc   17820
ctggccgaat cttatcagca gcaatttcag gagagcggca cctaatcgag aaacaaggca   17880
gttccgggct gaaagtagcg ccgggacaag tcccgtatta taaccgccta ggaggtgttg   17940
gatgcgcccg aaattcacct tctctgaaga ggtccgcgta gttcgcgcga ttcgtaatga   18000
tggcaccgtg gcgggttttg cgccaggtgc gctgctggtt cgtcgcggtt cgacgggctt   18060
tgtgcgtgac tggggtgtgt tcctgcaaga ccagatcatc tatcaaatcc actttccgga   18120
aaccgaccgc attatcggct gtcgcgagca ggagttaatc ccgattaccc agccgtggtt   18180
ggctggtaac ctccagtatc gtgacagcgt cacgtgccaa atggcactgg ctgtcaacgg   18240
tgacgtggtt gtgagcgccg gtcaacgtgg ccgtgtggag gccactgatc gtggcgaact   18300
tggcgattcc tacaccgtgg acttcagcgg ccgttggttc cgcgttccgg tccaggccat   18360
cgcgctgatt gaagagcgcg aagaataaac gccacgcgta gtgagacata cacgttcgtt   18420
gggttcactc agagactgaa gttattaccc aggaggtcta taatgaatcc gtggcagcgc   18480
tttgcccgtc aacgccttgc tcgcagccgc tggaaccgtg atccggctgc tctcgaccca   18540
gccgataccc cagcgttcga gcaggcgtgg cagcgtcaat gccatatgga acaaaccatc   18600
gtagcgcgtg tcccggaagg cgatattccg gctgccttac tggaaaacat cgcggccagc   18660
ctggcgatct ggctggacga gggtgacttc gctccgccgg agcgcgctgc gattgtgcgt   18720
catcatgcac gtctggagct ggcgtttgcc gacattgccc gccaggcacc gcaaccggat   18780
ctgagcacgg ttcaagcgtg gtatctgcgt caccagactc aattcatgcg tccggagcag   18840
cgtctgaccc gtcacctgct cctgacggtc gataatgatc gcgaggcggt gcatcaacgc   18900
atccttggcc tgtatcgtca gatcaacgcg agccgtgacg ccttcgcccc actggcacag   18960
cgccactctc attgcccgtc cgccttggaa gaaggccgtc tgggctggat ctcccgtggt   19020
ctgctgtacc cgcagctcga aaccgcgttg tttagcctgg cggaaaacgc actgtcgctg   19080
ccgattgcgt cggaattggg ttggcacctg ttatggtgcg aggccattcg tccggcagcc   19140
ccgatggagc cgcaacaggc ccttgaatct gcgcgcgact acttgtggca gcagagccag   19200
cagcgccacc agcgtcaatg gctggagcag atgatttccc gccaaccggg cctgtgtggt   19260
```
taatagcata accccttggg gcctctaaac gggtcttgag gggttttttg t    19311

<210> SEQ ID NO 2
<211> LENGTH: 19332
<212> TYPE: DNA
<213> ORGANISM: Artificial Sequence
<220> FEATURE:
<223> OTHER INFORMATION: Synthetic Polynucleotide

<400> SEQUENCE: 2

```
taatacgact cactattggg agatacaaat atataatata tttaaggagg tttcatatat    60
gaccatgcgt cagtgcgcga tttatggcaa aggtggtatt ggcaaaagca cgacgaccca   120
gaacttggtg gcggccctgg ccgagatggg taaaaaggtt atgattgtgg gttgcgaccc   180
gaaggccgac agcacgcgcc tgattctgca cgcgaaagca caaaacacga ttatggagat   240
ggctgccgag gttggtagcg tggaggatct ggagctggag gacgttctgc aaattggtta   300
cggtgatgtt cgttgcgcag agagcggtgg tccggaacca ggtgtcggct gtgcgggtcg   360
tggtgtaatt accgctatca atttcctgga agaagagggt gcgtacgaag atgatctgga   420
tttcgttttc tacgatgtgc tgggtgatgt cgtgtgcggt ggttttgcaa tgccgattcg   480
cgagaataag gcacaagaaa tttacattgt ctgtagcggc gagatgatgg caatgtacgc   540
tgctaacaac atcagcaagg gtattgttaa atacgcaaaa agcggtaagg ttcgcttggg   600
tggtttgatt tgcaacagcc gtcagaccga ccgtgaggac gaactgatca tcgccctggc   660
tgagaaactg ggcacccaaa tgatccactt cgtgccacgc gataatattg ttcaacgtgc   720
agaaatccgc cgtatgaccg tcattgagta tgacccggca tgcaagcaag cgaacgagta   780
ccgcaccttg gcacagaaaa tcgtgaacaa caccatgaag gttgttccga cgccgtgtac   840
gatggacgag ctggagagcc tgctgatgga gttcggcatt atggaggagg aggacaccag   900
cattatcggt aagaccgcag cggaggagaa tgcggcataa tactcgaacc cctagcccgc   960
tcttatcggt cggctagggg ttttttgtcg aagaacagat atgaaagtgt tagaactgta  1020
atacgactca ctataggtag agcgtgcgta caccttaatc accgcttcat gctaaggtcc  1080
tggctgcatg caaaaattca cattttatc tagcggagga gccggatgat gactaatgct  1140
actggcgaac gtaacctggc actgattcaa gaagtactgg aagtgttccc ggaaaccgcg  1200
cgcaaagagc gccgtaaaca catgatggtt tctgacccgg aaatggaatc tgtgggtaaa  1260
tgcatcatct ctaatcgcaa atctcagccg ggtgtcatga ctgttcgtgg ctgtgcgtac  1320
gcaggttcta aaggtgtcgt attcggcccg atcaaagata tggcgcatat ctctcatggc  1380
ccggtaggct gtggccagta ctctcgcgcg ggacgtcgta actactacac gggcgtttct  1440
ggcgttgact ctttcggcac gctgaacttc acctctgact tccaggaacg tgacatcgtt  1500
ttcggtggcg ataaaaagct gtccaaactg atcgaagaaa tggaactgct gttcccgctg  1560
actaaaggca ttactatcca aagcgaatgt ccggtgggtc tgatcggtga tgacatcagc  1620
gcggtcgcaa acgcatcttc caaagccctg gataagccgg tgatcccggt tcgttgcgag  1680
ggcttccgcg gcgttctca gtctctgggt catcacatcg caaacgatgt tgtgcgtgac  1740
tggattctga caaccgtga aggtcagcct tttgaaacca ccccttatga cgttgcgatt  1800
attggcgact ataacatcgg cggcgacgcc tgggcatccc gcatcctgct ggaggagatg  1860
ggtctgcgtg ttgtcgcaca gtggtctggc gatggcaccc tggttgaaat ggaaaacacc  1920
ccgtttgtta aactgaacct ggttcactgc taccgctcca tgaactacat tgcccgtcac  1980
atggaagaaa acatcagat cccttggatg gaatacaact tcttcggtcc gactaaaatc  2040
```

```
gcagaatccc tgcgtaaaat cgccgatcag tttgatgata ccattcgcgc gaacgctgaa    2100
gcagtaattg cgcgctacga aggccagatg gcagcaatca ttgctaagta ccgtccgcgc    2160
ctggaaggtc gtaaagtgct gctgtacatg ggtggtctgc gtccacgtca tgtgatcggt    2220
gcctacgagg acctgggcat ggagatcatc gcagcgggtt acgaatttgc acacaacgac    2280
gactatgatc gtacgctgcc agacctgaaa gaaggtacgc tgctgtttga cgacgccagc    2340
tcttatgaac tggaagcctt cgtgaaagcg ctgaaaccag acctgatcgg ctccggcatc    2400
aaggaaaaat acattttcca gaaatgggc gtgccgttcc gccagatgca ctcctgggac    2460
tactccggtc cgtaccacgg ctacgacggt ttcgctatct tcgctcgtga catggatatg    2520
accctgaata cccagcgtg gaatgaactg accgcaccgt ggctgaaatc tgcataacaa    2580
acaccccatg tcgatactga acgaatcgac gcacactccc ttccttgcaa tctcatactc    2640
tcaaaaatta ggcgaggtaa catgtctcaa actatcgata aaatcaactc ttgttacccg    2700
ctgttcgagc aggacgaata tcaggaactg ttccgtaaca acgtcagct ggaagaagcg    2760 cacgacgcac agcgcgtgca ggaagtgttc gcatggacca ccaccgcgga atacgaagct    2820
ctgaacttcc agcgcgaagc cctgacggtt gatccggcga aagcgtgcca gcctctgggt    2880
gcggttctgt gcagcctggg ttttgccaac accctgccgt atgtccacgg ttcccagggc    2940
tgcgtagcct acttccgtac ctatttcaac cgccacttta agaaccaat cgcgtgcgtg    3000 tccgacagca tgacggagga cgcggcagtt ttcggtggta caacaacat gaacctgggc    3060 ctgcaaaatg cttccgcact gtacaaaccg gaaatcatcg cagtgtctac cacctgcatg    3120
gcagaggtta ttggtgatga tctgcaagca tttattgcca acgcaaagaa agacggtttc    3180
gttgacagct ctatcgcggt tccgcacgct catacccgt ccttcatcgg ttctcacgta    3240
actggttggg acaacatgtt cgaaggcttc gcaaaaactt ttaccgcaga ctatcaaggc    3300
caaccgggta aactgccgaa gctgaacctg gtgaccggct ttgaaaccta cctgggcaac    3360
tttcgtgtcc tgaagcgcat gatggagcag atggcggttc cgtgttctct gctgtctgac    3420
ccgtctgagg ttctggacac tccagcggac ggccactatc gcatgtattc tggtggcacc    3480
actcagcagg aaatgaaaga ggccccagac gcgattgaca ccctgctgct gcaaccgtgg    3540
cagctgctga aaagcaagaa agttgttcag gaaatgtgga accagccggc aacggaagtt    3600
gcaatcccgc tgggtctggc agctactgac gaactgctga tgaccgtgtc ccaactgagc    3660
ggcaaaccaa tcgcggatgc tctgaccctg gaacgcggtc gcctggtgga catgatgctg    3720
gacagccaca cgtggctgca tgcaagaaa tttggcctgt acggtgaccc ggacttcgta    3780
atgggcctga cccgtttcct gctggaactg ggctgcgagc cgactgttat cctgtctcac    3840
aacgctaaca acgttggca gaaggccatg aacaaaatgc tggatgcgag cccatacggc    3900
cgtgatagcg aagtgttcat caactgcgac ctgtggcatt ccgctctct gatgtttacg    3960 cgtcagccgg atttcatgat cggtaactct tacggcaaat tcatccagcg tgacactctg    4020
gccaaaggca aagcgtttga agtgccgctg attcgtctgg gctttccgct gttcgaccgt    4080
caccacctgc accgccagac cacctgggt tacgaaggcg cgatgaacat cgtaactact    4140
ctggtaaacg cagtactgga aaagctggac agcgatactt cccagctggg caaaaccgac    4200
tattctttcg atctggttcg ttaacctgat tgtatccgca tctgatgcta ccgtggttga    4260
gttaccatac tcactcccgg aggtacttct atgtctgaca atgatacccg gtttggcgc    4320 atgctggcgc tgtttcagtc gctgccggat ttgcagccgc ctcaaatcgt cgattggctg    4380
```

```
gcgcaggaat ccggcgaaac cctgacgccg agcgccttg ccaccctgac ccaaccgcaa      4440
ctcgcggcgt cgttcccatc cgcgacggca gtgatgagcc cggctcgctg agccgcgtt      4500 atggcttctc tgcaaggcgc cctcccagcc cacttgcgca tcgtacgtcc ggcgcagcgt      4560
accccgcaac tgctcgccgc gttttgcagc caagacggcc ttgttatcaa tggtcatttc      4620
ggccagggtc gtctgttctt catttacgcc tttgacgagc agggcggctg gctgtatgac      4680
ttgcgccgct atccgagcgc accgcaccag caggaagcga atgaggtgcg tgctcgtctg      4740
attgaagatt gccagctgct gttctgccag gagattggcg gtccggcagc agcgcgtctg      4800
atccgccacc gcatccatcc gatgaaggcg cagccgggta ctacgattca ggcgcagtgt      4860
gaagctatca cacccctgct ggccggtcgc ctgccgccgt ggctcgccaa acgtttgaac      4920
cgtgataacc cgctggaaga gcgtgtgttt aacattttt gccttgcgac agacctccta      4980
cttagattgc cacactattc aattcatcac tggaggttat tacaaatgaa gggtaacgag      5040
attcttgctc tgctggacga accggcctgt gaacacaacc ataaacagaa atccggctgt      5100
agcgccccaa agccgggtgc gacggcggct ggctgcgctt cgatggtgc gcagatcacc      5160 ctgctcccga ttgcggacgt tgcccacctc gtgcatggcc caatcggttg cgcaggtagc      5220
tcttgggaca accgtggcag cgcctccagc ggtccgaccc tgaatcgttt gggctttacc      5280
actgacttga atgaacaaga tgtgatcatg gtcgcggcg agcgtcgcct gttccacgct      5340
gtgcgccata ttgtcacccg ttaccaccca gcggcagtat tcatctacaa tacgtgcgtg      5400
ccggctatgg aaggcgatga cctggaggcc gtgtgtcagg cagcccagac tgcgaccggc      5460
gtcccggtaa tcgcaattga tgcggctggc ttctacggtt cgaagaacct gggcaaccgt      5520
ccggcaggcg atgtcatggt taaacgcgtc attggccaac gtgagccagc gccgtggccg      5580
gagagccacc tgtttgcccc ggagcaacgt catgacattg gcttgatcgg tgagttcaac      5640
attgcgggcg agttttggca cattcagccg ctgcttgatg agctgggtat ccgcgttttg      5700
ggttcgctca gcgcgatgg tcgtttcgcc gagattcaaa ccatgcaccg tgcccaggcg      5760
aacatgctgg tgtgcagccg tgctctgatc aatgttgcgc gtgctctgga acagcgctat      5820
ggcaccccgt ggtttgaagg ctcgttctat ggtatccgcg cgaccagcga cgccctgcgc      5880
cagttagcgg cgctgctggg cgatgacgac ctccgtcagc gcaccgaggc gctgatcgcg      5940
cgtgaagaac aggcggctga gctggccctg caaccgtggc gtgaacagct gcgtggccgc      6000
aaggccctgc tctacacggg tggtgtcaaa agctggtctg tggtgtccgc gcttcaggat      6060
ctgggtatga ccgtggttgc cacgggcacg cgtaagagca cggaagagga taaacagcgc      6120
atccgcgaat tgatgggcga agaggccgtg atgcttgaag aaggcaacgc acgtaccttc      6180
ttggatgtag tttatcgcta tcaagcagac ctgatgattg ccggtggccg caacatgtat      6240
accgcctaca aagcgcgctt gccgttcctg gacatcaacc aggaacgcga gcacgcgttt      6300
gcgggctacc aaggcatcgt gaccttagcg cgccagctgt gccaaacgat taacagcccg      6360
atctggccgc agactcattc ccgcgcaccg tggcgctaat gtcacgctag gaggcaattc      6420
tataagaatg cacactgcac ctaaacctac cacacctgga agaagtaatt atggcagaca      6480
ttttccgcac tgataagccg ttggctgtgt cgccgatcaa gaccgccag ccgctgggtg      6540 cgatcctggc gtccctgggt atcgagcact cgattccgct ggtacatggc gcgcagggct      6600
gttcggcttt tgccaaggtt ttctttatcc agcacttcca cgatccggtc ccgctgcaaa      6660
gcacggcaat ggaccgacc agcaccatca tgggcgctga tggtaacatc ttcaccgcgc      6720
tggacactct ctgccaacgc aataacccgc aagcaattgt gctgctgagc accggcctct      6780
```

```
ccgaggcgca gggcagcgac atttcccgtg tagtgcgtca gttccgtgaa gaatatccgc   6840
gtcataaagg cgtggcgatt ctgactgtta acaccccgga cttttacggt agcatggaga   6900
acggcttttc cgctgtcctg gagtctgtga ttgaacagtg ggttccgcca gccccacgtc   6960
cggcgcagcg caatcgtcgc gtcaatcttt tggtgagcca tctctgtagc ccaggcgata   7020
ttgagtggct gcgccgttgc gtcgaggcct tcggtctgca accgatcatt ctgccggatc   7080
tggctcagag catggacggc caccttgctc agggtgactt ttcgccgctg acgcagggcg   7140
gcacgccgtt gcgccaaatc gagcagatgg gccagagcct tgctctttt gcgattggcg    7200 tcagcctgca ccgtgcgagc agcctgctgg ctccgcgttg tcgtggcgaa gtcatcgcct   7260
tgccgcacct catgaccttg aacgctgcg acgcctttat ccatcagttg gcgaaaatca    7320
gcggtcgcgc cgttccggag tggctggaac gccagcgcgg tcagctgcaa gacgccatga   7380
tcgattgcca catgtggctg caaggccagc gcatggcgat tgccgccgaa ggcgacctgc   7440
tggcagcgtg gtgcgatttc gcgaactctc aaggtatgca gccgggtcca ctggttgctc   7500
cgacgggtca tccgagcctg cgtcagttgc cggtggagcg cgtggtgccg ggtgatctgg   7560
aggatcttca gaccctctta tgcgcacatc cggccgactt actggtggcg aactcccacg   7620
cccgtgattt agcagagcaa ttcgccctgc cgctggtgcg cgcaggcttc ccgctgtttg   7680
acaaactggg cgaatttcgt cgtgttcgcc agggttatag cggtatgcgt gatatccctgt  7740 tcgagttggc gaacctgatc cgtgaacgcc atcatcatct ggctcattat cgcagcccgc   7800
tgcgccagaa cccagaatcc tcgttgtcta cgggtggcgc gtacgcagcg gattaactag   7860
agattaatat ggagaaatta agcatgaaaa ctatggacgg taacgctgcg gctgcatgga   7920
ttagctacgc cttaaccgaa gtggctgcga tctacccgat tacgccgagc accccgatgg   7980
cggaaaatgt ggacgaatgg gctgcgcagg gcaagaagaa cctcttcggc cagccggtgc   8040
gcctgatgga gatgcagtcg gaagcgggtg cagcaggtgc tgtgcatggc gccttgcaag   8100
ctggcgcact gacgaccacc tacaccgcgt cgcagggcct gttgctgatg atcccaaaca   8160
tgtacaaaat cgcgggtgaa ctgctgccgg gtgtctttca tgtttcggca cgcgcactgg   8220
ccaccaatag cctcaacatc tttggcgatc atcaggatgt aatggcggtg cgccaaacgg   8280
gctgcgcgat gttggccgag aataacgtcc agcaagttat ggatttgtcc gcggtagccc   8340
acttggcagc gatcaaaggt cgcattccgt tcgtgaactt cttcgatggc tttcgcacca   8400
gccacgaaat ccagaagatc gaggttctgg aatatgaaca gctggccacc ttgttggatc   8460
gtccggccct ggacagcttc cgccgtaacg cccttcaccc ggaccaccccg gtcatccgtg   8520 gcaccgccca gaacccggac atctacttcc aggaacgtga ggccggtaac cgtttctatc   8580
aggcgctccc ggatattgtg gaatcttaca tgacccagat ttctgccctg actggtcgcg   8640
agtatcacct gtttaactac actggtgctg cggatgcgga gcgcgtgatc atcgcgatgg   8700
gctctgtctg tgacaccgtc caagaggtgg ttgacacgct gaatgcagcg ggtgagaaag   8760
ttggtctgct ctccgttcat cttttccgcc cgttttcgtt agcgcacttc ttcgcccaac   8820
tgccgaaaac tgtacagcgt atcgcagtat tggaccgtac gaaagagcca ggtgctcaag   8880
cagagccgct gtgcctcgat gtgaagaatg ccttttacca ccatgacgat gccccgttga   8940
ttgtgggtgg tcgctatgcc ttgggcggta aggacgtgtt gccgaacgat attgcggccg   9000
tgtttgataa cctgaacaaa ccgctgccga tggacgcct cacgctgggt atcgtggacg   9060
atgttacctt cacctctctc ccgccagcgc agcagaccct ggcggtttct cacgacggca   9120
```

```
tcacggcatg taagttttgg ggcatgggct ccgacggcac ggttggtgcg aacaagtccg    9180
cgatcaagat tatcggcgac aaaacgccac tgtatgcgca agcgtacttt tcctacgact    9240
cgaagaagag cggtggtatt accgtcagcc atctgcgttt tggtgatcgc ccgatcaact    9300
ccccgtattt gatccatcgc gcggatttca tctcgtgcag ccagcaaagc tatgttgaac    9360
gctacgatct gctggatggc cttaaaccgg gtggcacctt tctgctgaac tgctcctgga    9420
gcgatgccga actggagcaa catctgccgg tcggtttcaa acgttatctg gcacgcgaga    9480
atatccactt ctacactctc aacgctgtgg acatcgcccg tgagcttggt ttgggtggcc    9540
gtttcaacat gctgatgcag gctgccttct caaactggc cgcgatcatt gacccgcaga     9600
ctgctgcgga ctatctgaag caggctgttg agaaaagcta tggcagcaaa ggtgcggcgg    9660
tcatcgagat gaaccagcgt gccatcgagc ttggcatggc cagcctgcac caggtgacga    9720
tcccggcaca ttgggccacc ctggatgagc cagcggcgca ggcgtccgcg atgatgccgg    9780
actttatccg cgacatcctg caaccgatga accgtcagtg cggcgaccag cttccggtgt    9840
cggcttttgt cggcatggaa gatggcacct tcccgtccgg cacggccgca tgggagaaac    9900
gtggcatcgc ccttgaggtg ccagtctggc agccggaagg ctgcacgcag tgcaaccagt    9960
gcgccttcat ttgtccgcac gccgcgattc gtccggcgtt gttgaatggc gaagagcatg    10020
atgctgcccc ggttggcctg ctgagcaaac cggcacaagg cgctaaagaa tatcactatc    10080
atctggcgat tagcccgctg gactgctccg gctgtggcaa ctgcgttgac atttgtccag    10140
ctcgtggcaa agcgttgaag atgcagtctc tggatagcca acgccagatg gctccggtgt    10200
gggattatgc gctggcgctg accccgaagt ctaacccgtt tcgtaaaacc accgtcaaag    10260
gctcgcagtt cgaaaccccg ctgctggagt ttagcggtgc gtgcgctggt tgtggcgaaa    10320
cgccgtatgc gcgcctcatt acccagctgt ttggcgaccg catgctgatt gccaatgcca    10380
ccggctgttc cagcatctgg ggcgcatctg cgccgagcat cccgtatacc accaatcatc    10440
gtggtcatgg tccggcctgg gcgaatagcc tgtttgagga caatgccgaa tttggtttag    10500
gtatgatgct gggcggtcaa gctgtgcgtc aacagatcgc ggacgatatg acggctgcgt    10560
tagcgctccc ggtttccgat gagctgagcg acgcgatgcg ccagtggttg gcgaaacagg    10620
acgagggtga aggcacgcgt gagcgtgcgg accgtctgag cgagcgctta gccgcggaga    10680
aagagggcgt tccgctgtta gagcagctgt ggcaaaatcg tgattacttt gtgcgtcgca    10740
gccagtggat tttcggcggt gacggctggg cctatgatat tggcttcggt ggcctggacc    10800
acgtcctcgc cagcggtgag gatgtgaaca ttctggtatt tgacaccgaa gtctactcga    10860
acaccggcgg tcaaagcagc aaatcgaccc cggtcgcggc catcgccaag ttcgcggctc    10920
agggcaagcg cacccgcaag aaagacctgg gtatgatggc gatgagctac ggcaacgtct    10980
atgtagccca ggtggcgatg ggtgcggata aagatcaaac tctgcgcgcc attgcggaag    11040
ctgaagcgtg gccaggcccg tcgctggtga ttgcgtatgc ggcctgcatc aatcatggcc    11100
tgaaggccgg tatgcgttgc agccaacgtg aggcgaagcg cgctgttgag gcgggctact    11160
ggcacctgtg gcgttatcac ccgcagcgcg aagcggaagg caagacgccg tttatgttag    11220
atagcgaaga accggaagag tcgttccgtg actttctgtt gggtgaggtg cgctacgcat    11280
ccctgcacaa gaccacccg cacctcgccg atgcccttt cagccgtacc gaagaagatg      11340
cgcgtgcgcg ctttgcgcaa taccgtcgcc tggctggcga agtaataa tactctaacc     11400 ccatcggccg tcttaggggt ttttttgtccg tggttagtta gttagccctt agtgactcta    11460
atacgactca ctagagagag acgcgacttc cagagaagaa gactactgac ttgagcgttc    11520
```

```
cctctctgta atacatcaaa tcaatcatag gagggctaaa atgacctctt gttcgtcgtt    11580
ttctggcggt aaagcgtgcc gtccggccga tgactccgcg ctgactccgc tggtggccga    11640
caaggcagct gcgcacccgt gctatagccg ccacggccat caccgcttcg cgcgtatgca    11700
cctgccagtc gctccggcct gcaacttaca atgcaactac tgcaaccgca agttcgattg    11760
cagcaatgaa agccgtccgg gcgtgtcctc taccctgctg acgccggaac aggctgtggt    11820
gaaggtgcgc caggtcgccc aagctatccc gcagctgtcg gtggtcggta ttgctggtcc    11880
gggcgatccg cttgcgaata tcgcccgcac cttccgtacc ttggagctta ttcgcgaaca    11940
gttgccggac ctgaaactgt gcctgagcac caacggcttg gtgctgccag atgccgttga    12000
tcgtctgctc gatgtgggcg tggatcacgt taccgtcacc attaacaccc tggacgcaga    12060
aatcgcagcg caaatctacg cgtggttgtg gctggatggc gaacgctact ccggtcgcga    12120
agccggcgaa attctcattg cccgccagct ggaaggcgta cgtcgcctga ccgcgaaagg    12180
tgtgctcgtc aagatcaaca gcgtattgat tccgggcatc aatgacagcg gcatggcggg    12240
tgttagccgt gcgctgcgcg cgtctggtgc gttcatccac aacatcatgc cactgattgc    12300
gcgtccggag catggcactg ttttcggtct gaacggccag ccggaaccgg acgcggaaac    12360
cctggcggcg acgcgctccc gctgcggcga ggttatgcca caaatgaccc actgccacca    12420
gtgccgtgcc gacgcgattg gcatgcttgg tgaggatcgc tcgcaacagt ttacgcaatt    12480
accggctccg gagtccctcc cggcctggct gccgatcctg catcagcgtg ctcagttgca    12540
tgcgagcatc gccacgcgcg gtgagagcga agccgatgac gcctgcctgg tggccgttgc    12600
gtcgagccgt ggcgatgtaa ttgactgcca tttcggccat gccgaccgtt tctatatcta    12660
tagcctgtct gcggctggta tggttctggt taacgaacgt ttcacccga aatactgcca    12720 gggtcgcgat gactgcgagc cgcaggacaa tgccgcacgc tttgctgcca tccttgagtt    12780
gctggcggac gtcaaagcgg tgttttgtgt gcgtatcggc catacccgt ggcaacagct    12840 ggagcaggaa ggcatcgaac cgtgcgtgga tggcgcctgg cgtccggtat ccgaggtcct    12900
gccggcatgg tggcagcagc gccgtggtag ctggccggct gcattgccgc acaaaggcgt    12960
tgcgtaaact acgagatttg aggtaaacca aataagcacg tagtggcatt aaagaggaga    13020
aattaagcat gccgccattg gactggttgc gtcgtttgtg gttactctat cacgccggca    13080
aaggcagctt tccgcttcgt atgggcttgt cgccgcgtga ctggcaagct ctgcgccgtc    13140
gcctgggcga ggtggaaacg ccgctggatg gcgaaaccct gacccgtcgc gtctgatgg    13200 cggagctgaa tgcgacccgc gaagaagaac gccagcagct gggtgcctgg ctggccggtt    13260
ggatgcaaca ggatgccggt ccgatggcgc agattatcgc agaggtgagc ctggcgttca    13320
accatctctg gcaggacctt ggcctcgcga gccgcgctga actgcgtctg ctgatgtctg    13380
actgcttccc gcagctggtt gttatgaacg agcacaacat gcgctggaag aaattctttt    13440
accgccagct tgcctgctg caacaggcg aagtcatctg tcgcagcccg tcttgcgatg    13500
aatgctggga acgttctgcg tgctttgagt aatacatatc ggggggtag gggttttttg    13560 tgtctgtagc acgtgcatct aatacgactc actaatggga gagacaagag tctcaattat    13620
aaggaggctt tactacatgg cgaacatcgg catcttcttt ggtacggata ccggcaaaac    13680
ccgcaagatt gcgaagatga ttcacaaaca gctgggcgag ctgccgatg ccccggttaa    13740 catcaatcgt accactttgg atgactttat ggcttaccca gtcctgttgc tcggcacgcc    13800
gacgcttggt gatggtcaac tgccgggctt agaggcgggc tgcgagagcg aaagctggtc    13860
```

```
tgagtttatc tccggtctgg atgacgcttc cctgaagggc aaaaccgtgg cgctgtttgg    13920
cctgggcgac cagcgtggtt acccggacaa cttcgtgtcg ggtatgcgtc cgctgttcga    13980
cgcgctgagc gcccgtggcg cccagatgat tggtagctgg ccgaacgaag gttatgagtt    14040
tagcgcatcg tccgcgctgg aaggcgaccg cttcgtcggc ttggtgctgg atcaagacaa    14100
tcagttcgac cagaccgaag cgcgcctggc gtcttggctt gaagagatca aacgcaccgt    14160
tctgtaataa tacatatcgg gggggtaggg gttttttgtg gtcattacaa cggttatggt    14220
ctcaggagta atacgactca ctagagagag aggtcgcgga cccggccgat ccgggggcct    14280
caaagccgcc tcaccagata ctgacaaata aaccagcgaa ggaggttcct aatgtggaac    14340
tacagcgaga aagtcaagga ccatttcttc aatccgcgca acgcgcgtgt tgtggataac    14400
gcaaatgcgg tgggcgacgt cggcagctta tcttgtggcg atgctctccg cttgatgctg    14460
cgcgtggacc cgcagagcga aatcatcgaa gaagcgggct ttcagacctt cggctgcggc    14520
agcgcgattg cgtcgtccag cgcactgacg gagctgatca tcggtcacac cctggcggaa    14580
gcgggtcaga tcaccaacca gcagatcgcc gactatctgg acggcttacc gccggaaaag    14640
atgcactgct ctgtaatggg ccaggaagct cttcgtgcgg ccattgctaa ctttcgcggt    14700
gaatcgctgg aagaggagca tgacgagggt aagctgatct gcaagtgctt cggcgtcgat    14760
gaaggccata ttcgccgtgc tgtccagaac aacggtctta cgacgctggc cgaggtgatc    14820
aattacacca aggcaggtgg cggttgtacc agctgccatg agaaaatcga gctggccctg    14880
gccgagattc tcgcccaaca gccgcaaacc accccggcag ttgcgtccgg taaagatccg    14940
cactggcaga gcgtcgtgga taccatcgct gaactgcgtc cacatatcca gcggacggt     15000 ggtgacatgg cgctgttgtc cgtgacgaac caccaagtga ctgtttcgct gtcgggcagc    15060
tgttctggct gcatgatgac cgacatgacc ctggcgtggc tgcaacagaa attgatgag    15120 cgtaccggct gctatatgga agttgttgcc gcctaagacc gcgcgcccg tcagagcaat    15180 gcgtatacca gctctcctgt cagcagaatg gctccagtac atctaacggg gcagtatccg    15240
cggcaagtcc tagtccaatc gatacccgta gaccattctg aaatcgaagg aggttttcca    15300
tgaaacaagt gtacctggac aacaacgcga ccacccgcct ggacccgatg gttctggaag    15360
cgatgatgcc gtttctcacg gatttctatg gcaatccgtc cagcatccat gacttcggca    15420
tcccggcaca agcggcgctg gaacgtgcgc accagcaagc tgcggcactg ctgggcgcag    15480
agtacccgtc tgaaatcatt ttcacgagct gtgcgaccga ggccactgca accgccattg    15540
cgtcggccat cgcgttattg ccggaacgcc gcgaaatcat cacctcggta gtggagcacc    15600
cggctacgct ggcggcgtgc gagcacctgg aacgccaagg ctatcgcatc catcgcattg    15660
cggtggatag cgaaggtgcg ctggacatgg cccagttccg tgcagcgctc tcgccgcgtg    15720
tcgcgttggt gagcgtgatg tgggccaaca acgaaaccgg cgtgctgttc ccgattggcg    15780
aaatggccga gcttgcccac gagcagggcg ctctgttcca ctgcgatgcc gttcaggtcg    15840
ttggcaaaat cccaattgct gttggccaga gcgcatcga catgctgtct tgctccgcgc    15900
acaagtttca tggtccgaag ggtgttggtt gcttgtactt acgtcgtggc acgcgctttc    15960
gtccgctgct tcgcggtggc catcaagaat atggtcgccg tgccggcact gagaatatct    16020
gtggcatcgt cggcatgggc gctgcgtgcg aactggcgaa catccatctg ccgggtatga    16080
cccatattgg ccagttacgc aatcgcctgg agcaccgtct gctcgccagc gtgccgtccg    16140
tgatggttat gggcggtggt cagccgcgtg taccgggtac tgtcaacctg gcgttcgagt    16200
ttatcgaagg tgaagcgatc ctgctcttgc tgaaccaggc tggcattgcc gcaagctccg    16260
```

```
gctccgcgtg tacctctggc agcttggagc cgagccatgt gatgcgcgcc atgaacattc   16320
catacaccgc ggctcacggc accattcgtt ttagcctgag ccgttatacg cgcgagaaag   16380
agatcgacta cgtcgttgcg accctcccgc caatcattga tcgtctgcgt gccttgtccc   16440
cgtattggca gaatggtaag ccgcgtccgg cagatgcagt ctttaccccg gtttacggtt   16500
aagcgactag gagcctaact cgccacaagg aaacatatgg agcgcgtctt gatcaacgat   16560
actaccctgc gtgatggcga acaatctccg ggcgtagcgt tcgtacctc cgagaaagtt    16620 gccatcgcgg aggcactgta cgctgcgggt atcaccgcga tggaagtcgg cactccggcg   16680
atgggtgatg aagagatcgc ccgcattcag ctggtgcgtc gtcaactgcc ggacgcgacg   16740
cttatgacct ggtgccgtat gaacgctctg gaaatccgtc agagcgcgga tctgggtatt   16800
gactgggtgg atatctcgat cccagcatcc gacaagctgc gtcagtacaa gctgcgtgag   16860
ccgctggccg tgctgctgga gcgccttgcg atgtttatcc atctggccca cacgttaggc   16920
ctcaaagtat gtattggttg cgaggatgcg agccgtgcgc ctggtcagac cctgcgcgcc   16980
attgccgagg tggcccagca atgcgcggct gcgcgcttgc gttacgctga caccgtgggc   17040
ctgctggacc cgttcaccac cgcagcccag atcagcgccc tgcgtgacgt ttggtcgggc   17100
gagatcgaga tgcatgctca caatgatctg ggcatggcta ccgcgaacac gctggcggca   17160
gtttcggctg gcgccacgtc ggtgaacact accgtcctcg gtctgggtga acgtgcaggc   17220
aacgcagccc tggaaaccgt tgcgctgggc ctggaacgct gcctgggcgt ggaaaccggc   17280
gtccatttca gcgcgctccc agcgctctgt cagcgcgtcg cggaggctgc acagcgcgca   17340
atcgacccgc aacagccgct ggtgggtgaa ttggttttca cccacgaatc tggtgttcac   17400
gttgcggcgc tgctgcgcga cagcgaatcc tatcaatcta ttgccccaag cctcatgggc   17460
cgtagctacc gtctggtgct cggcaagcat tcgggtcgtc aggctgtcaa cggtgttttc   17520
gaccagatgg gttaccacct gaatgcggcg cagatcaatc agttgctgcc ggccattcgc   17580
cgcttcgccg agaattggaa acgctctccg aaagactacg aactggttgc gatctatgac   17640
gaattgtgcg gtgaatccgc ccttcgtgct cgcggctaac cgatagtttc aagagaaagg   17700
gagtagaaac agaatggagt ggttttacca gattccgggt gtagacgaat tgcgcagcgc   17760
tgaatccttc tttcagttct tcgcggttcc ataccagccg gaactgctgg ccgctgctc    17820 gcttccggtg ttagcgacgt tccaccgtaa actgcgtgcg gaggtcccgc tgcaaaaccg   17880
tctggaggac aatgatcgtg cgccgtggct cttggcgcgc cgcctcctgg ccgaatctta   17940
tcagcagcaa tttcaggaga gcggcaccta attcaccagc ccgaatcaat ataggtcata   18000
caatgcgccc gaaattcacc ttctctgaag aggtccgcgt agttcgcgcg attcgtaatg   18060
atggcaccgt ggcgggtttt cgccaggtg cgctgctggt tcgtcgcggt tcgacgggct    18120
ttgtgcgtga ctgggtgtg ttcctgcaag accagatcat ctatcaaatc cactttccgg    18180
aaaccgaccg cattatcggc tgtcgcgagc aggagttaat cccgattacc cagccgtggt   18240
tggctggtaa cctccagtat cgtgacagcg tcacgtgcca aatggcactg ctgtcaacg    18300 gtgacgtggt tgtgagcgcc ggtcaacgtg ccgtgtgga ggccactgat cgtggcgaac    18360
ttggcgattc ctacaccgtg gacttcagcg gccgttggtt ccgcgttccg gtccaggcca   18420
tcgcgctgat tgaagagcgc gaagaataat cagagactga agttattacc caggaggtct   18480
ataatgaatc cgtggcagcg ctttgcccgt caacgccttg ctcgcagccg ctggaaccgt   18540
gatccggctg ctctcgaccc agccgatacc ccagcgttcg agcaggcgtg gcagcgtcaa   18600
```

| | |
|---|---|
| tgccatatgg aacaaaccat cgtagcgcgt gtcccggaag gcgatattcc ggctgcctta | 18660 |
| ctggaaaaca tcgcggccag cctggcgatc tggctggacg agggtgactt cgctccgccg | 18720 |
| gagcgcgctg cgattgtgcg tcatcatgca cgtctggagc tggcgtttgc cgacattgcc | 18780 |
| cgccaggcac cgcaaccgga tctgagcacg gttcaagcgt ggtatctgcg tcaccagacg | 18840 |
| caattcatgc gtccggagca gcgtctgacc cgtcacctgc tcctgacggt cgataatgat | 18900 |
| cgcgaggcgt tgcatcaacg catccttggc ctgtatcgtc agatcaacgc gagccgtgac | 18960 |
| gccttcgccc cactggcaca cgccactct cattgcccgt ccgccttgga agaaggccgt | 19020 |
| ctgggctgga tctcccgtgg tctgctgtac ccgcagctcg aaaccgcgtt gtttagcctg | 19080 |
| gcggaaaacg cactgtcgct gccgattgcg tcggaattgg gttggcacct gttatggtgc | 19140 |
| gaggccattc gtccggcagc cccgatggag ccgcaacagg cccttgaatc tgcgcgcgac | 19200 |
| tacttgtggc agcagagcca gcagcgccac cagcgtcaat ggctggagca gatgatttcc | 19260 |
| cgccaaccgg gcctgtgtgg ttaatagcat aaccccttgg ggcctctaaa cgggtcttga | 19320 |
| ggggtttttt gt | 19332 |

<210> SEQ ID NO 3
<211> LENGTH: 10746
<212> TYPE: DNA
<213> ORGANISM: Paenibacillus WLY78

<400> SEQUENCE: 3

| | |
|---|---|
| gtagggcgca ttaatgcagc tggactagtg aattgaggat aaatgtcagg gatttcatgg | 60 |
| agaagtgaat tgactgtatt tgtccctgtc tctaagatgt aattatattc cagacaaaaa | 120 |
| cagagattta tgtaagggaa tataacgtag agaggaggga atgaatggac tctttagctg | 180 |
| atctctcgga aaccccctta gcattagaaa ctctcagacg catccctgt tataacgaag | 240 |
| aggcacatcg ctattttgcg cgcattcatc ttccagtagc cccggcatgc aatattcagt | 300 |
| gccattattg caaccgcaaa ttcgattgcg tcaatgaaag ccgtcccggc gttgttagtg | 360 |
| aactgcttac gccggagcag gcggcgagca agacctatgg cgtagcggca cagctgatgc | 420 |
| agctgtccgt tgtcggcatt gcgggacctg gagatccgct ggccaatgcg gaggcaacct | 480 |
| tcgataccct ccgccgggtc cgtgagacag ttaaggacgt catattctgt ctcagcacga | 540 |
| atggccttac tttgatcagg catatcgaca ggattgtaga gttgggtatt tcgcatgtca | 600 |
| cgatcacgat caatgctgta gatccagtgg tggggagccg catttatgga tgggtctacg | 660 |
| atgaaggaaa acgctatgcg ggtgaggagg ccgcacgact gttgattgac cgccagctgg | 720 |
| caggcttgaa gatgctggct tcgagaggtg tattgtgcaa ggtgaactcg gtgctgattc | 780 |
| ccgaagtcaa tgatgcccat ctgccggagg tagcgagggt ggtcaaggag cacggcgcgg | 840 |
| tgctgcacaa cattatgccg ctcatcatcg cacctggtag ccgatatgag caggaaggga | 900 |
| tgcgggcacc ccgtccccgt ctggtccggc agctgcagga gcaatgtgct gaagcgggag | 960 |
| ctgtcattat gcgccattgc cgtcagtgca ggcggatgc gattggactg ctgggcgagg | 1020 |
| atcgcaatca ggattttaca tgggagaaca ttgctgctgc tcctcccatg gatgaagagg | 1080 |
| caagggcaca atttcagaaa gaactggatg agaaggtgag agtgagaatg gaacgcaagg | 1140 |
| agggacaatc gcaccacaaa caaccgtcaa ccggtgctgg ttgtagctgc ccgttatctg | 1200 |
| gggataagcc tgaagcgagc tttacctcaa agccggtctt aatcgctgtg gctagtcgtg | 1260 |
| gtggagggaa ggtgaatcag catttcggtc gtgccaagga atttatgatc tatgaaagcg | 1320 |
| acgggaccat cgtaaatttc ataggcattc gtaaggtgca atcctactgt cacgggaaag | 1380 |

```
ccgattgcaa tggagataag gccgagacga tcaaggagat cctttccatg gtacatgatt    1440
gtgcattgct gctgtcgtcc ggcataggcg aagcccccaa agaggcattg caggaagcgg    1500
gcgtgctgcc tattgtgtgc ggcggggata ttgaggagtc cgttctggaa tatgtaaaat    1560
ttctgcgtta tatgtatcct gtgcagacgg gtaaggaag taagcgtaat aagggagtta    1620
agggcaatca ttcggattta cccattgaac attttggagg ctgagaaaat atgagacaaa    1680
ttgcgtttta cggtaagggc ggtatcggca atcgacaac ctcgcagaat acactggctc     1740
aacttgcgac caaattcaaa caaaaaatta tgatcgtagg ctgtgatccc aaggcagact    1800
ccacccgtct tattttgaat acgaaggccc aacagaccgt actgcatctg gcagctgaaa    1860
ggggtacggt ggaggacttg gaactggagg atgttgtcca gaagggcttc ggtgatattc    1920
tgaacgtgga atgcggcggg ccagagcccg tgtcggctg tgcaggacgc ggtatcatca     1980
cagccattaa ttttctggag aagaggggg cctacgaagg gctggatttc gtttcctacg     2040
atgtactggg ggacgtcgtg tgcgggggt cgccatgcc gatccgggag aagaaggcgc      2100
aggaaatcta catcgtatgc tcaggcgaga tgatggctat gtacgctgcc aacaatattg    2160
cgcgcgggat cttgaagtat gccaacagcg gcggggtgcg tttgggcggc ttaatctgca    2220
acagccggaa tacggacctg gaagcggaat tgatcacaga gcttgcaaga agattgaaca    2280
cgcagatgat ccacttttg ccgcgtgaca atgttgtgca gcacgctgag ctgcgccgta     2340
tgaccgttac ccaatataac ccggaacata agcaggctgc ggagtatgaa gagctggcag    2400
gtaagatttt gaataatgac atgctaacgg ttcccacgcc catttccatg gaagatctgg    2460
aggatctatt gatggaattc ggcattattg aggatgaaga accgcaatt aacaaagctg     2520
aggcgtccgg gcagtaggct gtagccagaa ggcttaatga cggaaccatc gtgtaatgat    2580
gggaggagct gaacgcgcag ctcgcaggag ggaggaatag gccaaatgag cagtattgtg    2640
gataagggta agcagatcgt agaggagata ctggaggtat atcccaagaa ggccaagaag    2700
gatcggacca agcattttga gatcgcggat gaggagcttg tgaactgcgg aacctgttcc    2760
atcaagtcca acatgaaatc acggcctggc gtcatgacag caaggggctg tgcttatgca    2820
ggctccaagg gtgtggtatg gggcccgatt aaagacatgg tgcacattag ccatggtccc    2880
atcggctgcg gacagtacag ttggggtacc cgacgcaatt atgcgaatgg gatattggga    2940
atcgataatt ttaccgccat gcagattaca agcaattttc aggaaaaaga tatcgtgttc    3000
ggtggagata agaagttgga ggtgatctgc agggaaatta aggagatgtt cccgctggct    3060
aagggtatct ccgtgcaatc tgaatgtccg gtcggactga ttggtgatga tatcggggcc    3120
gtggccaaga agatgacaga ggagctgggc attccggtca ttcctgtacg ctgtgagggc    3180
tttcgcgggg tgagtcagtc tctgggccat cacattgcca atgatgctat ccgcgatttt    3240
ctaatggggc gccgagaact gaaggagtgc gggccttatg atgtctccat tatcggagac    3300
tacaatatcg gcggtgatgc ctgggcgtcg cgcattttgc tggaggaaat gggactgcgg    3360
gtcatagcgc agtggtcggg tgacggtacg atcaatgagc tggggattgc gcataaatcc    3420
aagctcaacc tgatccattg tcatcgttcc atgaattata tgtgcacaac aatggagcag    3480
gaatacggaa ttccctggat ggaatataac ttcttcggcc cgaccaagac gatggagagc    3540
ctcagagcga ttgctgcccg cttcgacgag acgattcagg aaaaatgtga gcaggtcatc    3600
gcccaatata tgccgcagat ggaggcggtc atccgtaaat atcgcccacg tctggaaggt    3660
aaaaaggtga tgcttctgat tggcgggctg cgggcaaggc ataccatcgg ggcctatgag    3720
```

```
gatctgggta tggaaattgt ggctacaggc tatgaatttg cccataagga tgattacgaa    3780
aagacgtttc ccgatgtaaa agaaggcacc attctgtacg atgatccaac ggcatatgag    3840
ctggaggaac tggcccagcg gctgaatatt gacttaatgg gcgccggagt caaggagaaa    3900
tacgtgtatc acaaaatggg cattcccttc cgtcaaatgc actcctggga ttacagcggg    3960
ccttatcatg gttttgacgg ctttaagatt tttgcacgtg atatggatat gaccataaac    4020
agtccagtat ggagcctgct gccctcacgg cagactgcgg aggtgccggt atgagcgagc    4080
gtccgaatat tgtcgatcac aatcagctgt ttcggcagga taaatatgtg cgccagcgtg    4140
aagaaaaacg agccttcgag gccccatgtt cgccggagga ggttaccgac accctggagt    4200
acaccaagac caaggaatac aaagacaaga attttgcccg tacagccgta gtcgtgaatc    4260
cggccaaggc ttgtcagccg ctgggagcgg ttatggctgc actgggcttc gaaaaaacgc    4320
tcccgttcat tcatggttca cagggctgta cggcttattt tcgcagtcat cttgcccgcc    4380
acttcaaaga gcctgttcct gccgtctcca cctcgatgac cgaggatgcc gccgtattcg    4440
gcggcatgcg caacctcatt gacggtatag agaactgcat tgccttgtat cagccggaga    4500
tgattgcggt atgcacgacc tgtatggcag aggtgatcgg ggatgatctg tctgccttcc    4560
tggccaatgc ccgtcaggag ggagtccttc ctgaggatat gccagttcct tttgccaata    4620
cccccagctt ctctggttca catattacag gctatgacgc catgctgcgc tctgtactgg    4680
agacgctgta taacaagtca ggccggacgg cgcagcctgg tcatgaattg aagctgaatg    4740
tactgctcgg gtttgacggg tatacgggca attttgcgga aatgcggcgc atgctgggga    4800
tgttcggcgc tacgtatacc attctgggtg accacagcag taattttgat tcaggggcca    4860
ctggagagta cagctactat tacgggggaa cgccgcttga ggatgtgcct aaggccgcag    4920
atgctgccgg cacgttggcg attcagcagt actctcttcg taaaacacta ggctatatga    4980
agcaaacctg ggggcagcag gtgtcctcca tctccacacc gctgggcatc cgggctacag    5040
atcgcttgct tgaggagatt agccgcctgt ctggaaggga aattcccgag gcattgaagc    5100
aggagcgcgc ccgaattgtg gatgccatga tggattcaca tgcttatctg cacggcaaac    5160
gagtggctat ggcaggagac ccggacatgc tcatcggctt gattggcttt tgtctggagc    5220
tgggcatgga gccggtgcat attgtttgct ccaatgggga ccgaaaattt gagaaggaag    5280
cagagcttct gctgaagtcc agcccttacg gtgcagaagc cacggttcat tccggtcagg    5340
atttgtggca tatgcgttcg ctgctgttcc aggacccggt ggacctggct attggcagct    5400
cccatctgaa gtttgcagcg aaagaggcgg aaattccttt gcttcgtgta ggctttccga    5460
tcttcgacag gcatcatctg catcgttatc cgattatcgg ctaccagggt gcgctgaatc    5520
tgctcaccca attcgtgaat accatactag atgtcatgga ggagcaggct ccggatcata    5580
gctttgatct ggtgcgctaa ttgctgtatc gcgtagaagg aagttgacag cttggcttgt    5640
gatttcaatg gattctatct gaaataaggg ggtgtgtgga tggagccggc tgtgtctaac    5700
ggaaggctgg aggtatcctg cggcaataaa attcccaaaa gcacgccctg tccccggcct    5760
gtgccgggag aggcttcggg tggctgctcc tttgacgggg cccagattac actgatcccc    5820
attgcagatg cggctcatct ggtgcacggg ccaattgcgt gtctcggcaa tagctgggag    5880
agcagaggca gtctgtccag cggcccagag ctgtcggctt atggcttcac tactgatctt    5940
ggagaacagg acatcatttt tggtagtgaa cagaagctgc atgaatcgat ccgctacatt    6000
gtcagccgct ttgctcctcc cgctgtgttt gtctatacca catgtgtcac agccctcact    6060
ggtgaagata tcgaggggt ttgcaaggct gaatcggagc ggctggggac gccgatcatt    6120
```

```
ccggtgaaca gtccgggatt tgtgggcagt aagaatctcg gaacccggct ggccggagat    6180
gtgctgttcc agcatattat cggcagcacc gagccggaac agacaacctc ccatgatatc    6240
aatctcattg gggaatacaa tattgcgggc gagatgtggc atatcgagcg gctgatgcag    6300
caggcgggaa tgagtatcct gtcccgaatt accggggacg tcggttccg cgaggtgggc    6360 tgggcgcacc gtgccaaggc caacatggtc gtatgcagcc gggctttgct gggtctggca    6420
gtccaaatgg agcgtaaata cggcattcct tattttgaag gttcatttta tggagcaaag    6480
gagacgagtt attccttgcg gcagatggct tacctgaccg gagatcgtga tgtggagcga    6540
cgggtggata agctggccgc acgggaggaa atgaggctat cgctggagct ggagccctac    6600
cgcaagcagc tgaaaggaaa gcgggcagtg ctctataccg ggggtgtaaa gagctggtct    6660
gtcattacgg ctttgcagga gctgggcata aggtggttg tgtaggcac gaacaagagc     6720 actgccgagg atgtatcccg gattgctgac cgtatcgggg atgatgcaga atacatcccg    6780
gaaggaggcg cccggcagat tctcaagacc gtacggagcc gcaaggcaga catggtcatt    6840
gccggaggcc ggaacatgta tatggcgctt aaggaacaga ttccttttgt ggacatcaat    6900
caagagcgga caaagccta tgcgggctat gacgggctgt tgtctctggc gaaacagctt    6960
gtgcatacgc tgcagcatcc agtatgggag ctgaccgcca aattggctcc atgggaggag    7020
gagacggaat tgctgatta aatccgccac gaagcctgtc agtgtcaacc cgctcaaggt    7080
aggacagcct ttgggcggcg tgctggctct gcagggatg tatcgctcaa tgcctttgct     7140
gcacggcgct cagggctgct cggccttctc caaggcgctg ctgactcgcc attttcgaga    7200
gccgattgcc gttcagacct ctgcgttgca agagatggac gttatatttg atgcagaccg    7260
gaatctggag gaggcgctgg atcatatctg gtccaaacac catccagatg tcatcggcgt    7320
tatcagcacg gccctcactg aggtggcagg cgttgacttt cagtctaggg taaaggcgtt    7380
caagcgagaa cgggcattga aggacagtct gctgttttct gtatcgctgc ctgattttca    7440
cggctctctg gagacgggct acagcagtac agtagagtca ctaatggatg ccgtactcgg    7500
gttggccggg ggcaagtccc ccaaaaaaca gcgccggacg caggtcaatc tgctgccggc    7560
ttcttatctg actgccggag atgtcatgga aatcaaggat attatcgctt ccttcggcct    7620
ggaggttatt acgctccccg atatttccac ttccttgtcc ggtcacctgc tgacaggctt    7680 ttccccttg acgagagggg ggactccgct ggattcagcc tgccagatgc tggagtcttc    7740
ctgcaccatt gccattggcg cgagcatgga gcgtccggcg cgcaggctga ctcatgctgc    7800
aggtattccc taccacttgt tcgctggtct gtctggcttg gccgcgagtg atgcgttcat    7860
acattttctg cagaaaatca gccgcgagcc agccccgtt cgcttccgtt ggcagcgtga    7920
aaatctgttg gacagcatgc tggatgccca tttctattat tctggcgctt cggctgtagt    7980
ggcgctagaa ccggatcata tgctgtcgac cgcagcctgg ctggaggaga tgggagtgga    8040
actgaagcgg ctaattacac cctgcagcac gcccgcactg caaaagacag aacgggaagt    8100
ctggatcggt gacctggatg atgcagagga gagcgcgcag ggtgttgatt tgtggatcag    8160
caactcacat ggaagaaagg gagcggcacg ggctggggcc tcattcgtac cggcaggctt    8220
gccggtgtat gacgagctag gcgcccacac atccgtaagc gtcggatacc gtggaaccat    8280
ggagtgggtg aacaaagtag gcaatgtatt gcttgccgag aggggagggg gaggatgaag    8340
gttgcatttg cgacggaaga cggcgtgctt gtgaatgctc attttgggca gagtcccatg    8400
ttcactatat tcgaaatccg gcactcaggc gtccagttcc tggagcatcg gcggatagcc    8460
```

```
ctggggagcg atgagaatga ggcgggcaag atcgccagcc gaattggcct gatcgaggat    8520
tgtgccttga tcttcctggt acagattggc gcttccgccg ccgcacaggt taccaagcgg    8580
accattatgc ctgtgaaggt ggccttcggt agcaccattg aggagcaggt ccagcgtctc    8640
cagaatatgc tgactcgcaa tccgcccatg tggcttgcca aaatcctgca tgctgaggag    8700
ggcagcggca aagccgaatc atgagccctc ctgtaaggaa gagcaaccat atagggtatt    8760
aagatcctgc agaccgaata tcttaaaggc gggagccgca catggagggg gtggacgaat    8820
ggtacaactg ctggaagaca gtagatacgg acgccagttg aagctgctgg gagtggaagg    8880
tcagaacagg ctaaagcagg ctacggttat ggttgcaggc atcggaggat tgggagggggc   8940 agcggccatg tacctggccg ctgccggagt aggaaagctg atattggccc atgagggcgt    9000
aatccatctg cccgatatga accggcaggt gctgatggac agcggacgaa tcggggagga    9060
acggatggag acggcattac agcatttgca tcgtatcaat ccggagaccg agcttgaggg    9120
ccacgcccac agaatcacgg aagaatcctc tggaccatgg gtagaagcgt cggatatcgt    9180
gattgatgca cgatatgact tccggaaaag atatgcgctg aacagactat gtgttcgaca    9240
tggaagaccg atgatagaag cggccatgta cgcctatgaa gtatcattga tgaccattga    9300
tcccggtaag acggcatgcc tggaatgtct ttacccggaa ggcggacagc cttgggaacc    9360
tctgggattc ccggtcctgg gagccacctc cggcttgatt ggctgcatgg ctgcactgga    9420
agcggtcaaa tggattacag atgcgggcaa tctgttcact gaccgcatgt accgtatgaa    9480
tgtgctggat atgagcagct gcaccatagc ggtcaaacgc aacccgcgtt gtccgtgctg    9540
cggaacggga ggggatacag atgagtcggt tgcatatttg tgatacgaca cttcgtgacg    9600
gagaacaggc tccgggcgtt gccttttcag ccgaggaaaa aactgaaatt gccatcatgc    9660
tggactcggc ggggtggag caggctgaga tcggaattcc ggcaatggga aagacggagt    9720
gcaggtctat tgccaggatt gctgctctcg gacttcagat gaagctaatg acctggaatc    9780
gcgcggtgtt cacggatatt gatgcaactg aatcgacagg tgtcggctgg gcccatattt    9840
cggttcccgt gtcgacggtg cagatgaagt ccaagctggg tatgaatcct gagcaggtga    9900
cggagctgat ccgcaagtct gtcgattacg ctctgtgtaa aggattgact gtttccgtag    9960
gctttgagga tgcttcaagg gcagatgacc tgttccttga gcagttggcg aatcagctct   10020 ataggggatgg catccggcgc ttcagatatg ccgatacgct gtccgttcac catcccgctg   10080
ccatagctgc ccgtatagac aggcttgtat cgcgcgtgcc acaggatgtg gagcttgaga   10140
ttcactgtca taatgattat ggcctggcgc ttgccaatac cctggcagct ttgcaagcgg   10200
gagctgtctg ggccagtacc acggtgtcgg gacttgggga aagggcaggt aataccgcgc   10260
tggaggaggt ggtgatgtcg tggagggacc tatatcaagg aacctgcagc gtccgtcccg   10320
aactgctgaa cccgctggct gcactggtgt ccaaagcctc caaccgaatc attcctgaag   10380
gcaagcccat tgtgggagac atggtattcg cccatgaatc cggcatacat atcaacggtc   10440
tgctaaagga gcgcgccgcc tatcaggcgc ttgatccgac tgagctgggc actgaccatt   10500
ccttcgtact cggcaagcat tcgggcagaa gtgcagttca atatatgctg gagcaggaag   10560
gaatcgaggc aggctccggt gaaatcaagt tcctgctgga gcggcttcgc ctagtcggtg   10620
aagatcccaa gcgtgtcatc catagcgcgg atttaagacg ctggctgcag tattatccgg   10680
cagagctgcc gaaataaccg aaaaagcgtt cccgtccggt aagtgtgacc gtgactggaa   10740
cgcttt                                                              10746
```

```
<210> SEQ ID NO 4
<211> LENGTH: 23467
<212> TYPE: DNA
<213> ORGANISM: Klebsiella oxytoca
<220> FEATURE:
<221> NAME/KEY: misc_feature
<222> LOCATION: (16445)..(16445)
<223> OTHER INFORMATION: n is a, c, g, or t

<400> SEQUENCE: 4
```

| | | | | | |
|---|---|---|---|---|---|
| gaattctaga | ctgctggata | cgctgcttaa | ggtcatgcag | caggagaact | aaaggcccgc | 60 |
| tactcctcgc | cggccagccg | ccgatactgg | gcaaagcggg | cccgcgcgtc | ctcctcggtt | 120 |
| cggctaaaga | gcgcatccgc | cagatgcggc | gtcgttttgt | gcagcgaggc | gtagcgcact | 180 |
| tcgccaagca | aaaagtcgcg | gaagctctcc | tccggctctt | cggaatcgag | cataaacggc | 240 |
| gtcttacctt | ccgcttcccg | ctgcggatga | tagcgccaca | ggtgccagta | tcccgcctca | 300 |
| accgcccgtt | tcgcctcgcg | ctggctgcag | cgcataccgg | ctttcagccc | gtggttaatg | 360 |
| caggcggcgt | aggcaatcac | cagcgacggt | cccggccagg | cttcggcctc | ggcgatcgcc | 420 |
| cgtagggtct | gatctttatc | agcgcccatc | gcgacctggg | ccacgtacac | attgccgtag | 480 |
| ctcatcgcca | tcatgccgag | atcttttttc | cgcgtgcgtt | tgccctgcgc | ggcaaacttc | 540 |
| gcgatggccg | ccaccggggt | cgatttagac | gactggccgc | cggtattgga | gtaaacctcg | 600 |
| gtgtcaaaca | ccagaatatt | gacgtcttcc | ccgctcgcca | gcacgtgatc | gagaccgccg | 660 |
| aagccgatat | cgtaggccca | gccgtcgccg | ccgaaaatcc | actgcgaacg | acgaacaaaa | 720 |
| tagtcgcggt | tctgccacag | ctgctccaac | agcggcacgc | cctcttttc | cgccgccagc | 780 |
| cgttcgctga | gccggtccgc | gcgctcgcgg | gtgccctcgc | cttcatcctg | cttcgccagc | 840 |
| cactggcgca | ttgcgtcgct | aagttcgtcg | ctgaccggta | gcgccagcgc | ggcggtcata | 900 |
| tcatcggcga | tttgttgacg | caccgcctgg | ccgccgagca | tcatgccgag | gccaaactcc | 960 |
| gcattatcct | caaacagcga | gttcgcccat | gccgggccat | ggccgcggtg | gttggtggta | 1020 |
| tagggaatcg | acggcgcgct | ggctccccag | atagaagagc | agccggtggc | gttagcgatc | 1080 |
| agcatccggt | cgccaaacag | ctgggttatc | aggcgggcat | aaggcgtttc | accgcatccc | 1140 |
| gcgcaggcgc | cggaaaactc | cagcagcggg | gtttcaaact | ggctgccttt | gaccgtcgtc | 1200 |
| ttacgaaacg | gattgctctt | cggcgtcagc | gccagcgcat | agtcccagac | cggcgccatc | 1260 |
| tgacgctggc | tatcgagaga | ctgcattttt | aacgccttgc | cgcgcgcggg | acagatatcc | 1320 |
| acgcagttgc | cgcagccgga | acaatccagc | ggcgagatag | ccagatggta | gtgatactcc | 1380 |
| ttcgctccct | gcgcgggttt | gctcagcagc | ccaaccggcg | cggcgtcatg | ctcttcgccg | 1440 |
| ttgagcagcg | ccgggcggat | cgccgcatgc | gggcagataa | aggcgcactg | gttacactgc | 1500 |
| gtgcagcccc | ccgctgcca | gaccggcact | tccagcgcga | tcccgcgttt | ctcccacgcg | 1560 |
| gcggtgcccg | aaggaaaggt | cccgtcctcc | ataccgacga | acgcgctcac | cggcagctgg | 1620 |
| tcgccgcact | ggcggttcat | cggctgcaga | atatcgcgga | tgaaatccgg | catcatggct | 1680 |
| gatgcttgcg | ccgcgggttc | atccagcgtc | gcccagtgcg | ccggaatcgt | cacctgatgc | 1740 |
| agcgaggcca | tgcccagctc | gatcgcccgc | tggttcatct | caatcaccgc | cgcccctttg | 1800 |
| ctgccgtagc | ttttttcaac | cgcctgcttg | aggtaatccg | ccgcggtctg | cgggtcgata | 1860 |
| atcgccgcca | gcttaaagaa | cgccgcctgc | atcagcatat | taaagcgccc | gcccagcccg | 1920 |
| agctcgcggg | cgatatccac | ggcgttcagg | gtataaaaat | ggatattttc | ccgcgccaga | 1980 |
| tagcgtttaa | agccgaccgg | cagatgctgc | tccagctccg | catcggacca | gctgcagttg | 2040 |

```
agtaaaaagg tcccgcccgg ctttaatccg tccagcagat cgtagcgctc aacgtaggac    2100
tgctgcgaac aggagataaa atcggcccga tggatcaggt agggcgaatt gatcggccgg    2160
tcgccgaagc gtaaatgtga acggtaatg ccgccggatt ttttcgagtc ataagaaaag     2220
taggcctgcg cgtagagcgg cgttttatcg ccgataattt tgatcgcgct tttattggcc    2280
ccgacggtgc cgtccgagcc catgcccccaa aatttacagg cggtgatgcc gtcatgcgag   2340
accgccagcc tctgctggcg cggcggtaac gaagtaaagg ttacatcatc gacaatcccg    2400
agggtaaacc cgtccatcgg cagcggttta ttgaggttat caaagacggc cgcgatatcg    2460
ttgggcagaa catccttccc gccaagcgca tagcggccgc cgacgattag cggcgcatcg    2520
tcgtggtggt agaaggcgtt tttcacatcc aggcacagcg gttcagcctg agcgccgggc    2580
tctttggtac ggtcaaggac ggcaatccgc tgcacggttt tcggcagctg ggcgaagaag    2640
tgggccagcg aaaaagggcg aaacagatgc acgctgagca gcccgacctt ctctcccgcc    2700
gcgttcagcg tatccaccac ttcctgaacg gtatcgcaga ccgatcccat tgcgataatc    2760
acccgttcgg catccgccgc gccggtatag ttaaacagat gatactcccg gccggtgagc    2820
gcgctgattt gcgtcatata gctttcgaca atgtcgggca gcgcctgata aaaacggttg    2880
cccgcctccc gctcctggaa gtagatatcc gggttctgcg ccgttccgcg gatgaccgga    2940
tgatccggat gcagcgcgtt acggcggaag ctgtcgagcg cgggccggtc cagcagcgtc    3000
gccagctgct catattccaa cacctcgatt ttttgaattt cgtgcgaggt gcgaaaaccg    3060
tcgaagaagt taacaaacgg gatgcgtccc ttaatcgccg ccagatgcgc caccgccgac    3120
aaatccatca cctgctgcac gttgttctcc gccagcatcg cgcagccggt ctggcggacc    3180
gccatcacat cctggtgatc gccaaaaata ttcagcgaat tggtcgccag cgcccgggcg    3240
ctgacgtgaa agacgcccgg cagcagttca ccggcgattt tgtacatgtt ggggatcatc    3300
agcagcagcc cctgggaggc cgtataggtg gtggtgagcg ccccggcctg cagcgcgccg    3360
tggaccgcgc ctgccgcgcc ggcctccgac tgcatctcca ttaagcgcac cggctggcca    3420
aaaaggttct ttttcccctg cgccgcccac tcgtcgacgt ttttccgccat cggcgtggag    3480 ggggttatgg ggtaaatcgc cgcgacctcg gtaaaggcat aagagatcca ggccgccgcg    3540
gcgttgccat ccattgtttt catttttccg gacattgttc aatcctcgaa ggtgagaggc    3600
atcttcgccg cctcaaataa gcggcaaacc cagttgttgc ctcaagcaca gcctgtgcca    3660
gctcgcggat gacagaagag ttagcgcgaa ttcaacgcgt tatgaagaga gtcgccgcgc    3720
agcgcgccaa gagattgcgt ggaataagac acaggggggcg acaagctgtt gaacaggcga    3780
caaagcgcca ccatggcccc ggcaggcgca attgttctgt ttcccacatt tggtcgcctt    3840
attgtgccgt tttgttttac gtcctgcgcg gcgacaaata actaacttca taaaaatcat    3900
aagaatacat aaacaggcac ggctggtatg ttccctgcac ttctctgctg gcaaacactc    3960
aacaacagga gaagtcacca tgaccatgcg tcaatgcgct atttacggta aaggcggtat    4020
cggtaaatcc accaccacgc agaacctcgt cgccgcgctg gcggagatgg gtaagaaagt    4080
gatgatcgtc ggctgcgatc cgaaggcgga ctccacccgt ctgattctgc acgccaaagc    4140
acagaacacc attatggaga tggccgcgga agtcggctcg gtcgaggacc tcgaactcga    4200
agacgtgctg caaattggct acggcgatgt gcgctgcgcg gaatccggcg gcccggagcc    4260
aggcgtcggc tgcgcgggac gcggcgtgat cacggcgatc aactttcttg aagaagaagg    4320
cgcctacgag gacgatctcg atttcgtgtt ctatgacgtg ctcggcgacg tggtctgcgg    4380
cggcttcgcc atgccgatcc gcgaaaacaa agcccaggag atctacatcg tctgctccgg    4440
```

```
cgaaatgatg gcgatgtacg cggccaacaa tatctccaaa gggatcgtta aatacgccaa    4500
atccggcaag gtgcgcctcg gcggcctgat ctgtaactca cgtcagaccg accgtgaaga    4560
cgaactgatt attgccctgg cggaaaagct cggtacccag atgatccact tgtgccccg     4620 cgacaacatc gtgcagcgcg cggagatccg ccgcatgacg gttatcgagt acgaccccgc    4680
ctgtaaacag gccaacgaat accgcaccct ggcgcagaag atcgtcaaca acaccatgaa    4740
agtggtgccg acgccctgca ccatggatga gctggaatcg ctgctgatgg agttcggcat    4800
catggaagag gaagacacca gcatcattgg caaaaccgcc gccgaagaaa acgcggcctg    4860
agcacaggac aattatgatg accaacgcaa cgggcgaacg taatctggcg ctgatccagg    4920
aagtcctgga ggtgttcccg gaaaccgcgc gaaaagagcg cagaaagcac atgatggtca    4980
gcgatccgga aatggagagc gtcggcaagt gcattatctc taaccgcaaa tcacaacccg    5040
gcgtaatgac cgtacgcggc tgcgcctacg ccggttccaa aggggtggta tttgggccga    5100
ttaaggatat ggcccatatt tcgcacggac cggtcggctg cggccagtat tcccgcgccg    5160
gacgacgcaa ctactacacc ggagtcagcg gcgtcgatag cttcggcacg ctgaacttca    5220
cctctgattt tcaggagcgc gacatcgtct tcggcggcga taaaaagctc agcaagctga    5280
ttgaagagat ggagttgctg ttcccgctca ccaaagggat caccattcag tcggaatgcc    5340
cggtggggct gatcggtgat gatatcagcg cggtggccaa cgccagcagc aaggcgctgg    5400
ataaaccggt gatcccggta cgctgcgaag gctttcgcgg cgtgtcgcag tctctggggc    5460
accatatcgc caacgacgtg gtgcgcgact ggatcctgaa caatcgcgaa ggacagccgt    5520
ttgaaaccac cccttacgat gtggcgatca tcggcgacta caacatcggc ggcgacgcct    5580
gggcctcgcg cattctgctg gaagagatgg ggctacgggt agtcgcgcag tggtccggcg    5640
acggcacgct ggtggagatg gagaatacccc cattcgtcaa gctgaacctg gttcactgct    5700
accgttcgat gaactatatc gcccgccata tggaggagaa acatcagatt ccgtggatgg    5760
agtacaactt cttcgggccg accaaaatcg ccgaatcgct gcgcaaaatc gccgaccagt    5820
tcgacgatac cattcgcgcg aacgccgaag cggtgatcgc ccggtatgag ggcagatgg    5880 cggcgattat cgccaaatat cgcccgcgcc tggaggggcg taaggtgctg ctctatatgg    5940
gcggcctgcg gccgcgccac gttattggcg cctatgagga tctcgggatg gagatcatcg    6000
ccgccggcta cgagtttgcc cataacgatg attacgaccg caccctgccg gatctgaaag    6060
agggcacgct gctgttcgat gacgccagca gctacgagct ggaagcgttc gtcaaggcgc    6120
tgaagcccga ccttatcggc tccggcatca aggaaaaata tatcttccag aaaatgggcg    6180
tgccgttccg ccagatgcac tcgtgggact attccggccc gtaccacggc tacgatggtt    6240
cgccattttt cgcccgcgat atggatatga ccctgaacaa cccggcgtgg aacgaactga    6300
ccgctccgtg gctgaagtct gcgtgattgc ccactcactg tcccgtctgt tcaccgattt    6360
gtggcgcggg aggagaacac catgagccaa acgattgata aaattaatag ctgttatccg    6420
ctattcgaac aggatgaata ccaggagctg ttccgcaata gcggcagct ggaagaggcg     6480 cacgatgcgc agcgcgtgca ggaggtctttt gcctggacca ccaccgccga gtatgaagcg    6540
ctgaatttcc agcgcgaggc gctgaccgtt gacccggcga agcctgcca gccgcttggc     6600 gcggtgcttt gctcgctggg atttgccaac accctgccgt atgtgcacgg ctctcagggg    6660
tgcgtggcct actttcgcac ctattttaac cgccatttca aagagccgat cgcctgcgtc    6720
tccgactcga tgaccgaaga cgcggcggtc ttcggcggca acaacaatat gaacctgggc    6780
```

```
ctgcagaacg ccagcgcgct gtacaaaccg gagatcattg cggtgtccac cacctgcatg    6840
gcggaagtta tcggcgatga cctgcaggcg tttatcgcca acgctaaaaa agatggcttc    6900
gtcgacagca gcatcgccgt gccccacgcc catacgccaa gctttatcgg cagccacgtc    6960
accggctggg ataacatgtt tgaaggcttc gccaaaacct tcactgcgga ctaccagggg    7020
cagccgggca aattgccgaa gctcaatctg gtgaccggct ttgaaaccta tctcggcaac    7080
ttccgcgtat aaagcggat gatggaacag atggcggtgc cgtgcagcct gctctccgat    7140
ccgtcggaag ttctcgacac gcccgccgac ggccactatc ggatgtattc cggcggcacc    7200
acgcagcagg agatgaaaga ggcccctgac gccatcgata cgctgctcct gcagccgtgg    7260
cagctgctga agagcaaaaa agtggtgcag gagatgtgga accagcccgc caccgaggtc    7320
gccattccgc tggggctggc cgccaccgat gaactgctga tgaccgtcag ccagcttagc    7380
ggcaagccga ttgccgacgc cctcacccTT gagcgcggcc ggctggttga catgatgctc    7440
gactcccaca cctggctgca cggcaagaag tttggcctgt acggcgatcc ggacttcgtg    7500
atgggcctca cccgcttcct gctggagctg ggctgcgagc caacggtgat cctgagccat    7560
aacgccaaca aacgctggca aaaagcgatg aacaaaatgc tcgatgcctc gccgtacggg    7620
cgcgatagcg aagtgtttat caactgcgat ttgtggcact tccgttcgct gatgttcacc    7680
cgtcagccgg actttatgat cggcaactcc tacggcaagt ttatccagcg cgataccctg    7740
gcgaagggta aagcctttga agtgccgctt atccgcctcg gctttccgct gttcgaccgc    7800
caccatctgc accgccagac aacctggggt tatgaagggg cgatgaacat tgtgacgacg    7860
ctggtgaacg ccgtgctgga gaaactggat agcgatacca gccagctggg caaaaccgat    7920
tacagcttcg atctcgtccg ttaaccatca ggtgccccgc gtcatgcggg gccaggaggg    7980
agtatgccca tcgtgatttt ccgtgagcgc ggcgcggacc tgtacgccta tatcgcgaaa    8040
caggatctgg aagcgcgagt gatccagatt gagcataacg acgctgaacg ctggggcggc    8100
gcgatttcgc tggagggggg acgccgctac tacgtgcatc cgcagccggg gcgtcccgtc    8160
tttccgataa gcctgcgcgc gacgcgcaat accttgatat aaggagctag tgatgtccga    8220
caacgatacc ctattctggc gtatgctggc gctgtttcag tctctgccgg acctacagcc    8280
ggcgcaaatc gtcgactggc tggcgcagga gagcggcgag acgctgacgc cagagcgtct    8340
ggcgaccctg acccagccgc agctggccgc cagcttTccc tccgcgacgg cggtgatgtc    8400
ccccgctcgc tggtcgcggg tgatggcgag cctgcagggc gcgctgcccg cccatttacg    8460
catcgttcgc cctgcccagc gcacgccgca gctgctggcg gcattttgct cccaggatgg    8520
gctggtgatt aacggccatt tcggccaggg acgactgttt tttatctacg cgttcgatga    8580
acaaggcggc tggttgtacg atctcgcgcc ctatccctcc gcccccaccc agcaggaggc    8640
caacgaagtg cgcgcccggc ttattgagga ctgtcagctg ctgttttgcc aggagatagg    8700
cgggcccgcc gccgcgcggc tgatccgcca tcgcatccac ccgatgaaag cgcagcccgg    8760
gacgacgatt caggcacagt gcgaggcgat caatacgctg ctggcggcc gtttgccgcc    8820
gtggctggcg aagcggctta acagggataa ccctctggaa gaacgcgttt tttaatccct    8880
gttttgtgct tgttgcccgc tgaccccgcg ggcttttttt cgcgtatgga cgctcttccc    8940
cacgttacgc tcagggggaat attccgttca cggttgttcc gggcttcttg atgcgcctaa    9000
ccccctcgct gccagccttt catcaacaaa tagccatccc agcgcgatag gtcataaagc    9060
atcacatgcc gccatccctt gtccgattgt tggcttTgtc gcaaagccaa caacctcttt    9120
tctttaaaaa tcaaggctcc gcttctggag cgcgaattgc atcttccccc tcatccccca    9180
```

```
ccgtcaacga ggtcactatg aagggaaatg aaattctggc gctgctggat gaaccggcct   9240
gtgaacacaa ccataaacaa aaatccggct gcagcgcgcc caaacccggc gccaccgccg   9300
gcggctgcgc gttcgacggc gcgcagataa ccctgctgcc catcgccgac gtggcgcatc   9360
tggtccacgg ccccatcggc tgcgccggaa gctcatggga taaccgcggc agcgccagct   9420
ccggccccac ccttaatcgg ctcgggttca ccaccgatct caacgaacag gacgtgatta   9480
tgggccgcgg cgaacgccgc ttgtttcacg ccgtgcgcca tcgtcacc cgctatcatc     9540 cggcggcggt ctttatctac aacacctgcg taccggccat ggagggcgat gacctggaag   9600
cggtatgcca ggccgcgcag accgccaccg gcgtaccggt tatcgctatt gacgccgccg   9660
gtttctacgg cagtaaaaat ctcggtaacc ggctggcggg cgacgtcatg gtcaaacggg   9720
tcatcggcca gcgcgagccc gcccctggc cggagagcac gctctttgcc ccggagcagc    9780
gtcacgatat tggcctgatt ggcgaattca atattgccgg cgagttctgg catattcagc   9840
cgctgctcga cgaactgggg atccgcgtgc tcggcagcct ctccggtgat ggccgcttcg   9900
ccgagatcca gaccatgcac cgggcgcagg ccaatatgct ggtctgctcg cgggcgttaa   9960
ttaacgtcgc cagagccctg gagcagcgct acggcacgcc gtggttcgaa ggcagcttt    10020 acgggatccg cgccacctct gacgccctgc gccagctggc ggcgctgctg ggcgacgacg   10080
accttcgcca gcgcaccgaa gcgctgattg cgcgggagga acaggcggcg gaactggcgc   10140
tacagccgtg gcgcgaacag ctgcgcggcc gcaaagcgct gctctatacc ggcggggtga   10200
aatcctggtc ggtggtatcg gcgctgcagg atttgggcat gaccgtggtg gcaaccggca   10260
cgcgtaaatc caccgaagag gataaacagc ggatccgcga gctgatgggc gaagaggcgg   10320
taatgctgga gagggcaac gcccgcacgc tgctggatgt ggtctatcgc tatcaggccg    10380
acctgatgat tgccggcgga cgcaatatgt acaccgccta taaagccagg ctgccgtttc   10440
tcgatatcaa tcaggagcgc gaacacgcct cgctggcta tcaggggatc gtcaccctcg    10500
cccgccagct gtgtcagacc atcaacagcc ccatctggcc gcaaacccat tctcgcgccc   10560
cgtggcgcta aggagctcac catggcagac atttccgca ccgataagcc gctggcggtc     10620
agccccatca aaaccggcca gccgctcggc gcaatcctcg ccagcctcgg gatcgaacac   10680
agcatccctc tggtccacgg cgcgcagggg tgcagcgcct cgccaaagt ctttttatt     10740 caacatttcc acgacccggt tcccctgcag tcgacgcga tggaccccac gtcgacgatt    10800
atgggcgcgg acggcaatat ttttaccgcc ctggataccc tctgccagcg caacaatccg   10860
caggctatcg tactgctcag caccgggctg tcggaggccc agggcagcga tatttcccgc   10920
gtggttcgcc agtttcgcga agagtatccc cggcataagg gggtggcgat attgacggtt   10980
aacacgccgg atttttatgg ctccatggag aacggcttca gcgcggtgtt agagagcgtc   11040
attgagcagt gggtgccgcc ggcgccgcgc ccggctcagc gcaatcgccg ggtcaatctg   11100
ctggtcagcc atctctgttc gccgggcgat atcgagtggc tgcgccgatg cgtcgaagcc   11160
tttggtctgc agccgataat cctgccggac ctggcgcaat cgatggacgg ccacctggcg   11220
cagggcgatt tctcgccgct gacccagggc gggacgccgc tgcgccagat agagcagatg   11280
gggcaaagcc tgtgcagctt cgccattggc gtctcccttc atcgcgcctc atcgctgctg   11340
gccccgcgct gccgcggcga ggttatcgcc ctgccgcacc tgatgaccct cgaacgctgc   11400
gacgccttta ttcatcaact ggcgaaaatt tccggacgcg ccgttccga gtggctggaa     11460 cgccagcgcg gccagctaca ggatgcgatg atcgactgcc atatgtggct ccagggccag   11520
```

```
cgcatggcga tagcggcgga aggcgatttg ctggcggcgt ggtgtgattt cgccaacagc   11580
cagggggatgc agcccggccc gctggtggcc cctaccggtc atcccagcct gcgccagctg   11640
ccggtggaac gggtggtgcc gggggatctg gaggatctgc aaaccctgct gtgcgcgcat   11700
cccgccgacc tgctggtggc gaactcgcac gcccgcgacc tggcggagca gtttgcgctg   11760
ccgctggtgc gcgcgggttt ccgctctttt gacaagctcg gcgaattccg ccgggtgcga   11820
cagggggtata gcgggatgcg cgatacgctg tttgagctgg caaacctgat acgcgagcgt   11880
caccaccacc tcgcccacta ccgatcgccg ctgcgccaga ccccgaatc gtcactctcc   11940
acaggaggcg cttatgccgc cgattaaccg tcagtttgat atggtccact ccgatgagtg   12000
gtctatgaag gtcgccttcg ccagctccga ctatcgtcac gtcgatcagc acttcggcgc   12060
taccccgcgg ctggtggtgt acggcgtcaa ggcggatcgg gtcactctca tccgggtggt   12120
tgatttctcg gtcgagaacg gccaccagac ggagaagatc gccaggcgga tccacgccct   12180
ggaggattgc gtcacgctgt tctgcgtggc gattggcgac gcggttttc gccagctgtt   12240
gcaggtgggc gtgcgtgccg aacgcgttcc cgccgacacc accatcgtcg gcttactgca   12300
ggagattcag ctctactggt acgacaaagg gcagcgcaaa aatacgcgcc agcgcgaccc   12360
ggagcgcttt acccgtctgc tgcaggagca ggagtggcat ggggatccgg acccgcgccg   12420
ctagccgtgt cgtttctgtg acaaagccca caaaacatcg cgacactgta ggacgaacct   12480
tgtcaggact aatacacaac catttgaaaa atattaattt tattctctgg tatcgcaatt   12540
gctagttcgt tatcgccacc gcgcttccgc ggtgaaccgc gccccggcgt tttccgtcaa   12600
catccctgga gctgacagca tgtggaatta ctccgagaaa gtgaaagacc attttttaa   12660
ccccccgcaat gcgcgcgtgg tggacaacgc caacgcggta ggcgacgtcg gttcgttaag   12720
ctgcggcgac gccctgcgcc tgatgctgcg cgtcgacccg caaagcgaaa tcattgagga   12780
ggcgggcttc cagaccttcg gctgcggcag cgccatcgcc tcctcctccg cgctgacgga   12840
gctgattatc ggccatacccc tcgccgaagc cgggcagata accaatcagc agattgccga   12900
ttatctcgac ggactgccgc cggagaaaat gcactgctcg gtgatgggcc aggaggccct   12960
gcgcgcggcc atcgccaact ttcgcggcga aagccttgaa gaggagcacg acgagggcaa   13020
gctgatctgc aaatgcttcg gcgtcgatga agggcatatt cgccgcgcgg tacagaacaa   13080
cgggctgacc acccttgccg aggtgatcaa ctacaccaaa gcgggcggcg gctgcacctc   13140
ttgccacgaa aaaatcgagc tggccctggc ggagatcctc gcccagcagc cgcagacgac   13200
gccagccgtg gccagcggca agatccgca ctggcagagc gtcgtcgata ccatcgcaga   13260
actgcggccg catattcagg ccgacggcgg cgatatggcg ctactcagcg tcaccaacca   13320
ccaggtgacc gtcagcctct ccggcagctg tagcggctgc atgatgaccg atatgacccct   13380
ggcctggctg cagcaaaaac tgatggaacg taccggctgt tatatggaag tggtggcggc   13440
ctgagccgcg gttaactgac ccaagggga caagatgaaa caggtttatc tcgataacaa   13500
cgccaccacc cgtctggacc cgatggtcct ggaagcgatg atgcccttt tgaccgattt   13560
ttacggcaac ccctcgtcga tacacgattt tggcattccg gcccaggcgg ctctggaacg   13620
cgcgcatcag caggctgcgg cgctgctggg gcgggagtat cccagcgaga tcatctttac   13680
ctcctgcgcc accgaagcca ccgccaccgc catcgcctcg gcgatcgccc tgctgcctga   13740
gcgtcgcgaa atcatcacca gcgtggtcga acatccggcg acgctggcgg cctgcgagca   13800
cctggagcgc cagggctacc ggattcatcg catcgcggtg gatagcgagg gggcgctgga   13860
catggcgcag ttccgcgcgg cgctcagccc gcgcgtcgcg ttggtcagcg tgatgtgggc   13920
```

```
gaataacgaa accggggtgc ttttcccgat cggcgaaatg gcggagctgg cccatgaaca    13980
aggggcgctg tttcactgcg atgcggtgca ggtggtcggg aaaataccga tcgccgtggg    14040
ccagacccgc atcgatatgc tctcctgctc ggcgcataag ttccacgggc caaaaggcgt    14100
aggctgtctt tatctgcggc ggggaacgcg ctttcgcccg ctgctgcgcg gcggtcacca    14160
ggagtacggt cggcgagccg ggacagaaaa tatctgcgga atcgtcggca tgggcgcggc    14220
ctgcgagctg gcgaatattc atctgccggg aatgacgcat atcggccaat tgcgcaacag    14280
gctggagcat cgcctgctgg ccagcgtgcc gtcggtcatg gtgatgggcg cggccagcc    14340 gcgggtgccc ggcacggtga atctggcctt tgagtttatt gaaggtgaag ccattctgct    14400
gctgttaaac caggccggga tcgccgcctc cagcggcagc gcctgcacct caggctcgct    14460
ggaaccctcc cacgtgatgc gggcgatgaa tatcccctac accgccgccc acggcaccat    14520
ccgcttttct ctctcgcgct acacccggga gaaagagatc gattacgtcg tcgccacgct    14580
gccgccgatt atcgaccggc tgcgcgcgct gtcgccctac tggcagaacg gcaagccgcg    14640
cccggcggac gccgtattca cgccggttta cggctaaggc ggaggtggct gatggaacgc    14700
gtgctgatta acgataccac cctgcgcgac ggcgagcaga gccccggcgt cgccttcgc    14760 accagcgaaa aggtcgccat tgccgaggcg ctttacgccg caggaataac ggcgatggag    14820
gtcggcaccc cggcgatggg cgacgaggag atcgcgcgga tccagctggt gcgtcgccag    14880
ctgcccgacg cgaccctgat gacctggtgt cggatgaacg cgctggagat ccgccagagc    14940
gccgatctgg gcatcgactg ggtggatatc tcgattccgg cttcggataa gctgcggcag    15000
tacaaactgc gcgagccgct ggcggtgctg ctggagcggg tggcgatgtt tatccatctt    15060
gcgcataccc tcggcctgaa ggtatgcatc ggctgcgagg acgcctcgcg ggccagcggc    15120
cagaccctgc gcgctatcgc cgaggtcgcg cagcaatgcg ccgccgcccg cctgcgctat    15180
gccgatacgg tcggcctgct cgacccttt accaccgcgg cgcaaatctc ggccctgcgc    15240
gacgtctggt ccggcgaaat cgaaatgcat gcccataacg atctgggtat ggcgaccgcc    15300
aatacgctgg cggcggtaag cgccggggcc accagcgtga atacgacggt cctcggtctc    15360
ggcgagcggg cgggcaacgc ggcgctggaa accgtcgcgc tgggccttga acgctgcctg    15420
ggcgtggaga ccggcgtgca ttttcggcg ctgcccgcgc tctgtcagag ggtcgcggaa    15480
gccgcgcagc gcgccatcga cccgcagcag ccgctggtcg gcgagctggt gtttacccat    15540
gagtcaggtg tccacgtggc ggcgctgctg cgcgacagcg agagctacca gtccatcgcc    15600
ccttccctga tgggccgcag ctaccggctg gtgctgggca acactccgg gcgtcaggcg    15660 gtcaacggcg tttttgacca gatgggctat cacctcaacg ccgcgcagat taaccagctg    15720
ctgcccgcca tccgccgctt cgccgagaac tggaagcgca gcccgaaaga ttacgagctg    15780
gtggctatct acgacgagct gtgcggtgaa tccgctctgc gggcgagggg gtaatgatgg    15840
agtggtttta tcaaattccc ggcgtggacg aacttcgctc cgccgaatct ttttttcagt    15900
ttttcgccgt ccccctatcag cccgagctgc ttggccgctg cagcctgccg gtgctggcaa    15960
cgtttcatcg caaactccgc gcggaggtgc cgctgcaaaa ccggctcgag gataacgacc    16020
gcgcgccctg gctgctggcg cgaagactgc tcgcggagag ctatcagcaa cagtttcagg    16080
agagcggaac atgagaccga aattcacctt tagcgaagag gtccgcgtcg tacgcgcgat    16140
tcgtaacgac ggcaccgtgg cgggcttcgc gcccggcgcg ctgctggtca ggcgcggcag    16200
caccggcttt gtgcgcgact ggggcgtttt tttgcaagat cagattatct accagatcca    16260
```

```
ctttccggaa accgatcgga tcatcggctg ccgcgagcag gagctgatcc ccatcaccca   16320
gccgtggctg gccggaaatt tgcaatacag ggatagcgtg acctgccaga tggcgctcgc   16380
ggtcaacggc gatgtggtcg tgagcgccgg ccagcgggga cgcgttgagg ctaccgatcg   16440
ggganagctc ggcgacagct acaccgtcga ctttagcggc cgctggttca gggtcccggt   16500
gcaggccatc gcccttatag aggaaagaga agaatgaacc catggcaacg ttttgcccgg   16560
cagcggctgg cgcgcagccg ctggaatcgc gatccggcgg ccctgatcc ggccgatacg   16620 ccggcttttg aacaggcctg gcaacgccag tgccatatgg agcagacgat cgtcgcgcgg   16680
gtccctgaag gcgatattcc ggcggcgttg ctggagaata tcgctgcctc ccttgccatc   16740
tggctcgacg aggggattt tgcgccgccc gagcgcgctg ccatcgtgcg ccatcacgcc   16800
cggctggaac tcgccttcgc cgatatcgcc cgccaggcgc cgcagccgga tctctccacg   16860
gtacaggcat ggtatctgcg ccaccagacg cagtttatgc gcccggaaca gcgtctgacc   16920
cgccatttac tgctgacggt cgataacgac cgcgaagccg tgcaccagcg gatcctcggc   16980
ctgtatcggc aaatcaacgc ctcgcgggac gctttcgcgc cgctggccca gcgccattcc   17040
cactgcccga gcgcgctgga agagggtcgt ttaggctgga ttagccgtgg cctgctctat   17100
ccgcagctcg agaccgcgct gttttcactg gcggaaaacg cgctaagcct tcccatcgcc   17160
agcgaactgg gctggcatct tttatggtgc gaagcgattc gccccgccgc gcccatggag   17220
ccgcagcagg cgctggagag cgcgcgcgat tatctttggc agcagagcca gcagcgccat   17280
cagcgccagt ggctggaaca gatgatttcc cgtcagccgg gactgtgcgg gtagcctcgg   17340
cggctacccg ttaacgccta cagcacggtg cgtttaatct cctcaagcca gctcgccaga   17400
cgcgcttcgg tctggtcgaa ctggttatcc tgatccagca ccagcccaac aaagcggtcg   17460
ccttccagcg ccgaggacgc gctgaattca taaccctcat ttggccagct gccaatcatc   17520
tgcgcgccgc gcgcgctcag ggcgtcgaac agcgggcgca tcccgctgac gaagttgtcc   17580
ggatagcctc tctgatcgcc gaggccgaac agcgccacgg ttttccctt caggctggcg   17640 tcgtcgaggc cgctgataaa ttcgctccat gactcgcttt cgcatccggc ctccagcccc   17700
ggcagctggc cgtcgccgag cgtcggcgtg cccagcagca gcaccggata ggccataaag   17760
tcgtccagcg tcgtgcggtt aatgttgacc ggggcatccg ccagctcgcc cagttgctta   17820
tggatcattt tcgcgatttt gcgggtttta ccggtatcgg tgccaaagaa ataccaatg   17880 ttcgccatgt tgcgctcctg tcggaaaagg gggttgaaaa tacgcgttct cgcaggggta   17940
ttgcgaaggc tgtgccaggt tgctttgcac taccgcggcc catccctgcc ccaaaacgat   18000
cgcttcagcc ctctcccgcc gcgcgcggcg gggctggcgg ggcgcttaaa atgcaaaaag   18060
cgcctgcttt tccctaccg gatcaatgtt tctgcacatc acgccgataa gggcgcacgg   18120
tttgcatggt tatcaccgtt cggaaaacac cgcggcgtcc ctgtcacggt gtcggacaaa   18180
ttgtcataac tgcgacacag gagtttgcga tgacctgaa tatgatgctc gataacgccg   18240
tacccgaggc gattgccggt gcgctgactc aacaacatcc ggggctgttt tttacaatgg   18300
tcgaacaggc atcggtagcg attcccctca ccgatgcccg ggcgaatatt atctacgcca   18360
acccggcgtt ttgccgccag actggatact cgctggcgca attgtcaat caaaacccgc   18420 gcctgctggc cagcagccag acgccgcgcg agatctacca ggagatgtgg caaaccctgc   18480
tccagcgcca gccgtggcgc ggtcagctaa ttaatcagcg ccgcgacggc ggcctgtatc   18540
tggtagatat cgatatcacg ccggtgctga atccgcaggg cgagctggag cattatctgg   18600
cgatgcagcg ggatatcagc gtcagctata ccctggaaca gcggctgcgc aatcatatga   18660
```

```
cgctaatgga agcggtgctc aataacatcc ccgccgccgt ggtcgtggtc gatgagcagg   18720
atcgggtggt gatggataat ctcgcctaca aaacgttctg cgcggactgc ggcgggaaag   18780
agctgctggt cgagctccag gtttccccgc gcaaaatggg gcccggcgcg gagcaaatcc   18840
tgccggtggt ggttcgcggc gcggtccgct ggctgtcggt aacctgctgg gcgctgcccg   18900
gcgtgagtga agaagccagc cgctacttcg tcgacagcgc cccggcgcgc acgctgatgg   18960
tgatcgccga ctgtacccag cagcgccagc agcaggagca gggccggctc gaccgtctga   19020
aacagcaaat gaccgccggt aagctgctgg ccgcgattcg cgagtcgctg gacgcggcgc   19080
tgattcagct taattgccca atcaatatgc tggcggcggc ccgccggctg aacggcgaag   19140
gcagcggcaa cgtggcgctg gacgcggcgt ggcgcgaagg tgaagaggcc atggcgcgcc   19200
tgcagcgctg ccgcccttct cttgagctgg aaagcaatgc cgtctggccg cttcagccct   19260
tttttgacga cctgtacgcc ctctaccgca cccgctttga cgatcgcgcg cggctgcagg   19320
tggacatggc atcgccgcat ctggtcggct tcggccagcg tacccagctg ctggcctgct   19380
tgagtttatg gctcgaccgg acgctggccc tcgccgccga gctgccctcc gtaccgctgg   19440
agatcgagct ttacgccgaa gaggacgagg gctggctctc tttgtatctc aacgacaatg   19500
tcccgctgct gcaggtgcgc tacgcccact cccccgatgc cctaaactct cccggcaaag   19560
ggatggagct gcggctgatc caaacgctgg tcgcctacca ccgcggcgcg attgaactgg   19620
cttcgcgacc gcagggaggc accagcctgg ttctgcgttt cccgctcttt aatacccctga   19680 ccggaggtga gcaatgatcc ataaatccga ttcggacacc accgtcagac gtttcgatct   19740
ctcccagcag tttaccgcca tgcagcggat aagcgtggtc ctgagtcgcg ccaccgaagc   19800
gagcaaaacc ctgcaggagg ttctgagcgt gctacataac gatgcccttta tgcagcacgg   19860 gatgatttgc ctgtacgaca gccagcagga gatcctgagc atcgaagcgc tgcagcaaac   19920
ggaagatcag acgctgcccg gcagtacgca aattcgctac cggccggggg aaggattagt   19980
cggtaccgtg ctggcgcagg gccagtcgct ggtgctgccg cgcgtcgccg acgaccagcg   20040
ttttctcgat cgtctgagcc tgtacgacta tgacctgccg tttatcgccg ttccgctgat   20100
gggcccccac tcccggccca tcggcgtact ggcggcgcag ccgatggcgc gtcaggaaga   20160
gcggctgccc gcctgcacgc gctttctcga aaccgtcgcc aatctgatcg cccagacgat   20220
tcgcctgatg atcctgccaa cctccgccgc gcaggcgccg cagcagagcc ccagaataga   20280
gcgcccgcgc gcctgtaccc cttcgcgcgg tttcggcctg gaaaatatgg tcggtaaaag   20340
cccggcgatg cggcagatta tggatattat tcgtcaggtt tcccgctggg ataccacggt   20400
gctggtacgc ggcgagagcg gcaccgggaa agagctcatc gccaacgcca tccaccataa   20460
ttctccgcgc gccgccgcgg cgttcgtcaa atttaactgc gcggcgctgc cggacaacct   20520
gctggagagc gagctgtttg gtcatgagaa aggcgcgttt accggcgcgg tgcgccagcg   20580
gaaaggccgc tttgagctgg cggacggcgg caccttattc ctcgatgaga tcggcgaaag   20640
cagcgcctcg tttcaggcta agctactgcg tattctgcaa gagggggaga tggagcgcgt   20700
cggcggcgac gaaaccctgc gggtcaacgt gcgcattatc gcggcgacca accgccatct   20760
ggaagaggag gtgcggctgg tcatttccg cgaggatcta tactaccgcc tgaacgtaat   20820
gcctatcgcg ctgccgccgc tgcgcgagcg ccaggaggat atcgccgagc tggcgcactt   20880
tctggtgcga aaaatcgccc acagccaggg gcgaacgctg cgcatcagcg atggggcgat   20940
tcgcctgctg atggagtaca gctggccggg aaacgtgcgc gaactggaaa actgtctcga   21000
```

```
acgttcggcg gtgctgtcgg aaagcggcct gatagaccgg gacgtgattc tgttcaacca   21060
tcgcgataac ccgccgaaag cgctcgccag cagcggcccg gcggaggacg gctggctcga   21120
taacagcctc gacgagcgcc agcggctgat cgccgccctg gaaaaagcgg gctgggtgca   21180
ggccaaagcg gcgcggctgc tcggcatgac ccgcgccag gtggcgtatc gcattcagat    21240
tatggatatc accatgccgc gactgtgaag ccttatgtga gattcaggac attgtcgcca   21300
gcgcggcgga attgcgacaa ttcagggacg cgggttgccg gttaaaaagt ctacttttca   21360
tgcggttgcg aaattaacct ctggtacagc atttgcagca ggaaggtatc gcccaaccac   21420
gaaggtacga ccatgacttc ctgctcctct ttttctggcg gcaaagcctg ccgcccggcg   21480
gatgacagcg cattgacgcc gcttgtggcc gataaagctg ccgcgcaccc ctgctactct   21540
cgccatgggc atcaccgttt cgcgcggatg catctgcccg tcgcgcccgc ctgcaatttg   21600
cagtgcaact actgtaatcg caaattcgat tgcagcaacg agtcccgccc cggggtatcg   21660
tcaacgctgc tgacgcctga acaggcggtc gtgaaagtgc gtcaggtcgc gcaggcgatc   21720
ccgcagcttt cggtggtggg catcgccggg cccggcgatc cgctcgccaa tatcgcccgc   21780
acctttcgca ccctggagct gatccgcgaa cagctgccgg acctgaaatt atgcctgtcg   21840
accaacggac tgatgctgcc tgacgcggtg gaccgcctgc tggatgtcgg cgttgaccac   21900
gtcacggtca ccattaacac cctcgacgcg gagattgccg cgcaaatcta cgcctggcta   21960
tggctggacg gcgaacgcta cagcgggcgc gaagcgggag agatcctgat tgcccgtcag   22020
cttgagggcg tacgcaggct gaccgccaaa ggcgtgctgg tgaaaataaa ttcggtgctg   22080
atccccggta tcaacgatag cggcatggcc gacgtgagcc gcgcgctgcg ggccagcggc   22140
gcgtttatcc ataatattat gccgctgatc gccaggccgg agcacggcac ggtgtttggc   22200
ctcaacggca gccggagcc ggacgccgag acgctcgccg ccacccgcag ccggtgcggc    22260
gaagtgatgc cgcagatgac ccactgccac cagtgtcgcg ccgacgccat tgggatgctc   22320
ggcgaagacc gcagccagca gtttacccag cttccggcgc cagagagtct cccggcctgg   22380
ctgccgatcc tccaccagcg cgcgcagctg cacgccagca ttgcgacccg cggcgaatct   22440
gaagccgatg acgcctgcct ggtcgccgtg gcgtcaagcc gcggggacgt cattgattgt   22500
cactttggtc acgccgaccg gttctacatt tacagcctct cggccgccgg tatggtgctg   22560
gtcaacgagc gctttacgcc caaatattgt caggggcgcg atgactgcga gccgcaggat   22620
aacgcagccc ggtttgcggc gatcctcgaa ctgctggcgg acgttaaagc cgtattctgc   22680
gtgcgtatcg gccatacgcc gtggcaacag ctggaacagg aaggcattga accctgcgtt   22740
gacggcgcgt ggcggccggt ctccgaagtg ctgcccgcgt ggtggcaaca cgtcggggg    22800 agctggcctg ccgcgttgcc gcataagggg gtcgcctgat gccgccgctc gactggttgc   22860
ggcgcttatg gctgctgtac cacgcgggga aaggcagctt tccgctgcgc atggggctta   22920
gcccgcgcga ttggcaggcg ctgccggcgg cctgggcga ggtggaaacg ccgctcgacg    22980
gcgagacgct caccgtcgc cgcctgatgg cggagctcaa cgccacccgc gaagaggagc    23040
gccagcagct gggcgcctgg ctggcgggct ggatgcagca ggatgccggg ccgatggcgc   23100
agattatcgc cgaggtttcg ctggcgttta accatctctg gcaggatctt ggtctggcat   23160
cgcgcgccga attgcgcctg ctgatgagcg actgcttttcc acagctggtg gtgatgaacg   23220
aacacaatat gcgctggaaa aagttctttt atcgtcagcg ctgtttgctg caacaggggg   23280
aagttatctg ccgttcgcca agctgcgacg agtgctggga acgcagcgcc tgttttgagt   23340 agccgttttcc cgaagggggc gctgcaaaca aaaaagccgg aggtttccct ccggcttttc   23400
```

```
acatcatcaa atgtgattat gcgacgtctt cgtactgcgg caccgggttg cggaagcttt   23460
tggtcac                                                              23467

<210> SEQ ID NO 5
<211> LENGTH: 32767
<212> TYPE: DNA
<213> ORGANISM: Pseudomonas stutzeri

<400> SEQUENCE: 5
gttaggttgg cctgaattcg gtgtgtatcc cccggagatc agcttcgcct cggcacgctc     60
agcctgcact cgccccagcc tagctttccg ccgcaagtgc ggcatcgagt cgcgccacca    120
ggctgccgtc ggcttccagg ccgaggatga tgtcgcaacc gccgaccagc tcgccacgca    180
ggaacagctg cgggtaggtc ggccactgcg agatcttcgg cagcttctcg cggatatgcg    240
gtgccagtag cacgttgacc gtggcgaacg gccggccgct gttcttcaat gcctccaccg    300
cggcgcggga gaaaccgcac tccggcacgc ccggcgtgcc cttcatgtac agcagcaccg    360
gatgctcggc gagttgctgg cgtatgcgtg cttcggtatc gagaacttgc atgcgttcac    420
tccattgcca gggtgcaggg ggagttgtag gcgcaggggc tggcatgggc ccgctgtggg    480
cgatccttcc aggcctcgta gccgccgtcc aggctgtagc aattgatgaa gccgaaatcg    540
ctgaacagct gtgccatgtc acggctggca tgaccgtgct cgcaacagat gatcagatgg    600
acgtgatttg gcgtgctctt gagcagcgtg cgcaagttca gctcgctgag gcgggtggcg    660
cgcgggtcat ggccctggca gtaggcgcgg gcatcgcgca tgtccagcag catggtgttt    720
tcggtcgcca acagccgctg ggcctgctcg acgctgatgc gttggtagtc gctcattgct    780
cttctccaaa acaatcgtga taggtcgggc aggcttcaca agaggggggag cggcatacgt    840 agccgccgtc ctgttcgcat agttgtttgt agaggaactt cttccagcgc atgtcctggg    900
tattgcgccg ggccagctgc gggaagttgt gcatcagcag cgcgtacagc tgcgcccgcg    960
aggccaggcc gaggtcgcgc cacaggtgtt cgccaccgag gcaggcggca gcgacgatgg   1020
ctgccatcgc cggttcgccg tggtcgtcct ggccgcccag cagcaggtcg tgcagcgcct   1080
gccattcttc ccggcgcagc gccagcaact cttcgcgcaa ggcgtcgcgc tcgccgagca   1140
aggcctcgtc ggcgctacgg gatggtggtc gcagcccatg gcgcgtcagg agctcggcgt   1200
actgcgccgc gtcgagcccg aggtgctgcg gcaggcaact acggccttcg cgctgggcgc   1260
ggatgatctg cgctagccag gccgggttgt cgttgactgc gacctccagg cacaacgcgg   1320
cccggctcat tgcggcgtgc tcgcggcggg gctgcaaccg agcaccgagc tggtgcccag   1380
cgaacagccg ctgatgctcg gtgccagcgc tggcagccgg cctttgcacg gcagccaggc   1440
attgatgccg accaggtcga agtcgaccat gtagtgcatg ccgcagcgga tcagcgggcg   1500
gcggatcaac agcggctggg ccaccatcag ctccagtgcc tgttcggcgc tcagttcgct   1560
gacatccagc tcgccgtact tgatcgccgg ggccgacggg ttgaaccact cggccaccgg   1620
cagccggccg aagaacggcc gcaggcgttc cggcgtccag gcctcgcgca gcaggtcgcg   1680
cacttccagc tcgatgcccg ctgaacgcag cagctcctcc tgcaggcggt tggtggcgca   1740
accgggcttc tcgtagaaga tgatgcagga catggcaacc tcctcaacgg gcctggatgg   1800
cgcgcatggc ctcggccaac cgctccggcg gaatgcccgt cagcgagccg gctgggttgg   1860
ccgggctgcc gtcggcgagc aggatcgcgc cttcgatggg gcagatgctc gcgcactgtt   1920
gctcggcgta gtcgccatcg cattcggtgc acttgtgcgc gctgatgcgg aagtacgcag   1980
```

```
tgccggggct gatcgcctcg ctcgggcaga cgtccacgca ggcccagcag ttgacgcagg    2040
attcgacgat ttgcagtgcc atactccacc tcctcatgcc atcaggcatt gctccgctgc    2100
gcccaccgac gcatcgagac ggccattggc gatcatttcc tggtacacct ccagcacggc    2160
ttcctcgatg ggctccatgg cgtgctcgcc attgggctgg atgccggcgg cttccagctc    2220
gccccagggt tcgaagccga tcttcgagca gagcaccgcc tcgcagccct tgagcgcgcg    2280
gatgctgccc gacagcgcac tgtccttgtc gccgcagctg tcgttgccga cgcagtactg    2340
ctcgaccttg cggtggccga tgaagcgcac cccggccggc gaggcctcgt agacgaggaa    2400
ttcgcgggca tggccgaagt gctggttgac caggccgccg ccgctggtgg ccacggccat    2460
cagtaccggg cgatggccct tgtccactgt gccggtgagc tgcgcagcgc tggggtggc     2520
caggcgcgcc ttcttcgccg cgcgttcgtc cagctcctcc ttgatcgccg cgtggatggc    2580
ggcgcgcttg accatcgccg cctcgtagtc gacgtccatg ctctcgatct tgtcgagggt    2640
gaactcgtcg ccgcggtcct cgccgagcag gcccaccgcg tcggcgcggc actggcggca    2700
gtggcgcatc atgttcatgt cgccggcaca ggcgtcctgc aggtcctgca gttcctccgg    2760
ctccgggctg cgctggccca tcacgccata aaggtgccg tgctcggcct cggcgatcag    2820
cggcatgacg ttgtgcagga aggcgccctt ggccttgacg atgcggctga cctctttcag    2880
gtgctcatcg ttgacgccgg ggatcagcac cgagttgacc ttcaccagga tgccacgctc    2940
gaccagcatc tccaggccct tctgctgccg ttcgatgagg atcttggccg ccttgcgccc    3000
acggatgcgc ttgttgttcc agtagatcca ggggtagatc tcggcgccga tgtccgggtc    3060
cacgcagttg atggtgatgg tcacgtggtc gatgttgtgc ttggccagct cgtcgacgca    3120
gtcgggcagg gccaggccgt tggtggagac gcacagcttg atgtccggcg cctgctcgga    3180
cagcatgcga aaggtctcga aggtgcgctg cgggttggcc agcgggtcgc ccgggccggc    3240
gatgccgagc acggtcatct gcgggatggt cgccgccacc gccttgacct tcttcaccgc    3300
ttgcaccggc tccagcagct cggacaccac gcccgggcgc gattcgttgg cgcagtcgta    3360
cttgcggttg cagtagtggc actggatgtt gcaggccggc gccaccgcca catgcatgcg    3420
cgcgaagtag tggtgcgcct cctcggagta gcaggggtg ttgtgcactt tctcgcggat    3480
gtgctcgggc aggtgcgcga gctggtcatc cgagctgcca caggaacccg ctgaacaacc    3540
gcccccggcg gttggcccgg cctcgctctg gcccagtacg ttcagttcca tgttcggtct    3600
ccgaatagag gtctgtcccc ggtacctgca gcaaggcttg tgcctgtttt caaatcattg    3660
tttcagaacg aatttttcag aaagcgggcg gaattcgttg tttcgcaacg aacaaagtgg    3720
cggggccggg cggggcggct gtcgcaaagg cgacaagctg cgcacgcccg gttcccgggc    3780
tgtcgcgacc cggtgctcca gacgattgcg catggcgggc cgcgatccgc accagcgccc    3840
cggcccgctg gtgccgggct actcctcgag gcgcccgctg gcgtcgcgat cgcgcacgta    3900
atggtgggtg agcggaaacg ccggcagcca ggactcgcgg cggacggtcc agagctcgta    3960
ggtgggcatc agctggtcgg gggcatccag ggctcccagg ctcacttcga tttcgtccgc    4020
ggtgcgtgcc ctgctagtga tgcgtagtgg gcacaaggct tcgcgggaag cgccatgcat    4080
ggggaacgct gcgccgcccg acccgggagt cgggcgggtc gttcagatct tgcgcatatg    4140
aatgttcagc gtctgcactc ggtaggcgat ctgccggggc gtcatgccga gcaggcgggc    4200
ggccttggcc tggacccagc cggcctgttc cagcgcggcg atgacgcgct cgcggtcgtc    4260
gaggctgtcg tcgcgaggt cgacttcggg gaccggcgcc agcggcgtgg cgtcgtggtc    4320
gaggccggtg agggagacca cgtcgcggct gatggtgcca tcctcgctca tgatggccga    4380
```

```
gcgttccagg cagttttcca gttcgcgcac gttgcccggc cagcggtggc tcatcagcag    4440
acgcagggcg ctgtcggtca gcttgagttt gcgaccctgc tggcgggcga tcttgtcgag    4500
gaggaattcg ccagttccg ggatgtcggc gctgcgctcg cgcagcggcg ggacgcggat    4560
ggccatgacg ttgaggcggt agtagaggtc ttcgcggaac ttgccttgct ccacctcgtg    4620
ctccaggtcg cggttggtgg cggcgacgat gcgcacgttg accttcaccg tctggctgcc    4680
gccgacgcgc tccagctcgc cttcctgcag cacgcgcagc agcttggcct ggaacatcgg    4740
cgagatctcg ccgatctcgt cgaggaacag ggtgccgccg tcggcctgtt cgaaacgtcc    4800
cttgcgctgc ttcacggcgc cggtgaaggc gcctttctcg tgaccgaaca gttccgattc    4860
gagcagggtt tccggtagcg cggcgcagtt caggcgtacc agcggctggt gagcgcgcgg    4920
tgagttgtag tggatggcgc tggcgatcag ctccttgccg gtgccggatt cgccgaggat    4980
cagcacggtg ctgttccact ggcgacccg tcgaacctgg tcgaaaaccc ggcgcatgga    5040
ggcggtgtgg cccaccacca tgttctcgaa gccgtacttg gcgcggactt cgcggcgtag    5100
ctcgtcgcgc tcgtcgacca cttcctggcc gtcctcgagg ttcaccacca ggcgcacggt    5160
ctgcgccagt aggcgggcga cgatttccat caaacgggtg cgttcgggca tcagctcgtc    5220
ggcgcggcgg tcgggctggg cagccagcac gccgatggtg gtgccgtcga cggccttgat    5280
cggcacggga atgaagggca ggtccatgtc gtacagcgcc agtcggtcga aaagcgcgg    5340 ttcggcgtcg atacgcccga gcaccacgct gttgccatgc ttgaggatgt tgccgaacac    5400
gccttcgccg atgcggtagc gggtgctttc gcaggcccgt accacggttt cggagtcgct    5460
gtgcacggcg cccacctgca ggctgccgtc cttcggttg cagatggaga ccagcccgtg    5520
cagcaggcca aggtcttcgt gcagcacggc gaggatctcg ccagcagtt cctcgatggg    5580 ccggccgcgg ttaaggatgc gggcgatctg cgccagcgcc tgcagttggg catccagcag    5640
ttcgttgcgg gttggcgcgc tggggcgttc ggcgaatgtg gcgttcatgc gagcttcccc    5700
tgtcagctgg ccgagaaggg cagttcgacg acgatcctgc agccctggtc gtagccgcta    5760
tcgatatgca ccgtgccggc atgctcggta acggtttcct gcaccatggc caggcccatg    5820
ccgcgaccgg tcttgtgcgg cggcttggtg ctgaagaagg gttcgaatac cttgagcgcc    5880
agctccggcg cgatgcccgg gccgctgtcg gcgatctcca ggcgcaccac ccgctggccc    5940
tggacacggg tgacgatcga cagcgtgcgc gggttgtcct ggttctggct catggcctcg    6000
atggcgtttt ccagcagctg cttgatcatg ctgcgcagcc ggccttcggc gcccatcacc    6060
cagggtaggc gcacgccgg ctgccagtcg acgacgatgc cctgggcgag caactggtcg    6120
gtcatcaggc tgaccacttc gcggatcagc tggttgatgt tgaccggcac gcagccgccg    6180
gcccggcgct gcggaatcga gccgctgagg ctttccagcg catccatgcc agcctggctg    6240
gcttcgcgca tggcgctgag caccggatcg ccctcggcgc tgtcgcccag gcgtcgttcg    6300
agcatgcgca gcgccgcact gatcaggttg accgggccct gcaggcggtg gatgcgccg    6360 ttgaaggttt cgcgcatgcc gtcgagcagc tcttcctcgg ccatcagcac cttcagggcg    6420
ttgagctggg aggcctgctg ttgctggcgc agcccggtga tgtcgttgac cgtcagcagc    6480
aggtagtttt cctcgcccgg gtcgaagaag tcgtcggcgc gttcgccttc gatgaggatg    6540
gcgcggccat ggcaggacag ccagcgcggt gtgtggccgc cgaggtcgaa ggtgacttcc    6600
ttgccggtga aggcctggcc atgcgccttc agcgcctcga tggcgccgcc gaggttgtcc    6660
tgcagcaggc tcaccagttg cgcgggcgtg gcctggtcgc cgagttccgc ggccaggcgg    6720
```

```
ttgaagctgg ggttggacag gcggatgcgc agggcgtgat cgagcaccac gatggccgcc      6780
ggtgcgctgt cgaccaccgc ctcgatgatc agccgctggt tgctgacgcg ctgttcgagc      6840
ttgtgctggt cgctgctgtc gcggtgcatg cccaggtaat ggatggtccg ctcgtgctcg      6900
tcgagcaccg gcgccaccgt cagctcggcg aggtagcagc tgtcgtcctt gcgccggttg      6960
accagcatgc cggaccaggc cttttctgc gccaggcggc tccagagcgc ctggtagacc       7020
agccgcgggg tggtgccgtt ggacagcacc gattcgttct tgccgatcac ctcgctgctg      7080
tcgtagccgg tgatggcgct gaaggcgcgg ttggcataga ggatgttggc cttcagatcg      7140
gtgatggaaa tggcgatcgg cgcgtgctcc acggcttgct ggaacacttc gggcgccaat      7200
ccatcggacg cagcgggttg ccccgcgtcg cgctcggggg tggcctgggt catgtgcatg      7260
tcctcatcga tgcggcgaag ccgacgtctg tgcgccggta ccgttgcaa agccatacgg       7320 ttaggggct gttgccgttc gcgagctgcg aatgaaacgg caacagaccc cttagggttt       7380
tgcaaaccgc gtgccgtcgg tcacattcct tgccgacagc cctgcggagc cgtaaatacg      7440
ctgtgcagat ggatttctgc cccgacaggt gccgctgggc tgttgcaaaa cccacaggga     7500
ggcgcgcgca cttctcccgg cctgtcgcaa accccacaaa gtccgtcgcg ccagcgtcgc      7560
caggggttgc gctatcacgg gattcgttga tctgcatcaa cgaatcccgg gctctcgggg     7620
cgctccggga cgcccggcgg ggcgtggcat gcttgatgca aaaccccta caacaaggcc      7680 tttgcccgac aacggtgcaa cgctgccaa taggctggga ggggttatgg aatatgcgct     7740
gtttctgatc ggcaccgtgc tggtcaacaa cgtggtgctg gtctacttcc tcggcctgtg     7800
tccgttcatg ggggtctccg gcaagctcga cccctcgctg gcatgggct tggcgacgac      7860 cctggtgatg accctgggcg gcgtcagcag ctggctgcta gaacgctacg tgctgcagcc     7920
gctgggcatc ggcttttttgc gcatcctctc ctacatcctg gtgatcgccg gcctggtgca    7980
gctgatcgag atgatcatcc gcagggttag cccgccgctg tatcgctcgc tgggcatcta    8040
cctgccgctg atcaccacca actgcgccgt gctgggcgtg ccgctgatca gcgtgcgcga     8100
aggccacagg ctggccgagg cggggctgtt cggcctgggc tcggcgctgg gcttcaccct    8160
ggtcatggtg atcttcgccg gcttgcgcga gcgcctggcg ctggccagcg tgccggcggc    8220
cttcgccggc gcaccgatcg cttttcgtcac cgccgggttg ctggcgatgg ctttcatggg    8280
cttcgccggc ctgatctgaa acgcacgccg ccggcgaggc tggcgaagga ggagcaatgc    8340
tggacgcaat tctggttctt gcactgatgg gcctgctgct cggcggcggc ctcggtctgg    8400
cggcgcgcta tctggcggtt tcgcaggaga accgctgat caaggaaatc gaggcgctgc      8460
tgcccggcag ccagtgcggg caatgcggct atccgggttg cagtgcggcg ccgacgcct    8520 tggtcgaggg cagcgccgcg gtcacctgct gcccgcccgg cggggccgcg ctggccgagc    8580
gcctggccga actgctcggc gtgccgctgg acgccagtgc gctcgccgcg cccatgctgg     8640
cgcgcatcga cgccgccgag tgcaccggct gcacgcgttg cttccgcgcc tgcccgaccg     8700
acgccatcgt cggcgccaac gggcagatcc attcgtgtt gagcaatgcc tgcattggct     8760
gcagcaaatg cctggaggcc tgcccggagg actgcatcgc cctcgcgccc cagacactga    8820
cgctggacca ctgcgctgg gccaaaccca gggccgcctg atttcgcctg atgaacaggg    8880
gcgtcagacc ccgggagtcg acaatgttca acctcgcgca ttttcgcggc ggcatccatc    8940
ccgccgccca aaggaccgc tcggccgccc tcggcatcgc cgtgcagccg ctgccgccgc     9000
gcctgtacct gccgtttcgc cagcatgccg gggccgaggc cttgccgctg gtgaaggcgg     9060
gcgagcgggt gctcaagggc cagctgctgg ccggctcgcc cactgagctc tcggcgccga    9120
```

```
tccatgcgcc gagttccggg cgcatcctct cgatcgggcc gatcgacgcg ccgcatccgt   9180
cggggctgca ggtcaacggt gtggtcctcg aatgcgatgg cgaggagcgc tggatcgagc   9240
tagacgtacc ggccgacccc ttcgccgagg acccgcagcg gctcgcccag cgcgtcgccg   9300
atgccggcgt ggtcgggctc ggcggggcga tcttcccggc cgcggtgaag ctcaagcagg   9360
gcgcccggca cgagatcaag accgtgctgg tcaacggcag cgagtgcgag ccgtacctga   9420
gctgcgacga ccggctgatg cgcgagcgcg ccgaggcggt ggtcgatggc gcgcggctga   9480
tccagcacat cctgcgtgcc tacagcatcg tcatcgccat cgaggacaac aagccggcgg   9540
cgctggcggc catgcgtgct cgagcgagc cctacgcgc catcgaggtg gtggcggtgc   9600
cggcgctcta cccgatgggc tcggccaagc agctgatccg ccaggtcacc ggccgcgagg   9660
tgccggccgg cgggcgcagt accgacgtcg gcgtgctggt acacaacgcc ggcacggtgt   9720
atgcgatcca gcaggcgctg cgccacggcc gcccgttgat ctcgcgggtg gtgacggtgg   9780
ctggtggttg cgtgagcaac ccgcgcaaca tcgagactct gatcggcacc ccggtgcagg   9840
cgctgttcga aagctgcggc ggactgctgc gcgagccgca gcaactgctg ctcggcgggc   9900
cgatgatggg catgctgctg ccatccacgg cggtgccggt gatcaagggc gccaccgggc   9960
tgctggcgct cgaccacggc gaagtgccgc gcagcgacag cgcgccgtgc atccgctgcg  10020
cgcgctgcgt cgacgcctgt ccgatgggcc tggctccgct ggagatggcc gcgcgcaccc  10080
gcgtcgacga tttcgacggc gccagcgaat acggcctgcg cgactgcatc ctctgtggct  10140
gctgcgccta tgtctgcccc tcgcacattc ccttggtgca gtacttccag tacgccgtcg  10200
gccagcagga cgagcgccgc agcgccgcgc gcaagaacga ttacgtcaag cagcttgccg  10260
aggcacgggc ggcgcgcttg gccgaggagg aagcggccaa ggcggcggcc aaggcggcga  10320
agaaacgcaa ggcggcggcg ccggccgcca gcgaggtatc gccatgagcg cgcagggtat  10380
cgcggcgggg ccgttcgccc atgatcgctc tcggtcgac cgcatcatgc tgcacgtctg  10440
cctggcgttg ctgccgacga cggcctgggg cctgtatctg ttcggctggc cggcgatcta  10500
cctgtggctg ctgacctgcg ccagcgcggt ggcctgcgag gccgcctgcc tgtacctgct  10560
cggccggccg ctgcgccgcc tgctggacgg cagcgcactg ctcagcggct ggctgttggc  10620
actgacgctg ccgccctggg cgccctggtg gatcgccgtc ggtggcagca tgttcgccat  10680
cggcattggc aagcagctgt acggcggcgt cgggcagaac gtgttcaacc cggcgatgct  10740
ggcgcgggtg gcgctgctga tcgccttccc gctgcagatg accacctggg ccctgccttt  10800
gccgctgggt acgagggcg cgcccggctg gctcgaaggc ctgcgcatca ccttcgccgg  10860
tggggcgctg gccgatggcc tgagcggcgc caccgcgctg gccacctgc agaccgagct  10920
gaccctgggg cacagtgccg cgcagatcct cgacgggcat ttcgcgttgc tgccggcctt  10980
tctcggctac agcggcggca gcctcggcga gacctcggag ctgctgatcc tgctcggcgg  11040
gctctgctg ctggcactgc gcatcatcca ctgggagatc ccgctgggca tgctgctgac  11100
ggtgggcgcg ctggcggcgc tggcgaacca gatcgacccg caggtacatg gcggcgggct  11160
gttccacctg acctcggcg gcttgctgct cggcgcgttg ttcatcgcca ccgatccggt  11220
gacctcgccg atcagccgca gtggccggct gatcttcgcc atcggttgcg gcgcgctggt  11280
cttcgtcatt cgcagctggg gcaatttccc cgaagccgtg gcgttcgccg tgttgctcat  11340
gaacgccctg gtgccgctga tcgaccgcgt ctgccggccg cgtgcctatg ccgcaacgc  11400
gcgcggcaag ccgctggtgg cggcgaagtg gaccgcagaa gtgaaggagg tcgacaaggt  11460
```

```
atgaacgagc tgacccagac gccgcccgtg gcagacggca cgaaccgcc gctcacccga    11520 cccggcctgg tcgagacctg gcgcgagcgg gtttcctacc aggcgctgtc gctgggcttg    11580
gtctgcgccc tggtggccgt ggcgctgctg ctcggcaacc agctgaccca ccagcggatt    11640
gtcgacgccg agcggcagga ccgcctcgcc gtgctgcgcc aggtgctgcc gcaggcgctc    11700
tacgacaacg atccgctggc cgatgccttc aacgtcgagg atgccgagct gggcctgatc    11760
gaggtgtacc cggcgcggcg cgcggggcaa ctgacggcca ccgccttcca gatcagcacc    11820
gtcggctacg gcggcccgat cgtccagttc atcgccctcg acagcgaagg ccgcatcctc    11880
ggcgtgcggg tgctcagcca caaggaaacc cctggcctgg cggacaagat cgaagtcacc    11940
cgcagcgact ggatcaaggc cttcgacggc ctgtcgctgg ccagcacacc gctggatcag    12000
tgggcggtga agaaggacgg tggccagttc gaccagttcg ccggcgccac catcaccccg    12060
cgggccatcg tcaagggcgt gctccgggcg ctcgagttcc aggcccgcca gtccaccgcc    12120
cagtccaacc aggagactcg gccatgagca gccaatgcgg atcagcggat gtcacggcgc    12180
ccaagcccaa ggggctgttc aactacttca gctcggcgct gtgggactac aacgtcgccc    12240
tggtgcagat gctcgcgttg tgcccggcgc tggcggtgac caccaccgct accaacggcc    12300
tgggcatggg cctggccacc accctggtgc tgatgatcac caatgcgatc atttccgcgc    12360
tgcgccacag catttcgccg gcggtgcgca accgctgat gatcggcatc atcgccggcg    12420
tggtgaccct catcgacatg gcgatcaatg cctggatgca cgaactgtac aaggtgctgg    12480
ggctgttcat cgccttgatc gtgaccaact gcgcggtact cggccgtgcc gaatcgttct    12540
gcagccgcaa cccggtgctg ccctcgatcc tcgacggcgc cggcatgggc atcggcttca    12600
cctgggtact ggtggtgatc ggcgggatac gcgagatcct cggcagcggc acgttgttcg    12660
cccaggcctc gctgctgctc ggtgagcact tccgctggct ggagatcacc gtcctgcccg    12720
gcttccaggg catcctgctg gcgatcctgc cgcccggggc gttcattgtt ctgggcttcg    12780
tgctggcgtt caagcgagta gttgatcgcc ggcgcgccga gcgacggatc aggacccatg    12840
gcgaactggt agtgttgcag tgagcccggc cgaggagcga agcagacgat gaagatttcc    12900
gttgtatacg ccgcaccccg gcagcccctg ctgttcgatt gccgggtggc ggaaggctcc    12960
agcgtggccg aggccatcga gcactccggg gtgctgcgct actgcccgga catcgacctg    13020
agcaagcaaa aggtcggggt ctacggcaag ttcgtcaaac tcgacagccc gctgaaggag    13080
ggcgatcggg tggaaatcta ccaacgcatc acgcgcgtgc tggatgaaga cgacgatgac    13140
gacgactgac agccgccgcg gatgaccata gccgagagag gagcgaccga tgaacagcca    13200
gcccccgagc atgaaccgtg aaaccgcatt acgcatcgca ctggccgccc gggcattgcc    13260
cgaggtgggc gtcggccggt tgctggatat cctgcaccag cggatcgatg gagaactgaa    13320
cgaagagagc ctgcagcgcg tgaccgtcac cgacctcaag acggcgttcg ccagcgccga    13380
cggcgaggag gatggcgagg acatcggcat cggcctgccg gcgctgaagg aagcggtgcg    13440
catcctctgg ggcgaaggcg tcggcgacga cctgccgcag ccggaggtcc tggaccgcgt    13500
gccggaaggc tcgatccggg tggccatcgc ctccaacaac ggcgagcgcc tggacggcca    13560
tttcggctcg tgcctgcgtt ttctgatcta ccagatcggc ctcgacagcc tggcgctggt    13620
ggacgtgcgc tcggcgctgg agaccgagtt cgccgaggat cgcaatggcg cgcgtgccga    13680
gctgatcggc gactgccagg tgctctatgt ggtctccatc ggcggtccgg cggcggcaa    13740 ggtggtcaag accggcctgt acccgatcaa gaaggccggt ggcgaggccc ggcagattct    13800
cgccgacctg cagaccgtca tggccggcaa cccgccgccg tggctggcca agctgctggg    13860
```

```
cgtgagcgcc gagcagcgag tgcgcttcga ccgctccgac gacgaggcgg cctgggcatg   13920
agcgatgtgc gcaggctggt cgccgtggcc atcgaccgcc agggcaaggt cgccggtcac   13980
gccggtcggg cgcaccactg gcaggtgtac gacatctggc ccggcgaggc gccggaatcc   14040
gtctatcgcc tggcgctgga cgaacaggcc tgcctgcacg agtggcatgt cagcgcgcaa   14100
ccggaacgcc atccgctgca cgccgtggac gtggcgatcg ccgccagcgc cggcgacggc   14160
gtggtgcgtc gcctgggcga gcgcggccgtg acgctgttga ccaccgccga gagcgacccg   14220
gaacatgccg ttaaagcctg gctcgccggc agcctgccgc caggcttgcc gcacgaggag   14280
ccgggctgcg gcggcgaggg gcaccggcat ccctgagcgt gcggggatgg gacggatggc   14340
aaccccaggc tgggtcgagc cgcgcagcgg cgaagcccaa cgtcgtgcgg gctcaagccc   14400
gtgcaaccgg cattgttcgt gagaacacca tgggcgatg tggcgcctga tgatccgcga   14460
tgttgggctt cgcttcgctc aacccaacct acggcaccgg ggcgataggc aaaaaaactc   14520
ccctgggagc gcaggggagt ggctcatcgc caatatgggg atgtcaaacc gttgcacgtg   14580
acccgggctg cgcccgggct ctgcgagccc agggcaacct agggtggaat cgagccccat   14640
gctggccaag cccaatacgc ccctgggtgg ttcagatcgg cccgcgcgcc tcgcgacgat   14700
gggcgacggt gcagccaagg gcggcctcgt agctcagcgt ctccagcttc ggccggtagt   14760
cgcgcagcgc ggcgtagacg tgagtacct tgtcctcggc gctctggccc ttgaagtctt   14820
ccttgtccag gcgcaggtcg tcggccaggg tgttccacac cgcgccttcc tcgtgcgcct   14880
gcagctgcag ggtcatgccg tcgagctcgg tgtacagcga ctggccgagg ttctccacgt   14940
agaagatcac cggtgcgccg tcggccaggt cgcggcgata gcgttcgagg aacagcggca   15000
ggtgggccca ttcgatcagg gcgccggcca tcatcgccag tttcccctgc tgctcgagca   15060
tgaccgcctg cttgaccacg gcggtcggcg gcaggcggcg gccggaggcg tcggcgatct   15120
cgccttcttc gagcaccagg tcgccgcgga aggcgtaggt gtccggcgtc gtggtcgcgc   15180
cattgacgct gacgttgcac agcaggtttt gcgtttcgta ggttttcaac agcatggtca   15240
tggtctctcg tggaaaaaat ggtcaggcga cttgtggggc gccctgggtc aggccaagca   15300
ggtcgtgcca atcggtctcg accagttcca gttgcttgcg caggcagacc ctgcggtcct   15360
ttgcgctggg cgaggggatc agcgcccagc cggcgggcgc ggctgcatcg tggatcaggt   15420
cgctcatcag catgcgctcg gtgtcgcggt tgaactgcat gccgaggaac aggtagcggc   15480
attccttgcg ctgcagcttg agccagccgg gaatggcgaa accgcccatc agttcggtga   15540
tgtagtcgac gaagtcggcg tcgctggcga cgtaggaagg gctcggcagc ggcgtgccca   15600
gcggcttgaa cagcaccggt agcgcgggat tgacctcgct ctggtcgatg cgctggtagc   15660
ggcctgcgtc gaagcgatag atgtcgaagc ggtaggggct ggcggcgatg cgcgcggcgc   15720
cgaccaccag ggtatgcgga cggtcggcat agcagcgctg cagctgggtg tcgcgattgc   15780
aatcgatgac gtagggcagg ttcagcccgg ccagccagcg gtgcagcggc gcgggcgtcc   15840
agttgtcgcc gccgtaggtc tgagtcagga agcgctcgat gaagctgcgg cccttcttgt   15900
tctccaggtg catggcggca cgcgggaatt cgtacatcag ccgcggcgcc atcggctgcc   15960
cgccgttcat ggcgaggatc aggctttcat tgtcggccgg catcggctga cctgtgtcgc   16020
ggtcgaccac gccgcccagc acaccggggc ccagataggg caccagttca tgggcggcga   16080
ggcggtcggc gatttcctgc aaaggatcgt tcacggcaaa tctcctgcgg ccagtggatt   16140
taccgatagc cgatcgcaat aaccgagcca gccgggagcg tgcatgcaac cccttgatat   16200
```

```
atgggcttt gaatgcggcg atagttgccg ttcaggtgtt ttcgaaagta tcgaacgcga    16260
caattgtcat gttcgcaaca gttgccgaaa gtgtggaaaa ccggcgcttg cccggccga    16320 tcttttgtc gccattgcaa cagtcaggcc tgtcggttgt taactatcga accgccgaag    16380
gatgttgcta gtaattaaat tattctaatt aaaacaagtg cttagattat tttagaaacg    16440
ctggcacaaa ggctgctatt gccctgttgc gcaggcttgt tcgtgcctat agcccacgtc    16500
aagtggtaac gaaacctgag gaacttaatt atggcaatgc gtcaatgcgc tatttacggg    16560
aagggtggaa tcggcaaatc caccacgacc cagaacctcg tggcggccct ggccgaactc    16620
ggcaagaagg tcatgatcgt cggctgcgac cccaaggccg actccactcg cctgatcctg    16680
cactccaagg cgcagaacac catcatggaa atggccgccg aggccggtac cgtggaagac    16740
ctggaactcg aggacgtgct caagaccggc tacggcgaca tcaagtgcgt cgagtcgggc    16800
ggtccggagc cgggcgtggg ctgcgccggt cgcggcgtga tcaccgcgat caacttcctc    16860
gaagaggaag cgcctacga ggatgacctg gacttcgtct tctacgacgt gctcggcgac    16920
gtggtctgtg gcggcttcgc catgcccatc cgcgagaaca aggcccagga gatctacgtg    16980
gtctgctccg gcgagatgat ggcgatgtat gccgccaaca acatctgcaa gggcatcgtg    17040
aagtacgcca actccggcag cgtgcggctc ggcgggctga tctgcaacag ccgcaacacc    17100
gaccgcgagg acgagctgat catggcccctg gccgacaagc tgggctcgca gatgatccac    17160
ttcgtcccgc gcgacaacgt cgtgcagcgc gccgaaatcc gccgcatgac cgtcatcgag    17220
tacgaccccg ccgccaagca ggccgacgaa taccggaccc tggcgaagaa gatcgtcgag    17280
aacaagaaac tggtcatccc cacccccgatc agcatggacg agctggaagc cttgcttatg    17340
gagttcggga tcatggacga ggaagacatg accatcgtcg gcaagaccgc cgccgaggaa    17400
gtcgttgcct gatcgcttca gcagaacggg gcagggcgga tgggcccctgc cggggtgtcg    17460 caccgtgcct ggcacggtgc ggtgcgcccg tgacccgcac atgaacgcaa gaggaggtca    17520
atcatgaccg gtatgtcccg cgaagaggtg gaatccctca tccaggaagt cctggaagtc    17580
tatccggaga aggcccgcaa ggaccgcgcc aagcacttgt cgcccaacga cccggcgctt    17640
gagcaatcga agaaatgcat cacttccaac aagaaatccc agccgggtct gatgaccatc    17700
cggggctgcg cctacgccgg ctcgaagggt gtggtctggg ggccgatcaa ggacatgatc    17760
cacatttccc acgggccggt gggctgtggc cagtactcgc gcgccgggcg cgcaactac    17820 tacatcggta ccaccggggt gaacgccttt gtgaccatga acttcacctc ggatttccag    17880
gagaaggaca tcgtcttcgg cggcgacaag aagctggcca agctgatcga cgagatcgag    17940
acgctgttcc cgctgaacaa gggcatctcc gtgcagtccg aatgccccat cggcctgatc    18000
ggcgacgaca ttgaggcggt cgccaagaag aaggccgccg agcacgaaac caccgtggta    18060
ccggtgcgct gcgaaggttt ccgcggggtg tcgcagtccc tcggccacca catagccaac    18120
gacgccatcc gcgactgggt gctggacaag cgcgacgatg acaccagctt cgagaccacg    18180
ccctacgacg tttccatcat cggtgactac aacatcggcg gcgatgcctg gtcctcgcgc    18240
atcctgctcg aggaaatggg cctgcgcgtg gtcgcgcagt ggtccggcga cggcacgatt    18300
tccgagatgg aactgacgcc caaggtcaag ctcaacctgg tgcactgcta ccgctcgatg    18360
aactacatct cgcggcacat ggaagagaag tacggcattc cgtggatgga gtacaacttc    18420
ttcggcccaa ccaagaccgc cgagtcgctg cgggccatcg ccgagcattt cgacgacagc    18480
atcaaggcca agtgcgagca agtgatcgcc aagtaccagt cggagtggga ggcggtgatc    18540
gccaagtatc gcccgcgcct ggaaggcaag cgcgtgatgc tctacgtcgg cggcctgcgt    18600
```

```
ccgcgccacg tgatcggcgc ctacgaggac ctgggcatgg aagtggtcgg caccggctac    18660
gagttcggcc acaacgacga ctacgaccgc accctcaagg aaatgggcaa cgccacgctg    18720
ctctacgacg acgtcaccgg ctacgagttc gaggagttcg tcaagcgcat caagcccgac    18780
ctgatcggct ccggcatcaa ggaaaaatac atcttccaga agatgggcat tccgttccgc    18840
cagatgcact cctgggatta ttccggcccg taccacggct ttgacggctt cgccatcttc    18900
gcccgtgaca tggacatgac cctgaacaac cgtgctgga agaagctgca ggcgccctgg     18960
cagaaggccg aggaatcggc cgagaaggtc gccgccagcg cctgatggtc cgcagtcgta    19020
cgcaacgtcc gcggcggccg cgcaggccg gtcgctgccg acatccgtga tcgccgttca    19080
cagatgagtg aggcgaagga gagagtcatg agccagcaag tcgataacat caaacccagc    19140
tatccgctgt ccgcgacga agactacaag gacatgcttg ccaagaagcg cgatgccttc    19200
gaggagaagc atccgcagga caagatcgac gaagtcttcc agtggaccac cacccaggaa    19260
taccaggagc tcaacttcca gcgcgaagcc ctgaccgtga acccggccaa ggcctgccag    19320
ccgctgggct cggtgctctg cgccctgggc tttgagaaga ccatgcccta cgtgcatggc    19380
tcgcagggtt gcgtcgccta cttccgtacc tacttcaacc ggcatttcaa ggaacccatc    19440
tcctgcgtgt cggactccat gactgaagat gcggcggtgt cggcggcca gcagaacatg     19500 aaggacggcc tggccaactg caaggccacc tacaagccgg acatgatcgc cgtgtccacc    19560
acctgcatgg ccgaggtcat cggcgacgac ctcaacgcct tcatcaacaa ctcgaagaag    19620
gagggcttca tccccgagga ctacccggtc ccctatgccc acaccccgag cttcgtcggc    19680
agccacgtca ccggctggga caacatgttc gagggcatcg cccgctactt caccctcaat    19740
cacatggacg acaaggtggt cggtagcaac cacaagatca acgtcgttcc cggcttcgag    19800
acctacctgg gcaacttccg cgtgatcaag cgcatgctca aggaaatgga cgtcggctac    19860
agcctgctct ccgacccgga agaagtgctc gataccccgg ccgacggcca gttccgcatg    19920
tactccggcg gcaccaccca ggacgagatc aaggatgcgc ccaacgccct gaacaccctg    19980
ctgctgcaac cctggcagtt ggaaaagacc aagaagttcg tcgaaggcac ctggaagcac    20040
gagacgccca agctgagcat ccccatgggc ctggactgga ccgacgagtt cctgatgaag    20100
gtcagcgaga tcaccggcca gccgatccct gaaagcctgg ccaaggagcg cggccgcctg    20160
gtcgacatga tgaccgactc gcacacctgg ctgcacggca gcgcttcgc gctctggggc     20220 gatccggact tcgtcatggg catggccaag ttcctcctgg agctgggcgc cgagccggtg    20280
cacatcctcg cccacaacgg caacaagcgc tggaagaagg ccatggacgc gatcctggag    20340
tcctcgccct acggcaagaa ctgcaccgtg tacatcggca aggatctctg gcacatgcgc    20400
tcgctggtgt tcaccgacaa gccggacttc atgatcggca atagctacgg caagttcatc    20460
cagcgcgaca cgctgcacaa gggcaaggaa ttcgaggtgc gcctgatccg tctcggcttc    20520
ccgatcttcg accgccacca cctgcatcgc cagaccaccc tgggctacga aggcgccatg    20580
cagatgctga ccacccctcgt caatgccgtg ctcgagcgcc tcgacgacga acccgcggc    20640 atgcagagca ccgactacaa ctacgacctg gttcgttgac cgctagcggg gagggcgacc    20700
tccccatcct ggccggccga cgcaccgcaa tggtcgtcgg ccggccagcc ctattttcag    20760
gaagcctccc atgcccagtg tcatgatcag ccgtaacaag aatggccagc tgaccttcta    20820
catcgccaag aaggaccagg aagaaatcgt cgtcagcctg aacacgaca gccccgagcg    20880 ctggggcggc gaagtcgccc tggccgatgg ctccagctac tacctcgaac ccctctcggc    20940
```

```
accgccgaaa ctgccgatca ccctgcgcgc caaacgggcc ggcgagggct gaacgatggc   21000
gcccagcaac ggacgggctc cgctgccggc tcacctggcc ctgcgcatcg ccctggcggc   21060
gcgcgagctg aacggcgtgg ataccgggca actgctgcgc accctgctca gcgtcaccgg   21120
cgagccgatc accgaagcgc ggctggccag gctgcgccta aaccgcctgc gcaaccgcct   21180
gctgagcagc gtcgacgggc caccgccggt gctcagcgag cggcaattgc agcgtgcgct   21240
cggcctgctc aaggggcgtg gcgtgcgaat gcccgaggaa ccgttgccgg ccatcgagcc   21300
ctatcgcgaa ggcgagttgc cggattcgat ccgcatcgcc tgcacctccg acggcggcga   21360
gcgcctggac ggcagcttcg gcagctgcgc gcgctttctc gtctaccaga tctcgccgag   21420
cgccagccgc ctgatcgacc tgcgcgagcc ggggccggcc gcgccccacg aggatcgcca   21480
tgcccgccgc gccgaactgc tgcacgactg ccagctgctc tacaccctga gcatcggcgg   21540
gccggcggcg gccaaggtga ttcgcgtcgg cacccacccg gtcaaggtca tgcggccgat   21600
cccggcccgc gagatcgtcg aggaactgca acaggtactg gccagtgcgc cgccgccctg   21660
gctggccaag gctatgggca gcgagccggc accccgcgtt tccatgtctg aaaaagagga   21720 cacccccatga tcagtcagac ccagctcgac gcggtcatcc gccaggccga gaacggcccg   21780
ctgaacgagg cgctgctcgc caggctgcgc agcgagcacc tggtatcca cttcacctgt   21840 tgcatggacg acgacgtggt ggtcaacgcc aagccggttg ccgagcggcc ggggttcaac   21900
gtctatctgg tcaactccag ccagcactgc tcggtgctga gcaacgacct ggacgccgcc   21960
tcgggcatcg tcctggccga agtcatcgcc gattagagag cgcccatgca gaacgacggt   22020
agcgaggaca ttatccccct ggcggactgc cgcgattgca gctttcgcgg cgacctgctg   22080
cccagcggcc gctgcacgcc gggcgaccgc tgcgtagcga tccacagcgg ccggcagatc   22140
gaccgtttct tccggcagaa tccgcagctg gccgtacact acctggccga tccgttctgg   22200
gagcggcgcg ccatcgccgt gcgctacgcc ccggtggagg cgctgctgtc gatgatccac   22260
gacgtcgacg aggcggtgcg tcgtgccgtc gcctaccgcc tgccgcgcga gcgcctgggc   22320
gaactcatgc gcgacccgga tcgggaagta cgcatcaccg tcgccgaccg cctgccggcc   22380
gagcagctga acggatggc tgccgacccg gattacctag tgcgcgccta cgtggtccag   22440
cgcatcgccc cagggcggct gttccgcttc atccgcgacg aggaccgcca ggtgcgcaag   22500
ttcgtcgccc agcgtctgcc tgaggaaagc ctcggactga tggtcaccga ccccgaaccg   22560
gaagtccgcc gcctggttgc cgcgcgcctg catggccagg acgtgctgga aatgctccac   22620
gaccccgact ggacggtacg cctggccgcc gtggaaaacg ccccgctcga ggccctgcgc   22680
gagctgaacg aagacgatcc cgaagtccag gctgcgatcg cgcaacggtt ggggtaggtt   22740
gggtggacgc ccgacccgag atgatgcttt ttaggctttg gtaggcctgc cggcctgcat   22800
cgccgcgagg gcgcgcctcc cacaggtccg caggctgctt gctgcctttg tgagcccgac   22860
cacggggcga tgcttttcgc tagggtgggc cgggcggcgt tccgcttcag cccaccaatc   22920
aagccagcga tcgcgaagga tgctggtggg ctgatgccca ccctacggat ccgtaccgcc   22980
cgacccggcc tacggggcca ctcgccgaat cctttgttgc gaacccgaca tctgggcgcg   23040
tttgcgacaa tttttatttca atgaaaatca tataaatcaa tgagttaatt tttggtacag   23100
gcattgcact cacctcgttg cgcataacca cgacgaccgg agggtgcgat gaaagccaag   23160
gacattgccg agctgctcga cgagcccgcc tgcacgcaca acaagaagga gaagtccggc   23220
tgcgccaagc cggcgccggg cgccaccgat ggcggctgcg ccttcgacgg cgcgcagatc   23280
gcgctgctgc cgatcgccga tgtggcgcac atcgtccatg ggcccatcgc ctgcgccggc   23340
```

```
agttcctggg acaaccgcgg cacccgctcc agcggcccgc agttgtaccg catcggcatg   23400
accaccgatc tctccgagca ggacgtgatc atggggcgcg ccgagaagcg cctgttccac   23460
gccatccgcc aggcggtgga gagctacgcg ccgccggcgg tgttcgtcta caacacctgc   23520
gtgccggcgc tgatcggcga cgacctcgac gccgtgtgca aggccgccag cgagcatttc   23580
gccaccccgg tggtgccggt ggacggcgcc ggtttctacg gtaccaagaa cctcggcaac   23640
cgcatcgccg gcgatgccat ggtcaagcac gtgatcggca cccgcgagcc cgacccgctg   23700
ccggccggcg ccgagcgcgc cggtattcgc gtgcacgacg tcaacctgat cggtgaatac   23760
aacatcgccg gcgagttctg gcacgtgctg ccgctgctcg acgagctggg cctgcgcgtg   23820
ctctgcacgc tgtcgggcga tgcgcgtttt cgcgaggtgc agaccatgca ccgcgccgag   23880
gtgaacatga tggtctgctc caaggccatg ctcaatgtcg cgcgcaagct gcaggagcgc   23940
ttcggcacgc cctggttcga gggcagcttc tacggcatca ccgacacctc gcaggcgctg   24000
cgcgacttcg cccggctgat cggcgacgac gacctcgccg cgcgcaccga agcgctgatc   24060
gcgcgcgagg aagcgaggat tcgcgcggcg ctggagccct ggcgcgaacg cctggccggc   24120
aagcgcgtgc tgctctacac cggcggggtc aagtcctggt cggtgatctc cgcgctgcag   24180
gacctgggca tgaaggtggt cgccaccggc accaagaaat ccaccgagga ggacaaggcg   24240
cgcatccgcg agctgatggg cgacgacgtc aagatgctcg acgagggcaa cccgcgcgcg   24300
ttgttgcgca cggtggagga ataccgcgcc gacatcctca tcgccggcgg tcgcaacatg   24360
tacaccgcgc tcaaggggcg catccccttc ctcgacatca accaggaacg cgaattcggc   24420
tatgccggct acgacggcat gcgggaactg gtgcgccagc tgtgcctgac cctcgagagc   24480
ccggtgtggc cggcggtgcg ccagccgcgg ccgtgggagc ggcccgcgtc ggccgaggca   24540
caaccccgca cgctggcgaa cgcctgagga ggtcgcgatg gcacagatca tcaaccgcaa   24600
caaggcgctg gcggtcagcc cgctgaaggc cagccagacc atgggtgccg cgctggcctt   24660
cctcggcctg gcgcgcagca tgccgttgct gcacggttcg cagggctgca cggcgttcgc   24720
caaggtgttc ttcgtccggc acttccgcga gccggtgccg ttgcagacca cggcgatgga   24780
tcaggtcagc tcggtgatgg cgccgacga gaacgtggtc gaggcgctgc gcaccatttg   24840
cgacaagcag catccagcgg tgatcggcct gctcagcacc gcgctggcgg agacccaggg   24900
ctgcgacctg cacagcgccg tgcatcagtt ccgccgcgaa tatcccgagt acggcgacgt   24960
ggccgtggtg tcggtgaaca gcccggactt cagcggttgc ttcgagagcg gtttcgccgc   25020
cgcgctcaag gcgatgatcg aggcgctggt gcccgagcgc cgtgaccagg tcggccagcg   25080
gccgcgccag gtcaacgtgc tgtgcagcgc cagcctgaca cccggcgacc tggaattcgt   25140
cgccgagagc atcgagagct tcggcctgcg gccgttgctg atccccgacc tgtccggctc   25200
gctggacggc catctcgacg aggcggcctt caacccgctg accaccggcg ggctgaccct   25260
cgacgagttg gccagtgccg ggcagagcgc cgccaccctg gtgatcggcc agagcctgac   25320
cgccgccgcc gatgcgctgg ccgcccgcag cggcgtaccg gaccggcgtt tcggcctgct   25380
gctgggcctg gaggcggtgg atgcctggtt gatggcgctg agcgagatca gcggcaaccc   25440
ggtgccggag cgctggcagc gccagcgccg gcaactgcag gacgccatgc tcgataccca   25500
tttcatgctc ggcgacgcgc gtctgggcat cgccgccgac cccgacctgc tgctcggttt   25560
ctccaccctg gcgcgcggca tgggcgcgca actggtggcc gccgtggtgc cggcgcgcgc   25620
gccggcgctg gccgatgcgc cgctggcgcg catccaggtc ggtgacctgg aggacctgga   25680
```

```
gcaggccgcc cgcgacggtg gtgcccaact gctgctcggc aacagccacg cgctggccag   25740
cgccgaccgc ctgggcattc cgctgctgcg cgtgggcttt ccgcagtacg acctgctggg   25800
cggcttccag cgctgctgga gcggttaccg ggccagcgcg caggcgctgt tcgacctggc   25860
caacctgctc accgaacacc atcagggtat cgcgccgtat cgctcgatct atgcgcagaa   25920
gcccgcctcc gaccattcgc aatggagcca ctgagccatg ccagccccca tccgacaact   25980
gcaggtactc gacggcgaga acgacggcac gctgctcaag gtggccttcg cctcgtccga   26040
tcggcgcacg gtcgaccagc atttcggttc gtcgcggtcg ttcgtgttct acggcatcga   26100
ccccgagcgg gccgagctgc aatcggtggt ggaattcggc gagctcgacc aggacggcaa   26160
cgaggacaag ctggcggcca agctggaact gctcgatggc tgcatcgcgg tgtactgccg   26220
cgcctgcggc gcctcggcgg tacgccagct gctggcgatc ggcgtgcagc cggtcaaggt   26280
cagcgaggcc gagggcatcg ccgaactgat cgaaacgctg caggccgagc tgcgcgaagg   26340
cccttcggcc tggctggcca aggcgatccg gcgtacccgt ggcacgccgg accagcaacg   26400
tttcgaggcc atgccggcg aggcctggga cgaatagccc gacacccgca atcgaggaca   26460
gcgttatgta tgcagaagaa caacaggcgg tcgttcgcga cgacgccccg gccctgcagg   26520
acccggtgat caagcagatg gtggtgcaac tgcgcgccat ggacagctac ggcacctacg   26580
acacctggag cgacgcgcgg gtgctcgacc cgctggtgct gacccgcgag cggcgccgcg   26640
cgatccccat cgtcggcgat ccggacgagg tcaccctgtc gcgggtcaag gccttctaca   26700
acgccctggc gcagatgatc gagcgcgaga ccgggctgct cgcggtaccg gtgatcaaca   26760
tcacccacga gggcttcggc cgcgcgctga tcctggtcgg caagctggtg gcgctggaca   26820
agaccctgcg cgacgtccat cgcttcggct tcgaatcgct cgaggcgttg tcgctcgacg   26880
cgcagaagct gctgggcaag gcgaccgcgc tggtcgccga gcaccgtacg gtcgccgagt   26940
tgtaagggga gacgagccga tgaccgaaga ggaactcaag gcgttgaaga aggaagtcag   27000
ccagaagaag cgcatcgcca ccgaatgggc gtcgcagatc cacgacctgg tcgaggaccg   27060
gctgctgatc gattaccggc aattgccgga actggcgacg caggcacacc aggcctgcct   27120
cgactgggcc gaggccaacg cccggctgga agccggcggc aacgcctgac cgccaataca   27180
gagcgggccc gagcccgccg tatccctaac cgtaggccgc cgccatgcca ttggcgggca   27240
ggagatgaca gatggaagca gtgataaccg ggcgtacgcg cggtggcgcc gaatgggtgc   27300
cgcagttcgt caccgccgtc gatgcgcaga agtgcatcgg ttgcgggcgt tgctacaagg   27360
tgtgcccgcg cgacgtgttc gagctggtgg agcgctccgg catggtgggc gaggacgacg   27420
acctctacga cgaggacgac gagatgatgg tcatggccat cgccgacggc ctcgactgca   27480
tcggctgcaa ggcctgttcg gcggtctgcc cgaaacaatg ccatacccat caggccctgg   27540
ccggctgagg agctgctgac atgccaagac ccgactacca catcttcctc tgcctgcagc   27600
gccgcgccga ggggcacccg cgcggcagtt gtgctgcgaa gggcggcgaa gcccgtttcg   27660
acgccttctc ccaggccctg atccggcgca acctgatcgg ccgcatcgcc ttgaccggca   27720
ccggctgcct ggggccctgc caggccggcg ccaatgtgct gatctacccg ggcgcattga   27780
tgtacagctg ggtggagccg gcggatgtcg acagcatcct cacgcatctg ctcgaaggcg   27840
agcccttcgc cgacaagctc acccccgcgg agctctggtg aggcatgggt gaagtgctgt   27900
tgctggagcc cgaacgggcg ttcttttccg accgcacgcc gaccgggctg cgctacctgc   27960
tgaacagcgc gcgcggcctc gagcatccgg cggcggtcga agccctgctg ctggaggccc   28020
ggcagcgctg gagcgaggag ccggacgcgc atgtcggcct gtacaagttc tactttctcc   28080
```

```
aggcccgcta cgcggaggcc gaagccgccg tatgggaagc cctgcggcgg gccgcggcct   28140
gtgccggctt cagccgcaac taccggcgcc tgcaccctgc cagcgccgac tggcagacac   28200
gccgcggtgc cacgcggttg tacctgttca gcctcaaggc gctgggcgtg atccgcctgc   28260
gccgtggcaa ggtggacaac gcgcggcggg tgctggagaa gctgctggag ctcgatccgg   28320
gcaacgagat cggcggcgag gcgttcctgc agatcgcccg cgccttcgag gaggaaaact   28380
gatggcggca tcgttcgaag cacgcctgca ggcggcgcgg ccgctgttcg gcgaaatcca   28440
gcgcgcgctg caggattgcc tgcagcgttc ggccatccgc ctgcaactgc ccgacgagcg   28500
tgaaccgtcg cgcagcgaag tgcgggtcga cccgttcgat cgcagcgaat gcttctacag   28560
cgaatggcgc agcgcccagg gcgatttcct cggcagcatg cagatcaacg cgacggtca   28620 ggtctatgcc gagttcgacg tgctgctgaa gcacccgcac gagccggcct ggctggtgga   28680
ggcggtcgcc gcctggggtt ggccggggc gctgaaaagc gagttgcgcc tgctgccggc   28740
gctcgatcat gaatgagctc tacgactggc tgctggccag cgccgcgcag gcgcggaccg   28800
tcgaacatct gtgcctgggg ttgaactgga cactggccga agtcgacggc aaccagggct   28860
tcgccttcag cccgcgccag gtgccgcgca cgctcggctg gtcgggcaca ctcgccggcc   28920
agggcaacgc cgcgctgctg ccctggctgc tgtcgtggaa cagcgccgaa gccgcggtcg   28980
gcctggccgt gctcaatgcc agcgtgaaca cggcggcggg ctgccagcgc gaggcgcagg   29040
cactgcgcac gcaggcaccg gggcatctgc aggtgttcgc acatttccgt ccacggctgg   29100
cgggccagcg ggtcgtggtg atcggccatt atcccggcct cgaacggctc tggcaggacc   29160
agccctacca gtgcctggag cgccagcagc aggagggcga cctgcccgat gcgccgccg   29220 agtacctgct gcccgaggcc gactgggtgt tcgtcagcgc gagcagcatc gccaacaaga   29280
ccttgccgcg cctgctcgag ctgtcgcgcc aggcccaggt ggtgctgatg gggccgagcc   29340
tgccctggct ggacggttgg cggcgcttcg gcgtggacta cctggccggg gttcgcgtgc   29400
tcgacccgga cggcgtgcgg cgggtgattg ccgagggtgg cggtacgcgg ctgttcgccg   29460
ggccggtgga gtatgccttg atggcgctcg ggaaatgatg gggtctcacg gccggctggg   29520
ctggcggatg ctgatctgtc acaagcaccc ggtcagcgcg cgcctgcatt tcctcgtgcc   29580
gcagcgcggc ggggtggtct tgccgcagcc ccttccggcc ctcgcggtat tcgccgaacc   29640
gccgatgcag ggcgatctgc tggtccatcc tgcgggcgct ctgcgcagcc tgcagcgcga   29700
cctggggatc gagaaaccgc tggagctggt ggccgattac cgggtcggcc tcgaagtgtc   29760
gggcggggtt ctgccggtat tcctcgccgc actggacggg cacgatcggt gccggcggc   29820 catcggaacc cactggatcg aactgacgca gagcatcggc atgccctggc tggaccgcga   29880
actgctcagg cgggcctatg aagtgctgat cgggtgaagc gtaggcgcgt ggatcgggcg   29940
gtcgcctagc ctgaatttcc agacatatgg acgccaccca tcctactgca ccgaaaagca   30000 tcgcccgag ggcgggcccc ccacaaaagc agccagcagc accgagcccc cgtgggcgc   30060 gccctcgcgg tgatgcaggc cggtaggcct gccaaagact gaaaagcatc gccccgaggg   30120
cgggcctccc acaaaagcag ccagcagcac cgagccccg tggcgcgct ctcgcggcga   30180 tgcaggccgt aggcctgcc aaagactgaa aagcatcgcc ccggggtcgg gcctccacaa   30240
agcagtcccg tagggtgggc cgggtggcgt tccgcttcag cccacccatt ccaggcaatg   30300
ggcgtcatcg aagtgggctg aagcccaccc tgctgctgcg tgccgaaatg taacctcgtg   30360
acggatgcgc ggaccgatgg ctgacgtgtt ggcgctcagc cacctcccgc acctcaggcg   30420
```

```
cgcagcagcg ccttggccat cttcggcgac agctgggctt cgctgaactg tggctcgttc    30480
ggcggataga gcaggtcctc gatgatgctg tagccgtgtt ccttgccgag ggcgatcacg    30540
tcgcggacct tttcacaggc cttgagtttt cgccgagcg ccgggtcgtt cagggcttgg    30600
ttcgagaagg cttggatttc cttgatggac atagggttct ctctgttgcg atgactggaa    30660
ccagcgccga acggctggcg aggcatgcca tagcaacatc gatgcctgag atcattccat    30720
tgaatatcaa tggcttatga ggttttgacg agctgccgat tgtcgtattg gcgacaatcg    30780
gacaacagcc gggctcaacc cagcagggcc acggccttga tctgtgccca cagcggcagc    30840
ccgggagcga tgcccaactg gtcggccgag cggcgagtga tgcgcgccag cagcggcgtg    30900
ccgccggcat ccaggcgcac cagcacgtgg gccggggtat ctgccgcggc cagcgcttcg    30960
actcgcgccg gcagcaggtt ggtgatgctg ctgccctcgg cacgggtcag cgccaggctg    31020
acgtcgcggg catgcacgcg aaagcgcagg cgctggccga gcgcttccgg ccgctgcgcc    31080
accagtacct cgccgccggg gaaggtcagg cgggtcagat ggtaggcgtc gtcgtgttcg    31140
gccacgtggg attcgaccac cacgccgcg tcctcgccga gggcggtggg caggtccagt    31200
cgtgccaggg tttcgcgcag gccgccggcg gctaccgccc ggccctggtc gagcaacacc    31260
acgtgatcgg ccagccgcgc cacttcgtcc ggcgaatggc tgacgtagag cagcgggatg    31320
tcgagttcgt cgtgcaggcg ttccagatag gcaggatttt cgttcttgcg cttgaggtcc    31380
agcgccgcca gcggttcgtc catcagcagc aggcgcgggc tggtgagcag ggcgcgggcg    31440
atgccgacgc gctggcgctc accccggac agcgttcccg gcaggcgctc cagcaggtgg    31500 tcgatacccca gcaggttcac cacatggtcc cagtccaccc ggcgctgggc ggccttgacc    31560
cgacgcaggc cgtattcgag gttgcgccgt gccgtgaggt gcgggaacag gctggcttcc    31620
tggaatacat aacccagggc gcgcgcgtgc gtcgggacga acagcccgcg cgcactgtcc    31680
tgccagcgtt cgccgttgac ttccaggtac gcctcgccgg cgcgctccag gccggcgacg    31740
cagcgcaggc aggtggtctt gcccgagccc gaatggccga acagcgccgt cacgccgcgg    31800
ccaggcaggg cgaggtcgac gtccagttcg aagccgggcc aggtcaggcg gaagcgggcg    31860
tggatctgcc cggcggttgg tgagtcgttc atgcacgagt cccttcaatt gaggccggac    31920
ttgaaacggc ggctggagta cagcgccagc agcacgcaga aggagaacgc cagcatgccg    31980
ccggccagcc agtgggcctg gcgtactcc atggcctcga cgtggtcgaa gatctgtacc    32040
gagaccgtgc gggtgacacc ggggatgttg ccgccgatca tcaacaccac gccgaactcg    32100
ccgacggtat gggcgaagcc gaggatcgag gcggtgacga gcccggccg cgccagcggc    32160 agtaccacgc tgaagaaggt gtcccaggga ctggcgcgca gggtggcggc tacttccagc    32220
gggcgctcac cgatggcttc gaaggcgttc tgcaggggtt gcacgacgaa gggcatggag    32280
taaagcaccg agcccaccac cagaccggcg aaggtaaagg gcagcagacc gaggccgagg    32340
ctctgggtca gctggccaac caggccgtta gggcccatgg cggtgagcag atagaagccc    32400
agcacggtcg gcggcaacac cagtggcagt gccaccactg cgccgaccgg ccccttgagc    32460
ggcgaatgag tacgcgccag ccaccatgcc agcggcgtgc cgatcagcaa cagcagtgcg    32520
gtggtgaggc tggccagctt gaaggtcagc cagatagctg cgaaatcgac gctgtcgagc    32580
atcatcgcgg ttcagtccag ctcatagccg taggcgcgaa tcagcgcggc ggcggtatcg    32640
cccctgaggt agtcgagcag cgcctgtgcc gccgggttgc cctcgccatg gcgaagcagc    32700
agggcgtcct ggcggatcgc cgcgtgctgg tcggccggca ccacccaggc cgagccgcgg    32760
gcgatgc                                                              32767
```

<210> SEQ ID NO 6
<211> LENGTH: 7217
<212> TYPE: DNA
<213> ORGANISM: Artificial Sequence
<220> FEATURE:
<223> OTHER INFORMATION: Synthetic Polynucleotide

<400> SEQUENCE: 6

```
ggcgtatcac gaggcccttt cgtcttcacc tcgagaaaat ttatcaaaaa gagtgttgac      60
ttgtgagcgg ataacaatga tacttagatt caattgtgag cggataacaa tttcacacat     120
ctagagctaa tcttctcgta ctcatgacgc aagtaatgaa cacgattaac atcgctaaga     180
acgacttctc tgacatcgaa ctggctgcta tcccgttcaa cactctggct gaccattacg     240
gtgagcgttt agctcgcgaa cagttggccc ttgagcatga gtcttacgag atgggtgaag     300
cacgcttccg caagatgttt gagcgtcaac ttaaagctgg tgaggttgcg ataacgctg      360
ccgccaagcc tctcatcact accctactcc ctaagatgat tgcacgcatc aacgactggt     420
ttgaggaagt gaaagctaag cgcggcaagc gcccgacagc cttccagttc ctgcaagaaa     480
tcaagccgga agccgtagcg tacatcacca ttaagaccac tctggcttgc ctaaccagtg     540
ctgacaatac aaccgttcag gctgtagcaa gcgcaatcgg tcgggccatt gaggacgagg     600
ctcgcttcgg tcgtatccgt gaccttgaag ctaagcactt caagaaaaac gttgaggaac     660
aactcaacaa gcgcgtaggg cacgtctaca gaaagcatt tatgcaagtt gtcgaggctg     720
acatgctctc taagggtcta ctcggtggcg aggcgtggtc ttcgtggcat aaggaagact     780
ctattcatgt aggagtacgc tgcatcgaga tgctcattga gtcaaccgga atggttagct     840
tacaccgcca aaatgctggc gtagtaggtc aagactctga gactatcgaa ctcgcacctg     900
aatacgctga ggctatcgca acccgtgcag gtgcgctggc tggcatctct ccgatgttcc     960
aaccttgcgt agttcctcct aagccgtgga ctggcattac tggtggtggc tattgggcta    1020
acggtcgtcg tcctctggcg ctggtgcgta ctcacagtaa gaaagcactg atgcgctacg    1080
aagacgttta catgcctgag gtgtacaaag cgattaacat tgcgcaaaac accgcatgga    1140
aaatcaacaa gaaagtccta gcggtcgcca acgtaatcac caagtggaag cattgtccgg    1200
tcgaggacat ccctgcgatt gagcgtgaag aactcccgat gaaaccggaa gacatcgaca    1260
tgaatcctga ggctctcacc gcgtggaaac gtgctgccgc tgctgtgtac cgcaaggaca    1320
aggctcgcaa gtctcgccgt atcagccttg agttcatgct tgagcaagcc aataagtttg    1380
ctaaccataa ggccatctgg ttcccttaca acatggactg gcgcggtcgt gtttacgctg    1440
tgtcaatgtt caacccgcaa ggtaacgata tgaccaaagg actgcttacg ctggcgaaag    1500
gtaaaccaat cggtaaggaa ggttactact ggctgaaaat ccacggtgca aactgtgcgg    1560
gtgtcgacaa ggttccgttc cctgagcgca tcaagttcat tgaggaaaac cacgagaaca    1620
tcatggcttg cgctaagtct ccactggaga cacttggtg ggctgagcaa gattctccgt     1680
tctgcttcct tgcgttctgc tttgagtacg ctggggtaca gcaccacggc ctgagctata    1740
actgctccct tccgctggcg tttgacgggt cttgctctgg catccagcac ttctccgcga    1800
tgctccgaga tgaggtaggt ggtcgcgcgg ttaacttgct tcctagtgaa accgttcagg    1860
acatctacgg gattgttgct aagaaagtca cgagattct acaagcagac gcaatcaatg     1920
ggaccgataa cgaagtagtt accgtgaccg atgagaacac tggtgaaatc tctgagaaag    1980
tcaagctggg cactaaggca ctggctggtc aatggctggc ttacggtgtt actcgcagtg    2040
```

```
tgactaagag ttcagtcatg acgctggctt acgggtccaa agagttcggc ttccgtcaac    2100
aagtgctgga agataccatt cagccagcta ttgattccgg caagggtctg atgttcactc    2160
agccgaatca ggctgctgga tacatggcta agctgatttg ggaatctgtg agcgtgacgg    2220
tggtagctgc ggttgaagca atgaactggc ttaagtctgc tgctaagctg ctggctgctg    2280
aggtcaaaga taagaagact ggagagattc ttcgcaagcg ttgcgctgtg cattgggtaa    2340
ctcctgatgt tttccctgtg tggcaggaat acaagaagcc tattcagacg cgcttgaacc    2400
tgatgttcct cggtcagttc cgcttacagc ctaccattaa caccaacaaa gatagcgaga    2460
ttgatgcaca caaacaggag tctggtatcg ctcctaactt tgtacacagc caagacggta    2520
gccaccttcg taagactgta gtgtgggcac acgagaagta cggaatcgaa tcttttgcac    2580
tgattcacga ctccttcggt acgattccgg ctgacgctgc gaacctgttc aaagcagtgc    2640
gcgaaactat ggttgacaca tatgagtctt gtgatgtact ggctgatttc tacgaccagt    2700
tcgctgacca gttgcacgag tctcaattgg acaaaatgcc agcacttccg gctaaaggta    2760
acttgaacct ccgtgacatc ttagagtcgg acttcgcgtt cgcgtaacag atctcatcac    2820
catcaccatc actaagctta attagctgag cttggactcc tgttgataga tccagtaatg    2880
acctcagaac tccatctgga tttgttcaga acgctcggtt gccgccgggc gttttttatt    2940
ggtgagaatc caagctagct tggcgagatc cttgcagcac atccccttt cgccagctgg     3000 cgtaatagcg aagaggcccg caccgatcgc aggccaacca gataagtgaa atctagttcc    3060
aaactatttt gtcattttta attttcgtat tagcttacga cgctacaccc agttcccatc    3120
tattttgtca ctcttcccta aataatcctt aaaaactcca tttccacccc tcccagttcc    3180
caactatttt gtccgcccac agcggggcat ttttcttcct gttatgtttg ggcgctgcat    3240
taatgaatcg gccaacgcgc ggggagaggc ggtttgcgta ttgggcgctc ttccgcttcc    3300
tcgctcactg actcgctgcg ctcggtcgtt cggctgcggc gagcggtatc agctcactca    3360
acaccacttc aagaactctg tagcaccgcc tacatacctc gctctgctaa tcctgttacc    3420
agccggttgt cagccgttaa gtgttcctgt gtcactcaaa attgctttga gaggctctaa    3480
gggcttctca gtgcgttaca tccctggctt gttgtccaca accgttaaac cttaaaagct    3540
ttaaaagcct tatatattct ttttttttctt ataaaactta aaaccttaga ggctatttaa    3600
gttgctgatt tatattaatt ttattgttca aacatgagag cttagtacgt gaaacatgag    3660
agcttagtac gttagccatg agagcttagt acgttagcca tgagggttta gttcgttaaa    3720
catgagagct tagtacgtta aacttgagag cttagtacgt gaaacatgag agcttagtac    3780
gtactatcaa caggttgaac tgcccatgtt ctttcctgcg ttatcagagc ttatcggcca    3840
gcctcgcaga gcaggattcc cgttgagcac cgccaggtgc gaataaggga cagtgaagaa    3900
ggaacacccg ctcgcgggtg ggcctacttc acctatcctg cccggctgac gccgttggat    3960
acaccaagga aagtctacac gaaccctttg gcaaaatcct gtatatcgtg cgaaaaagga    4020
tggatatacc gaaaaaatcg ctataatgac cccgaagcag ggttatgcag cggaaagtat    4080
accttaacat gttctttcct gcgttatccc ctgattctgt ggataaccgt attaccgcct    4140
gcggttgagt aataaatgga tgccctgcgt aagcgggtgt gggcggacaa taaagtctta    4200
aactgaacaa aatagatcta aactatgaca ataaagtctt aaactagaca gaatagttgt    4260
aaactgaaat cagtccagtt atgctgtgaa aaagcatact ggactttgt tatggctaaa     4320 gcaaactctt cattttctga agtgcaaatt gcccgtcgta ttaaagaggg gcgtggggtt    4380
cgaggtcgac ggtatcgata agctagctta attagctgag cttggaagta cctattccga    4440
```

```
agttcctatt ctctagaaag tataggaact tcagcggaaa aggacaattg tctcaggtcg    4500
aggtggcccg gctccatgca ccgcgacgca acgcggggag gcagacaagg tatagggcgg    4560
cgcctacaat ccatgccaac ccgttccatg tgctcgccga ggcggcataa atcgccgtga    4620
cgatcagcgg tccagtgatc gaagttaggc tggtaagagc cgcgagcgat ccttgaagct    4680
gtccctgatg gtcgtcatct acctgcctgg acagcatggc ctgcaacgcg gcatcccga     4740 tgccgccgga agcgagaaga atcataatgg ggaaggccat ccagcctcgc gtcgcgaacg    4800
ccagcaagac gtagcccagc gcgtcggccg ccatgccggc gataatggcc tgcttctcgc    4860
cgaaacgttt ggtggcggga ccagtgacga aggcttgagc gagggcgtgc aagattccga    4920
ataccgcaag cgacaggccg atcatcgtcg cgctccagcg aaagcggtcc tcgccgaaaa    4980
tgacccagag cgctgccggc acctgtccta cgagttgcat gataaagaag acagtcataa    5040
gtgcggccac aatggtcatg ccccgcgccc accggaagga gctgactggg ttgaaggctc    5100
tcaagggcat cggacggcgc tctcccttat gcgactcctg cattaggaag cagcccagta    5160
gtaggttgag gccgttgagc accgccgccg caaggaatgg tgcgtgcagg gagatggcgc    5220
ccaacagtcc cccggccacg gggcctgcca ccatacccac gccgaaacaa gcgctcatga    5280
gcccgaagtg gcgagcccga tcttccccat cggtgatgtc ggcgatatag gcgccagcaa    5340
ccgcacctgt ggcgccggtg atgccggcca cgatgcgtcc ggcgtagaga atccacagga    5400
cgggtgtggt cgccatgatc gcgtagtcga tagtggctcc aagtagcgaa gcgagcagga    5460
ctgggcggcg gccaaagcgg tcggacagtg ctccgagaac gggtgcgcat agaaaattgca    5520 tcaacgcata tagcgctagc agcacgccat agtgactggc gatgctgtcg gaatggacga    5580
tatcccgcaa gaggcccggc agtaccggca taaccaagcc tatgcctaca gcatccaggg    5640
tgacggtgcc gaggatgacg atgagcgcat tgttagattt catacacggt gcctgactgc    5700
gttagcaatt taactgtgat aaactaccgc attacagttt atcgatgata agctgtcaag    5760
aagttcctat tccgaagttc ctattctcta gaaagtatag gaacttctgc atttacgttg    5820
acaccataat aaaaaagccc ccggaatgat cttccggggg ctcactgccc gctttccagt    5880
cgggaaacct gtcgtgccag ctgcattaat gaatcggcca acgcgcgggg agaggcggtt    5940
tgcgtattgg gcgccagggt ggtttttctt ttcaccagtg agactggcaa cagctgattg    6000
cccttcaccg cctggccctg agagagttgc agcaagcggt ccacgctggt ttgccccagc    6060
aggcgaaaat cctgtttgat ggtggttaac ggcgggatat aacatgagct atcttcggta    6120
tcgtcgtatc ccactaccga gatatccgca ccaacgcgca gcccggactc ggtaatggcg    6180
cgcattgcgc ccagcgccat ctgatcgttg gcaaccagca tcgcagtggg aacgatgccc    6240
tcattcagca tttgcatggt ttgttgaaaa ccggacatgg cactccagtc gccttcccgt    6300
tccgctatcg gctgaatttg attgcgagtg agatatttat gccagccagc cagacgcaga    6360
cgcgccgaga cagaacttaa tgggcccgct aacagcgcga tttgctggtg acccaatgcg    6420
accagatgct ccacgcccag tcgcgtaccg tcctcatggg agtaaataat actgttgatg    6480
ggtgtctggt cagagacatc aagaaataac gccggaacat tagtgcaggc agcttccaca    6540
gcaatggcat cctggtcatc cagcggatag ttaatgatca gcccactgac gcgttgcgcg    6600
agaagattgt gcaccgccgc tttacaggct tcgacgccgc ttcgttctac catcgacacc    6660
accacgctgg cacccagttg atcggcgcga gatttaatcg ccgcgacaat ttgcgacggc    6720
gcgtgcaggg ccagactgga ggtggcaacg ccaatcagca acgactgttt gcccgccagt    6780
```

-continued

```
tgttgtgcca cgcggttggg aatgtaattc agctccacca tcgccgcttc cacttttcc    6840 cgcgttttcg cagaaacgtg gctggcctgg ttcaccacgc gggaaacggt catataagag   6900
acaccggcat actctgcgac atcgtataac gttactggtt tcacattcac caccctgaat   6960
tgactctctt ccgggcgcta tcatgccata ccgcgaaagg ttttgcacca ttcgatggtg   7020
tcaacgtaaa tgcatgccgc ttcgccttcg cgcgcgaatt gcaggtacca tttatcaggg   7080
ttattgtctc atgagcggat acatatttga atgtatttag aaaaataaac aaatagggt    7140 tccgcgcaca tttccccgaa aagtgccacc tgacgtctaa gaaaccatta ttatcatgac   7200
attaacctat aaaaata                                                  7217
```

NITROGEN FIXATION USING REFACTORED NIF CLUSTERS

RELATED APPLICATION

This application is national stage filing under U.S.C. § 371 of PCT International Application PCT/US2016/055429entitled, "NITROGEN FIXATION USING REFACTORED NIF CLUSTERS" filed Oct. 5, 2016, which claims the benefit under 35 U.S.C. § 119(e) of U.S. provisional application No. 62/237,426, entitled "NITROGEN FIXATION IN SALMONELLA USING REFACTORED NIF CLUSTERS", filed Oct. 5, 2015, which are herein incorporated by reference herein in their entirety.

GOVERNMENT SUPPORT

This invention was made with government support under IOS1331098 awarded by the National Science Foundation. The government has certain rights in the invention.

BACKGROUND OF INVENTION

Availability of nitrogen is one of the principal elements limiting growth and development of crops, particularly in agricultural soils for plant production of food, feed, fiber and fuel. Excessive use of synthetic fertilizer to meet the food demands of growing population poses an environmental threat in that it can cause harmful algal blooms and disrupt beneficial soil microbial community [1]. On the other hand, over-farming in many developing countries with a scant supply of fertilizer damages agricultural land and makes small farmers suffer from the poor yield of their crops [2].

Successful endophytic colonization of plants by human-pathogenic bacteria such as *Salmonella enterica, Pseudomonas aeruginosa, Burkholderia cepacia, Escherichia coli* O157:H7 has been demonstrated [3-5]. *Salmonella* can recognize plants as a suitable host and colonize in root tissues of alfalfa and barley [6,7].

SUMMARY OF INVENTION

The invention, in various aspects, relates to a method for providing fixed nitrogen from atmospheric nitrogen, comprising delivering a modified bacteria having an exogenous nif cluster to a cereal plant, or to soil where a cereal plant or seed is growing or is to be planted, wherein the modified bacteria provides fixed nitrogen.

In some embodiments, the nif cluster is a native nif cluster. In some embodiments, the nif cluster is a refactored nif cluster.

In other embodiments, the modified bacteria is a gamma-proteobacteria. In some embodiments, the modified bacteria is a *Salmonella typhimurium*.

In some embodiments, the *Salmonella typhimurium* strain is selected from SL1344, LT2, and DW01.

In other embodiments, the modified bacteria is a *E. coli*, optionally of strain H7:0157.

In other embodiments, the nif cluster is a *Klebsiella* wild-type nif cluster, a *Pseudomonas* Stutzi nif cluster, or a *paenibacillus* cluster. In some embodiments, the nif cluster is a refactored nif clusters.

In some embodiments, the cereal plant is selected from wheat, rye, barley, triticale, oats, millet, sorghum, teff, fonio, buckwheat, *quinoa*, corn and rice.

In some embodiments, the invention further comprises an exogenous gene encoding a plant growth-stimulating peptide.

In some embodiments, the exogenous gene encoding the plant growth-stimulating peptide is regulated by a type 3 secretion system (T3SS).

In some embodiments, the plant growth stimulating peptide is directly delivered into root or stem tissues.

Aspects of the invention include a method, comprising delivering a modified non-pathogenic bacteria having exogenous genes for enabling plant endosymbiosis to a cereal plant, or to soil where a cereal plant or seed is growing or is to be planted.

In some embodiments, the non-pathogenic bacteria is *E. coli*.

In some embodiments, the genes encode effectors or apparatus for a secretion system.

In other embodiments, the apparatus for a secretion system is type 3 secretion system (T3SS).

Aspects of the invention include compositions comprising an agriculturally suitable or compatible carrier, and a gamma-proteobacteria having an exogenous nif cluster present on or in the agriculturally suitable or compatible carrier.

In some embodiments, the proteobacteria is a *Salmonella typhimurium* or *E. coli*.

In other embodiments, the nif cluster is a native nif cluster.

In some embodiments, the nif cluster is a refactored nif cluster.

In some embodiments, the invention further comprises an exogenous gene encoding a plant growth-stimulating peptide.

In some embodiments, the agriculturally suitable or compatible carrier is selected from the group consisting of seeds, seed coats, granular carriers, soil, solid carriers, liquid slurry carriers, and liquid suspension carriers. In other embodiments the agriculturally suitable carrier includes a wetting agents, a synthetic surfactant, a water-in-oil emulsion, a wettable powder, granules, gels, agar strips or pellets, thickeners, microencapsulated particles, or liquids such as aqueous flowables or aqueous suspensions.

In other embodiments the exogenous nif cluster or gene includes a controller. The controller may be a nucleic acid encoding an IPTG inducible T7 RNA polymerase. Alternatively the controller may be a partitioning system encoded by the two par operons (parCBA and parDE). In some embodiments the partitioning system is a RK2 par system.

A seed or seedling of a cereal plant having a modified bacteria associated with an external surface of the seed or seedling is provided in other aspects of the invention. In some embodiments the modified bacteria has an exogenous nif cluster.

In other aspects the invention is a cereal plant having a modified bacteria in the plant, wherein the modified bacteria has an exogenous nif cluster.

The nif cluster may be a native nif cluster or a refactored nif cluster. In some embodiments the nif cluster is a *Klebsiella* wild-type nif cluster, a *Pseudomonas* Stutzi nif cluster, or a *paenibacillus* cluster. In some embodiments the modified bacteria is a gamma-proteobacteria such as a *Salmonella typhimurium*, optionally a *Salmonella typhimurium* strain selected from SL1344, LT2, and DW01 or an *E. coli*, optionally of strain H7:0157.

The cereal plant in some embodiments is selected from wheat, rye, barley, triticale, oats, millet, sorghum, teff, fonio, buckwheat, *quinoa*, corn and rice.

Optionally the seed or seedling further includes an exogenous gene encoding a plant growth-stimulating peptide. The exogenous gene encoding the plant growth-stimulating peptide, in some embodiments, is regulated by a type 3 secretion system (T3SS).

In some embodiments the exogenous gene is in root or stem tissues of the cereal plant.

In some embodiments the modified bacteria may be provided in form of solutions, dispersions, sclerotia, gel, layer, cream, coating, or dip.

In some embodiments the plant, parts of plants or the area surrounding the plants is selected from leaf, seed, branches, soil, stems, roots. In some embodiments the modified bacteria is associated with (i.e. admixed, in physical contact with or present near) the plant, parts of plants or the area surrounding the plants or is incorporated therein. In some embodiments the seeds are inoculated or coated with the modified bacteria. In certain embodiments, the modified bacteria is disposed in an amount effective to be detectable within a target tissue of the mature agricultural plant selected from a fruit, a seed, a leaf, or a root, or portion thereof.

In other embodiments, the plant, the seed or seedling comprises at least about 100 CFU, for example, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more, of the modified bacteria on its exterior surface.

In another embodiment, the modified bacteria is disposed on an exterior surface or within a tissue of the plant, the seed or seedling in an amount effective to be detectable in an amount of at least about 100 CFU, for example, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 shows nitrogenase activity in *Salmonella* strains. Nitrogenase activity of native and refactored nif clusters in diverse *Salmonella* strains were measured by acetylene reduction assay. Non-detectable ethylene production was indicated by asterisks.

FIG. 2 shows endophytic colonization of *Zea mays* B73 by enteric bacteria. Internal colonization of maize roots by either *S. typhi* ATCC 14028 or *E. coli* MG1655 (a control) was investigated. While there is no CFU of *E. coli* MG1655 from the crushed maize roots which is surface sterilized, *S. typhi* ATCC 14028 cells were recovered from inside the root tissues. Error bars represent standard deviation (n=6 for MG1655 and n=10 for ATCC14028).

FIG. 3 shows ethylene production in maize plant seedlings. The box plot shows the distribution of ethylene production between the plant seedlings inoculated with the engineered *S. typhi* ATCC 14028 and the control wild-type *S. typhi* ATCC14028 (no nif cluster). Dots represent ethylene production from individual plants in a group (n=33 (control), 39 (native nif), 39 (refactored nif)). The box extends from 25% to 75% quartile. The central line represents the median of the ethylene production in a group. The whiskers represent 75% quartile plus 1.5 times the interquartile range (upper whiskers) and 25% quartile minus 1.5 times the interquartile range (lower whiskers). Asterisk indicates statistically significant difference between the refactored nif and the control group (Student's t-test, ***$P<0.0001$).

FIGS. 4A and 4B are graphs showing the stability of genetic systems in the *Salmonella* strains obtained from the surface-sterilized roots. FIG. 4A shows a controller device composed of a sensor, T7 RNA polymerase and a selective marker showed no loss from the genome-based expression system. FIG. 4B shows the RK2 par system on the nif plasmid based on the pBBR1 origin of replication leads to an increase in the plasmid stability.

FIG. 5 shows a schematic of a controller for mini-Tn7 insertion (pR6K-T7RM).

DETAILED DESCRIPTION

Endophytic bacteria that are symbiotic with host plants can be genetically engineered to deliver proteins to the host and thereby regulate properties of plants. In non-cereal plants bacteria can be used to provide fixed nitrogen, reducing the need for nitrogen rich fertilizer. In cereal plants, however, bacterial systems for providing fixed nitrogen have never been developed despite many attempts over the years to develop such systems. A method for manipulating endophytic bacteria such that they are capable of providing fixed nitrogen to cereal plants has been discovered according to the invention. Endophytes may occupy the intracellular or extracellular spaces of plant tissue, including the leaves, stems, flowers, fruits, seeds, or roots.

The methods of the invention are useful for several purposes such as reducing fertilization needs, reducing fertilization pollution, providing an eco-friendly crop production, enhanced crop production, improved oil content in plants, improved protein content in plants, the reduction of nitrogen contamination of water, and the enrichment of the carbon content relative to nitrogen and carbon in relation to a soil's organic phase.

A limiting factor for crop productivity of agricultural crops is the nitrogen content in soil and water. The supply of this element has dwindled over time as crop demands increased. Nitrogen is one of the primary nutrients essential to all forms of life, including plants. However, nitrogen must first be converted to a form that plants can utilize. Biological Nitrogen Fixation (BNF) is the conversion of atmospheric nitrogen ($N_2$) to ammonia ($NH_3$) using the enzyme nitrogenase. This reaction consumes a tremendous amount of energy as $N_2$ contains a triple bond. The bond energy in a nitrogen molecule is about 225 kcal/mol. Few BNFs are performed in nature as a result of a symbiotic relationship between plants and several bacterial species that make up a "nitrogenase enzymatic complex."

The bacterial species that produce the nitrogenase enzymatic complex include diazotrophs such as cyanobacteria, azotobacteraceae, *rhizobia*, and *frankia*. However, only a few plant species can live in a symbiotic relationship with diazotrophs. For example, the pea plant from the legume family lives in symbiosis with bacteria from the *rhizobia* family. In particular, *rhizobia* bacteria penetrate the pea plant's roots creating root nodules that contain bacteria that fix nitrogen (to ammonia) while the plant donates carbon (sugar). Improving either the symbiosis, or extending the host range would therefore be beneficial for plant survival, but achieving this goal includes many challenges including the complexity of the process and lack of basic knowledge.

Biological nitrogen fixation is carried out by a complex of three proteins (nitrogenase), encoded by nifH, rufD and nifK, which are assembled and activated by an additional 17 genes [8]. Transferring a nif cluster to a new host is challenging because of the fact that the pathway is very sensitive to small changes in gene expression and the regulatory control in many organisms is not well established [8,9]. As shown in the Examples, a refactoring method was applied to a 16 gene nif cluster from *Klebsiella oxytoca* M5a1 to engineer a system for regulating nif. The method modularized the gene cluster into a set of well-characterized genetic parts. Refactoring can be used as a platform for large-scale part substitutions that facilitate the swapping of regulation to that which will function in a new host. Refactoring also is valuable in eliminating the response to signals that repress the native nif cluster, including ammonia and oxygen.

Quite surprisingly, it was discovered that nif clusters, both wild type and refactored nif, transferred into endophytic bacteria enable the bacteria to provide fixed nitrogen in cereal plants. This is the first demonstration that the transfer of native and synthetic nif clusters into endophytic bacteria can be used to provide fixed nitrogen to crops. The experiments presented in the Examples below demonstrate that genetic sensors connected to refactored nif clusters successfully regulated nitrogen fixation pathway at three different *Salmonella* strains in response to a chemical signal. The refactored nif clusters allows the testing of large populations of enteric bacteria isolated from plants for efficient symbiosis that delivers nitrogen to crops.

Synthetic nucleic acids encoding wild type and refactored nif clusters can be used to produce genetically modified bacteria. The modified bacteria useful according to the invention are endophytes which are endosymbionts. Endosymbionts do not cause apparent disease in plants for some or all of its life cycle. Bacterial endophytes may belong to a broad range of taxa, including α-Proteobacteria, β-Proteobacteria, γ-Proteobacteria, Firmicutes, and Actinobacteria. It is particularly preferred according to methods of the invention to use γ-Proteobacteria.

In some embodiments, examples of endophytic bacteria that are γ-Proteobacteria include but are not limited to *Salmonella* spp., *Yersinia pestis, Vibrio cholerae, Pseudomonas aeruginosa, Escherichia coli, Xanthomonas axonopodis* pv. *citri* and *Pseudomonas syringae* pv. *actinidiae*. In preferred embodiments γ-Proteobacteria include *Salmonella* and *Escherichia coli*.

The modified bacteria of the invention, are used to promote fixed nitrogen from atmospheric nitrogen. The term "plant" as used herein refers to cereal plants. The term includes all parts of a plant such as germinating seeds, emerging seedlings and vegetation including all below ground portions (such as the roots) and above ground portions. Cereals are the cultivated forms of grasses (Poaceae) and include for example wheat (inclusive spelt, einkorn, emmer, kamut, durum and triticale), rye, barley, rice, wild rice, maize (corn), millet, sorghum, teff, fonio and oats. The term cereal plants also includes pseudocereals, such as amaranth, *quinoa* and buckwheat.

Additionally, the modified bacteria can be genetically engineered to deliver other factors such as plant growth-stimulating peptides directly into root or stem tissues. For instance, genes expressing proteins that affect plants can be engineered into a type 3 secretion system (T3SS). Synthetic control will be able to be regulated by expressing of T3SS in bacteria. Methods of engineering bacteria in this manner are described in Widmaier, D. M. et al. [3].

Thus, the methods according to the invention can also involve genetically modifying bacteria to further treat the cereal plants. The term "genetically modified bacteria" refers to bacteria whose genetic material has been modified by the use of recombinant DNA techniques to include an inserted sequence of DNA that is not native to that bacterial genome or to exhibit a deletion of DNA that was native to that species' genome. Often, a particular genetically modified bacteria will be one that has obtained its genetic modification(s) by a recombinant DNA technique. Typically, one or more genes have been integrated into the genetic material of a genetically modified bacteria. The gene may be inserted into the T3SS region.

A nif cluster is a collection of genes encoding enzymes involved in the fixation of atmospheric nitrogen into a form of nitrogen available to living organisms. The primary enzyme encoded by the nif genes is the nitrogenase complex which is in charge of converting atmospheric nitrogen ($N_2$) to other nitrogen forms such as ammonia which the organism can use for various purposes. Besides the nitrogenase enzyme, the nif genes also encode a number of regulatory proteins involved in nitrogen fixation. The nif genes are found in both free-living nitrogen-fixing bacteria and in symbiotic bacteria associated with various plants. The expression of the native nif genes are induced as a response to low concentrations of fixed nitrogen and oxygen concentrations (the low oxygen concentrations are actively maintained in the root environment of host plants). Refactored nif clusters can be designed to be regulated by exogenous factors and/or constitutively regulated.

As used herein, a "genetic cluster" refers to a set of two or more genes that encode gene products. A target, naturally occurring, or wild type genetic cluster is one which serves as the original model for the refactoring. In some embodiments, the gene products are enzymes. In some embodiments, the gene cluster that is refactored is the nif nitrogen fixation pathway.

Each genetic cluster is organized into transcriptional units which are composed of a plurality of modular units. A modular unit is a discreet nucleic acid sequence that is made up of one or more genetic components. A genetic component may include anything typically found in a genetic fragment. For instance a genetic component includes but is not limited to genes, regulatory elements, spacers, non-coding nucleotides. Some or all of these are found within each modular unit. Within the modular unit one or more of the synthetic regulatory elements may be genetically linked to one or more protein coding sequences of the genetic cluster.

While multiple modular units may be composed of the same gene and regulatory elements, the units may differ from one another in terms of the orientation, position, number etc. of the gene and regulatory elements. Other modular units may have some elements in common with other modular units but include some different elements. Yet other modular units may be completely distinct and do not overlap with other modular units. The great diversity of the modular units is what leads to the diversity of the assembled genetic clusters in a library.

The modular units within the genetic cluster are arranged such that the plurality of distinct non-naturally occurring genetic clusters are distinct from a naturally occurring genetic cluster based on the number, the order, and/or the orientation of particular genetic components. The number of genetic components within a modular unit may be easily varied. For instance, one modular unit may have a single promoter or terminator, whereas another modular unit may have 5 promoters and 2 terminators. The variation that may be achieved by manipulation of this factor is significant. Additionally the order of the components within a modular unit may be varied dramatically. Multiple sets of modular units may be generated where a single order of two components may be switched. This factor would also generate significant diversity. Switching the orientation of a component in the modular unit is also a viable way of generating diversity. While it may be expected that switching the orientation of one or more genetic components might interfere with functionality it has been demonstrated herein that genetic nif clusters having different orientations are actually functional.

The refactoring process involves several levels of restructuring genetic clusters. For example, the codons of essential genes in a genetic cluster, such as the nif cluster, are changed to create a DNA sequence divergent from the wild-type (WT) gene. This may be achieved through codon optimization. Recoded genes may be computationally scanned to identify internal regulators. These regulatory components may then be removed. They are organized into operons and placed under the control of synthetic parts (promoters, ribosome binding sites, and terminators) that are functionally separated by spacer parts. Finally, a controller consisting of genetic sensors and circuits that regulate the conditions and dynamics of gene expression may be added.

The genetic components in the refactored genetic cluster typically will include at least one synthetic regulatory element. A synthetic regulatory element is any nucleic acid sequence which plays a role in regulating gene expression and which differs from the naturally occurring regulatory element. It may differ for instance by a single nucleotide from the naturally occurring element. Alternatively it may include one or more non-natural nucleotides. Alternatively it may be a totally different element. In each case, it may be considered to be an exogenous regulatory element (i.e. not identical to the naturally occurring version). Thus, a "regulatory element" refers to a nucleic acid having nucleotide sequences that influence transcription or translation initiation or rate, or stability and/or mobility of a transcription or translation product. Regulatory regions include, without limitation, promoter sequences, ribosome binding sites, ribozymes, enhancer sequences, response elements, protein recognition sites, inducible elements, protein binding sequences, 5' and 3' untranslated regions (UTRs), transcriptional start sites, transcription terminator sequences, polyadenylation sequences, introns, and combinations thereof.

In some embodiments, the regulatory sequence will increase the expression of a gene. In other embodiments, the regulatory sequence will decrease the expression of a gene. In some embodiments the regulatory sequence may be a protein-binding sequence, for example a transcription factor binding site. In some embodiments, the regulatory sequence may be a polymerase-binding site. In some embodiments, the regulatory sequence is a terminator. The terminator may require an additional factor to indicated the end of the sequence for transcription, for example a rho-dependent terminator. In some embodiments, a regulatory sequence is a sequence that binds a ribosome, such as a ribosome-binding site (RBS). In some embodiments, the regulatory sequence indicates where translation will begin. It will be evident to one of ordinary skill in the art that regulatory sequences differ in their strength of regulation. For example, there exist strong promoter sequences, gene expression from which is higher than gene expression from a weak promoter sequence. Similarly, there exist strong RBS sequences that recruit and bind ribosomes with higher affinity than a RBS sequence that is characterized as weak. In some embodiments, the regulatory sequence may be an inducible or conditional regulatory sequence. In some embodiments, the regulatory sequence will exist 5' or upstream of a protein-coding sequence. In other some embodiments, the regulatory sequence will exist 3' or downstream of a protein-coding sequence. In still other embodiments, the regulatory sequence may be present within a protein-coding sequence. Any given protein-coding sequence may be regulated by one or more regulatory sequences. Non-limiting examples of regulatory sequences include the bacteriophage T7 promoter, sigma 70 promoter, sigma 54 promoter, lac promoter, rho-dependent terminator, stem-loop/rho-independent terminator.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid also can be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. The exogenous elements may be added to a construct, for example using genetic recombination. Genetic recombination is the breaking and rejoining of DNA strands to form new molecules of DNA encoding a novel set of genetic information.

"Expression" refers to the process of converting genetic information of a polynucleotide into RNA through transcription, which is catalyzed by an enzyme, RNA polymerase, and into protein, through translation of mRNA on ribosomes.

Promoters may be constitutive or inducible. Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268:1766-1769 (1995), see also Harvey et al, Curr. Opin. Chem. Biol., 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J. Clin. Invest., 100:2865-2872 (1997)]. Still other types of inducible promoters which may be useful in this context are those which are regulated by a specific physiological state, e.g., temperature, acute phase, a particular differentiation state of the cell, or in replicating cells only.

The regulatory elements may be in some instances tissue-specific. Tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TB G) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some instances the modular units or genetic clusters may be designed to lack in restriction recognition sites. Restriction endonucleases cleave DNA with extremely high sequence specificity and due to this property they have become indispensable tools in molecular biology and molecular medicine. Over three thousand restriction endonucleases have been discovered and characterized from a wide variety of bacteria and archae. Comprehensive lists of their recognition sequences and cleavage sites can be found at REBASE.

As used herein the term "isolated nucleic acid molecule" refers to a nucleic acid that is not in its natural environment, for example a nucleic acid that has been (i) extracted and/or purified from a cell, for example, an algae, yeast, plant or mammalian cell by methods known in the art, for example, by alkaline lysis of the host cell and subsequent purification of the nucleic acid, for example, by a silica adsorption procedure; (ii) amplified in vitro, for example, by polymerase chain reaction (PCR); (iii) recombinantly produced by cloning, for example, a nucleic acid cloned into an expression vector; (iv) fragmented and size separated, for example, by enzymatic digest in vitro or by shearing and subsequent gel separation; or (v) synthesized by, for example, chemical synthesis. In some embodiments, the term "isolated nucleic acid molecule" refers to (vi) an nucleic acid that is chemically markedly different from any naturally occurring nucleic acid. In some embodiments, an isolated nucleic acid can readily be manipulated by recombinant DNA techniques well known in the art. Accordingly, a nucleic acid cloned into a vector, or a nucleic acid delivered to a host cell and integrated into the host genome is considered isolated but a nucleic acid in its native state in its natural host, for example, in the genome of the host, is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein.

Methods to deliver expression vectors or expression constructs into cells are well known to those of skill in the art. Nucleic acids, including expression vectors, can be delivered to prokaryotic and eukaryotic cells by various methods well known to those of skill in the relevant biological arts. Methods for the delivery of nucleic acids to a cell in accordance to some aspects of this invention, include, but are not limited to, different chemical, electrochemical and biological approaches, for example, heat shock transformation, electroporation, transfection, for example liposome-mediated transfection, DEAE-Dextran-mediated transfection or calcium phosphate transfection. In some embodiments, a nucleic acid construct, for example an expression construct comprising a fusion protein nucleic acid sequence, is introduced into the host cell using a vehicle, or vector, for transferring genetic material. Vectors for transferring genetic material to cells are well known to those of skill in the art and include, for example, plasmids, artificial chromosomes, and viral vectors. Methods for the construction of nucleic acid constructs, including expression constructs comprising constitutive or inducible heterologous promoters, knockout and knockdown constructs, as well as methods and vectors for the delivery of a nucleic acid or nucleic acid construct to a cell are well known to those of skill in the art.

In one embodiment, a genetic clusters includes a nucleotide sequence that is at least about 85% or more homologous or identical to the entire length of a naturally occurring genetic cluster sequence, e.g., at least 5%, 10%, 15%, 20%, 25%, 30%, 35%, 40%, 50% or more of the full length naturally occurring genetic cluster sequence). In some embodiments, the nucleotide sequence is at least about 90%, 91%, 92%, 93%, 94%, 95%, 96%, 97%, 98%, 99% or 100% homologous or identical to a naturally occurring genetic cluster sequence. In some embodiments, the nucleotide sequence is at least about 85%, e.g., is at least about 90%, 91%, 92%, 93%, 94%, 95%, 96%, 97%, 98%, 99% or 100% homologous or identical to a genetic cluster sequence, in a fragment thereof or a region that is much more conserved, such as an essential, but has lower sequence identity outside that region.

Calculations of homology or sequence identity between sequences (the terms are used interchangeably herein) are performed as follows. To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

In many cases the nucleic acids described herein having naturally occurring nucleotides and are not modified. In some instances, the nucleic acids may include non-naturally occurring nucleotides and/or substitutions, i.e. Sugar or base substitutions or modifications.

One or more substituted sugar moieties include, e.g., one of the following at the 2' position: OH, SH, SCH$_3$, F, OCN, OCH$_3$OCH$_3$, OCH$_3$O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of a nucleic acid; or a group for improving the pharmacodynamic properties of a nucleic acid and other substituents having similar properties. Similar modifications may also be made at other positions on the nucleic acid, particularly the 3' position of the sugar on the 3' terminal nucleotide and the 5' position of 5' terminal nucleotide. Nucleic acids may also have sugar mimetics such as cyclobutyls in place of the pentofuranosyl group.

Nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methyl-amino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-'7'7; and Gebeyehu, G., et al. Nucl. Acids Res., 15:4513 (1987)). A "universal" base known in the art, e.g., inosine, can also be included.

In the context of the present disclosure, hybridization means base stacking and hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as the term is used in the art, refers to the capacity for precise pairing between two nucleotides. For example, if a nucleotide at a certain position of an nucleic acid is capable of hydrogen bonding with a nucleotide at the same position of a second nucleic acid, then the two nucleic acids are considered to be complementary to each other at that position. The nucleic acids are complementary to each other when a sufficient number of corresponding positions in each molecule are occupied by nucleotides that can hydrogen bond with each other through their bases. Thus, "specifically hybridizable" and "complementary" are terms which are used to indicate a sufficient degree of complementarity or precise pairing such that stable and specific binding occurs between the nucleic acids. 100% complementarity is not required.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

As shown in the examples, the refactoring approach has been applied to the nif gene cluster from *Klebsiella oxytoca* encoding the nitrogen fixation pathway for converting atmospheric N2 to ammonia. The native gene cluster consists of 20 genes in seven operons and is encoded in 23.5 kb of DNA. The refactored gene cluster may share little DNA sequence identity with the wild type (WT).

When the nif cluster is a native nif cluster, it may have the DNA sequence of any naturally occurring nif cluster. For example it may have the sequence of a naturally occurring nif cluster from *Klebsiella oxytoca* (SEQ ID NO. 4) *Pseudomonas* stutzi nif cluster (SEQ ID NO. 5) and *paenibacillus* nif cluster. Refactored nif clusters may be any refactored nif cluster which is active in producing the proteins involved in promoting N$_2$ conversion to other nitrogen forms.

The following exemplary DNA sequences of nif clusters are useful according to the invention.

refactored nif cluster v1.0

(SEQ ID NO. 1)

taatacgactcactatagggagaacaataaactaacataaggaggataaatatgaccatgcgtcagtgcgcgatt
tatggcaaaggtggtattggcaaaagcacgacgacccagaacttggtggcggccctggccgagatgggtaaaaag
gttatgattgtgggttgcgacccgaaggccgacagcacgcgcctgattctgcacgcgaaagcacaaaacacgatt
atggagatggctgccgaggttggtagcgtggaggatctggagctggaggacgttctgcaaattggttacggtgat
gttcgttgcgcagagagcggtggtccggaaccaggtgtcggctgtgcgggtcgtggtgtaattaccgctatcaat
ttcctggaagaagagggtgcgtacgaagatgatctggatttcgttttctacgatgtgctgggtgatgtcgtgtgc
ggtggttttgcaatgccgattcgcgagaataaggcacaagaaatttacattgtctgtagcggcgagatgatggca
atgtacgctgctaacaacatcagcaagggtattgttaaatacgcaaaaagcggtaaggttcgcttgggtggtttg
atttgcaacagccgtcagaccgaccgtgaggacgaactgatcatcgccctggctgagaaactgggcacccaaatg
atccacttcgtgccacgcgataatattgttcaacgtgcagaaatccgccgtatgaccgtcattgagtatgacccg
gcatgcaagcaagcgaacgagtaccgcaccttggcacagaaaatcgtgaacaacaccatgaaggttgttccgacg
ccgtgtacgatggacgagctggagagcctgctgatggagttcggcattatggaggaggaggacaccagcattatc
ggtaagaccgcagcggaggagaatgcggcataagcgtgcgtacaccttaatcaccgcttcatgctaaggtcctgg
ctgcatgcaaaaattcacatccctatctagcggaggagccggatgatgactaatgctactggcgaacgtaacctg
gcactgattcaagaagtactggaagtgttcccggaaaccgcgcgcaaagagcgccgtaaacacatgatggtttct
gacccggaaatggaatctgtgggtaaatgcatcatctctaatcgcaaatctcagccgggtgtcatgactgttcgt
ggctgtgcgtacgcaggttctaaaggtgtcgtattcggcccgatcaaagatatggcgcatatctctcatggcccg
gtaggctgtggccagtactctcgcgcgggacgtcgtaactactacacggvcgtttctggcgttgactctttcggc
acgctgaacttcacctctgacttccaggaacgtgacatcgttttcggtggcgataaaaagctgtccaaactgatc
gaagaaatggaactgctgttcccgctgactaaaggcattactatccaaagcgaatgtccggtgggtctgatcggt
gatgacatcagcgcggtcgcaaacgcatcttccaaagccctggataagccggtgatcccggttcgttgcgagggc
ttccgcggcgtttctcagtctctgggtcatcacatcgcaaacgatgttgtgcgtgactggattctgaacaaccgt
gaaggtcagccttttgaaaccaccccttatgacgttgcgattattggcgactataacatcggcggcgacgcctgg
gcatcccgcatcctgctggaggagatgggtctgcgtgttgtcgcacagtggtctggcgatggcaccctggttgaa
atggaaaacaccccgtttgttaaactgaacctggttcactgctaccgctccatgaactacattgcccgtcacatg
gaagaaaaacatcagatcccttggatggaatacaacttcttcggtccgactaaaatcgcagaatccctgcgtaaa
atcgccgatcagtttgatgataccattcgcgcgaacgctgaagcagtaattgcgcgctacgaaggccagatggca
gcaatcattgctaagtaccgtccgcgcctggaaggtcgtaaagtgctgctgtacatgggtggtctgcgtccacgt
catgtgatcggtgcctacgaggacctgggcatggagatcatcgcagcgggttacgaatttgcacacaacgacgac
tatgatcgtacgctgccagacctgaaagaaggtacgctgctgtttgacgacgccagctcttatgaactggaagcc
ttcgtgaaagcgctgaaaccagacctgatcggctccggcatcaaggaaaaatacattttccagaaaatgggcgtg
ccgttccgccagatgcactcctgggactactccggtccgtaccacggctacgacggtttcgctatcttcgctcgt
gacatggatatgacccctgaataacccagcgtggaatgaactgaccgcaccgtggctgaaatctgcataacaaaca
ccccatgtcgatactgaacgaatcgacgcacactcccttccttgcaatctcatactctcaaaaattaggcgaggt
aacatgtctcaaactatcgataaaatcaactcttgttacccgctgttcgagcaggacgaatatcaggaactgttc
cgtaacaaacgtcagctggaagaagcgcacgacgcacagcgcgtgcaggaagtgttcgcatggaccaccaccgcg
gaatacgaagctctgaacttccagcgcgaagccctgacggttgatccggcgaaagcgtgccagcctctgggtgcg
gttctgtgcagcctgggtttttgccaacaccctgccgtatgtccacggttcccagggctgcgtagcctacttccgt
acctatttcaaccgccacttttaaagaaccaatcgcgtgcgtgtccgacagcatgacggaggacgcggcagttttc
ggtggtaacaacaacatgaacctgggcctgcaaaatgcttccgcactgtacaaaccggaaatcatcgcagtgtct -continued

```
accacctgcatggcagagagttattggtgatgatctgcaagcatttattgccaacgcaaagaaagacggtttcgtt gacagctctatcgcggttccgcacgctcatacccgtccttcatcggttctcacgtaactggtttgggacaacatg ttcgaaggcttcgcaaaaacttttaccgcagactatcaaggccaaccgggtaaactgccgaagctgaacctggtg accggctttgaaacctacctgggcaactttcgtgtcctgaagcgcatgatggagcagatggcggttccgtgttct ctgctgtctgacccgtctgaggttctggacactccagcggacggccactatcgcatgtattctggtggcaccact cagcaggaaatgaaagaggccccagacgcgattgacaccctgctgctgcaaccgtggcagctgctgaaaagcaag aaagttgttcaggaaatgtggaaccagccggcaacggaagttgcaatcccgctgggtctggcagctactgacgaa ctgctgatgaccgtgtcccaactgagcggcaaaccaatcgcggatgctctgaccctggaacgcggtcgcctggtg gacatgatgctggacagccacacgtggctgcatggcaagaaatttggcctgtacggtgacccggacttcgtaatg ggcctgacccgtttcctgctggaactgggctgcgagccgactgttatcctgtctcacaacgctaacaaacgttgg cagaaggccatgaacaaaatgctggatgcgagcccatacggccgtgatagcgaagtgttcatcaactgcgacctg tggcatttccgctctctgatgtttacgcgtcagccggatttcatgatcggtaactcttacggcaaattcatccag cgtgacactctggccaaaggcaaagcgtttgaagtgccgctgattcgtctgggctttccgctgttcgaccgtcac cacctgcaccgccagaccacctgggggttacgaaggcgcgatgaacatcgtaactactctggtaaacgcagtactg gaaaagctggacagcgatacttcccagctgggcaaaaccgactattctttcgatctggttcgttaacctgattgt atccgcatctgatgctaccgtggttgagttaccatactcactcccggaggtacttctatgtctgacaatgatacc ctgttttggcgcatgctggcgctgtttcagtcgctgccggatttgcagccggctcaaatcgtcgattggctggcg caggaatccggcgaaaccctgacgccggagcgccttgccaccctgacccaaccgcaactcgcggcgtcgttccca tccgcgacggcagtgatgagcccggctcgctggagccgcgttatggcttctctgcaaggcgccctcccagcccac ttgcgcatcgtacgtccggcgcagcgtaccccgcaactgctcgccgcgttttgcagccaagacggccttgttatc aatggtcatttcggccagggtcgtctgttcttcatttacgcctttgacgagcagggcggctggctgtatgacttg cgccgctatccgagcgcaccgcaccagcaggaagcgaatgaggtgcgtgctcgtctgattgaagattgccagctg ctgttctgccaggagattggcggtccggcagcagcgcgtctgatccgccaccgcatccatccgatgaaggcgcag ccgggtactacgattcaggcgcagtgtgaagctatcaacaccctgctggccggtcgcctgccgccgtggctcgcc aaacgtttgaaccgtgataacccgctggaagagcgtgtgttttaacattttgccttgcgacagacctcctactt agattgccacactattcaatacatcactggaggttattacaaatgaagggtaacgagattcttgctctgctggac gaaccggcctgtgaacacaaccataaacagaaatccggctgtagcgccccaaagccgggtgcgacggcggctggc tgcgctttcgatggtgcgcagatcaccctgctcccgattgcggacgttgcccacctcgtgcatggcccaatcggt tgcgcaggtagctcttgggacaacgtggcagcgcctccagcggtccgaccctgaatcgtttgggctttaccact gacttgaatgaacaagatgtgatcatgggtcgcggcgagcgtcgcctgttccacgctgtgcgccatattgtcacc cgttaccacccagcggcagtattcatctacaatacgtgcgtgccggctatggaaggcgatgacctggaggccgtg tgtcaggcagcccagactgcgaccggcgtcccggtaatcgcaattgatgcggctggcttctacggttcgaagaac ctgggcaaccgtccggcaggcgatgtcatggttaaacgcgtcattggccaacgtgagccagcgccgtggccggag agcaccctgtttgccccggagcaacgtcatgacattggcttgatcggtgagttcaacattgcgggcgagttttgg cacattcagccgctgcttgatgagctgggtatccgcgttttgggttcgctcagcggcgatggtcgtttcgccgag attcaaaccatgcaccgtgcccaggcgaacatgctggtgtgcagccgtgctctgatcaatgttgcgcgtgctctg gaacagcgctatggcaccccgtggtttgaaggctcgttctatggtatccgcgcgaccagcgacgccctgcgccag ttagcggcgctgctgggcgatgacgacctccgtcagcgcaccgaggcgctgatcgcgcgtgaagaacaggcggct gagctggccctgcaaccgtggcgtgaacagctgcgtggccgcaaggccctgctctacacgggtggtgtcaaaagc tggtctgtggtgtccgcgcttcaggatctgggtatgaccgtggttgccacgggcacgcgtaagagcacggaagag
```

-continued

```
gataaacagcgcatccgcgaattgatgggcgaagaggccgtgatgcttgaagaaggcaacgcacgtaccttattg gatgtagtttatcgctatcaagcagacctgatgattgccggtggccgcaacatgtataccgcctacaaagcgcgc ttgccgttcctggacatcaaccaggaacgcgagcacgcgtttgcgggctaccaaggcatcgtgaccttagcgcgc cagctgtgccaaacgattaacagcccgatctggccgcagactcattcccgcgcaccgtggcgctaatgtcacgct aggaggcaattctataagaatgcacactgcacctaaacctaccacacctggaagaagtaattatggcagacattt tccgcactgataagccgttggctgtgtcgccgatcaagaccggccagccgctgggtgcgatcctggcgtccctgg gtatcgagcactcgattccgctggtacatggcgcgcagggctgttcggcttttgccaaggttttctttatccagc acttccacgatccggtcccgctgcaaagcacggcaatggacccgaccagcaccatcatgggcgctgatggtaaca tcttcaccgcgctggacactctctgccaacgcaataacccgcaagcaattgtgctgctgagcaccggcctctccg aggcgcagggcagcgacatttcccgtgtagtgcgtcagttccgtgaagaatatccgcgtcataaaggcgtggcga ttctgactgttaacaccccggacttttacggtagcatggagaacggcttttccgctgtcctggagtctgtgattg aacagtgggttccgccagccccacgtccggcgcagcgcaatcgtcgcgtcaatcttttggtgagccatctctgta gcccaggcgatattgagtggctgcgccgttgcgtcgaggccttcggtctgcaaccgatcattctgccggatctgg ctcagagcatggacggccaccttgctcagggtgacttttcgccgctgacgcagggcggcacgccgttgcgccaaa tcgagcagatgggccagagcctttgctcttttgcgattggcgtcagcctgcaccgtgcgagcagcctgctggctc cgcgttgtcgtggcgaagtcatcgccttgccgcacctcatgaccttggaacgctgcgacgcctttatccatcagt tggcgaaaatcagcggtcgcgccgttccggagtggctggaacgccagcgcggtcagctgcaagacgccatgatcg attgccacatgtggctgcaaggccagcgcatggcgattgccgccgaaggcgacctgctggcagcgtggtgcgatt tcgcgaactctcaaggtatgcagccgggtccactggttgctccgacgggtcatccgagcctgcgtcagttgccgg tggagcgcgtggtgccgggtgatctggaggatcttcagaccctcttatgcgcacatccggccgacttactggtgg cgaactcccacgcccgtgatttagcagagcaattcgccctgccgctggtgcgcgcaggcttcccgctgtttgaca aactgggcgaatttcgtcgtgttcgccagggttatagcggtatgcgtgataccctgttcgagttggcgaacctga tccgtgaacgccatcatcatctggctcattatcgcagcccgctgcgccagaacccagaatcctcgttgtctacgg gtggcgcgtacgcagcggattaactagagattaaagaggagaaattaagcatgaaaactatggacggtaacgctg cggctgcatggattagctacgcctttaccgaagtggctgcgatctacccgattacgccgagcaccccgatggcgg aaaatgtggacgaatgggctgcgcagggcaagaagaacctcttcggccagccggtgcgcctgatggagatgcagt cggaagcgggtgcagcaggtgctgtgcatggcgccttgcaagctggcgcactgacgaccacctacaccgcgtcgc agggcctgttgctgatgatcccaaacatgtacaaaatcgcgggtgaactgctgccgggtgtctttcatgtttcgg cacgcgcactggccaccaatagcctcaacatcttttggcgatcatcaggatgtaatggcggtgcgccaaacgggct gcgcgatgttggccgagaataacgtccagcaagttatggatttgtccgcggtagcccacttggcagcgatcaaag gtcgcattccgttcgtgaacttcttcgatggctttcgcaccagccacgaaatccagaagatcgaggttctggaat atgaacagctggccaccttgttggatcgtccggccctggacagcttccgccgtaacgcccttcacccggaccacc cggtcatccgtggcaccgcccagaacccggacatctacttccaggaacgtgaggccggtaaccgtttctatcagg cgctcccggatattgtggaatcttacatgacccagatttctgccctgactggtcgcgagtatcacctgtttaact acactggtgctgcggatgcggagcgcgtgatcatcgcgatgggctctgtctgtgacaccgtccaagaggtggttg acacgctgaatgcagcgggtgagaaagttggtctgctctccgttcatcttttccgcccgttttcgttagcgcact tcttcgcccaactgccgaaaactgtacagcgtatcgcagtattggaccgtacgaaagagccaggtgctcaagcag agccgctgtgcctcgatgtgaagaatgccttttaccaccatgacgatgccccgttgattgtgggtggtcgctatg ccttgggcggtaaggacgtgttgccgaacgatattgcggccgtgtttgataacctgaacaaaccgctgccgatgg acggcttcacgctgggtatcgtggacgatgttaccttcacctctctcccgccagcgcagcagaccctggcggttt ctcacgacggcatcacggcatgtaagttttggggcatgggctccgacggcacggttggtgcgaacaagtccgcga
```

-continued

```
tcaagattatcggcgacaaaacgccactgtatgcgcaagcgtacttttcctacgactcgaagaagagcggtggta
ttaccgtcagccatctgcgttttggtgatcgcccgatcaactcccgtatttgatccatcgcgcggatttcatct
cgtgcagccagcaaagctatgttgaacgctacgatctgctggatggccttaaaccgggtggcacctttctgctga
actgctcctggagcgatgccgaactggagcaacatctgccggtcggtttcaaacgttatctggcacgcgagaata
tccacttctacactctcaacgctgtggacatcgcccgtgagcttggtttgggtggccgtttcaacatgctgatgc
aggctgccttcttcaaactggccgcgatcattgacccgcagactgctgcggactatctgaagcaggctgttgaga
aaagctatggcagcaaaggtgcggcggtcatcgagatgaaccagcgtgccatcgagcttggcatggccagcctgc
accaggtgacgatcccggcacattgggccaccctggatgagccagcggcgcaggcgtccgcgatgatgccggact
ttatccgcgacatcctgcaaccgatgaaccgtcagtgcggcgaccagcttccggtgtcggcttttgtcggcatgg
aagatgcaccttcccgtccggcacggccgcatgggagaaacgtggcatcgcccttgaggtgccagtctggcagc
cggaaggctgcacgcagtgcaaccagtgcgccttcatttgtccgcacgccgcgattcgtccggcgttgttgaatg
gcgaagagcatgatgctgccccggttggcctgctgagcaaaccggcacaaggcgctaaagaatatcactatcatc
tggcgattagcccgctggactgctccggctgtggcaactgcgttgacatttgtccagctcgtggcaaagcgttga
agatgcagtctctggatagccaacgccagatggctccggtgtgggattatgcgctggcgctgaccccgaagtcta
acccgtttcgtaaaaccaccgtcaaaggctcgcagttcgaaaccccgctgctggagtttagcggtgcgtgcgctg
gttgtggcgaaacgccgtatgcgcgcctcattacccagctgtttggcgaccgcatgctgattgccaatgccaccg
gctgttccagcatctggggcgcatctgcgccgagcatcccgtataccaccaatcatcgtggtcatggtccggcct
gggcgaatagcctgttttgaggacaatgccgaatttggtttaggtatgatgctgggcggtcaagctgtgcgtcaac
agatcgcggacgatatgacggctgcgttagcgctcccggtttccgatgagctgagcgacgcgatgcgccagtggt
tggcgaaacaggacgagggtgaaggcacgcgtgagcgtgcggaccgtctgagcgagcgcttagccgcggagaaag
agggcgttccgctgttagagcagctgtggcaaaatcgtgattactttgtgcgtcgcagccagtggattttcggcg
gtgacggctgggcctatgatattggcttcggtggcctggaccacgtcctcgccagcggtgaggatgtgaacattc
tggtatttgacaccgaagtctactcgaacaccggcggtcaaagcagcaaatcgacccggtcgcggccatcgcca
agttcgcggctcagggcaagcgcacccgcaagaaagacctgggtatgatggcgatgagctacggcaacgtctatg
tagcccaggtggcgatgggtgcggataaagatcaaactctgcgcgccattgcggaagctgaagcgtggccaggcc
cgtcgctggtgattgcgtatgcggcctgcatcaatcatggcctgaaggccggtatgcgttgcagccaacgtgagg
cgaagcgcgctgttgaggcgggctactggcacctgtggcgttatcacccgcagcgcgaagcggaaggcaagacgc
cgtttatgttagatagcgaagaaccggaagagtcgttccgtgactttctgtttgggtgaggtgcgctacgcatccc
tgcacaagaccaccccgcacctcgccgatgcccttttcagccgtaccgaagaagatgcgcgtgcgcgctttgcgc
aataccgtcgcctggctggcgaagagtaataatactctaaccccatcggccgtcttagggggttttttgtccgtgg
ttgagtcagcgtcgagcacgcggctaatacgactcactagagagagacgcgacttccagagaagaagactactga
cttgagcgttccctctctgtaatacatcaaatcaatcataggagggctaaaatgacctcttgttcgtcgttttct
ggcggtaaagcgtgccgtccggccgatgactccgcgctgactccgctggtggccgacaaggcagctgcgcacccg
tgctatagccgccacggccatcaccgcttcgcgcgtatgcacctgccagtcgctccggcctgcaacttacaatgc
aactactgcaaccgcaagttcgattgcagcaatgaaagccgtccgggcgtgtcctctaccctgctgacgccggaa
caggctgtggtgaaggtgcgccaggtcgcccaagctatcccgcagctgtcggtggtcggtattgctggtccgggc
gatccgcttgcgaatatcgcccgcaccttccgtaccttggagcttattcgcgaacagttgccggacctgaaactg
tgcctgagcaccaacggcttggtgctgccagatgccgttgatcgtctgctcgatgtgggcgtggatcacgttacc
gtcaccattaacaccctggacgcagaaatcgcagcgcaaatctacgcgtggtttgtggctggatggcgaacgctac
tccggtcgcgaagccggcgaaattctcattgcccgccagctggaaggcgtacgtcgcctgaccgcgaaaggtgtg
```

-continued

```
ctcgtcaagatcaacagcgtattgattccgggcatcaatgacagcggcatggcgggtgttagccgtgcgctgcgc gcgtctggtgcgttcatccacaacatcatgccactgattgcgcgtccggagcatggcactgttttcggtctgaac ggccagccggaaccggacgcggaaaccctggcggcgacgcgctcccgctgcggcgaggttatgccacaaatgacc cactgccaccagtgccgtgccgacgcgattggcatgcttggtgaggatcgctcgcaacagtttacgcaattaccg gctccggagtccctcccggcctggctgccgatcctgcatcagcgtgctcagttgcatgcgagcatcgccacgcgc ggtgagagcgaagccgatgacgcctgcctggtggccgttgcgtcgagccgtggcgatgtaattgactgccatttc ggccatgccgaccgtttctatatctatagcctgtctgcggctggtatggttctggttaacgaacgtttcaccccg aaatactgccagggtcgcgatgactgcgagccgcaggacaatgccgcacgctttgctgccatccttgagttgctg gcggacgtcaaagcggtgttttgtgtgcgtatcggccataccccgtggcaacagctggagcaggaaggcatcgaa ccgtgcgtggatggcgcctggcgtccggtatccgaggtcctgccggcatggtggcagcagcgccgtggtagctgg ccggctgcattgccgcacaaaggcgttgcgtaaactacgagatttgaggtaaaccaaataagcacgtagtggcat taaagaggagaaattaagcatgccgccattggactggttgcgtcgtttgtggttactctatcacgccggcaaagg cagctttccgcttcgtatgggcttgtcgccgcgtgactggcaagctctgcgccgtcgcctgggcgaggtggaaac gccgctggatggcgaaaccctgacccgtcgccgtctgatggcggagctgaatgcgacccgcgaagaagaacgcca gcagctgggtgcctggctggccggttggatgcaacaggatgccggtccgatggcgcagattatcgcagaggtgag cctggcgttcaaccatctctggcaggaccttggcctcgcgagccgcgctgaactgcgtctgctgatgtctgactg cttcccgcagctggttgttatgaacgagcacaacatgcgctggaagaaattcttttaccgccagcgttgcctgct gcaacagggcgaagtcatctgtcgcagcccgtcttgcgatgaatgctgggaacgttctgcgtgctttgagtaata catatcggggggtagggttttttgtgtctgtagcacgtgcatctaatacgactcactaatgggagagacaaga gtctcaattataaggaggctttactacatggcgaacatcggcatcttctttggtacggataccggcaaacccgc aagattgcgaagatgattcacaaacagctgggcgagctggccgatgccccggttaacatcaatcgtaccactttg gatgactttatggcttaccagtcctgttgctcggcacgccgacgcttggtgatggtcaactgccgggcttagag gcgggctgcgagagcgaaagctggtctgagtttatctccggtctggatgacgcttccctgaagggcaaaaccgtg gcgctgtttggcctgggcgaccagcgtggttaccccggacaacttcgtgtcgggtatgcgtccgctgttcgacgcg ctgagcgcccgtggcgcccagatgattggtagctggccgaacagaaggttatgagtttagcgcatcgtccgcgctg gaaggcgaccgcttcgtcggcttggtgctggatcaagacaatcagttcgaccagaccgaagcgcgcctggcgtct tggcttgaagagatcaaacgcaccgttctgtaataatacatatcggggggtagggttttttgtggtcattaca acggttattaatacgactcactagagagagaaacatagcgttccatgagggctagaattacctaccggcctcaga tactgacaaataaaccagcgaaggaggttcctaatgtggaactacagcgagaaagtcaaggaccatttcttcaat ccgcgcaacgcgcgtgttgtggataacgcaaatgcggtgggcgacgtcggcagcttatcttgtggcgatgctctc cgcttgatgctgcgcgtggacccgcagagcgaaatcatcgaagaagcgggctttcagaccttcggctgcggcagc gcgattgcgtcgtccagcgcactgacggagctgatcatcggtcacaccctggcggaagcgggtcagatcaccaac cagcagatcgccgactatctggacggcttaccgccggaaaagatgcactgctctgtaatgggccaggaagctctt cgtgcggccattgctaactttcgcggtgaatcgctggaagaggagcatgacgagggtaagctgatctgcaagtgc ttcggcgtcgatgaaggccatattcgccgtgctgtccagaacaacggtcttacgactctggccgaggtgatcaat tacaccaaggcaggtggcggttgtaccagctgccatgagaaaatcgagctggccctggccgagattctcgcccaa cagccgcaaaccaccccggcagttgcgtccggtaaagatccgcactggcagagcgtcgtggataccatcgctgaa ctgcgtccacatatccaagcggacggtggtgacatggcgctgttgtccgtgacgaaccaccaagtgactgtttcg ctgtcgggcagctgttctggctgcatgatgaccgacatgaccctggcgtggctgcaacagaaattgatggagcgt accggctgctatatggaagttgttgccgcctaacattgtaatagccaccaaaagagtgatgatagtcatgggtga tacccgtagaccattctgaaatcgaaggaggttttccatgaaacaagtgtacctggacaacaacgcgaccacccg
```

-continued cctggacccgatggttctggaagcgatgatgccgtttctcacggatttctatggcaatccgtccagcatccatga cttcggcatcccggcacaagcggcgctggaacgtgcgcaccagcaagctgcggcactgctgggcgcagagtaccc gtctgaaatcattttcacgagctgtgcgaccgaggccactgcaaccgccattgcgtcggccatcgcgttattgcc ggaacgccgcgaaatcatcacctcggtagtggagcacccggctacgctggcggcgtgcgagcacctggaacgcca aggctatcgcatccatcgcattgcggtggatagcgaaggtgcgctggacatggcccagttccgtgcagcgctctc gccgcgtgtcgcgttggtgagcgtgatgtgggccaacaacgaaaccggcgtgctgttcccgattggcgaaatggc cgagcttgcccacgagcagggcgctctgttccactgcgatgccgttcaggtcgttggcaaaatcccaattgctgt tggccagacgcgcatcgacatgctgtcttgctccgcgcacaagtttcatggtccgaagggtgttggttgcttgta cttacgtcgtggcacgcgctttcgtccgctgcttcgcggtggccatcaagaatatggtcgccgtgccggcactga gaatatctgtggcatcgtcggcatgggcgctgcgtgcgaactggcgaacatccatctgccgggtatgacccatat tggccagttacgcaatcgcctggagcaccgtctgctcgccagcgtgccgtccgtgatggttatgggcggtggtca gccgcgtgtaccgggtactgtcaacctggcgttcgagtttatcgaaggtgaagcgatcctgctcttgctgaacca ggctggcattgccgcaagctccggctccgcgtgtacctctggcagcttggagccgagccatgtgatgcgcgccat gaacattccatacaccgcggctcacggcaccattcgttttagcctgagccgttatacgcgcgagaaagagatcga ctacgtcgttgcgaccctcccgccaatcattgatcgtctgcgtgccttgtcccgtattggcagaatggtaagcc gcgtccggcagatgcagtctttaccccggtttacggttaagagttactggccctgatttctccgcttctaatacc gcacagcgactaggagcctaactcgccacaaggaaacatatggagcgcgtcttgatcaacgatactaccctgcgt gatggcgaacaatctccgggcgtagcgtttcgtacctccgagaaagttgccatcgcggaggcactgtacgctgcg ggtatcaccgcgatggaagtcggcactccggcgatgggtgatgaagagatcgcccgcattcagctggtgcgtcgt caactgccggacgcgacgcttatgacctggtgccgtatgaacgctctggaaatccgtcagagcgcggatctgggt attgactgggtggatatctcgatcccagcatccgacaagctgcgtcagtacaagctgcgtgagccgctggccgtg ctgctggagcgccttgcgatgtttatccatctggcccacacgttaggcctcaaagtatgtattggttgcgaggat gcgagccgtgcgtctggtcagaccctgcgcgccattgccgaggtggcccagcaatgcgcggctgcgcgcttgcgt tacgctgacaccgtgggcctgctggacccgttcaccaccgcagcccagatcagcgccctgcgtgacgtttggtcg ggcgagatcgagatgcatgctcacaatgatctgggcatggctaccgcgaacacgctggcggcagtttcggctggc gccacgtcggtgaacactaccgtcctcggtctgggtgaacgtgcaggcaacgcagccctggaaaccgttgcgctg ggcctggaacgctgcctgggcgtggaaaccggcgtccatttcagcgcgctcccagcgctctgtcagcgcgtcgcg gaggctgcacagcgcgcaatcgacccgcaacagccgctggtgggtgaattggttttcacccacgagtctggtgtt cacgttgcggcgctgctgcgcgacagcgaatcctatcaatctattgccccaagcctcatgggccgtagctaccgt ctggtgctcggcaagcattcgggtcgtcaggctgtcaacggtgttttcgaccagatgggttaccacctgaatgcg gcgcagatcaatcagttgctgccggccattcgccgcttcgccgagaattggaaacgctctccgaaagactacgaa ctggttgcgatctatgacgaattgtgcggtgaatccgcccttcgtgctcgcggctaagactcaacacgctaggga cgtgaagtcgattccttcgatgcagaaggcgagaactagatttaagggccattatagatggagtggttttaccag attccgggtgtagacgaattgcgcagcgctgaatccttctttcagttcttcgcggttccataccagccggaactg ctgggccgctgctcgcttccggtgttagcgacgttccaccgtaaactgcgtgcggaggtcccgctgcaaaaccgt ctggaggacaatgatcgtgcgccgtggctcttggcgcgccgcctcctggccgaatcttatcagcagcaatttcag gagagcggcacctaatcgagaaacaaggcagttccgggctgaaagtagcgccgggacaagtcccgtattataacc gcctaggaggtgttggatgcgcccgaaattcaccttctctgaagaggtccgcgtagttcgcgcgattcgtaatga tggcaccgtggcgggttttgcgccaggtgcgctgctggttcgtcgcggttcgacgggctttgtgcgtgactgggg tgtgttcctgcaagaccagatcatctatcaaatccactttccggaaaccgaccgcattatcggctgtcgcgagca -continued ggagttaatcccgattacccagccgtggttggctggtaacctccagtatcgtgacagcgtcacgtgccaaatggc actggctgtcaacggtgacgtggttgtgagcgccggtcaacgtggccgtgtggaggccactgatcgtggcgaact tggcgattcctacaccgtggacttcagcggccgttggttccgcgttccggtccaggccatcgcgctgattgaaga gcgcgaagaataaacgccacgcgtagtgagacatacacgttcgttgggttcactcagagactgaagttattaccc aggaggtctataatgaatccgtggcagcgctttgcccgtcaacgccttgctcgcagccgctggaaccgtgatccg gctgctctcgacccagccgataccccagcgttcgagcaggcgtggcagcgtcaatgccatatggaacaaaccatc gtagcgcgtgtcccggaaggcgatattccggctgccttactggaaaacatcgcggccagcctggcgatctggctg gacgagggtgacttcgctccgccgagcgcgctgcgattgtgcgtcatcatgcacgtctggagctggcgtttgcc gacattgcccgccaggcaccgcaaccggatctgagcacggttcaagcgtggtatctgcgtcaccagactcaattc atgcgtccggagcagcgtctgacccgtcacctgctcctgacggtcgataatgatcgcgaggcggtgcatcaacgc atccttggcctgtatcgtcagatcaacgcgagccgtgacgccttcgcccactggcacagcgccactctcattgc ccgtccgccttggaagaaggccgtctgggctggatctcccgtggtctgctgtacccgcagctcgaaaccgcgttg tttagcctggcggaaaacgcactgtcgctgccgattgcgtcggaattgggttggcacctgttatggtgcgaggcc attcgtccggcagccccgatggagccgcaacaggcccttgaatctgcgcgcgactacttgtggcagcagagccag cagcgccaccagcgtcaatggctggagcagatgatttcccgccaaccgggcctgtgtggttaatagcataacccc ttggggcctctaaacgggtcttgaggggttttttgt refactored nif cluster v2.1

(SEQ ID NO. 2)

taatacgactcactattgggagatACAAATATATAATATATTTAAGGAGGTTTCATATATGACCATCCGTCAGTG

CGCGATTTATGGCAAAGGTGGTATTGCCAAAAGCACGACGACCCAGAACTTGGTCGCCGCCGTGGCCGAGATGGG

TAAAAAGGTTATGATTGTGGGTTGCGACCCGAAGGCCGACAGCACGCGCCTGATTCTCCACGCGAAAGGACAAAA

CACGATTATGGAGATGGCTGCCGAGGTTGCTAGCGTGGAGGATCTGGAGCTGGAGGACGTTCTGCAAATTGGTTA

CGGTGATGTTCGTTGCGCAGAGAGCGGTGGTGCGGAACCAGGTGTCGGCTGTGGGGGTCGTGGTGTAATTACCGC

TATCAATTTCCTGGAAGAAGAGGGTGCGTACGAAGATGATCTGGATTTCGTTTTCTACGATGTGCTGGGTGATGT

CGTGTGCGGTGGTTTTGCAATGCCGATTCGCGAGAATAAGGCACAAGAAATTTACATTGTCTGTAGCGGCGAGAT

GATGGCAATGTACGCTGCTAACAACATCAGCAAGGGTATTGTTAAATACGCAAAAAGCGGTAAGGTTCGCTTGGG

TGGTTTGATTTGCAACAGCCGTCAGACCGACCGTGAGGACGAACTGATCATCGCCCTGGCTGAGAAACTGGGCAC

CCAAATGATCCACTTCGTGCCACGCGATAATATTGTTCAACGTGCAGAAATCCGCCGTATGACCGTCATTGAGTA

TGACCCGGCATGCAAGCAAGCGAACGAGTACCGCACCTTGGCACAGAAAATCGTGAACAACACCATGAAGGTTGT

TCCGACGCCGTGTACGATGGACGAGCTGGAGAGCCTGCTGATGGAGTTCGGCATTATGGAGGAGGAGGACACCAG

CATTATCGGTAAGACCGCAGCGGAGGAGAATGCGGCATAATACTCGAACCCCTAGCCCGCTCTTATCGGGCGGCT

AGGGGTTTTTGTCGAAGAACAGATATGAAAGTGTTAGAACTGTAATACGACTCACTATAGGTAGAGCGTGCGTA

CACCTTAATCACCGCTTCATGCTAAGGTCCTGGCTGCATGCAAAAATTCACATTTTTATCTAGCGGAGGAGCCGG atgatgactaatgctactggcgaacgtaacctggcactgattcaagaagtactggaagtgttcccggaaaccgcg cgcaaagagcgccgtaaacacatgatggtttctgacccgGaaatgGaatctgtgggtaaatgcatcatctctaat cgcaaatctcagccgggtgtcatgactgttcgtggctgtgcgtacgcaggttctaaaggtgtcgtattcggcccg atcaaagatatggcgcatatctctcatggcccggTaggctgtggccagtactctcgcgcggGacgtcgtaactac tacacgggcgtttctggcgttgactctttcggcacgctgaacttcacctctgacttccaggaacgtgacatcgtt ttcggtggcgataaaaagctgtccaaactgatcgaagaaatggaactgctgttcccgctgactaaaggcattact atccaaagcgaatgtccggtgggtctgatcggtgatgacatcagcgcggtcgcaaacgcatcttccaaagccctg gataagccggtgatcccggttcgttgcgagggcttccgcggcgtttctcagtctctgggtcatcacatcgcaaac gatgttgtgcgtgactggattctgaacaaccgtgaaggtcagccttttgaaaccacccctatgacgttgcgatt -continued

```
attggcgactataacatcggcggcgacgcctgggcatcccgcatcctgctggaggagatgggtctgcgtgttgtc
gcacagtggtctggcgatggcaccctggttgaaatggaaaacaccccgtttgttaaactgaacctggttcactgc
taccgctccatgaactacattgcccgtcacatggaagaaaaacatcagatcccttggatggaatacaacttcttc
ggtccgactaaaatcgcagaatccctgcgtaaaatcgccgatcagtttgatgataccattcgcgcgaacgctgaa
gcagtaattgcgcgctacgaaggccagatggcagcaatcattgctaagtaccgtccgcgcctggaaggtcgtaaa
gtgctgctgtacatgggtggtctgcgtccacgtcatgtgatcggtgcctacgaggacctgggcatggagatcatc
gcagcgggttacgaatttgcacacaacgacgactatgatcgtacgctgccagacctgaaagaaggtacgctgctg
tttgacgacgccagctcttatgaactggaagccttcgtgaaagcgctgaaaccagacctgatcggctccggcatc
aaggaaaaatacattttccagaaaatgggcgtgccgttccgccagatgcactcctgggactactccggtccgtac
cacggctacgacggtttcgctatcttcgctcgtgacatggatatgaccctgaataacccagcgtggaatgaactg
accgcaccgtggctgaaatctgcataaCAAACACCGCATGTCGATACTGAACGAATCGACCCACACTCGCTTCCT
TGCAATCTCATACTGTCAAAAATTAGGCGAGGTAACatgtctcaaactatcgataaaatcaactcttgttacccg
ctgttcgagcaggacgaatatcaggaactgttccgtaacaaacgtcagctggaagaagcgcacgacgcacagcgc
gtgcaggaagtgttcgcatggaccaccaccgcggaatacgaagctctgaacttccagcgcgaagccctgacggtt
gatccggcgaaagcgtgccagcctctgggtgcggttctgtgcagcctgggttttgccaacaccctgccgtatgtc
cacggttcccagggctgcgtagcctacttccgtacctatttcaaccgccactttaaagaaccaatcgcgtgcgtg
tccgacagcatgacggaggacgcggcagttttcggtggtaacaacaacatgaacctgggcctgcaaaatgcttcc
gcactgtacaaaccggaaatcatcgcagtgtctaccacctgcatggcagaggttattggtgatgatctgcaagca
tttattgccaacgcaaagaaagacggtttcgttgacagctctatcgcggttccgcacgctcataccccgtccttc
atcggttctcacgtaactggttgggacaacatgttcgaaggcttcgcaaaaacttttaccgcagactatcaaggc
caaccgggtaaactgccgaagctgaacctggtgaccggctttgaaacctacctgggcaactttcgtgtcctgaag
cgcatgatggagcagatggcggttccgtgttctctgctgtctgacccgtctgaggttctggacactccagcggac
ggccactatcgcatgtattctggtggcaccactcagcaggaaatgaaagaggccccagacgcgattgacaccctg
ctgctgcaaccgtggcagctgctgaaaagcaagaaagttgttcaggaaatgtggaaccagccggcaacggaagtt
gcaatcccgctgggtctggcagctactgacgaactgctgatgaccgtgtcccaactgagcggcaaaccaatcgcg
gatgctctgaccctggaacgcggtcgcctggtggacatgatgctggacagccacacgtggctgcatggcaagaaa
tttggcctgtacggtgacccggacttcgtaatgggcctgacccgtttcctgctggaactgggctgcgagccgact
gttatcctgtctcacaacgctaacaaacgttggcagaaggccatgaacaaaatgctggatgcgagcccatacggc
cgtgatagcgaagtgttcatcaactgcgacctgtggcatttccgctctctgatgtttacgcgtcagccggatttc
atgatcggtaactcttacggcaaattcatccagcgtgacactctggccaaaggcaaagcgtttgaagtgccgctg
attcgtctgggctttccgctgttcgaccgtcaccacctgcaccgccagaccacctggggttacgaaggcgcgatg
aacatcgtaactactctggtaaacgcagtactggaaaagctggacagcgatacttcccagctgggcaaaaccgac
tattctttcgatctggttcgttaaCCTGATTGTATCCGCATCTGATGCTACCGTGGTTGAGTTACCATACTCACT
CCCGGAGGTACTTCTATGTCTGACAATGATACCCTGTTTTGGCGCATGCTGGCGCTGTTTCAGTCGCTGCCGGAT
TTGCACCCGGCTCAAATCGTCGATTGGCTGGCGCAGGAATCCGGCGAAACCCTGACGCCGGAGCCCCTTGCCACC
CTGACCCAACCGCAACTCGCGGCGTCGTTCCCATCCGCGACGGCAGTGATGAGCCCGGCTCGCTCGAGCCGCGTT
ATGGCTTCTCTGCAAGGCGCCCTCCCAGCCCACTTGCGCATCGTACGTCCGGCGCAGCGTACCCCGCAACTGCTC
GCCGCGTTTTGCAGCCAAGACGGCCTTGTTATCAATGGTCATTTCGGCCAGGGTCGTCTGTTCTTCATTTACGCC
TTTGACGAGCAGGGCGGCTGGCTGTATGACTTGCGCCGCTATCCGAGCGCACCGCACCAGCAGGAAGCGAATGAG
GTGCGTGCTCGTCTGATTGAAGATTGCCAGCTGCTGTTCTGCCAGGAGATTGGCGGTCCGGCAGCAGCGCGTCTG
```

-continued

```
ATCCGCCACCGCATCCATCCGATGAAGGCGCAGCCGGGTACTACGATTCAGGCGCAGTGTGAAGCTATCAACACC
CTGCTGGCCGGTCGCCTGCCGCCGTGGCTCGCCAAACGTTTGAACCGTGATAACCCGCTGGAAGAGCGTGTGTTT
TAACATTTTTGCCTTGCGACAGACCTCCTACTTAGATTGCCACACTATTCAATTCATCACTGGAGGTTATTACAA
ATGAACGGTAACGAGATTCTTGCTCTGCTGGACCAACCGGCCTGTGAACACAACCATAAACAGAAATCCGGCTGT
AGCGCCCCAAAGCCGGGTGCGACGGCGGCTGGCTGCGCTTTCGATGGTGCGCAGATCACCCTGCTCCCGATTGCG
GACGTTGCCCACCTCGTGCATGGCCCAATCGGTTGCGCAGGTAGCTCTTGGGACAACCGTGGCAGCGCCTCCAGC
GGTCCGACCCTGAATCGTTTGGGCTTTACCACTGACTTGAATGAACAAGATGTGATCATGGGTCGCGGCGAGCGT
CGCCTGTTCCACGCTGTGCGCCATATTGTCACCCGTTACCACCCAGCGGCAGTATTCATCTACAATACGTGCGTG
CCGGCTATGGAAGGCGATGACCTGGAGGCCGTGTGTCAGGCAGCCCAGACTGCGACCGGCGTCCCGGTAATCGCA
ATTGATGCGGCTGGCTTCTACGGTTCGAAGAACCTGGGCAACCGTCCGGCAGGCGATGTCATGGTTAAACGCGTC
ATTGGCCAACGTGAGCCAGCGCCGTGGCCGGAGAGCACCCTGTTTGCCCCGGAGCAACGTCATGACATTGGCTTG
ATCGGTGAGTTCAACATTGCGGGCGAGTTTTGGCACATTCAGCCGCTGCTTGATGAGCTGGGTATCCGCGTTTTG
GGTTCGCTCAGCGGCGATGGTCGTTTCGCCGAGATTCAAACCATGCACCGTGCCCAGGCGAACATGCTGGTGTGC
AGCCGTGCTCTGATCAATGTTGCGCGTGCTCTGCAACAGCGCTATGGCACCCCGTGGTTTGAAGCCTCGTTCTAT
GGTATCCGCGCGACCAGCGACGCCCTGCGCCAGTTAGCGGCGCTGCTGGGCGATGACGACCTCCGTCAGCGCACC
GAGGCGCTGATCGCGCGTGAAGAACAGGCGGCTGAGCTGGCCCTGCAACCGTGGCGTGAACAGCTGCGTGGCCGC
AAGGCCCTGCTCTACACGGGTGGTGTCAAAAGCTGGTCTGTGGTGTCCGCGCTTCAGGATCTGGGTATGACCGTG
GTTGCCACGGGCACGCGTAAGAGCACGGAAGAGGATAAACAGCGCATCCGCGAATTGATGGGCGAAGAGGCCGTG
ATGCTTGAAGAAGGCAACGCACGTACCTTATTGGATGTAGTTTATCGCTATCAAGCAGACCTGATGATTGCCGGT
GGCCGCAACATGTATACCGCCTACAAAGCGCGCTTGCCGTTCCTGGACATCAACCAGGAACGCGAGCACGCGTTT
GCGGGCTACCAAGGCATCGTGACCTTAGCGCGCCAGCTGTGCCAAACGATTAACAGCCCGATCTGGCCGCAGACT
CATTCCCGCGCACCGTGGCGCTAATGTCACGCTAGGAGGCAATTCTATAAGAATGCACACTGCACCTAAACCTAC
CACACCTGGAAGAAGTAATTATGGCAGACATTTTCCGCACTGATAAGCCGTTGGCTGTGTCGCCGATCAAGACCG
GCCAGCCGCTGGGTGCGATCCTGGCGTCCCTGGGTATCGAGCACTCGATTCCGCTGGTACATGGCGCGCAGGGCT
GTTCGGCTTTTGCCAAGGTTTTCTTTATCCAGCACTTCCACGATCCGGTCCCGCTGCAAAGCACGGCAATGGACC
CGACCAGCACCATCATGGGCGCTGATGGTAACATCTTCACCGCGCTGGACACTCTCTGCCAACGCAATAACCCGC
AAGCAATTGTGCTGCTGAGCACCGGCCTCTCCGAGGCGCAGGGCAGCGACATTTCCCGTGTAGTGCGTCAGTTCC
GTGAAGAATATCCGCGTCATAAAGGCGTGGCGATTCTGACTGTTAACACCCCGGACTTTTACGGTAGCATGGAGA
ACGGCTTTTCCGCTGTCCTGGAGTCTGTGATTGAACAGTGGGTTCCGCCAGCCCCACGTCCGGCGCAGCGCAATC
GTCGCGTCAATCTTTTGGTGAGCCATCTCTGTAGCCCAGGCGATATTGAGTGGCTGCGCCGTTGCGTCGAGGCCT
TCGGTCTGCAACCGATCATTCTGCCGGATCTGGCTCAGAGCATGGACGGCCACCTTGCTCAGGGTGACTTTTCGC
CGCTGACGCAGGGCGGCACGCCGTTGCGCCAAATCGAGCAGATGGGCCAGAGCCTTTGCTCTTTTGCGATTGGCG
TCAGCCTGCACCGTGCGAGCAGCCTGCTGGCTCCGCGTTGTCGTGGCGAAGTCATCGCCTTGCCGCACCTCATGA
CCTTCCAACGCTGCCACCCCTTTATCCATCAGTTGCCGAAAATCACCGCTCCCGCCGTTCCGGACTGGCTGGAAC
CCCAGCGCGGTCAGCTGCAAGACGCCATGATCGATTGCCACATGTGGCTGCAAGGCCAGCGCATGGCGATTGCCG
CCGAAGGCGACCTGCTGCCAGCGTGGTGCGATTTCGCGAACTCTCAAGGTATGCAGCCGGTCCACTGGTTGCTC
CGACGGGTCATCCGAGCCTGCGTCAGTTGCCGGTGGAGCGCGTGGTGCCGGGTGATCTGGAGGATCTTCAGACCC
TCTTATGCGCACATCCGCCCGACTTACTGGTGGCGAACTCCCACGCCCGTGATTTAGCAGAGCAATTCGCCCTGC
CGCTGGTGCGCGCAGGCTTCCCGCTGTTTGACAAACTGGGCGAATTTCGTCGTGTTCGCCAGGGTTATAGCGGTA
TGCGTGATACCCTGTTCCAGTTGGCGAACCTGATCCGTGAACGCCATCATCATCTGGCTCATTATCGCAGCCCGC
TGCGCCAGAACCCAGAATCCTCGTTGTCTACGGGTGGCGCGTACGCAGCGGATTAActagagattaaTATggaga
```

-continued

```
aattaagcATGAAAACTATGGACGGTAACGCTGCGGCTGCATGGATTAGCTACGCCTTTACCGAAGTGGCTGCGA
TCTACCCGATTACGCCGAGCACCCCGATGGCGGAAAATGTGGACGAATGGGCTGCGCAGGGCAAGAAGAACCTCT
TCGGCCAGCCGGTGCGCCTGATGGAGATGCAGTCGGAAGCGGGTGCAGCAGGTGCTGTGCATGGCGCCTTGCAAG
CTGGCGCACTGACGACCACCTACACCGCGTCGCAGGGCCTGTTGCTGATGATCCCAAACATGTACAAATCGCGG
GTGAACTGCTGCCGGGTCTCTTTCATGTTTCGGCACGCGCACTGGCCACCAATAGCCTCAACATCTTTGGCGATC
ATCAGGATGTAATGGCGCTGCGCCAAACGGGCTGCGCGATGTTGGCCGAGAATAACGTCCAGCAAGTTATGGATT
TGTCCGCGGTAGCCCACTTGGCAGCGATCAAAGGTCGCATTCCGTTCGTGAACTTCTTCGATGGCTTTCGCACCA
CCCACGAAATCCAGAAGATCGAGGTTCTCGAATATGAACAGCTGGCCACCTTGTTGGATCGTCCGGCCCTGGACA
GCTTCCGCCGTAACGCCGTTCACCCGGACCACCCGGTCATCCGTGGCACCGCCCAGAACCCGGACATCTACTTCC
AGGAACGTGAGGCCGGTAACCGTTTCTATCAGGCGCTCCCGGATATTGTGGAATCTTACATGACCCAGATTTCTG
CCCTGACTGGTCGCGAGTATCACCTGTTTAACTACACTGGTGCTGCGGATGCGGAGCGCGTGATCATCGCGATGG
GCTCTGTCTGTGACACCCTCCAAGAGGTGGTTGACACGCTGAATGCAGCGGGTGAGAAAGTTGGTCTGCTCTCCG
TTCATCTTTTCCGCCCGTTTTCGTTAGCGCACTTCTTCGCCCAACTGCCGAAAACTGTACAGCGTATCGCAGTAT
TGGACCGTACGAAAGAGCCAGGTGCTCAAGCAGAGCCGCTGTGCCTCGATGTGAAGAATGCCTTTTACCACCATG
ACGATGCCCCGTTGATTGTGGGTGGTCGCTATGCCTTGGGCGGTAAGGACGTGTTGCCGAACGATATTGCGGCCG
TGTTTGATAACCTGAACAAACCGCTGCCGATGGACGGCTTCACGCTGGGTATCGTGGACGATGTTACCTTCACCT
CTCTCCCGCCAGCGCAGCAGACCCTGGCGGTTTCTCACGACGGCATCACGGCATGTAAGTTTTGGGGCATGGGCT
CCGACGGCACGGTTGGTCCGAACAAGTCCGCGATCAAGATTATCGGCGACAAAACGCCACTGTATGCGCAAGCGT
ACTTTTCCTACGACTCGAAGAAGAGCGGTGGTATTACCGTCAGCCATCTGCGTTTTGGTGATCGCCCGATCAACT
CCCCGTATTTGATCCATCGCGCGGATTTCATCTCGTGCAGCCAGCAAAGCTATGTTGAACGCTACGATCTGCTGG
ATGGCCTTAAACCGGGTCGCACCTTTCTGCTGAACTGCTCCTGGAGCGATGCCGAACTGGAGCAACATCTGCCGG
TCGGTTTCAAACGTTATCTGGCACGCGAGAATATCCACTTCTACACTCTCAACGCTGTGGACATCGCCCGTGAGC
TTGGTTTGGGTGGCCGTTTCAACATGCTGATGCAGGCTGCCTTCTTCAAACTGGCCGCGATCATTGACCCGCAGA
CTGGTGGGACTATCTGAAGCAGGCTGTTGAGAAAAGCTATGGCAGCAAAGGTGGGGCGGTCATCGAGATGAACC
AGCGTGCCATCGAGCTTCGCATGGCCAGCCTGCACCAGGTGACGATCCCGGCACATTGGGCCACCCTGGATGAGC
CAGCGGCGCAGGCGTCCCCGATGATGCCGGACTTTATCCGCGACATCCTGCAACCGATGAACCGTCAGTGCGGCG
ACCAGCTTCCGGTGTCGCCTTTTGTCGGCATGGAAGATGGCACCTTCCCGTCCGGCACGGCCGCATGGGAGAAAC
GTGGCATCGCCCTTGAGCTGCCAGTCTGGCAGCCGGAAGGCTGCACGCAGTGCAACCAGTGCGCCTTCATTTGTC
CGCACGCCGCGATTCGTCCGGCGTTGTTGAATGGCGAAGAGCATGATGCTGCCCCGGTTGGCCTGCTGAGCAAAC
CGGCACAAGGCGCTAAACAATATCACTATCATCTGGCGATTAGCCCGCTGGACTGCTCCGGCTGTGGCAACTGCG
TTGACATTTGTCCAGCTCGTGGCAAAGCGTTGAAGATGCAGTCTCTGGATAGCCAACGCCAGATGGCTCCGGTGT
GGGATTATGCGCTGGCGCTGACCCCGAAGTCTAACCCGTTTCGTAAAACCACCGTCAAAGGCTCGCAGTTCGAAA
CCCCGCTGCTGGAGTTTAGCGGTGCGTGCGCTGGTTGTGGCGAAACGCCGTATGCGCGCCTCATTACCCAGCTGT
TTGGCGACCGCATGCTGATTGCCAATGCCACCGGCTGTTCCAGCATCTGGGGCGCATCTGCGCCGAGCATCCCGT
ATACCACCAATCATCGTCGTCATGGTCCGGCCTGGGCGAATAGCCTGTTTGAGGACAATGCCGAATTTGGTTTAG
GTATGATGCTGGGCGGTCAAGCTGTGCGTCAACAGATCGCGGACGATATGACGGCTGCGTTAGCGCTCCCGGTTT
CCGATGAGCTGAGCGACCCGATGCGCCAGTGGTTGGCGAAACAGGACGAGGGTGAAGGCACGCGTGAGCGTGCGG
ACCGTCTGAGCGAGCGCTTAGCCGCGGAGAAAGAGGGCGTTCCGCTGTTAGAGCAGCTGTGGCAAAATCGTGATT
ACTTTGTGCGTCGCAGCCAGTGGATTTTCGGCGGTGACGGCTGGGCCTATGATATTGGCTTCGGTGGCCTGGACC
ACGTCCTCGCCAGCGGTCAGGATGTGAACATTCTGGTATTTGACACCGAAGTCTACTCGAACACCGGCGGTCAAA
```

-continued

```
GCAGCAAATCGACCCCGCTCGCGGCCATCGCCAAGTTCGCGGCTCAGGGCAAGCGCACCCGCAAGAAAGACCTGG
GTATGATGGCGATGAGCTACGGCAACGTCTATGTAGCCCAGGTGGCGATGGGTGCGGATAAAGATCAAACTCTGC
GCGCCATTGCGGAAGCTCAAGCGTGGCCAGGCCCGTCGCTGGTGATTGCGTATGCGGCCTGCATCAATCATGGCC
TGAAGGCCGGTATGCGTTGCAGCCAACGTGAGGCGAAGCGCGCTGTTGAGGCGGGCTACTGGCACCTGTGGCGTT
ATCACCCGCAGCGCGAACCGGAAGGCAAGACGCCGTTTATGTTAGATAGCGAAGAACCGGAAGAGTCGTTCCGTG
ACTTTCTGTTGGGTGAGCTGCGCTACGCATCCCTGCACAAGACCACCCCGCACCTCGCCGATGCCCTTTTCAGCC
GTACCGAAGAAGATGCGCGTGCGCGCTTTGCGCAATACCGTCGCCTGGCTGGCGAAGAGTAATAATACTCTAACC
CCATCGGCCGTCTTAGGCGTTTTTTGTCCGTGGttagttagttagcccttagtgactcTAATACGACTCACTAGA
GAGAGACGCGACTTCCACAGAAGAAGACTACTGACTTGAGCGTTCCCTCTCTGTAATACATCAAATCAATCATAG
GAGGGCTAAAATGACCTCTTGTTCGTCGTTTTCTGGCGGTAAAGCGTGCCGTCCGGCCGATGACTCCGCGCTGAC
TCCGCTGGTGGCCGACAAGGCAGCTGCGCACCCGTGCTATAGCCGCCACGGCCATCACCGCTTCGCGCGTATGCA
CCTGCCAGTCGCTCCGGCCTGCAACTTACAATGCAACTACTGCAACCGCAAGTTCGATTGCAGCAATGAAAGCCG
TCCGCTGGTGGCCGACAAGGCAGCTGCGCACCCGTGCTATAGCCGCCACGGCCATCACCGCTTCGCGCGTATGCA
GCAGCTGtcgGTGGTCGCTATTGCTGGTCCGGGCGATCCGCTTGCGAATATCGCCCGCACCTTCCGTACCTTGGA
GCTTATTCGCGAACAGTTGCCGGACCTGAAACTGTGCCTGAGCACCAACGGCTTGGTGCTGCCAGATGCCGTTGA
TCGTCTGCTCGATGTGGCCGTGGATCACGTTACCGTCACCATTAACACCCTGGACGCAGAAATCGCAGCGCAAAT
CTACGCGTGGTTGTGGCTGGATGGCGAACGCTACTCCGGTCGCGAAGCCGGCGAAATTCTCATTGCCCGCCAGCT
GGAAGGCGTACGTCGCCTGACCGCGAAAGGTGTGCTCGTCAAGATCAACAGCGTATTGATTCCGGGCATCAATGA
CAGCGGCATGGCGGGTGTTAGCCGTGCGCTGCGCGCGTCTGGTGCGTTCATCCACAACATCATGCCACTGATTGC
GCGTCCGGAGCATGGCACTGTTTTCGGTCTGAACGGCCAGCCGGAACCGGACGCGGAAACCCTGGCGGCGACGCG
CTCCCGCTGCGGCGAGGTTATGCCACAAATGACCCACTGCCACCAGTGCCGTGCCGACGCGATTGGCATGCTTGG
TGAGGATCGCTCGCAACAGTTTACGCAATTACCGGCTCCGGAGTGCCTCCGGGCCTGGCTGCCGATCCTGCATCA
GCGTGCTCAGTTGCATGCGAGCATCGCCACGCGCGGTGAGAGCGAAGCCGATGACGCCTGCCTGGTGGCCGTTGC
GTCGAGCCGTGGCGATGTAATTGACTGCCATTTCGGCCATGCCGACCGTTTCTATATCTATAGCCTGTCTGCGGC
TGGTATCGTTCTGGTTAACGAACGTTTCACCCCGAAATACTGCCAGGGTCGCGATGACTGCGAGCCGCAGGACAA
TGCCGCACGCTTTGCTGCCATCCTTGAGTTGCTGGCGGACGTCAAAGCGGTGTTTTGTGTGCGTATCGGCCATAC
CCCGTGGCAACAGCTGGAGCAGGAAGGCATCGAACCGTGCGTGGATGGCGCCTGGCGTCCGGTATCCGAGGTCCT
GCCGGCATGGTGGCAGCAGCGCCGTGGTAGCTGGCCGGCTGCATTGCCGCACAAAGGCGTTGCGTAAACTACGAG
ATTTGAGGTAAACCAAATAAGCACGTAGTGGCATTAAAGAGGAGAAATTAAGCATGCCGCCATTGGACTGGTTGC
GTCGTTTGTGGTTACTCTATCACGCCGGCAAAGGCAGCTTTCCGCTTCGTATGGGCTTGTCGCCGCGTGACTGGC
AAGCTCTGCGCCGTCGCCTGGGCGAGGTGGAAACGCCGCTGGATGGCGAAACCCTGACCCGTCGCCGTCTGATGG
CGGAGCTGAATCCGACCCGCGAAGAAGAACGCCAGCAGCTGGCTGCCTGGCTGGCCGGTTGGATGCAACAGGATG
CCGGTCCGATGGCGCAGATTATCGCAGAGGTGAGCCTGGCGTTCAACCATCTCTGGCAGGACCTTGGCCTCGCGA
GCCGCGCTGAACTGCGTCTGCTGATGTCTGACTGCTTCCCGCAGCTGGTTGTTATGAACGAGCACAACATGCGCT
GGAAGAAATTCTTTTACCGCCAGCGTTGCCTGCTGCAACAGGGCGAAGTCATCTGTCGCAGCCCGTCTTGCGATG
AATGCTGGGAACGTTCTCCGTGCTTTGAGTAATACATATCGGGGCGTAGGGGTTTTTGTGTCTGTAGCACGTG
CATCTAATACGACTCACTAATGGGAGAGACAAGAGTCTCAATTATAAGGAGGCTTTACTACATGGCGAACATCGG
CATCTTCTTTGGTACGGATACCGGCAAAACCCGCAAGATTGCGAAGATGATTCACAAACAGCTGGGCGAGCTGGC
CGATGCCCCGGTTAACATCAATCGTACCACTTTGGATGACTTTATGGCTTACCCAGTCCTGTTGCTCGGCACGCC
GACGCTTGGTGATGGTCAACTGCCGGGCTTAGAGGCGGGCTGCGAGAGCGAAAGCTGGTCTGAGTTTATCTCCGG
TCTGGATGACGCTTCCCTGAAGGGCAAAACCGTGGCGCTGTTTGGCCTGGGCGACCAGCGTGGTTACCCGGACAA
```

-continued

```
CTTCGTGTCGGGTATGCGTCCGCTGTTCGACGCGCTGAGCGCCCGTGGCGCCCAGATGATTGGTAGCTGGCCGAA
CGAAGGTTATGAGTTTAGCGCATCGTCCGCGCTGGAAGGCGACCGCTTCGTCGGCTTGGTGCTGGATCAAGACAA
TCAGTTCGACCAGACCGAAGCGCGCCTGGCGTCTTGGCTTGAAGAGATCAAACGCACCGTTCTGTAATAATACAT
ATCGGGGGGGTAGGGGTTTTTTGTGGTCATTACAACGGTTATggtctcaggagtaatacgactcactagagagag
aggtcgcggacccggccgatccgggggcctcaaagccgcctcaccagatactgacaaataaaccagcgaaggagg
ttcctaatgtggaactacagcgagaaagtcaaggaccatttcttcaatccgcgcaacgcgcgtgttgtggataac
gcaaatgcggtgggcgacgtcggcagcttatcttgtggcgatgctctccgcttgatgctgcgcgtggacccgcag
agcgaaatcatcgaagaagcgggctttcagaccttcggctgcggcagcgcgattgcgtcgtccagcgcactgacg
gagctgatcatcggtcacaccctggcggaagcgggtcagatcaccaaccagcagatcgccgactatctggacggc
ttaccgccgaaaagatgcactgctctgtaatgggccaggaagctcttcgtgcggccattgctaactttcgcggt
gaatcgctggaagaggagcatgacgagggtaagctgatctgcaagtgcttcggcgtcgatgaaggccatattcgc
cgtgctgtccagaacaacggtcttacgacgctggccgaggtgatcaattacaccaaggcaggtggcggttgtacc
agctgccatgagaaaatcgagctggccctggccgagattctcgcccaacagccgcaaaccacccggcagttgcg
tccggtaaagatccgcactggcagagcgtcgtggataccatcgctgaactgcgtccacatatccaagcggacggt
ggtgacatggcgctgttgtccgtgacgaaccaccaagtgactgtttcgctgtcgggcagctgttctggctgcatg
atgaccgacatgaccctggcgtggctgcaacagaaattgatggagcgtaccggctgctatatggaagttgttgcc
gcctaagaccgcgcgccccgtcagagcaatgcgtataccagctctcctgtcagcagaatggctccagtacatcta
acggggcagtatccgcggcaagtcctagtccaatcgatacccgtagaccattctgaaatcgaaggaggttttcca
tgaaacaagtgtacctggacaacaacgcgaccacccgcctggacccgatggttctggaagcgatgatgccgtttc
tcacggatttctatggcaatccgtccagcatccatgacttcggcatcccggcacaagcggcgctggaacgtgcgc
accagcaagctgcggcactgctgggcgcagagtacccgtctgaaatcattttcacgagctgtgcgaccgaggcca
ctgcaaccgccattgcgtcggccatcgcgttattgccggaacgccgcgaaatcatcacctcggtagtggagcacc
cggctacgctggcggcgtgcgagcacctggaacgccaaggctatcgcatccatcgcattgcggtggatagcgaag
gtgcgctggacatggcccagttccgtgcagcgctctcgccgcgtgtcgcgttggtgagcgtgatgtgggccaaca
acgaaaccggcgtgctgttcccgattggcgaaatggccgagcttgcccacgagcagggcgctctgttccactgcg
atgccgttcaggtcgttggcaaaatcccaattgctgttggccagacgcgcatcgacatgctgtcttgctccgcgc
acaagtttcatggtccgaagggtgttggttgcttgtacttacgtcgtggcacgcgctttcgtccgctgcttcgcg
gtggccatcaagaatatggtcgccgtgccggcactgagaatatctgtggcatcgtcggcatgggcgctgcgtgcg
aactggcgaacatccatctgccgggtatgacccatattggccagttacgcaatcgcctggagcaccgtctgctcg
ccagcgtgccgtccgtgatggttatgggcggtggtcagccgcgtgtaccgggtactgtcaacctggcgttcgagt
ttatcgaaggtgaagcgatcctgctcttgctgaaccaggctggcattgccgcaagctccggctccgcgtgtacct
ctggcagcttggagccgagccatgtgatgcgcgccatgaacattccatacaccgcggctcacggcaccattcgtt
ttagcctgagccgttatacgcgcgagaaagagatcgactacgtcgttgcgacccctccgccaatcattgatcgtc
tgcgtgccttgtccccgtattggcagaatggtaagccgcgtccggcagatgcagtctttaccccggtttacggtt
aagcgactaggagcctaactcgccacaaggaaacatatggagcgcgtcttgatcaacgatactaccctgcgtgat
ggcgaacaatctccgggcgtagcgtttcgtacctccgagaaagttgccatcgcggaggcactgtacgctgcgggt
atcaccgcgatggaagtcggcactccggcgatgggtgatgaagagatcgcccgcattcagctggtgcgtcgtcaa
ctgccggacgcgacgcttatgacctggtgccgtatgaacgctctggaaatccgtcagagcgcggatctgggtatt
gactgggtggatatctcgatcccagcatccgacaagctgcgtcagtacaagctgcgtgagccgctggccgtgctg
ctggagcgccttgcgatgtttatccatctggcccacacgttaggcctcaaagtatgtattggttgcgaggatgcg
```

-continued

```
agccgtgcgtctggtcagaccctgcgcgccattgccgaggtggcccagcaatgcgcggctgcgcgcttgcgttac gctgacaccgtgggcctgctggacccgttcaccaccgcagcccagatcagcgccctgcgtgacgtttggtcgggc gagatcgagatgcatgctcacaatgatctgggcatggctaccgcgaacacgctggcggcagtttcggctggcgcc acgtcggtgaacactaccgtcctcggtctgggtaacgtgcaggcaacgcagccctggaaaccgttgcgctgggc ctggaacgctgcctgggcgtggaaaccggcgtccatttcagcgcgctcccagcgctctgtcagcgcgtcgcggag gctgcacagcgcgcaatcgacccgcaacagccgctggtgggtgaattggttttcacccacgaatctggtgttcac gttgcggcgctgctgcgcgacagcgaatcctatcaatctattgccccaagcctcatgggccgtagctaccgtctg gtgctcggcaagcattcgggtcgtcaggctgtcaacggtgttttcgaccagatgggttaccacctgaatgcggcg cagatcaatcagttgctgccggccattcgccgcttcgccgagaattggaaacgctctccgaaagactacgaactg gttgcgatctatgacgaattgtgcggtgaatccgcccttcgtgctcgcggctaaccgatagtttcaagagaaagg gagtagaaacagaatggagtggttttaccagattccgggtgtagacgaattgcgcagcgctgaatccttctttca gttcttcgcggttccataccagccggaactgctgggccgctgctcgcttccggtgttagcgacgttccaccgtaa actgcgtgcggaggtcccgctgcaaaaccgtctggaggacaatgatcgtgcgccgtggctcttggcgcgccgcct cctggccgaatcttatcagcagcaatttcaggagagcggcacctaattcaccagcccgaatcaatataggtcata caatgcgcccgaaattccacttctctgaagaggtccgcgtagttcgcgcgattcgtaatgatggcaccgtggcgg gttttgcgccaggtgcgctgctggttcgtcgcggttcgacgggctttgtgcgtgactgggggtgtgttcctgcaag accagatcatctatcaaatccactttccggaaaccgaccgcattatcggctgtcgcgagcaggagttaatcccga ttacccagccgtggttggctggtaacctccagtatcgtgacagcgtcacgtgccaaatggcactggctgtcaacg gtgacgtggttgtgagcgccggtcaacgtggccgtgtggaggccactgatcgtgcgaacttggcgattcctaca ccgtggacttcagcggccgttggttccgcgttccggtccaggccatcgcgctgattgaagagcgcgaagaataat cagagactgaagttattacccaggaggtctataatgaatccgtggcagcgctttgcccgtcaacgccttgctcgc agccgctggaaccgtgatccggctgctctcgacccagccgatacccagcgttcgagcaggcgtggcagcgtcaa tgccatatggaacaaaccatcgtagcgcgtgtcccggaaggcgatattccggctgccttactggaaaacatcgcg gccagcctggcgatctggctggacgagggtgacttcgctccgccggagcgcgctgcgattgtgcgtcatcatgca cgtctggagctggcgtttgccgacattgcccgccaggcaccgcaaccggatctgagcacggttcaagcgtggtat ctgcgtcaccagacgcaattcatgcgtccggagcagcgtctgacccgtcacctgctcctgacggtcgataatgat cgcgaggcggtgcatcaacgcatccttggcctgtatcgtcagatcaacgcgagccgtgacgccttcgccccactg gcacagcgccactctcattgcccgtccgccttggaagaaggccgtctgggctggatctcccgtggtctgctgtac ccgcagctcgaaaccgcgttgtttagcctggcggaaaacgcactgtcgctgccgattgcgtcggaattgggttgg cacctgttatggtgcgaggccattcgtccggcagcccgatggagccgcaacaggcccttgaatctgcgcgcgac tacttgtggcagcagagccagcagcgccaccagcgtcaatggctggagcagatgatttcccgccaaccgggcctg tgtggttaaTACCATAACCCGttggggcctctaaacgggtcttgaggggttttttgt
```

Paenibacillus WLY78 nif cluster (SEQ ID NO. 3)

```
gtagggcgcattaatgcagctggactagtGAATTGAGGATAAATGTCAGGGATTTCATGGAGAAGTGAATTGACT

GTATTTGTCCCTGTCTCTAAGATGTAATTATATTCCAGACAAAAACAGAGATTTATGTAAGGGAATATAACGTAG

AGAGGAGGGAATGAATGGACTCTTTAGCTGATCTCTCGGAAACCCCCTTAGCATTAGAAACTCTCAGACGACATC

CCTGTTATAACGAAGAGGCACATCGCTATTTTGCGCGCATTCATCTTCCAGTAGCCCCGGCATGCAATATTCAGT

GCCATTATTGCAACCGCAAATTCGATTGCGTCAATGAAAGCCGTCCCGGCGTTGTTAGTGAACTGCTTACGCCGG

AGCAGGCGGCGAGCAAGACCTATGGCGTAGCGGCACAGCTGATGCAGCTGTCCGTTGTCGGCATTGCGGGACCTG

GAGATCCGCTGGCCAATGCGGAGGCAACCTTCGATACCTTCCGCCGGGTCCGTGAGACAGTTAAGGACGTCATAT

TCTGTCTCAGCACGAATGGCCTTACTTTGATCAGGCATATCGACAGGATTGTAGAGTTGGGTATTTCGCATGTCA
```

-continued

```
CGATCACGATCAATGCTGTAGATCCAGTGGTGGGGAGCCGCATTTATGGATGGGTCTACGATGAAGGAAAACGCT
ATGCGGGTGAGGAGGCCGCACGACTGTTGATTGACCGCCAGCTGGCAGGCTTGAAGATGCTGGCTTCGAGAGGTG
TATTGTGCAAGGTGAACTCGGTGCTGATTCCCGAAGTCAATGATGCCCATCTGCCGGAGGTAGCGAGGGTGGTCA
AGGAGCACGGCGCGGTGCTGCACAACATTATGCCGCTCATCATCGCACCTGGTAGCCGATATGAGCAGGAAGGGA
TGCGGGCACCCCGTCCCCGTCTGGTCCGGCAGCTGCAGGAGCAATGTGCTGAAGCGGGAGCTGTCATTATGCGCC
ATTGCCGTCAGTGCAGGGCGGATGCGATTGGACTGCTGGGCGAGGATCGCAATCAGGATTTTACATGGGAGAACA
TTGCTGCTGCTCCTCCCATGGATGAAGAGGCAAGGGCACAATTTCAGAAAGAACTGGATGAGAAGGTGAGAGTGA
GAATGGAACGCAAGGAGGGACAATCGCACCACAAACAACCGTCAACCGGTGCTGGTTGTAGCTGCCCGTTATCTG
GGGATAAGCCTGAAGCGAGCTTTACCTCAAAGCCGGTCTTAATCGCTGTGGCTAGTCGTGGTGGAGGGAAGGTGA
ATCAGCATTTCGGTCGTGCCAAGGAATTTATGATCTATGAAAGCGACGGGACCATCGTAAATTTCATAGGCATTC
GTAAGGTGCAATCCTACTGTCACGGGAAAGCCGATTGCAATGGAGATAAGGCCGAGACGATCAAGGAGATCCTTT
CCATGGTACATGATTGTGCATTGCTCCTGTCGTCCGGCATAGGCGAAGCCCCCAAAGAGGCATTGCAGGAAGCGG
GCGTGCTGCCTATTGTGTGCGGCGGCGATATTGAGGAGTCCGTTCTGGAATATCTAAAATTTCTGCGTTATATGT
ATCCTGTGCAGACGGGTAAGGGAAGTAAGCGTAATAAGGGAGTTAAGGGCAATCATTCGGATTTACCCATTGAAC
ATTTTGGAGGCTGAGAAAATATGAGACAAATTGCGTTTTACGCTAAGGGCGGTATCGGCAAATCGACAACCTCGC
AGAATACACTGCCTCAACTTGCGACCAAATTCAAACAAAAAATTATGATCGTAGGCTGTGATCCCAAGGCAGACT
CCACCCCTCTTATTTTGAATACCAAGCCCCAACACACCGTACTCCATCTCCCACCTCAAAGCCGTACCCTCCACC
ACTTGCAACTGCAGCATCTTCTCCAGAACCCCTTCGCTGATATTCTCAACCTCGAATCCCGCCGCCCACACCCCC
CTCTCCCCTCTCCACCACCCCCTATCATCACACCCATTAATTTTCTCGACCAAGACCCCCCCTACCAACGCCTCC
ATTTCGTTTCCTACCATCTACTGGGGGACGTCGTGTCCGCGGCGTTCGCCATGCCGATCCGGGAGAACAACGCCC
AGGAAATCTACATCGTATGCTCAGGCGAGATGATGGCTATGTACGCTGCCAACAATATTGCGCGCGGGATCTTGA
AGTATGCCAACAGCGGCGGGGTGCGTTTGGGCGGCTTAATCTGCAACAGCCGGAATACGGACCTGGAAGCGGAAT
TGATCACAGAGCTTGCAAGAAGATTGAACACGCAGATGATCCACTTTTTGCCGCGTGACAATGTTGTGCAGCACG
CTGAGCTGCGCCGTATGACCGTTACCCAATATAACCCGGAACATAAGCAGGCTGCGGAGTATGAAGAGCTGGCAG
GTAAGATTTTGAATAATGACATGCTAACGGTTCCCACGCCCATTTCCATGGAAGATCTGGAGGATCTATTGATGG
AATTCGGCATTATTGAGGATGAAGAAACCGCAATTAACAAAGCTGAGGCGTCCGGGCAGTAGGCTGTAGCCAGAA
GGCTTAATGACGGAACCATCGTGTAATGATGGGAGGAGCTGAACGCGCAGCTCGCAGGAGGGAGGAATAGGCCAA
ATGAGCAGTATTGTGGATAAGGGTAAGCAGATCGTAGAGGAGATACTGGAGGTATATCCCAAGAAGGCCAAGAAG
GATCGGACCAACCATTTTGAGATCGCGGATGAGGAGCTTGTGAACTGCGGAACCTGTTCCATCAAGTCCAACATG
AAATCACGGCCTGGCGTCATGACAGCAAGGGGCTGTGCTTATCCAGGCTCCAAGGGTGTGGTATGGGGCCCGATT
AAAGACATGGTGCACATTAGCCATGGTCCCATCGGCTGCGGACAGTACAGTTGGGGTACCCGACGCAATTATGCG
AATGGGATATTGGGAATCGATAATTTTACCGCCATGCAGATTACAAGCAATTTTCAGGAAAAAGATATCGTGTTC
GGTGGAGATAAGAAGTTGGAGGTGATCTGCAGGGAAATTAAGGAGATGTTCCCGCTGGCTAAGGGTATCTCCGTG
CAATCTGAATGTCCGGTCGGACTGATTGGTGATGATATCGGGGCCGTGGCCAAGAAGATGACAGAGGAGCTGGGC
ATTCCGGTCATTCCTGTACGCTGTGAGGGCTTTCGCGGGGTGAGTCAGTCTCTGGGCCATCACATTGCCAATGAT
GCTATCCGCGATTTTCTAATGGGGCGCCGAGAACTGAAGGAGTGCGGGCCTTATGATGTCTCCATTATCGGAGAC
TACAATATCGGCGGTGATGCCTGGGCGTCGCGCATTTTGCTGGAGGGAAATGGGACTGCGGGTCATAGCGCAGTGG
TCGGGTGACGGTACGATCAATGAGCTGGGGATTGCGCATAAATCCAAGCTCAACCTGATCCATTGTCATCGTTCC
ATGAATTATATGTGCACAACAATGGAGCAGGAATACGGAATTCCCTGGATGGAATATAACTTCTTCGGCCCGACC
AAGACGATGGAGAGCCTCAGAGCGATTGCTGCCCGCTTCGACGAGACGATTCAGGAAAAATGTGAGCAGGTCATC
```

```
GCCCAATATATGCCGCAGATGGAGGCGGTCATCCGTAAATATCGCCCACGTCTGGAAGGTAAAAAGGTGATGCTT
CTGATTGGCGGGCTGCGGGCAAGGCATACCATCGGGGCCTATGAGGATCTGGGTATGGAAATTGTGGCTACAGGC
TATGAATTTGCCCATAAGGATGATTACGAAAAGACGTTTCCCGATGTAAAAGAAGGCACCATTCTGTACGATGAT
CCAACGGCATATGAGCTGGAGGAACTGGCCCAGCGGCTGAATATTGACTTAATGGGCGCCGGAGTCAAGGAGAAA
TACGTGTATCACAAAATGGGCATTCCCTTCCGTCAAATGCACTCCTGGGATTACAGCGGGCCTTATCATGGTTTT
GACGGCTTTAAGATTTTTGCACGTGATATGGATATGACCATAAACAGTCCAGTATGGAGCCTGCTGCCCTCACGG
CAGACTGCGGAGGTGCCGGTATGAGCGAGCGTCCGAATATTGTCGATCACAATCAGCTGTTTCGGCAGGATAAAT
ATGTGCGCCAGCGTGAAGAAAAACGAGCCTTCGAGGCCCCATGTTCGCCGGAGGAGGTTACCGACACCCTGGAGT
ACACCAAGACCAAGGAATACAAAGACAAGAATTTTGCCCGTACAGCCGTAGTCGTGAATCCGGCCAAGGCTTGTC
AGCCGCTGGGAGCGGTTATGGCTGCACTGGGCTTCGAAAAAACGCTCCCGTTCATTCATGGTTCACAGGGCTGTA
CGGCTTATTTTCGCAGTCATCTTGCCCGCCACTTCAAAGAGCCTGTTCCTGCCGTCTCCACCTCGATGACCGAGG
ATGCCGCCGTATTCGGCGGCATGCGCAACCTCATTGACGGTATAGAGAACTGCATTGCCTTGTATCAGCCGGAGA
TGATTGCGGTATGCACGACCTGTATGGCAGAGGTGATCGGGATGATCTGTCTGCCTTCCTGGCCAATGCCCGTC
AGGAGGGAGTCCTTCCTGAGGATATGCCAGTTCCTTTTGCCAATACCCCCAGCTTCTCTGGTTCACATATTACAG
GCTATGACGCCATGCTGCGCTCTGTACTGGAGACGCTGTATAACAAGTCAGGCCGGACGGCGCAGCCTGGTCATG
AATTGAAGCTGAATGTACTGCTCGGGTTTGACGGGTATACGGGCAATTTTGCGGAAATGCGGCGCATGCTGGGGA
TGTTCGGCGCTACGTATACCATTCTGGGTGACCACAGCAGTAATTTTGATTCAGGGGCCACTGGAGAGTACAGCT
ACTATTACGGGGAACGCCGCTTGAGGATGTGCCTAAGGCCGCAGATGCTGCCGGCACGTTGGCGATTCAGCAGT
ACTCTCTTCGTAAAACACTAGGCTATATGAAGCAAACCTGGGGGCAGCAGGTGTCCTCCATCTCCACACCGCTGG
GCATCCGGGCTACAGATCGCTTGCTTGAGGAGATTAGCCGCCTGTCTGGAAGGGAAATTCCCGAGGCATTGAAGC
AGGAGCGCGCCCGAATTGTGGATGCCATGATGGATTCACATGCTTATCTGCACGGCAAACGAGTGGCTATGGCAG
GAGACCCGGACATGCTCATCGGCTTGATTGGCTTTTGTCTGGAGCTGGGCATGGAGCCGGTGCATATTGTTTGCT
CCAATGGGGACCGAAAATTTGAGAAGGAAGCAGAGCTTCTGCTGAAGTCCAGCCCTTACGGTGCAGAAGCCACGG
TTCATTCCGGTCAGGATTTGTGGCATATGCGTTCGCTGCTGTTCCAGGACCCGGTGGACCTGGCTATTGGCAGCT
CCCATCTGAAGTTTGCAGCGAAAGAGGCGGAAATTCCTTTGCTTCGTGTAGGCTTTCCGATCTTCGACAGGCATC
ATGTCATGGAGGAGCAGGCTCCGGATCATAGCTTTGATCTGGTGCGCTAATTGCTGTATCGCGTAGAAGGAAGTT
GACAGCTTGGCTTGTGATTTCAATGGATTCTATCTGAAATAAGGGGGTGTGTGGATGGAGCCGGCTGTGTCTAAC
GGAAGGCTGGAGGTATCCTGCGGCAATAAAATTCCCAAAAGCACGCCCTGTCCCCGGCCTGTGCCGGGAGAGGCT
TCGGGTGGCTGCTCCTTTGACGGGGCCCAGATTACACTGATCCCCATTGCAGATGCGGCTCATCTGGTGCACGGG
CCAATTGCGTGTCTCGGCAATAGCTGGGAGAGCAGAGGCAGTCTGTCCAGCGGCCCAGAGCTGTCGGCTTATGGC
TTCACTACTGATCTTGGAGAACAGGACATCATTTTTGGTAGTGAACAGAAGCTGCATGAATCGATCCGCTACATT
GTCAGCCGCTTTGCTCCTCCCGCTGTGTTTGTCTATACCACATGTGTCACAGCCCTCACTGGTGAAGATATCGAG
GGGGTTTGCAAGGCTGAATCGGAGCGGCTGGGGACGCCGATCATTCCGGTGAACAGTCCGGGATTTGTGGGCAGT
AAGAATCTCGGAACCCGGCTGGCCGGAGATGTGCTGTTCCAGCATATTATCGGCAGCACCGAGCCGGAACAGACA
ACCTCCCATGATATCAATCTCATTGGGGAATACAATATTGCGGGCGAGATGTGGCATATCGAGCGGCTGATGCAG
CAGGCGGGAATGAGTATCCTGTCCCGAATTACCGGGGACGGTCGGTTCCGCGAGGTGGGCTGGGCGCACCGTGCC
AAGGCCAACATGGTCGTATGCAGCCGGGCTTTGCTGGGTCTGGCAGTCCAAATGGAGCGTAAATACGGCATTCCT
TATTTTGAAGGTTCATTTTATGGAGCAAAGGAGACGAGTTATTCCTTGCGGCAGATGGCTTACCTGACCGGAGAT
CGTGATGTGGAGCGACGGGTGGATAAGCTGGCCGCACGGGAGGAAATGAGGCTATCGCTGGAGCTGGAGCCCTAC
CGCAAGCAGCTGAAAGGAAAGCGGGCAGTGCTCTATACCGGGGGTGTAAAGAGCTGGTCTGTCATTACGGCTTTG
CAGGAGCTGGGCATAAAGGTGGTTGGTGTAGGCACGAACAAGAGCACTGCCGAGGATGTATCCCGGATTGCTGAC
```

-continued

```
CGTATCGGGGATGATGCAGAATACATCCCGGAAGGAGGCGCCCGGCAGATTCTCAAGACCGTACGGAGCCGCAAG
GCAGACATGGTCATTGCCGGAGGCCGGAACATGTATATGGCGCTTAAGGAACAGATTCCTTTTGTGGACATCAAT
CAAGAGCGGCACAAAGCCTATGCGGGCTATGACGGGCTGTTGTCTCTGGCGAAACAGCTTGTGCATACGCTGCAG
CATCCAGTATGGGAGCTGACCGCCAAATTGGCTCCATGGGAGGAGGAGACGGAATTTGCTGATTAAATCCGCCAC
GAAGCCTGTCAGTGTCAACCCGCTCAAGGTAGGACAGCCTTTGGGCGGCGTGCTGGCTCTGCAGGGGATGTATCG
CTCAATGCCTTTGCTGCACGGCGCTCAGGGCTGCTCGGCCTTCTCCAAGGCGCTGCTGACTCGCCATTTTCGAGA
GCCGATTGCCGTTCAGACCTCTGCGTTGCAAGAGATGGACGTTATATTTGATGCAGACCGGAATCTGGAGGAGGC
GCTGGATCATATCTGGTCCAAACACCATCCAGATGTCATCGGCGTTATCAGCACGGCCCTCACTGAGGTGGCAGG
CGTTGACTTTCAGTCTAGGGTAAAGGCGTTCAAGCGAGAACGGGCATTGAAGGACAGTCTGCTGTTTTCTGTATC
GCTGCCTGATTTTCACGGCTCTCTGGAGACGGGCTACAGCAGTACAGTAGAGTCACTAATGGATGCCGTACTCGG
GTTGGCCGGGGGCAAGTCCCCCAAAAAACAGCGCCGGACGCAGGTCAATCTGCTGCCGGCTTCTTATCTGACTGC
CGGAGATGTCATGGAAATCAAGGTATTATCGCTTCCTTCGGCCTGGAGGTTATTACGCTCCCCGATATTTCCAC
TTCCTTGTCCGGTCACCTGCTGACAGGCTTTTCCCCTTTGACGAGAGGGGGGACTCCGCTGGATTCAGCCTGCCA
GATGCTGGAGTCTTCCTGCACCATTGCCATTGGCGCGAGCATGGAGCGTCCGGCGCGCAGGCTGACTCATGCTGC
AGGTATTCCCTACCACTTGTTCGCTGGTCTGTCTGGCTTGGCCGCGAGTGATGCGTTCATACATTTTCTGCAGAA
AATCAGCCGCGAGCCAGCCCCCGTTCGCTTCCGTTGGCAGCGTGAAAATCTGTTGGACAGCATGCTGGATGCCCA
TTTCTATTATTCTGGCGCTTCGGCTGTAGTGGCGCTAGAACCGGATCATATGCTGTCGACCGCAGCCTGGCTGGA
GGAGATGGGAGTGGAACTGAAGCGGCTAATTACACCCTGCAGCACGCCCGCACTGCAAAAGACAGAACGGGAAGT
GGAGATGGGAGTGGAACTGAAGCGGCTAATTACACCCTGCAGCACGCCCGCACTGCAAAAGACAGAACGGGAAGT
CTGGATCGGTGACCTGGATGATGCAGAGGAGAGCGCGCAGGGTGTTGATTTGTGGATCAGCAACTCACATGGAAG
AAAGGGAGCGGCACGGGCTGGGGCCTCATTCGTACCGGCAGGCTTGCCGGTGTATGACGAGCTAGGCGCCCACAC
ATCCGTAAGCGTCGGATACCGTGGAACCATGGAGTGGGTGAACAAAGTAGGCAATGTATTGCTTGCCGAGAGGGG
GAGGGGAGGATGAAGGTTGCATTTGCGACGGAAGACGGCGTGCTTGTGAATGCTCATTTTGGGCAGAGTCCCATG
TTCACTATATTCGAAATCCGGCACTCAGGCGTCCAGTTCCTGGAGCATCGGCGGATAGCCCTGGGGAGCGATGAG
AATGAGGCGGGCAAGATCGCCAGCCGAATTGGCCTGATCGAGGATTGTGCCTTGATCTTCCTGGTACAGATTGGC
GCTTCCGCCGCCGCACAGGTTACCAAGCGGACCATTATGCCTGTGAAGGTGGCCTTCGGTAGCACCATTGAGGAG
CAGGTCCAGCGTCTCCAGAATATGCTGACTCGCAATCCGCCCATGTGGCTTGCCAAAATCCTGCATGCTGAGGAG
GGCAGCGGCAAAGCCGAATCATGAGCCCTCCTGTAAGGAAGAGCAACCATATAGGGTATTAAGATCCTGCAGACC
GAATATCTTAAAGGCGGGAGCCGCACATGGAGGGGTGGACGAATGGTACAACTGCTGGAAGACAGTAGATACGG
ACGCCAGTTGAAGCTGCTGGGAGTGGAAGGTCAGAACAGGCTAAAGCAGGCTACGGTTATGGTTGCAGGCATCGG
AGGATTGGGAGGGGCAGCGGCCATGTACCTGGCCGCTGCCGGAGTAGGAAAGCTGATATTGGCCCATGAGGGCGT
AATCCATCTGCCCGATATGAACCGGCAGGTGCTGATGGACAGCGGACGAATCGGGGAGGAACGGATGGAGACGGC
ATTACAGCATTTGCATCGTATCAATCCGGAGACCGAGCTTGAGGGCCACGCCCACAGAATCACGGAAGAATCCTC
TGGACCATGGGTAGAAGCGTCGGATATCGTGATTGATGCACGATATGACTTTCCGGAAAGATATGCGCTGAACAG
ACTATGTGTTCGACATGGAAGACCGATGATAGAAGCGGCCATGTACGCCTATGAAGTATCATTGATGACCATTGA
TCCCGGTAAGACGGCATGCCTGGAATGTCTTTACCCGGAAGGCGGACAGCCTTGGGAACCTCTGGGATTCCCGGT
CCTGGGAGCCACCTCCGGCTTGATTGGCTGCATGGCTGCACTGGAAGCGGTCAAATGGATTACAGATGCGGGCAA
TCTGTTCACTGACCGCATGTACCGTATGAATGTGCTGGATATGAGCAGCTGCACCATAGCGGTCAAACGCAACCC
GCGTTGTCCGTGCTGCGGAACGGGAGGGGATACAGATGAGTCGGTTGCATATTTGTGATACGACACTTCGTGACG
GAGAACAGGCTCCGGGCGTTGCCTTTTCAGCCGAGGAAAAAACTGAAATTGCCATCATGCTGGACTCGGCGGGGG
```

-continued

TGGAGCAGGCTGAGATCGGAATTCCGGCAATGGGAAAGACGGAGTGCAGGTCTATTGCCAGGATTGCTGCTCTCG

GACTTCAGATGAAGCTAATGACCTGGAATCGCGCGGTGTTCACGGATATTGATGCAACTGAATCGACAGGTGTCG

GCTGGGCCCATATTTCGGTTCCCGTGTCGACGGTGCAGATGAAGTCCAAGCTGGGTATGAATCCTGAGCAGGTGA

CGGAGCTGATCCGCAAGTCTGTCGATTACGCTCTGTGTAAAGGATTGACTGTTTCCGTAGGCTTTGAGGATGCTT

CAAGGGCAGATGACCTGTTCCTTGAGCAGTTGGCGAATCAGCTCTATAGGGATGGCATCCGGCGCTTCAGATATG

CCGATACGCTGTCCGTTCACCATCCCGCTGCCATAGCTGCCCGTATAGACAGGCTTGTATCGCGCGTGCCACAGG

ATGTGGAGCTTGAGATTCACTGTCATAATGATTATGGCCTGGCGCTTGCCAATACCCTGGCAGCTTTGCAAGCGG

GAGCTGTCTGGGCCAGTACCACGGTGTCGGGACTTGGGGAAAGGGCAGGTAATACCGCGCTGGAGGAGGTGGTGA

TGTCGTGGAGGGACCTATATCAAGGAACCTGCAGCGTCCGTCCCGAACTGCTGAACCCGCTGGCTGCACTGGTGT

CCAAAGCCTCCAACCGAATCATTCCTGAAGGCAAGCCCATTGTGGGAGACATGGTATTCGCCCATGAATCCGGCA

TACATATCAACGGTCTGCTAAAGGAGCGCGCCGCCTATCAGGCGCTTGATCCGACTGAGCTGGGCACTGACCATT

CCTTCGTACTCGGCAAGCATTCGGGCAGAAGTGCAGTTCAATATATGCTGGAGCAGGAAGGAATCGAGGCAGGCT

CCGGTGAAATCAAGTTCCTGCTGGAGCGGCTTCGCCTAGTCGGTGAAGATCCCAAGCGTGTCATCCATAGCGCGG

ATTTAAGACGCTGGCTGCAGTATTATCCGGCAGAGCTGCCGAAATAACCGAAAAAGCGTTCCCGTCCGGTAAGTG

TGACCGTGACTGGAACGCTTT

*Klebsiella oxytoca* M5a1 nif cluster (SEQ ID NO. 4)

GAATTCTAGACTGCTGGATACGCTGCTTAAGGTCATGCAGCAGGAGAACTAAAGGCCCGCTACTCCTCGCCGGCC

AGCCGCCGATACTGGGCAAAGCGGGCCCGCGCGTCCTCCTCGGTTCGGCTAAAGAGCGCATCCGCCAGATGCGGC

GTCGTTTTGTGCAGCGAGGCGTAGCGCACTTCGCCAAGCAAAAGTCGCGGAAGCTCTCCTCCGGCTCTTCGGAA

TCGAGCATAAACGGCGTCTTACCTTCCGCTTCCCGCTGCGGATGATAGCGCCACAGGTGCCAGTATCCCGCCTCA

ACCGCCCGTTTCGCCTCGCGCTGGCTGCAGCGCATACCGGCTTTCAGCCCGTGGTTAATGCAGGCGGCGTAGGCA

ATCACCAGCGACGGTCCCGGCCAGGCTTCGGCCTCGGCGATCGCCCGTAGGGTCTGATCTTTATCAGCGCCCATC

GCGACCTGGGCCACGTACACATTGCCGTAGCTCATCGCCATCATGCCGAGATCTTTTTTCCGCGTGCGTTTGCCC

TGCGCGGCAAACTTCGCGATGGCCGCCACCGGGGTCGATTTAGACGACTGGCCGCCGGTATTGGAGTAAACCTCG

GTGTCAAACACCAGAATATTGACGTCTTCCCCGCTCGCCAGCACGTGATCGAGACCGCCGAAGCCGATATCGTAG

GCCCAGCCGTCGCCGCCGAAAATCCACTGCGAACGACGAACAAAATAGTCGCGGTTCTGCCACAGCTGCTCCAAC

AGCGGCACGCCCTCTTTTTCCGCCGCCAGCCGTTCGCTGAGCCGGTCCGCGCGCTCGCGGGTGCCCTCGCCTTCA

TCCTGCTTCGCCAGCCACTGGCGCATTGCGTCGCTAAGTTCGTCGCTGACCGGTAGCGCCAGCGCGGCGGTCATA

TCATCGGCGATTTGTTGACGCACCGCCTGGCCGCCGAGCATCATGCCGAGGCCAAACTCCGCATTATCCTCAAAC

AGCGAGTTCGCCCATGCCGGGCCATGGCCGCGGTGGTTGGTGGTATAGGGAATCGACGGCGCGCTGGCTCCCCAG

ATAGAAGAGCAGCCGGTGGCGTTAGCGATCAGCATCCGGTCGCCAAACAGCTGGGTTATCAGGCGGGCATAAGGC

GTTTCACCGCATCCCGCGCAGGCGCCGGAAAACTCCAGCAGCGGGGTTTCAAACTGGCTGCCTTTGACCGTCGTC

TTACGAAACGGATTGCTCTTCGGCGTCAGCGCCAGCGCATAGTCCCAGACCGGCGCCATCTGACGCTGGCTATCG

AGAGACTGCATTTTTAACGCCTTGCCGCGCGCGGGACAGATATCCACGCAGTTGCCGCAGCCGGAACAATCCAGC

GGCGAGATAGCCAGATGGTAGTGATACTCCTTCGCTCCCTGCGCGGGTTTGCTCAGCAGCCCAACCGGCGCGGCG

TCATGCTCTTCGCCGTTGAGCAGCGCCGGGCGGATCGCCGCATGCGGGCAGATAAAGGCGCACTGGTTACACTGC

GTGCAGCCCTCCGGCTGCCAGACCGGCACTTCCAGCGCGATCCCGCGTTTCTCCCACGCGGCGGTGCCCGAAGGA

AAGGTCCCGTCCTCCATACCGACGAACGCGCTCACCGGCAGCTGGTCGCCGCACTGGCGGTTCATCGGCTGCAGA

ATATCGCGGATGAAATCCGGCATCATGGCTGATGCTTGCGCCGCGGGTTCATCCAGCGTCGCCCAGTGCGCCGGA

ATCGTCACCTGATGCAGCGAGGCCATGCCCAGCTCGATCGCCCGCTGGTTCATCTCAATCACCGCCGCCCCTTTG

CTGCCGTAGCTTTTTTTCAACCGCCTGCTTGAGGTAATCCGCCGCGGTCTGCGGGTCGATAATCGCCGCCAGCTTA

-continued

```
AAGAACGCCGCCTGCATCAGCATATTAAAGCGCCCGCCCAGCCCGAGCTCGCGGGCGATATCCACGGCGTTCAGG
GTATAAAAATGGATATTTTCCCGCGCCAGATAGCGTTTAAAGCCGACCGGCAGATGCTGCTCCAGCTCCGCATCG
GACCAGCTGCAGTTGAGTAAAAAGGTCCCGCCCGGCTTTAATCCGTCCAGCAGATCGTAGCGCTCAACGTAGGAC
TGCTGCGAACAGGAGATAAAATCGGCCCGATGGATCAGGTAGGGCGAATTGATCGGCCGGTCGCCGAAGCGTAAA
TGTGAAACGGTAATGCCGCCGGATTTTTTCGAGTCATAAGAAAAGTAGGCCTGCGCGTAGAGCGGCGTTTTATCG
CCGATAATTTTGATCGCGCTTTTATTGGCCCCGACGGTGCCGTCCGAGCCCATGCCCCAAAATTTACAGGCGGTG
ATGCCGTCATGCGAGACCGCCAGCGTCTGCTGGCGCGGCGGTAACGAAGTAAAGGTTACATCATCGACAATCCCG
AGGGTAAACCCGTCCATCGGCAGCGGTTTATTGAGGTTATCAAAGACGGCCGCGATATCGTTGGGCAGAACATCC
TTCCCGCCAAGCGCATAGCGGCCGCCGACGATTAGCGGCGCATCGTCGTGGTGGTAGAAGGCGTTTTTCACATCC
AGGCACAGCGGTTCAGCCTGAGCGCCGGGCTCTTTGGTACGGTCAAGGACGGCAATCCGCTGCACGGTTTTCGGC
AGCTGGGCGAAGAAGTGGGCCAGCGAAAAAGGGCGAAACAGATGCACGCTGAGCAGCCCGACCTTCTCTCCCGCC
GCGTTCAGCGTATCCACCACTTCCTGAACGGTATCGCAGACCGATCCCATTGCGATAATCACCCGTTCGGCATCC
GCCGCGCCGGTATAGTTAAACAGATGATACTCCCGGCCGGTGAGCGCGCTGATTTGCGTCATATAGCTTTCGACA
ATGTCGGGCAGCGCCTGATAAAAACGGTTGCCCGCCTCCCGCTCCTGGAAGTAGATATCCGGGTTCTGCGCCGTT
CCGCGGATGACCGGATGATCCGGATGCAGCGCGTTACGGCGGAAGCTGTCGAGCGCGGGCCGGTCCAGCAGCGTC
GCCAGCTGCTCATATTCCAACACCTCGATTTTTTGAATTTCGTGCGAGGTGCGAAAACCGTCGAAGAAGTTAACA
AACGGGATGCGTCCCTTAATCGCCGCCAGATGCGCCACCGCCGACAAATCCATCACCTGCTGCACGTTGTTCTCC
GCCAGCATCGCGCAGCCGGTCTGGCGGACCGCCATCACATCCTGGTGATCGCCAAAAATATTCAGCGAATTGGTC
AGCAGCAGCCCCTGGGAGGCCGTATAGGTGGTGGTGAGCGCCCCGGCCTGCAGCGCGCCGTGGACCGCGCCTGCC
GCGCCGGCCTCCGACTGCATCTCCATTAAGCGCACCGGCTGGCCAAAAAGGTTCTTTTTCCCCTGCGCCGCCCAC
TCGTCGACGTTTTCCGCCATCGGCGTGGAGGGGGTTATGGGTAAATCGCCGCGACCTCGGTAAAGGCATAAGAG
ATCCAGGCCGCCGCGGCGTTGCCATCCATTGTTTTCATTTTTCCGGACATTGTTCAATCCTCGAAGGTGAGAGGC
ATCTTCGCCGCCTCAAATAAGCGGCAAACCCAGTTGTTGCCTCAAGCACAGCCTGTGCCAGCTCGCGGATGACAG
AAGAGTTAGCGCGAATTCAACGCGTTATGAAGAGAGTCGCCGCGCAGCGCGCCAAGAGATTGCGTGGAATAAGAC
ACAGGGGCGACAAGCTGTTGAACAGGCGACAAAGCGCCACCATGGCCCCGGCAGGCGCAATTGTTCTGTTTCCC
ACATTTGGTCGCCTTATTGTGCCGTTTTGTTTTACGTCCTGCGCGGCGACAAATAACTAACTTCATAAAAATCAT
AAGAATACATAAACAGGCACGGCTGGTATGTTCCCTGCACTTCTCTGCTGGCAAACACTCAACAACAGGAGAAGT
CACCATGACCATGCGTCAATGCGCTATTTACGGTAAAGGCGGTATCGGTAAATCCACCACCACGCAGAACCTCGT
CGCCGCGCTGGCGGAGATGGGTAAGAAAGTGATGATCGTCGGCTGCGATCCGAAGGCGGACTCCACCCGTCTGAT
TCTGCACGCCAAAGCACAGAACACCATTATGGAGATGGCCGCGGAAGTCGGCTCGGTCGAGGACCTCGAACTCGA
AGACGTGCTGCAAATTGGCTACGGCGATGTGCGCTGCGCGGAATCCGGCGGCCCGGAGCCAGGCGTCGGCTGCGC
GGGACGCGGCGTGATCACGGCGATCAACTTTCTTGAAGAAGAAGGCGCCTACGAGGACGATCTCGATTTCGTGTT
CTATGACGTGCTCGGCGACGTGGTCTGCGGCGGCTTCGCCATCAAGATCCGCGAAAACAAAGCCCAGGAGATCTA
CATCGTCTGCTCCGGCGAAATGATGGCGATGTACGCGGCCAACAATATCTCCAAAGGGATCGTTAAATACGCCAA
ATCCGGCAAGGTGCGCCTCGGCGGCCTGATCTGTAACTCACGTCAGACCGACCGTGAAGACGAACTGATTATTGC
CCTGGCGGAAAAGCTCGGTACCCAGATGATCCACTTTGTGCCCCGCGACAACATCGTGCAGCGCGCGGAGATCCG
CCGCATGACGGTTATCGAGTACGACCCCGCCTGTAAACAGGCCAACGAATACCGCACCCTGGCGCAGAAGATCGT
CAACAACACCATGAAAGTGGTGCCGACGCCCTGCACCATGGATGAGCTGGAATCGCTGCTGATGGAGTTCGGCAT
CATGGAAGAGGAAGACACCAGCATCATTGGCAAAACCGCCGCCGAAGAAAACGCGGCCTGAGCACAGGACAATTA
TGATGACCAACGCAACGGGCGAACGTAATCTGGCGCTGATCCAGGAAGTCCTGGAGGTGTTCCCGGAAACCGCGC
```

-continued

```
GAAAAGAGCGCAGAAAGCACATGATGGTCAGCGATCCGGAAATGGAGAGCGTCGGCAAGTGCATTATCTCTAACC

GCAAATCACAACCCGGCGTAATGACCGTACGCGGCTGCGCCTACGCCGGTTCCAAAGGGGTGGTATTTGGGCCGA

TTAAGGATATGGCCCATATTTCGCACGGACCGGTCGGCTGCGGCCAGTATTCCCGCGCCGGACGACGCAACTACT

ACACCGGAGTCAGCGGCGTCGATAGCTTCGGCACGCTGAACTTCACCTCTGATTTTCAGGAGCGCGACATCGTCT

TCGGCGGCGATAAAAAGCTCAGCAAGCTGATTGAAGAGATGGAGTTGCTGTTCCCGCTCACCAAAGGGATCACCA

TTCAGTCGGAATGCCCGGTGGGGCTGATCGGTGATGATATCAGCGCGGTGGCCAACGCCAGCAGCAAGGCGCTGG

ATAAACCGGTGATCCCGGTACGCTGCGAAGGCTTTCGCGGCGTGTCGCAGTCTCTGGGGCACCATATCGCCAACG

ACGTGGTGCGCGACTGGATCCTGAACAATCGCGAAGGACAGCCGTTTGAAACCACCCCTTACGATGTGGCGATCA

TCGGCGACTACAACATCGGCGGCGACGCCTGGGCCTCGCGCATTCTGCTGGAAGAGATGGGGCTACGGGTAGTCG

CGCAGTGGTCCGGCGACGGCACGCTGGTGGAGATGGAGAATACCCCATTCGTCAAGCTGAACCTGGTTCACTGCT

ACCGTTCGATGAACTATATCGCCCGCCATATGGAGGAGAAACATCAGATTCCGTGGATGGAGTACAACTTCTTCG

GGCCGACCAAAATCGCCGAATCGCTGCGCAAAATCGCCGACCAGTTCGACGATACCATTCGCGCGAACGCCGAAG

CGGTGATCGCCCGGTATGAGGGGCAGATGGCGGCGATTATCGCCAAATATCGCCCGCGCCTGGAGGGGCGTAAGG

TGCTGCTCTATATGGGCGGCCTGCGGCCGCGCCACGTTATTGGCGCCTATGAGGATCTCGGGATGGAGATCATCG

CCGCCGGCTACGAGTTTGCCCATAACGATGATTACGACCGCACCCTGCCGGATCTGAAAGAGGGCACGCTGCTGT

TCGATGACGCCAGCAGCTACGAGCTGGAAGCGTTCGTCAAGGCGCTGAAGCCCGACCTTATCGGCTCCGGCATCA

AGGAAAAATATATCTTCCAGAAAATGGGCGTGCCGTTCCGCCAGATGCACTCGTGGGACTATTCCGGCCCGTACC

ACGGCTACGATGGTTTCGCCATTTTCGCCCGCGATATGGATATGACCCTGAACAACCCGGCGTGGAACGAACTGA

CCGCTCCGTGGCTGAAGTCTGCGTGATTGCCCACTCACTGTCCCGTCTGTTCACCGATTTGTGGCGCGGGAGGAG

AACACCATGAGCCAAACGATTGATAAAATTAATAGCTGTTATCCGCTATTCGAACAGGATGAATACCAGGAGCTG

TTCCGCAATAAGCGGCAGCTGGAAGAGGCGCACGATGCGCAGCGCGTGCAGGAGGTCTTTGCCTGGACCACCACC

GCCGAGTATGAAGCGCTGAATTTCCAGCGCGAGGCGCTGACCGTTGACCCGGCGAAAGCCTGCCAGCCGCTTGGC

GCGGTGCTTTGCTCGCTGGGATTTGCCAACACCCTGCCGTATGTGCACGGCTCTCAGGGGTGCGTGGCCTACTTT

CGCACCTATTTTAACCGCCATTTCAAAGAGCCGATCGCCTGCGTCTCCGACTCGATGACCGAAGACGCGGCGGTC

TTCGGCGGCAACAACAATATGAACCTGGGCCTGCAGAACGCCAGCGCGCTGTACAAACCGGAGATCATTGCGGTG

TCCACCACCTGCATGGCGGAAGTTATCGGCGATGACCTGCAGGCGTTTATCGCCAACGCTAAAAAAGATGGCTTC

GTCGACAGCAGCATCGCCGTGCCCCACGCCCATACGCCAAGCTTTATCGGCAGCCACGTCACCGGCTGGGATAAC

ATGTTTGAAGGCTTCGCCAAAACCTTCACTGCGGACTACCAGGGGCAGCCGGGCAAATTGCCGAAGCTCAATCTG

GTGACCGGCTTTGAAACCTATCTCGGCAACTTCCGCGTATTAAAGCGGATGATGAACAGATGGCGGTGCCGTGC

AGCCTGCTCTCCGATCCGTCGGAAGTTCTCGACACGCCCGCCGACGGCCACTATCGGATGTATTCCGGCGGCACC

ACGCAGCAGGAGATGAAAGAGGCCCCTGACGCCATCGATACGCTGCTCCTGCAGCCGTGGCAGCTGCTGAAGAGC

AAAAAAGTGGTGCAGGAGATGTGGAACCAGCCCGCCACCGAGGTCGCCATTCCGCTGGGGCTGGCCGCCACCGAT

GAACTGCTGATGACCGTCAGCCAGCTTAGCGGCAAGCCGATTGCCGACGCCCTCACCCTTGAGCGCGGCCGGCTG

GTTGACATGATGCTCGACTCCCACACCTGGCTGCACGGCAAGAAGTTTGGCCTGTACGGCGATCCGGACTTCGTG

ATGGGCCTCACCCGCTTCCTGCTGGAGCTGGGCTGCGAGCCAACGGTGATCCTGAGCCATAACGCCAACAAACGC

TGGCAAAAAGCGATGAACAAAATGCTCGATGCCTCGCCGTACGGGCGCGATAGCGAAGTGTTTATCAACTGCGAT

TTGTGGCACTTCCGTTCGCTGATGTTCACCCGTCAGCCGGACTTTATGATCGGCAACTCCTACGGCAAGTTTATC

CAGCGCGATACCCTGGCGAAGGGTAAAGCCTTTGAAGTGCCGCTTATCCGCCTCGGCTTTCCGCTGTTCGACCGC

CACCATCTGCACCGCCAGACAACCTGGGGTTATGAAGGGCGATGAACATTGTGACGACGCTGGTGAACGCCGTG

CTGGAGAAACTGGATAGCGATACCAGCCAGCTGGGCAAAACCGATTACAGCTTCGATCTCGTCCGTTAACCATCA

GGTGCCCCGCGTCATGCGGGGCCAGGAGGGAGTATGCCCATCGTGATTTTCCGTGAGCGCGGCGCGGACCTGTAC
```

-continued

```
GCCTATATCGCGAAACAGGATCTGGAAGCGCGAGTGATCCAGATTGAGCATAACGACGCTGAACGCTGGGGCGGC
GCGATTTCGCTGGAGGGGGACGCCGCTACTACGTGCATCCGCAGCCGGGGCGTCCCGTCTTTCCGATAAGCCTG
CGCGCGAGGCGCAATACCTTGATATAAGGAGCTAGTGATGTCCGACAACGATACCCTATTCTGGCGTATGCTGGC
GCGATTTCGCTGGAGGGGGACGCCGCTACTACGTGCATCCGCAGCCGGGGCGTCCCGTCTTTCCGATAAGCCTG
CGCGCGAGGCGCAATACCTTGATATAAGGAGCTAGTGATGTCCGACAACGATACCCTATTCTGGCGTATGCTGGC
GACGCCAGAGCGTCTGGCGACCCTGACCCAGCCGCAGCTGGCCGCCAGCTTTCCCTCCGCGACGGCGGTGATGTC
CCCCGCTCGCTGGTCGCGGGTGATGGCGAGCCTGCAGGGCGCGCTGCCCGCCCATTTACGCATCGTTCGCCCTGC
CCAGCGCACGCCGCAGCTGCTGGCGGCATTTTGCTCCCAGGATGGGCTGGTGATTAACGGCCATTTCGGCCAGGG
ACGACTGTTTTTTATCTACGCGTTCGATGAACAAGGCGGCTGGTTGTACGATCTGCGCCGCTATCCCTCCGCCCC
CCACCAGCAGGAGGCCAACGAAGTGCGCGCCCGGCTTATTGAGGACTGTCAGCTGCTGTTTTGCCAGGAGATAGG
CGGGCCCGCCGCCGCGCGGCTGATCCGCCATCGCATCCACCCGATGAAAGCGCAGCCCGGGACGACGATTCAGGC
ACAGTGCGAGGCGATCAATACGCTGCTGGCCGGCCGTTTGCCGCCGTGGCTGGCGAAGCGGCTTAACAGGGATAA
CCCTCTGGAAGAACGCGTTTTTTAATCCCTGTTTTGTGCTTGTTGCCCGCTGACCCCGCGGGCTTTTTTTCGCGT
ATGGACGCTCTTCCCCACGTTACGCTCAGGGGAATATTCCGTTCACGGTTGTTCCGGGCTTCTTGATGCGCCTAA
CCCCCTCGCTGCCAGCCTTTCATCAACAAATAGCCATCCCAGCGCGATAGGTCATAAAGCATCACATGCCGCCAT
CCCTTGTCCGATTGTTGGCTTTGTCGCAAAGCCAACAACCTCTTTTCTTTAAAAATCAAGGCTCCGCTTCTGGAG
CGCGAATTGCATCTTCCCCCTCATCCCCCACCGTCAACGAGGTCACTATGAAGGGAAATGAAATTCTGGCGCTGC
TGGATGAACCGGCCTGTGAACACAACCATAAACAAAAATCCGGCTGCAGCGCGCCCAAACCCGGCGCCACCGCCG
GCGGCTGCGCGTTCGACGGCGCGCAGATAACCCTGCTGCCCATCGCCGACGTGGCGCATCTGGTCCACGGCCCCA
TCGGCTGCGCCGGAAGCTCATGGGATAACCGCGGCAGCGCCAGCTCCGGCCCCACCCTTAATCGGCTCGGGTTCA
CCACCGATCTCAACGAACAGGACGTGATTATGGGCCGCGGCGAACGCCGCTTGTTTCACGCCGTGCGCCATATCG
TCACCCGCTATCATCCGGCGGCGGTCTTTATCTACAACACCTGCGTACCGGCCATGGAGGGCGATGACCTGGAAG
CGGTATGCCAGGCCGCGCAGACCGCCACCGGCGTACCGGTTATCGCTATTGACGCCGCCGGTTTCTACGGCAGTA
AAAATCTCGGTAACCGGCTGGCGGGCGACGTCATGGTCAAACGGGTCATCGGCCAGCGCGAGCCCGCCCCCTGGC
CGGAGAGCACGCTCTTTGCCCCGGAGCAGCGTCACGATATTGGCCTGATTGGCGAATTCAATATTGCCGGCGAGT
TCTGGCATATTCAGCCGCTGCTCGACGAACTGGGGATCCGCGTGCTCGGCAGCCTCTCCGGTGATGGCCGCTTCG
CCGAGATCCAGACCATGCACCGGGCGCAGGCCAATATGCTGGTCTGCTCGCGGGCGTTAATTAACGTCGCCAGAG
CCCTGGAGCAGCGCTACGGCACGCCGTGGTTCGAAGGCAGCTTTTACGGGATCCGCGCCACCTCTGACGCCCTGC
GCCAGCTGGCGGCGCTGCTGGGCGACGACGACCTTCGCCAGCGCACCGAAGCGCTGATTGCGCGGGAGGAACAGG
CGGCGGAACTGGCGCTACAGCCGTGGCGCGAACAGCTGCGCGGCCGCAAAGCGCTGCTCTATACCGGCGGGGTGA
AATCCTGGTCGGTGGTATCGGCGCTGCAGGATTTGGGCATGACCGTGGTGGCAACCGGCACGCGTAAATCCACCG
AAGAGGATAAACAGCGGATCCGCGAGCTGATGGGCGAAGAGGCGGTAATGCTGGAAGAGGGCAACGCCCGCACGC
TgctggatgtggtctATCGCTATCAGGCCGACCTGATGATTGCCGGCGGACGCAATATGTACACCGCCTATAAAG
CCAGGCTGCCGTTTCTCGATATCAATCAGGAGCGCGAACACGCCTTCGCTGGCTATCAGGGGATCGTCACCCTCG
CCCGCCAGCTGTGTCAGACCATCAACAGCCCCATCTGGCCGCAAACCCATTCTCGCGCCCCGTGGCGCTAAGGAG
CTCACCATGGCAGACATTTTCCGCACCGATAAGCCGCTGGCGGTCAGCCCCATCAAAACCGGCCAGCCGCTCGGC
GCAATCCTCGCCAGCCTCGGGATCGAACACAGCATCCCTCTGGTCCACGGCGCGCAGGGGTGCAGCGCCTTCGCC
AAAGTCTTTTTTATTCAACATTTCCACGACCCGGTTCCCCTGCAGTCGACGGCGATGGACCCCACGTCGACGATT
ATGGGCGCGGACGGCAATATTTTTACCGCCCTGGATACCCTCTGCCAGCGCAACAATCCGCAGGCTATCGTACTG
CTCAGCACCGGGCTGTCGGAGGCCCAGGGCAGCGATATTTCCCGCGTGGTTCGCCAGTTTCGCGAAGAGTATCCC
```

-continued

CGGCATAAGGGGGTGGCGATATTGACGGTTAACACGCCGGATTTTTATGGCTCCATGGAGAACGGCTTCAGCGCG

GTGTTAGAGAGCGTCATTGAGCAGTGGGTGCCGCCGGCGCCGCGCCCGGCTCAGCGCAATCGCCGGGTCAATCTG

CTGGTCAGCCATCTCTGTTCGCCGGGCGATATCGAGTGGCTGCGCCGATGCGTCGAAGCCTTTGGTCTGCAGCCG

ATAATCCTGCCGGACCTGGCGCAATCGATGGACGGCCACCTGGCGCAGGGCGATTTCTCGCCGCTGACCCAGGGC

GGGACGCCGCTGCGCCAGATAGAGCAGATGGGGCAAAGCCTGTGCAGCTTCGCCATTGGCGTCTCCCTTCATCGC

GCCTCATCGCTGCTGGCCCCGCGCTGCCGCGGCGAGGTTATCGCCCTGCCGCACCTGATGACCCTCGAACGCTGC

GACGCCTTTATTCATCAACTGGCGAAAATTTCCGGACGCGCCGTTCCCGAGTGGCTGGAACGCCAGCGCGGCCAG

CTACAGGATGCGATGATCGACTGCCATATGTGGCTCCAGGGCCAGCGCATGGCGATAGCGGCGGAAGGCGATTTG

CTGGCGGCGTGGTGTGATTTCGCCAACAGCCAGGGGATGCAGCCCGGCCCGCTGGTGGCCCCTACCGGTCATCCC

AGCCTGCGCCAGCTGCCGGTGGAACGGGTGGTGCCGGGGGATCTGGAGGATCTGCAAACCCTGCTGTGCGCGCAT

CCCGCCGACCTGCTGGTGGCGAACTCGCACGCCCGCGACCTGGCGGAGCAGTTTGCGCTGCCGCTGGTGCGCGCG

GGTTTTCCGCTCTTTGACAAGCTCGGCGAATTCCGCCGGGTGCGACAGGGGTATAGCGGGATGCGCGATACGCTG

TTTGAGCTGGCAAACCTGATACGCGAGCGTCACCACCACCTCGCCCACTACCGATCGCCGCTGCGCCAGAACCCC

GAATCGTCACTCTCCACAGGAGGCGCTTATGCCGCCGATTAACCGTCAGTTTGATATGGTCCACTCCGATGAGTG

GTCTATGAAGGTCGCCTTCGCCAGCTCCGACTATCGTCACGTCGATCAGCACTTCGGCGCTACCCCGCGGCTGGT

GGTGTACGGCGTCAAGGCGGATCGGGTCACTCTCATCCGGGTGGTTGATTTCTCGGTCGAGAACGGCCACCAGAC

GGAGAAGATCGCCAGGCGGATCCACGCCCTGGAGGATTGCGTCACGCTGTTCTGCGTGGCGATTGGCGACGCGGT

TTTTCGCCAGCTGTTGCAGGTGGGCGTGCGTGCCGAACGCGTTCCCGCCGACACCACCATCGTCGGCTTACTGCA

GGAGATTCAGCTCTACTGGTACGACAAAGGGCAGCGCAAAAATACGCGCCAGCGCGACCCGGAGCGCTTTACCCG

TCTGCTGCAGGAGCAGGAGTGGCATGGGGATCCGGACCCGCGCCGCTAGCCGTGTCGTTTCTGTGACAAAGCCCA

CAAAACATCGCGACACTGTAGGACGAACCTTGTCAGGACTAATACACAACCATTTGAAAAATATTAATTTTATTC

TCTGGTATCGCAATTGCTAGTTCGTTATCGCCACCGCGCTTCCGCGGTGAACCGCGCCCCGGCGTTTTCCGTCAA

CATCCCTGGAGCTGACAGCATGTGGAATTACTCCGAGAAAGTGAAAGACCATTTTTTTAACCCCCGCAATGCGCG

CGTGGTGGACAACGCCAACGCGGTAGGCGACGTCGGTTCGTTAAGCTGCGGCGACGCCCTGCGCCTGATGCTGCG

CGTCGACCCGCAAAGCGAAATCATTGAGGAGGCGGGCTTccagaccttcggctgCGGCAGCGCCATCGCCTCCTC

CTCCGCGCTGACGGAGCTGATTATCGGCCATACCCTCGCCGAAGCCGGGCAGATAACCAATCAGCAGATTGCCGA

TTATCTCGACGGACTGCCGCCGGAGAAAATGCACTGCTCGGTGATGGGCCAGGAGGCCCTGCGCGCGGCCATCGC

CAACTTTCGCGGCGAAAGCCTTGAAGAGGAGCACGACGAGGGCAAGCTGATCTGCAAATGCTTCGGCGTCGATGA

AGGGCATATTCGCCGCGCGGTACAGAACAACGGGCTGACCACCCTTGCCGAGGTGATCAACTACACCAAAGCGGG

CGGCGGCTGCACCTCTTGCCACGAAAAAATCGAGCTGGCCCTGGCGGAGATCCTCGCCCAGCAGCCGCAGACGAC

GCCAGCCGTGGCCAGCGGCAAAGATCCGCACTGGCAGAGCGTCGTCGATACCATCGCAGAACTGCGGCCGCATAT

TCAGGCCGACGGCGGCGATATGGCGCTACTCAGCGTCACCAACCACCAGGTGACCGTCAGCCTCTCCGGCAGCTG

TAGCGGCTGCATGATGACCGATATGACCCTGGCCTGGCTGCAGCAAAAACTGATGGAACGTACCGGCTGTTATAT

GGAAGTGGTGGCGGCCTGAGCCGCGGTTAACTGACCCAAGGGGGACAAGATGAAACAGGTTTATCTCGATAACAA

CGCCACCACCCGTCTGGACCCGATGGTCCTGGAAGCGATGATGCCCTTTTTGACCGATTTTTACGGCAACCCCTC

GTCGATACACGATTTTGGCATTCCGGCCCAGGCGGCTCTGGAACGCGCGCATCAGCAGGCTGCGGCGCTGCTGGG

CGCGGAGTATCCCAGCGAGATCATCTTTTACCTCCTGCGCCACCGAAGCCACCGCCACCGCCATCGCCTCGGCGAT

CGCCCTGCTGCCTGAGCGTCGCGAAATCATCACCAGCGTGGTCGAACATCCGGCGACGCTGGCGGCCTGCGAGCA

CCTGGAGCGCCAGGGCTACCGGATTCATCGCATCGCGGTGGATAGCGAGGGGGCGCTGGACATGGCGCAGTTCCG

CGCGGCGCTCAGCCCGCGCGTCGCGTTGGTCAGCGTGATGTGGGCGAATAACGAAACCGGGGTGCTTTTCCCGAT

CGGCGAAATGGCGGAGCTGGCCCATGAACAAGGGGCGCTGTTTCACTGCGATGCGGTGCAGGTGGTCGGGAAAAT

-continued

```
ACCGATCGCCGTGGGCCAGACCCGCATCGATATGCTCTCCTGCTCGGCGCATAAGTTCCACGGGCCAAAAGGCGT
AGGCTGTCTTTATCTGCGGCGGGGAACGCGCTTTCGCCCGCTGCTGCGCGGCGGTCACCAGGAGTACGGTCGGCG
AGCCGGGACAGAAAATATCTGCGGAATCGTCGGCATGGGCGCGGCCTGCGAGCTGGCGAATATTCATCTGCCGGG
AATGACGCATATCGGCCAATTGCGCAACAGGCTGGAGCATCGCCTGCTGGCCAGCGTGCCGTCGGTCATGGTGAT
GGGCGGCGGCCAGCCGCGGGTGCCCGGCACGGTGAATCTGGCCTTTGAGTTTATTGAAGGTGAAGCCATTCTGCT
GCTGTTAAACCAGGCCGGGATCGCCGCCTCCAGCGGCAGCGCCTGCACCTCAGGCTCGCTGGAACCCTCCCACGT
GATGCGGGCGATGAATATCCCCTACACCGCCGCCCACGGCACCATCCGCTTTTCTCTCTCGCGCTACACCCGGGA
GAAAGAGATCGATTACGTCGTCGCCACGCTGCCGCCGATTATCGACCGGCTGCGCGCGCTGTCGCCCTACTGGCA
GAACGGCAAGCCGCGCCCGGCGGACGCCGTATTCACGCCGGTTTACGGCTAAGGCGGAGGTGGCTGATGGAACGC
GTGCTGATTAACGATACCACCCTGCGCGACGGCGAGCAGAGCCCCGGCGTCGCCTTTCGCACCAGCGAAAAGGTC
GCCATTGCCGAGGCGCTTTACGCCGCAGGAATAACGGCGATGGAGGTCGGCACCCCGGCGATGGGCGACGAGGAG
ATCGCGCGGATCCAGCTGGTGCGTCGCCAGCTGCCCGACGCGACCCTGATGACCTGGTGTCGGATGAACGCGCTG
GAGATCCGCCAGAGCGCCGATCTGGGCATCGACTGGGTGGATATCTCGATTCCGGCTTCGGATAAGCTGCGGCAG
TACAAACTGCGCGAGCGCTGGCGGTGCTGCTGGAGCGGCTGGCGATGTTTATCCATCTTGCGCATACCCTCGGC
CTGAAGGTATGCATCGGCTGCGAGGACGCCTCGCGGGCCAGCGGCCAGACCCTGCGCGCTATCGCCGAGGTCGCG
CAGCAATGCGCCGCCGCCCGCCTGCGCTATGCCGATACGGTCGGCCTGCTCGACCCTTTTACCACCGCGGCGCAA
ATCTCGGCCCTGCGCGACGTCTGGTCCGGCGAAATCGAAATGCATGCCCATAACGATCTGGGTATGGCGACCGCC
AATACGCTGGCGGCGGTAAGCGCCGGGGCCACCAGCGTGAATACGACGGTCCTCGGTCTCGGCGAGCGGGCGGGC
AACGCGGCGCTGGAAACCGTCGCGCTGGGCCTTGAACGCTGCCTGGGCGTGGAGACCGGCGTGCATTTTTCGGCG
CTGCCCGCGCTCTGTCAGAGGGTCGCGGAAGCCGCGCAGCGCGCCATCGACCCGCAGCAGCCGCTGGTCGGCGAG
CTGGTGTTTACCCATGAGTCAGGTGTCCACGTGGCGGCGCTGCTGCGCGACAGCGAGAGCTACCAGTCCATCGCC
CCTTCCCTGATGGGCCGCAGCTACCGGCTGGTGCTGGGCAAACACTCCGGGCGTCAGGCGGTCAACGGCGTTTTT
GACCAGATGGGCTATCACCTCAACGCCGCGCAGATTAACCAGCTGCTGCCCGCCATCCGCCGCTTCGCCGAGAAC
TGGAAGCGCAGCCCGAAAGATTACGAGCTGGTGGCTATCTACGACGAGCTGTGCGGTGAATCCGCTCTGCGGGCG
AGGGGGTAATGATGGAGTGGTTTTATCAAATTCCCGGCGTGGACGAACTTCGCTCCGCCGAATCTTTTTTTCAGT
TTTTCGCCGTCCCCTATCAGCCCGAGCTGCTTGGCCGCTGCAGCCTGCCGGTGCTGGCAACGTTTCATCGCAAAC
TCCGCGCGGAGGTGCCGCTGCAAAACCGGCTCGAGGATAACGACCGCGCGCCCTGGCTGCTGGCGCGAAGACTGC
TCGCGGAGAGCTATCAGCAACAGTTTCAGGAGAGCGGAACATGAGACCGAAATTCACCTTTAGCGAAGAGGTCCG
CGTCGTACGCGCGATTCGTAACGACGGCACCGTGGCGGGCTTCGCGCCCGGCGCGCTGCTGGTCAGGCGCGGCAG
CACCGGCTTTGTGCGCGACTGGGGCGTTTTTTTGCAAGATCAGATTATCTACCAGATCCACTTTCCGGAAACCGA
TCGGATCATCGGCTGCCGCGAGCAGGAGCTGATCCCCATCACCCAGCCGTGGCTGGCCGGAAATTTGCAATACAG
GGATAGCGTGACCTGCCAGATGGCGCTCGCGGTCAACGGCGATGTGGTCGTGAGCGCCGGCCAGCGGGGACGCGT
TGAGGCTACCGATCGGGGANAGCTCGGCGACAGCTACACCGTCGACTTTAGCGGCCGCTGGTTCAGGGTCCCGGT
GCAGGCCATCGCCCTTATAGAGGAAAGAGAAGAATGAACCCATGGCAACGTTTTGCCCGGCAGCGGCTGGCGCGC
AGCCGCTGGAATCGCGATCCGGCGGCCCTGGATCCGGCCGATACGCCGGCTTTTGAACAGGCCTGGCAACGCCAG
TGCCATATGGAGCAGACGATCGTCGCGCGGGTCCCTGAAGGCGATATTCCGGCGGCGTTGCTGGAGAATATCGCT
GCCTCCCTTGCCATCTGGCTCGACGAGGGGGATTTTGCGCCGCCCGAGCGCGCTGCCATCGTGCGCCATCACGCC
CGGCTGGAACTCGCCTTCGCCGATATCGCCCGCCAGGCGCCGCAGCCGGATCTCTCCACGGTACAGGCATGGTAT
CTGCGCCACCAGACGCAGTTTATGCGCCCGGAACAGCGTCTGACCCGCCATTTACTGCTGACGGTCGATAACGAC
CGCGAAGCCGTGCACCAGCGGATCCTCGGCCTGTATCGGCAAATCAACGCCTCGCGGGACGCTTTCGCGCCGCTG
```

-continued

```
GCCCAGCGCCATTCCCACTGCCCGAGCGCGCTGGAAGAGGGTCGTTTAGGCTGGATTAGCCGTGGCCTGCTCTAT
CCGCAGCTCGAGACCGCGCTGTTTTCACTGGCGGAAAACGCGCTAAGCCTTCCCATCGCCAGCGAACTGGGCTGG
CATCTTTTATGGTGCGAAGCGATTCGCCCCGCCGCGCCCATGGAGCCGCAGCAGGCGCTGGAGAGCGCGCGCGAT
TATCTTTGGCAGCAGAGCCAGCAGCGCCATCAGCGCCAGTGGCTGGAACAGATGATTTCCCGTCAGCCGGGACTG
TGCGGGTAGCCTCGGCGGCTACCCGTTAACGCCTACAGCACGGTGCGTTTAATCTCCTCAAGCCAGCTCGCCAGA
CGCGCTTCGGTCTGGTCGAACTGGTTATCCTGATCCAGCACCAGCCCAACAAAGCGGTCGCCTTCCAGCGCCGAG
GACGCGCTGAATTCATAACCCTCATTTGGCCAGCTGCCAATCATCTGCGCGCCGCGCGCGCTCAGGGCGTCGAAC
AGCGGGCGCATCCCGCTGACGAAGTTGTCCGGATAGCCTCTCTGATCGCCGAGGCCGAACAGCGCCACGGTTTTC
CCTTTCAGGCTGGCGTCGTCGAGGCCGCTGATAAATTCGCTCCATGACTCGCTTTCGCATCCGGCCTCCAGCCCC
GGCAGCTGGCCGTCGCCGAGCGTCGGCGTGCCCAGCAGCAGCACCGGATAGGCCATAAAGTCGTCCAGCGTCGTG
CGGTTAATGTTGACCGGGGCATCCGCCAGCTCGCCCAGTTGCTTATGGATCATTTTCGCGATTTTGCGGGTTTTA
CCGGTATCGGTGCCAAAGAAAATACCAATGTTCGCCATGTTGCGCTCCTGTCGGAAAAGGGGGTTGAAAATACGC
GTTCTCGCAGGGGTATTGCGAAGGCTGTGCCAGGTTGCTTTGCACTACCGCGGCCCATCCCTGCCCCAAAACGAT
CGCTTCAGCCCTCTCCCGCCGCGCGGCGGGGCTGGCGGGGCGCTTAAAATGCAAAAAGCGCCTGCTTTTCCCC
TACCGGATCAATGTTTCTGCACATCACGCCGATAAGGGCGCACGGTTTGCATGGTTATCACCGTTCGGAAAACAC
CGCGGCGTCCCTGTCACGGTGTCGGACAAATTGTCATAACTGCGACACAGGAGTTTGCGATGACCCTGAATATGA
TGCTCGATAACGCCGTACCCGAGGCGATTGCCGGTGCGCTGACTCAACAACATCCGGGGCTGTTTTTTACAATGG
TCGAACAGGCATCGGTAGCGATTTCCCTCACCGATGCCCGGGCGAATATTATCTACGCCAACCCGGCGTTTTGCC
GCCAGACTGGATACTCGCTGGCGCAATTGCTCAATCAAAACCCGCGCCTGCTGGCCAGCAGCAGACGCCGCGCG
AGATCTACCAGGAGATGTGGCAAACCCTGCTCCAGCGCCAGCCGTGGCGCGGTCAGCTAATTAATCAGCGCCGCG
ACGGCGGCCTGTATCTGGTAGATATCGATATCACGCCGGTGCTGAATCCGCAGGGCGAGCTGGAGCATTATCTGG
CGATGCAGCGGGATATCAGCGTCAGCTATACCCTGGAACAGCGGCTGCGCAATCATATGACGCTAATGGAAGCGG
TGCTCAATAACATCCCCGCCGCCGTGGTCGTGGTCGATGAGCAGGATCGGGTGGTGATGGATAATCTCGCCTACA
AAACGTTCTGCGCGGACTGCGGCGGGAAAGAGCTGCTGGTCGAGCTCCAGGTTTCCCCGCGCAAAATGGGGCCCG
GCGCGGAGCAAATCCTGCCGGTGGTGGTTCGCGGCGCGGTCCGCTGGCTGTCGGTAACCTGCTGGGCGCTGCCCG
GCGTGAGTGAAGAAGCCAGCCGCTACTTCGTCGACAGCGCCCCGGCGCGCACGCTGATGGTGATCGCCGACTGTA
CCCAGCAGCGCCAGCAGCAGGAGCAGGGCCGGCTCGACCGTCTGAAACAGCAAATGACCGCCGGTAAGCTGCTGG
CCGCGATTCGCGAGTCGCTGGACGCGGCGCTGATTCAGCTTAATTGCCCAATCAATATGCTGGCGGCGGCCCGCC
GGCTGAACGGCGAAGGCAGCGGCAACGTGGCGCTGGACGCGCGTGGCGCGAAGGTGAAGAGGCCATGGCGCGCC
TGCAGCGCTGCCGCCCTTCTCTTGAGCTGGAAAGCAATGCCGTCTGGCCGCTTCAGCCCTTTTTTGACGACCTGT
ACGCCCTCTACCGCACCCGCTTTGACGATCGCGCGCGGCTGCAGGTGGACATGGCATCGCCGCATCTGGTCGGCT
TCGGCCAGCGTACCCAGCTGCTGGCCTGCTTGAGTTTATGGCTCGACCGGACGCTGGCCCTCGCCGCCGAGCTGC
CCTCCGTACCGCTGGAGATCGAGCTTTACGCCGAAGAGGACGAGGGCTGGCTCTCTTTGTATCTCAACGACAATG
TCCCGCTGCTGCAGGTGCGCTACGCCCACTCCCCCGATGCCCTAAACTCTCCCGGCAAAGGGATGGAGCTGCGGC
TGATCCAAACGCTGGTCGCCTACCACCGCGGCGCGATTGAACTGGCTTCGCGACCGCAGGGAGGCACCAGCCTGG
TTCTGCGTTTCCCGCTCTTTAATACCCTGACCGGAGGTGAGCAATGATCCATAAATCCGATTCGGACACCACCGT
CAGACGTTTCGATCTCTCCCAGCAGTTTACCGCCATGCAGCGGATAAGCGTGGTCCTGAGTCGCGCCACCGAAGC
GAGCAAAACCCTGCAGGAGGTTCTGAGCGTGCTACATAACGATGCCTTTATGCAGCACGGGATGATTTGCCTGTA
CGACAGCCAGCAGGAGATCCTGAGCATCGAAGCGCTGCAGCAAACGGAAGATCAGACGCTGCCCGGCAGTACGCA
AATTCGCTACCGGCCGGGGGAAGGATTAGTCGGTACCGTGCTGGCGCAGGGCCAGTCGCTGGTGCTGCCGCGCGT
CGCCGACGACCAGCGTTTTCTCGATCGTCTGAGCCTGTACGACTATGACCTGCCGTTTATCGCCGTTCCGCTGAT
```

-continued

```
GGGCCCCCACTCCCGGCCCATCGGCGTACTGGCGGCGCAGCCGATGGCGCGTCAGGAAGAGCGGCTGCCCGCCTG

CACGCGCTTTCTCGAAACCGTCGCCAATCTGATCGCCCAGACGATTCGCCTGATGATCCTGCCAACCTCCGCCGC

GCAGGCGCCGCAGCAGAGCCCCAGAATAGAGCGCCCGCGCGCCTGTACCCCTTCGCGCGGTTTCGGCCTGGAAAA

TATGGTCGGTAAAAGCCCGGCGATGCGGCAGATTATGGATATTATTCGTCAGGTTTCCCGCTGGGATACCACGGT

GCTGGTACGCGGCGAGAGCGGCACCGGGAAAGAGCTCATCGCCAACGCCATCCACCATAATTCTCCGCGCGCCGC

CGCGGCGTTCGTCAAATTTAACTGCGCGGCGCTGCCGGACAACCTGCTGGAGAGCGAGCTGTTTGGTCATGAGAA

AGGCGCGTTTACCGGCGCGGTGCGCCAGCGGAAAGGCCGCTTTGAGCTGGCGGACGGCGGCACCTTATTCCTCGA

TGAGATCGGCGAAAGCAGCGCCTCGTTTCAGGCTAAGCTACTGCGTATTCTGCAAGAGGGGGAGATGGAGCGCGT

CGGCGGCGACGAAACCCTGCGGGTCAACGTGCGCATTATCGCGGCGACCAACCGCCATCTGGAAGAGGAGGTGCG

GCTGGGTCATTTCCGCGAGGATCTATACTACCGCCTGAACGTAATGCCTATCGCGCTGCCGCCGCTGCGCGAGCG

CCAGGAGGATATCGCCGAGCTGGCGCACTTTCTGGTGCGAAAAATCGCCCACAGCCAGGGGCGAACGCTGCGCAT

CAGCGATGGGGCGATTCGCCTGCTGATGGAGTACAGCTGGCCGGGAAACGTGCGCGAACTGGAAAACTGTCTCGA

ACGTTCGGCGGTGCTGTCGGAAAGCGGCCTGATAGACCGGGACGTGATTCTGTTCAACCATCGCGATAACCCGCC

GAAAGCGCTCGCCAGCAGCGGCCCGGCGGAGGACGGCTGGCTCGATAACAGCCTCGACGAGCGCCAGCGGCTGAT

CGCCGCCCTGGAAAAAGCGGGCTGGGTGCAGGCCAAAGCGGCGCGGCTGCTCGGCATGACCCCGCGCCAGGTGGC

GTATCGCATTCAGATTATGGATATCACCATGCCGCGACTGTGAAGCCTTATGTGAGATTCAGGACATTGTCGCCA

GCGCGGCGGAATTGCGACAATTCAGGGACGCGGGTTGCCGGTTAAAAAGTCTACTTTTCATGCGGTTGCGAAATT

AACCTCTGGTACAGCATTTGCAGCAGGAAGGTATCGCCCAACCACGAAGGTACGACCATGACTTCCTGCTCCTCT

TTTTCTGGCGGCAAAGCCTGCCGCCCGGCGGATGACAGCGCATTGACGCCGCTTGTGGCCGATAAAGCTGCCGCG

CACCCCTGCTACTCTCGCCATGGGCATCACCGTTTCGCGCGGATGCATCTGCCCGTCGCGCCCGCCTGCAATTTG

CAGTGCAACTACTGTAATCGCAAATTCGATTGCAGCAACGAGTCCCGCCCCGGGGTATCGTCAACGCTGCTGACG

CCTGAACAGGCGGTCGTGAAAGTGCGTCAGGTCGCGCAGGCGATCCCGCAGCTTTCGGTGGTGGGCATCGCCGGG

CCCGGCGATCCGCTCGCCAATATCGCCCGCACCTTTCGCACCCTGGAGCTGATCCGCGAACAGCTGCCGGACCTG

AAATTATGCCTGTCGACCAACGGACTGATGCTGCCTGACGCGGTGGACCGCCTGCTGGATGTCGGCGTTGACCAC

GTCACGGTCACCATTAACACCCTCGACGCGGAGATTGCCGCGCAAATCTACGCCTGGCTATGGCTGGACGGCGAA

CGCTACAGCGGGCGCGAAGCGGGAGAGATCCTGATTGCCCGTCAGCTTGAGGGCGTACGCAGGCTGACCGCCAAA

GGCGTGCTGGTGAAAATAAATTCGGTGCTGATCCCCGGTATCAACGATAGCGGCATGGCCGACGTGAGCCGCGCG

CTGCGGGCCAGCGGCGCGTTTATCCATAATATTATGCCGCTGATCGCCAGGCCGGAGCACGGCACGGTGTTTGGC

CTCAACGGCCAGCCGGAGCCGGACGCCGAGACGCTCGCCGCCACCCGCAGCCGGTGCGGCGAAGTGATGCCGCAG

ATGACCCACTGCCACCAGTGTCGCGCCGACGCCATTGGGATGCTCGGCGAAGACCGCAGCCAGCAGTTTACCCAG

CTTCCGGCGCCAGAGAGTCTCCCGGCCTGGCTGCCGATCCTCCACCAGCGCGCGCAGCTGCACGCCAGCATTGCG

ACCCGCGGCGAATCTGAAGCCGATGACGCCTGCCTGGTCGCCGTGGCGTCAAGCCGCGGGGACGTCATTGATTGT

CACTTTGGTCACGCCGACCGGTTCTACATTTACAGCCTCTCGGCCGCCGGTATGGTGCTGGTCAACGAGCGCTTT

ACGCCCAAATATTGTCAGGGGCGCGATGACTGCGAGCCGCAGGATAACGCAGCCCGGTTTGCGGCGATCCTCGAA

CTGCTGGCGGACGTTAAAGCCGTATTCTGCGTGCGTATCGGCCATACGCCGTGGCAACAGCTGGAACAGGAAGGC

ATTGAACCCTGCGTTGACGGCGCGTGGCGGCCGGTCTCCGAAGTGCTGCCCGCGTGGTGGCAACAGCGTCGGGGG

AGCTGGCCTGCCGCGTTGCCGCATAAGGGGGTCGCCTGATGCCGCCGCTCGACTGGTTGCGGCGCTTATGGCTGC

TGTACCACGCGGGGAAAGGCAGCTTTCCGCTGCGCATGGGGCTTAGCCCGCGCGATTGGCAGGCGCTGCGGCGGC

GCCTGGGCGAGGTGGAAACGCCGCTCGACGGCGAGACGCTCACCCGTCGCCGCCTGATGGCGGAGCTCAACGCCA

CCCGCGAAGAGGAGCGCCAGCAGCTGGGCGCCTGGCTGGCGGGCTGGATGCAGCAGGATGCCGGGCCGATGGCGC
```

-continued

```
AGATTATCGCCGAGGTTTCGCTGGCGTTTAACCATCTCTGGCAGGATCTTGGTCTGGCATCGCGCGCCGAATTGC
GCCTGCTGATGAGCGACTGCTTTCCACAGCTGGTGGTGATGAACGAACACAATATGCGCTGGAAAAAGTTCTTTT
ATCGTCAGCGCTGTTTGCTGCAACAGGGGGAAGTTATCTGCCGTTCGCCAAGCTGCGACGAGTGCTGGGAACGCA
GCGCCTGTTTTGAGTAGCCGTTTCCCGAAGGGGGCGCTGCAAACAAAAAAGCCGGAGGTTTCCCTCCGGCTTTTC
ACATCATCAAATGTGATTATGCGACGTCTTCGTACTGCGGCACCGGGTTGCGGAAGCTTTTGGTCAC
```

*Pseudomonas stutzeri* A1501 nitcluster (SEQ ID NO. 5)
```
gttaggttggcctgaattcggtgtgtatccccggagatcagcttcgcctcggcacgctcagcctgcactcgccc
cagcctagctttccgccgcaagtgcggcatcgagtcgcgccaccaggctgccgtcggcttccaggccgaggatga
tgtcgcaaccgccgaccagctcgccacgcaggaacagctgcgggtaggtcggccactgcgagatcttcggcagct
tctcgcggatatgcggtgccagtagcacgttgaccgtggcgaacggccggccgctgttcttcaatgcctccaccg
cggcgcgggagaaaccgcactccggcacgcccggcgtgcccttcatgtacagcagcaccggatgctcggcgagtt
gctggcgtatgcgtgcttcggtatcgagaacttgcatgcgttcactccattgccagggtgcaggggagttgtag
gcgcaggggctggcatgggcccgctgtgggcgatccttccaggcctcgtagccgccgtccaggctgtagcaattg
atgaagccgaaatcgctgaacagctgtgccatgtcacggctggcatgaccgtgctcgcaacagatgatcagatgg
acgtgatttggcgtgctcttgagcagcgtgcgcaagttcagctcgctgaggcgggtggcgcgcgggtcatggccc
tggcagtaggcgcgggcatcgcgcatgtccagcagcatggtgttttcggtcgccaacagccgctgggcctgctcg
acgctgatgcgttggtagtcgctcattgctcttctccaaaacaatcgtgataggtcgggcaggcttcacaagagg
gggagcggcatacgtagccgccgtcctgttcgcatagttgtttgtagaggaacttcttccagcgcatgtcctggg
tattgcgccgggccagctgcgggaagttgtgcatcagcagcgcgtacagctgcgcccgcgaggccaggccgaggt
cgcgccacaggtgttcgccaccgaggcaggcggcagcgacgatggctgccatcgccggttcgccgtggtcgtcct
ggccgcccagcagcaggtcgtgcagcgcctgccattcttcccggcgcagcgccagcaactcttcgcgcaaggcgt
cgcgctcgccgagcaaggcctcgtcggcgctacgggatggtggtcgcagcccatggcgcgtcaggagctcggcgt
actgcgccgcgtcgagcccgaggtgctgcggcaggcaactacggccttcgcgctgggcgcggatgatctgcgcta
gccaggccgggttgtcgttgactgcgacctccaggcacaacgcggcccggctcattgcggcgtgctcgcggcggg
gctgcaaccgagcaccgagctggtgcccagcgaacagccgctgatgctcggtgccagcgctggcagccggccttt
gcacggcagccaggcattgatgccgaccaggtcgaagtcgaccatgtagtgcatgccgcagcggatcagcgggcg
gcggatcaacagcggctgggccaccatcagctccagtgcctgttcggcgctcagttcgctgacatccagctcgcc
gtacttgatcgccggggccgacgggttgaaccactcggccaccggcagccggccgaagaacggccgcaggcgttc
cggcgtccaggcctcgcgcagcaggtcgcgcacttccagctcgatgcccgctgaacgcagcagctccttctgcag
gcggttggtggcgcaaccgggcttctcgtagaagatgatgcaggacatggcaacctcctcaacgggcctggatgg
cgcgcatggcctcggccaaccgctccggcggaatgcccgtcagcgagccggctgggttggccgggctgccgtcgg
cgagcaggatcgcgccttcgatggggcagatgctcgcgcactgttgctcggcgtagtcgccatcgcattcggtgc
acttgtgcgcgctgatgcggaagtacgcagtgccggggctgatcgcctcgctcgggcagacgtccacgcaggccc
agcagttgacgcaggattcgacgatttgcagtgccatactccacctcctcatgccatcaggcattgctccgctgc
gcccaccgacgcatcgagacggccattggcgatcatttcctggtacacctccagcacggcttcctcgatgggctc
catggcgtgctcgccattgggctggatgccggcggcttccagctcgcccccagggttcgaagccgatcttcgagca
gagcaccgcctcgcagcccttgagcgcgcggatgctgcccgacagcgcactgtccttgtcgccgcagctgtcgtt
gccgacgcagtactgctcgaccttgcggtggccgatgaagcgcacccgccggcgaggcctcgtagacgaggaa
ttcgcgggcatggccgaagtgctggttgaccaggccgccgccgctggtggccacggccatcagtaccgggcgatg
gcccttgtccactgtgccggtgagctgcgcagcgctggggggtggccaggcgcgccttcttcgccgcgcgttcgtc
cagctcctccttgatcgccgcgtggatggcggcgcgcttgaccatcgccgcctcgtagtcgacgtccatgctctc
```

```
gatcttgtcgagggtgaactcgtcgccgcggtcctcgccgagcaggcccaccgcgtcggcgcggcactggcggca gtggcgcatcatgttcatgtcgccggcacaggcgtcctgcaggtcctgcagttcctccggctccgggctgcgctg gcccatcacgccatagaaggtgccgtgctcggcctcggcgatcagcggcatgacgttgtgcaggaaggcgccctt ggccttgacgatgcggctgacctcttcaggtgctcatcgttgacgccgggatcagcaccgagttgaccttcac caggatgccacgctcgaccagcatctccaggcccttctgctgccgttcgatgaggatcttggccgccttgcgccc acggatgcgcttgttgttccagtagatccaggggtagatctcggcgccgatgtccgggtccacgcagttgatggt gatggtcacgtggtcgatgttgtgcttggccagctcgtcgacgcagtcgggcagggccaggccgttggtggagac gcacagcttgatgtccggcgcctgctcggacagcatgcgaaaggtctcgaaggtgcgctgcgggttggccagcgg gtcgcccgggccggcgatgccgagcacggtcatctgcgggatggtcgccgccaccgccttgaccttcttcaccgc ttgcaccggctccagcagctcggacaccacgcccgggcgcgattcgttggcgcagtcgtacttgcggttgcagta gtggcactggatgttgcaggccggcgccaccgccacatgcatgcgcgcgaagtagtggtgcgcctcctcggagta gcaggggtggttgtgcactttctcgcggatgtgctcgggcaggtgcgcgagctggtcatccgagctgccacagga acccgctgaacaaccgcccccggcggttggcccggcctcgctctggcccagtacgttcagttccatgttcggtct ccgaatagaggtctgtccccggtacctgcagcaaggcttgtgcctgttttcaaatcattgtttcagaacgaattt ttcagaaagcgggcggaattcgttgtttcgcaacgaacaaagtggcggggccgggcggggcggctgtcgcaaagg cgacaagctgcgcacgcccggttcccgggctgtcgcgacccggtgctccagacgattgcgcatggcgggccgcga tccgcaccagcgccccggcccgctggtgccgggctactcctcgaggcgcccgctggcgtcgcgatcgcgcacgta atggtgggtgagcggaaacgccggcagccaggactcgcggcggacggtccagagctcgtaggtgggcatcagctg gtcgggggcatccagggctcccaggctcacttcgatttcgtccgcggtgcgtgccctgctagtgatgcgtagtgg gcacaaggcttcgcggggaagcgccatgcatggggaacgctgcgccgcccgacccgggagtcgggcgggtcgttca gatcttgcgcatatgaatgttcagcgtctgcactcggtaggcgatctgccggggcgtcatgccgagcaggcgggc ggccttggcctggacccagccggcctgttccagcgcggcgatgacgcgctcgcggtcgtcgaggctgtcgtcggc gaggtcgacttcggggaccggcgccagcggcgtggcgtcgtggtcgaggccggtgagggagaccacgtcgcggct gatggtgccatcctcgctcatgatggccgagcgttccaggcagttttccagttcgcgcacgttgcccggccagcg gtggctcatcagcagacgcagggcgctgtcggtcagcttgagtttgcgaccctgctggcgggcgatcttgtcgag gaggaattcggccagttccgggatgtcggcgctgcgctcgcgcagcggcgggacgcggatggccatgacgttgag gcggtagtagaggtcttcgcggaacttgccttgctccacctcgtgctccaggtcgcggttggtggcggcgacgat gcgcacgttgaccttcaccgtctggctgccgccgacgcgctccagctcgccttcctgcagcacgcgcagcagctt ggcctggaacatcggcgagatctcgccgatctcgtcgaggaacagggtgccgccgtcggcctgttcgaaacgtcc cttgcgctgcttcacggcgccggtgaaggcgcctttctcgtgaccgaacagttccgattcgagcagggtttccgg tagcgcggcgcagttcaggcgtaccagcggctggtgagcgcgcggtgagttgtagtggatggcgctggcgatcag ctccttgccggtgccggattcgccgaggatcagcacggtgctgttccacttggcgacccgtcgaacctggtcgaa aacccggcgcatggaggcggtgtggcccaccaccatgttctcgaagccgtacttggcgcggacttcgcggcgtag ctcgtcgcgctcgtcgaccacttcctggccgtcctcgaggttcaccaccaggcgcacggtctgcgccagtaggcg ggcgacgatttccatcaaacgggtgcgttcgggcatcagctcgtcggcgcggcgtcgggctgggcagcagcac gccgatggtggtgccgtcgacggccttgatcggcacggcgatgaagggcaggtccatgtcgtacagcgccagtcg gtcgagaaagcgcggttcggcgtcgatacgcccgagcaccacgctgttgccatgcttgaggatgttgccgaacac gccttcgccgatgcggtagcgggtgctttcgcaggcccgtaccacggtttcggagtcgctgtgcacggcgcccac ctgcaggctgccgtccttcgggttgcagatggagaccagcccgtgcagcaggccgaggtcttcgtgcagcacggc gaggatctcggccagcagttcctcgatgggccggccgcggttaaggatgcgggcgatctgcgccagcgcctgcag
```

-continued ttgggcatccagcagttcgttgcgggttggcgcgctggggcgttcggcgaatgtggcgttcatgcgagcttcccc tgtcagctggccgagaagggcagttcgacgacgatcctgcagccctggtcgtagccgctatcgatatgcaccgtg ccggcatgctcggtgacggtttcctgcaccatggccaggcccatgccgcgaccggtcttgtgcggcggcttggtg ctgaagaagggttcgaataccttgagcgccagctccggcgcgatgcccgggccgctgtcggcgatctccaggcgc accaccgctggccctggacacgggtgacgatcgacagcgtgcgcgggttgtcctggttctggctcatggcctcg atggcgttttccagcagctgcttgatcatgctgcgcagccggccttcggcgcccatcacccagggtaggcgcagc gccggctgccagtcgacgacgatgccctgggcgagcaactggtcggtcatcaggctgaccacttcgcggatcagc tggttgatgttgaccggcacgcagccgccggcccggcgctgcggaatcgagccgctgaggctttccagcgcatcc atgccagcctggctggcttcgcgcatggcgctgagcaccggatcgccctcggcgctgtcgcccaggcgtcgttcg agcatgcgcagcgccgcactgatcaggttgaccgggccctgcaggcggtggatggcgccgttgaaggtttcgcgc atgccgtcgagcagctcttcctcggccatcagcaccttcagggcgttgagctgggaggcctgctgttgctggcgc agcccggtgatgtcgttgaccgtcagcagcaggtagttttcctcgcccgggtcgaagaagtcgtcggcgcgttcg ccttcgatgaggatggcgcggccatggcaggacagccagcgcggtgtgtggccgccgaggtcgaaggtgacttcc ttgccggtgaaggcctggccatgcgccttcagcgcctcgatggcgccgccgaggttgtcctgcagcaggctcacc agttgcgcgggcgtggcctggtcgccgagttccgcggccaggcggttgaagctggggttggacaggcggatgcgc agggcgtgatcgagcaccacgatggccgccggtgcgctgtcgaccaccgcctcgatgatcagccgctggttgctg acgcgctgttcgagcttgtgctggtcgctgctgtcgcggtgcatgcccaggtaatggatggtccgctcgtgctcg tcgagcaccggcgccacggtcagctcggcgaggtagcagctgtcgtccttgcgccggttgaccagcatgccggac caggccttttctgcgccaggcggctccagagcgcctggtagaccagccgcggggtggtgccgttggacagcacc gattcgttcttgccgatcacctcgctgctgtcgtagccggtgatggcgctgaaggcgcggttggcatagaggatg ttggccttcagatcggtgatggaaatggcgatcggcgcgtgctccacaggcttgctggaacacttcgggcgccaat ccatcggacgcagcgggttgccccgcgtcgcgctcggggtggcctgggtcatgtgcatgtcctcatcgatgcgg cgaagccgacgtctgtgcgccggtatccgttgcaaagccatacggttaggggcgtgttgccgttcgcgagctgcg aatgaaacggcaacagacccctaggggttttgcaaaccgcgtgccgtcggtcacattccttgccgacagccctgc ggagccgtaaatacgctgtgcagatggatttctgccccgacaggtgccgctgggctgttgcaaaacccacaggga ggcgcgcgcacttctcccggcctgtcgcaaaccccacaaagtccgtcgcgccagcgtcgccaggggttgcgctat cacgggattcgttgatctgcatcaacgaatcccgggctctcggggcgctccgggacgcccggcggggcgtggcat gcttgatgcaaaaccctcacaacaaggcctttgcccgacaacggtgcaagcgctgccaataggctgggaggggt tatggaatatgcgctgtttctgatcggcaccgtgctggtcaacaacgtggtgctggtctacttcctcggcctgtg tccgttcatgggggtctccggcaagctcgaccctcgctgggcatgggcttggcgacgaccctggtgatgaccct gggcggcgtcagcagctggctgctagaacgctacgtgctgcagccgctgggcatcggcttttttgcgcatcctctc ctacatcctggtgatcgccggcctggtgcagctgatcgagatgatcatccgcagggttagcccgccgctgtatcg ctcgctgggcatctacctgccgctgatcaccaccaactgcgccgtgctgggcgtgccgctgatcagcgtgcgcga aggccacaggctggccgaggcggggctgttcggcctgggctcggcgctgggcttcaccctggtcatggtgatctt cgccggcttgcgcgagcgcctggcgctggccagcgtgccggcggccttcgccggcgcaccgatcgctttcgtcac cgccgggttgctggcgatggctttcatgggcttcgccggcctgatctgaaacgcacgccgccggcgaggctggcg aaggaggagcaatgctggacgcaattctggttcttgcactgatgggcctgctgctcggcggcggcctcggtctgg cggcgcgctatctggcggtttcgcaggagaacccgctgatcaaggaaatcgaggcgctgctgcccggcagcagt gcgggcaatgcggctatccgggttgcagtgcggcggccgacgccttggtcgagggcagcgccgcggtcacctgct gcccgccggcggggccgcgctggccgagcgcctggccgaactgctcggcgtgccgctggacgccagtgcgctcg ccgcgcccatgctggcgcgcatcgacgccgccgagtgcaccggctgcacgcgttgcttccgcgcctgcccgaccg -continued

```
acgccatcgtcggcgccaacgggcagatccattgcgtgttgagcaatgcctgcattggctgcagcaaatgcctgg
aggcctgcccggaggactgcatcgccctcgcgccccagacactgacgctggaccactggcgctgggccaaaccca
gggccgcctgatttcgcctgatgaacaggggcgtcagaccccggggagtcgacaatgttcaacctcgcgcattttc
gcggcggcatccatcccgccgcccacaaggaccgctcggccgccctcggcatcgccgtgcagccgctgccgccgc
gcctgtacctgccgtttcgccagcatgccggggccgaggccttgccgctggtgaaggcgggcgagcgggtgctca
agggccagctgctggccggctcgcccactgagctctcggcgccgatccatgcgccgagttccgggcgcatcctct
cgatcgggccgatcgacgcgccgcatccgtcggggctgcaggtcaacggtgtggtcctcgaatgcgatggcgagg
agcgctggatcgagctagacgtaccggccgacccctttcgccgaggacccgcagcggctcgcccagcgcgtcgccg
atgccggcgtggtcgggctcggcggggcgatcttcccggccgcggtgaagctcaagcagggcgcccggcacgaga
tcaagaccgtgctggtcaacgcagcgagtgcgagccgtacctgagctgcgacgaccggctgatgcgcgagcgcg
ccgaggcggtggtcgatggcgcgcggctgatccagcacatcctgcgtgcctacagcatcgtcatcgccatcgagg
acaacaagccggcggcgctggcggccatgcgtgctgcgagcgagccctacggcgccatcgaggtggtggcggtgc
cggcgctctacccgatgggctcggccaagcagctgatccgccaggtcaccggccgcgaggtgccggccggcgggc
gcagtaccgacgtcggcgtgctggtacacaacgccggcacggtgtatgcgatccagcaggcgctgcgccacggcc
gcccgttgatctcgcgggtggtgacggtggctggtggttgcgtgagcaacccgcgcaacatcgagactctgatcg
gcacccggtgcaggcgctgttcgaaagctgcggcggactgctgcgcgagccgcagcaactgctgctcggcgggc
cgatgatgggcatgctgctgccatccacggcggtgccggtgatcaagggcgccaccgggctgctggcgctcgacc
acggcgaagtgccgcgcagcgacagcgcgccgtgcatccgctgcgcgcgctgcgtcgacgcctgtccgatgggcc
tggctccgctggagatggccgcgcgcacccgcgtcgacgatttcgacggcgccagcgaatacggcctgcgcgact
gcatcctctgtggctgctgcgcctatgtctgcccctcgcacattcccttggtgcagtacttccagtacgccgtcg
gccagcaggacgagcgccgcagcgccgcgcgcaagaacgattacgtcaagcagcttgccgaggcacgggcggcgc
gcttggccgaggaggaagcggccaaggcggcggccaaggcggcgaagaaacgcaaggcggcggcgccggccgcca
gcgaggtatcgccatgagcgcgcagggtatcgcggcggggccgttcgcccatgatcgctcctcggtcgaccgcat
catgctgcacgtctgcctggcgttgctgccgacgacggcctggggcctgtatctgttcggctggccggcgatcta
cctgtggctgctgacctgcgccagcgcggtggcctgcgaggccgcctgcctgtacctgctcggccggccgctgcg
ccgcctgctggacggcagcgcactgctcagcggctggctgttggcactgacgctgccgccctgggcgccctggtg
gatcgccgtcggtggcagcatgttcgccatcggcattggcaagcagctgtacggcggcgtcgggcagaacgtgtt
caacccggcgatgctggcgcgggtggcgctgctgatcgccttcccgctgcagatgaccacctgggccctgcctttt
gccgctgggtacggagggcgcgcccggctggctcgaaggcctgcgcatcaccttcgccggtggggcgctggccga
tggcctgagcggcgccaccgcgctgggccacctgcagaccgagctgaccctggggcacagtgccgcgcagatcct
cgacgggcatttcgcgttgctgccggccttctcggctacagcggcggcagcctcggcgagacctcggagctgct
gatcctgctcggcgggctctggctgctggcactgcgcatcatccactgggagatcccgctgggcatgctgctgac
ggtgggcgcgctggcggcgctggcgaaccagatcgacccgcaggtacatggcggcgggctgttccacctgacctc
gggcggcttgctgctcggcgcgttgttcatcgccaccgatccggtgacctcgccgatcagccgcagtggccggct
gatcttcgccatcggttgcggcgcgctggtcttcgtcattcgcagctggggcaatttcccccgaagccgtggcgtt
cgccgtgttgctcatgaacgccctggtgccgctgatcgaccgcgtctgccggccgcgtgcctatggccgcaacgc
gcgcggcaagccgctggtggcggcgaagtggaccgccaggtgaaggaggtcgacaaggtatgaacgagctgacc
cagacgccgcccgtggcagacggcaacgaaccgccgctcacccgacccggcctggtcgagacctggcgcgagcgg
gtttcctaccaggcgctgtcgctgggcttggtctgcgccctggtggccgtggcgctgctgctcggcaaccagctg
acccaccagcggattgtcgacgccgagcggcaggaccgcctcgccgtgctgcgccaggtgctgccgcaggcgctc
```

-continued

```
tacgacaacgatccgctggccgatgccttcaacgtcgaggatgccgagctgggcctgatcgaggtgtacccggcg cggcgcgcggggcaactgacggccaccgccttccagatcagcaccgtcggctacggcggcccgatcgtccagttc atcgccctcgacagcgaaggccgcatcctcggcgtgcgggtgctcagccacaaggaaacccctggcctggcggac aagatcgaagtcacccgcagcgactggatcaaggccttcgacggcctgtcgctggccagcacaccgctggatcag tgggcggtgaagaaggacggtggccagttcgaccagttcgccggcgccaccatcaccccgcgggccatcgtcaag ggcgtgctccgggcgctcgagttccaggcccgccagtccaccgcccagtccaaccaggagactcggccatgagca gccaatgcggatcagcggatgtcacggcgcccaagcccaaggggctgttcaactacttcagctcggcgctgtggg actacaacgtcgccctggtgcagatgctcgcgttgtgcccggcgctggcggtgaccaccaccgctaccaacggcc tgggcatgggcctggccaccaccctggtgctgatgatcaccaatgcgatcatttccgcgctgcgccacagcattt cgccggcggtgcgcaacccgctgatgatcggcatcatcgccggcgtggtgaccctcatcgacatggcgatcaatg cctggatgcacgaactgtacaaggtgctggggctgttcatcgccttgatcgtgaccaactgcgcggtactcggcc gtgccgaatcgttctgcagccgcaacccggtgctgccctcgatcctcgacggcgccggcatgggcatcggcttca cctgggtactggtggtgatcggcgggatacgcgagatcctcggcagcggcacgttgttcgcccaggcctcgctgc tgctcggtgagcacttccgctggctggagatcaccgtcctgcccggcttccagggcatcctgctggcgatcctgc cgcccggggcgttcattgttctgggcttcgtgctggcgttcaagcgagtagttgatcgccggcgcgccgagcgac ggatcaggacccatggcgaactggtagtgttgcagtgagcccggccgaggagcgaagcagacgatgaagatttcc gttgtatacgccgcaccccggcagccctgctgttcgattgccgggtggcggaaggctccagcgtggccgaggcc atcgagcactccggggtgctgcgctactgcccggacatcgacctgagcaagcaaaaggtcggggtctacggcaag ttcgtcaaactcgacagcccgctgaaggagggcgatcgggtggaaatctaccaacgcatcacgcgcgtgctggat gaagacgacgatgacgacgactgacagccgccgcggatgaccatagccgagagaggagcgaccgatgaacagcca gcccccgagcatgaaccgtgaaaccgcattacgcatcgcactggccgcccgggcattgcccgaggtgggcgtcgg ccggttgctggatatcctgcaccagcggatcgatggagaactgaacgaagagagcctgcagcgcgtgaccgtcac cgacctcaagacggcgttcgccagcgccgacggcgaggaggatggcgaggacatcggcatcggcctgccggcgct gaaggaagcggtgcgcatcctctggggcgaaggcgtcggcgacgacctgccgcagccggaggtcctggaccgcgt gccggaaggctcgatccgggtggccatcgcctccaacaacggcgagcgcctggacggccatttcggctcgtgcct gcgttttctgatctaccagatcggcctcgacagcctggcgctggtggacgtgcgctcggcgctggagaccgagtt cgccgaggatcgcaatggcgcgcgtgccgagctgatcggcgactgccaggtgctctatgtggtctccatcggcgg tccggcggcggccaaggtggtcaagaccggcctgtacccgatcaagaaggccggtggcgaggcccggcagattct cgccgacctgcagaccgtcatggccggcaacccgccgccgtggctggccaagctgctgggcgtgagcgccgagca gcgagtgcgcttcgaccgctccgacgacgaggcggcctgggcatgagcgatgtgcgcaggctggtcgccgtggcc atcgaccgccagggcaaggtcgccggtcacgccggtcgggcgcaccactggcaggtgtacgacatctggcccggc gaggcgccggaatccgtctatcgcctggcgctggacgaacaggcctgcctgcacgagtggcatgtcagcgcgcaa ccggaacgccatccgctgcacgcggtggacgtggcgatcgccgccagcgccggcgacggcgtggtgcgtcgcctg ggcgagcgcggcgtgacgctgttgaccaccgccgagagcgacccggaacatgccgttaaagcctggctcgccggc agcctgccgccaggcttgccgcacgaggagccggctgcggcggcgaggggcaccggcatccctgagcgtgcggg gatgggacggatggcaaccccaggctgggtcgagccgcgcagcggcgaagcccaacgtcgtgcgggctcaagccc gtgcaaccggcattgttcgtgagaacaccatgggcggatgtggcgcctgatgatccgcgatgttgggcttcgctt cgctcaacccaacctacggcaccggggcgataggcaaaaaaaactcccctgggagcgcaggggagtggctcatcgc caatatggggatgtcaaaccgttgcacgtgacccgggctgcgcccgggctctgcgagcccagggcaacctagggt ggaatcgagcccatgctggccaagcccaatacgcccctgggtggttcagatcggcccgcgcgcctcgcgacgat gggcgacggtgcagccaagggcggcctcgtagctcagcgtctccagcttcggccggtagtcgcgcagcgcggcgt
```

-continued

```
agacggtgagtaccttgtcctcggcgctctggcccttgaagtcttccttgtccaggcgcaggtcgtcggccaggg
tgttccacaccgcgccttcctcgtgcgcctgcagctgcagggtcatgccgtcgagctcggtgtacagcgactggc
cgaggttctccacgtagaagatcaccggtgcgccgtcggccaggtcgcggcgatagcgttcgaggaacagcggca
ggtgggccagttcgatcagggcgccggccatcatcgccagtttcccctgctgctcgagcatgaccgcctgcttga
ccacggcggtcggcggcaggcggcggccggaggcgtcggcgatctcgccttcttcgagcaccaggtcgccgcgga
aggcgtaggtgtccggcgtcgtggtcgcgccattgacgctgacgttgcacagcaggttttgcgtttcgtaggttt
tcaacagcatggtcatggtctctcgtggaaaaaatggtcaggcgacttgtggggcgccctgggtcaggccaagca
ggtcgtgccaatcggtctcgaccagttccagttgcttgcgcaggcagaccctgcggtcctttgcgctgggcgagg
ggatcagcgcccagccggcgggcgcggctgcatcgtggatcaggtcgctcatcagcatgcgctcggtgtcgcggt
tgaactgcatgccgaggaacaggtagcggcattccttgcgctgcagcttgagccagccgggaatggcgaaaccgc
ccatcagttcggtgatgtagtcgacgaagtcggcgtcgctggcgacgtaggaagggctcggcagcggcgtgccca
gcggcttgaacagcaccggtagcgcgggattgacctcgctctggtcgatgcgctggtagcggcctgcgtcgaagc
gatagatgtcgaagcggtaggggctggcggcgatgcgcgcggcgccgaccaccagggtatgcggacggtcggcat
agcagcgctgcagctgggtgtcgcgattgcaatcgatgacgtagggcaggttcagcccggccagccagcggtgca
gcggcgcgggcgtccagttgtcgccgccgtaggtctgagtcaggaagcgctcgatgaagctgcggcccttcttgt
tctccaggtgcatggcggcacgcgggaattcgtacatcagccgcggcgccatcggctgcccgccgttcatggcga
ggatcaggctttcattgtcggccggcatcggctgacctgtgtcgcggtcgaccacgccgcccagcacaccggggc
ccagatagggcaccagttcatgggcggcgaggcggtcggcgatttcctgcaaaggatcgttcacggcaaatctcc
tgcggccagtggatttaccgatagccgatcgcaataaccgagccagccgggagcgtgcatgcaaccccttgatat
atggggctttgaatgcggcgatagttgccgttcaggtgttttcgaaagtatcgaacgcgacaattgtcatgttcg
caacagttgccgaaagtgtggaaaaccggcgcttggcccggccgatcttttgtcgccattgcaacagtcaggcc
tgtcggttgttaactatcgaaccgccgaaggatgttgctagtaattaaattattctaattaaaacaagtgcttag
attattttagaaacgctggcacaaaggctgctattgccctgttgcgcaggcttgttcgtgcctatagcccacgtc
aagtggtaacgaaacctgaggaacttaattatggcaatgcgtcaatgcgctatttacgggaagggtggaatcggc
aaatccaccacgacccagaacctcgtggcggccctggccgaactcggcaagaaggtcatgatcgtcggctgcgac
cccaaggccgactccactcgcctgatcctgcactccaaggcgcagaacaccatcatggaaatggccgccgaggcc
ggtaccgtggaagacctggaactcgaggacgtgctcaagaccggctacggcgacatcaagtgcgtcgagtcgggc
ggtccggagccgggcgtgggctgcgccggtcgcggcgtgatcaccgcgatcaacttcctcgaagaggaaggcgcc
tacgaggatgacctggacttcgtcttctacgacgtgctcggcgacgtggtctgtggcggcttcgccatgcccatc
cgcgagaacaaggcccaggagatctacgtggtctgctccggcgagatgatggcgatgtatgccgccaacaacatc
tgcaagggcatcgtgaagtacgccaactccggcagcgtgcggctcggcgggctgatctgcaacagccgcaacacc
gaccgcgaggacgagctgatcatggccctggccgacaagctgggctcgcagatgatccacttcgtcccgcgcgac
aacgtcgtcagcgcgccgaaatccgccgcatgaccgtcatcgagtacgaccccgccgccaagcaggccgacgaa
taccggaccctggcgaagaagatcgtcgagaacaagaaactggtcatccccaccccgatcagcatggacgagctg
gaagccttgcttatggagttcgggatcatggacgaggaagacatgaccatcgtcggcaagaccgccgccgaggaa
gtcgttgcctgatcgcttcagcagaacggggcagggcggatgggccctgccggggtgtcgcaccgtgcctggcac
ggtgcggtgcgcccgtgacccgcacatgaacgcaagaggaggtcaatcatgaccggtatgtcccgcgaagaggtg
gaatccctcatccaggaagtcctggaagtctatccggagaaggcccgcaaggaccgcgccaagcacttgtcgccc
aacgacccggcgcttgagcaatcgaagaaatgcatcacttccaacaagaaatcccagccgggtctgatgaccatc
cggggctgcgcctacgccggctcgaagggtgtggtctgggggccgatcaaggacatgatccacatttcccacggg
```

-continued

```
ccggtgggctgtggccagtactcgcgcgcgggcggcgcaactactacatcggtaccaccggggtgaacgccttt
gtgaccatgaacttcacctcggatttccaggagaaggacatcgtcttcggcggcgacaagaagctggccaagctg
atcgacgagatcgagacgctgttcccgctgaacaagggcatctccgtgcagtccgaatgcccatcggcctgatc
ggcgacgacattgaggcggtcgccaagaagaaggccgccgagcacgaaaccaccgtggtaccggtgcgctgcgaa
ggtttccgcggggtgtcgcagtccctcggccaccacatagccaacgacgccatccgcgactgggtgctggacaag
cgcgacgatgacaccagcttcgagaccacgccctacgacgttccatcatcggtgactacaacatcggcggcgat
gcctggtcctcgcgcatcctgctcgaggaaatgggcctgcgcgtggtcgcgcagtggtccggcgacggcacgatt
ccgagatggaactgacgcccaaggtcaagctcaacctggtgcactgctaccgctcgatgaactacatctcgcgg
cacatggaagagaagtacggcattccgtggatggagtacaacttcttcggcccaaccaagaccgccgagtcgctg
cgggccatcgccgagcatttcgacgacagcatcaaggccaagtgcgagcaagtgatcgccaagtaccagtcggag
tgggaggcggtgatcgccaagtatcgcccgcgcctggaaggcaagcgcgtgatgctctacgtcggcggcctgcgt
ccgcgccacgtgatcggcgcctacgaggacctgggcatggaagtggtcggcaccggctacgagttcggccacaac
gacgactacgaccgcaccctcaaggaaatgggcaacgccacgctgctctacgacgacgtcaccggctacgagttc
gaggagttcgtcaagcgcatcaagcccgacctgatcggctccggcatcaaggaaaaatacatcttccagaagatg
ggcattccgttccgccagatgcactcctgggattattccggcccgtaccacggctttgacggcttcgccatcttc
gcccgtgacatggacatgaccctgaacaacccgtgctggaagaagctgcaggcgccctggcagaaggccgaggaa
tcggccgagaaggtcgccgccagcgcctgatggtccgcagtcgtacgcaacgtccgcggcggccggcgcaggccg
gtcgctgccgacatccgtgatcgccgttcacagatgagtgaggcgaaggagagagtcatgagccagcaagtcgat
aacatcaaacccagctatccgctgttccgcgacgaagactacaaggacatgcttgccaagaagcgcgatgccttc
gaggagaagcatccgcaggacaagatcgacgaagtcttccagtggaccaccacccaggaataccaggagctcaac
ttccagcgcgaagccctgaccgtgaacccggccaaggcctgccagccgctgggctcggtgctctgcgccctgggc
tttgagaagaccatgccctacgtgcatggctcgcagggttgcgtcgcctacttccgtacctacttcaaccggcat
ttcaaggaacccatctcctgcgtgtcggactccatgactgaagatgcggcggtgttcggcggccagcagaacatg
aaggacggcctggccaactgcaaggccacctacaagccggacatgatcgccgtgtccaccacctgcatggccgag
gtcatcggcgacgacctcaacgccttcatcaacaactcgaagaaggagggcttcatccccgaggactacccggtc
ccctatgcccacaccccgagcttcgtcggcagccacgtcaccggctgggacaacatgttcgagggcatcgcccgc
tacttcaccctcaatcacatggacgacaaggtggtcggtagcaaccacaagatcaacgtcgttcccggcttcgag
acctacctgggcaacttccgcgtgatcaagcgcatgctcaaggaaatggacgtcggctacagcctgctctccgac
ccggaagaagtgctcgatacccggccgacggccagttccgcatgtactccggcggcaccacccaggacgagatc
aaggatgcgcccaacgccctgaacaccctgctgctgcaaccctggcagttggaaaagaccaagaagttcgtcgaa
ggcacctggaagcacgagacgcccaagctgagcatccccatgggcctggactggaccgacgagttcctgatgaag
gtcagcgagatcaccggccagccgatccctgaaagcctggccaaggagcgcggccgcctggtcgacatgatgacc
gactcgcacacctggctgcacggcaagcgcttcgcgctctggggcgatccggacttcgtcatgggcatggccaag
ttcctcctggagctgggcgccgagccggtgcacatcctcgcccacaacgcaacaagcgctggaagaaggccatg
gacgcgatcctggagtcctcgcccctacggcaagaactgcaccgtgtacatcggcaaggatctctggcacatgcgc
tcgctggtgttcaccgacaagccgacttcatgatcggcaatagctacggcaagttcatccagcgcgacacgctg
cacaagggcaaggaattcgaggtgccgctgatccgtctcggcttcccgatcttcgaccgccaccacctgcatcgc
cagaccaccctgggctacgaaggcgccatgcagatgctgaccaccctcgtcaatgccgtgctcgagcgcctcgac
gacgagacccgcggcatgcagagcaccgactacaactacgacctggttcgttgaccgctagcggggagggcgacc
tccccatcctgccggccgacgcaccgcaatggtcgtcggccggccagcccttatttttcaggaagcctcccatgcc
cagtgtcatgatcagccgtaacaagaatggccagctgaccttctacatcgccaagaaggaccaggaagaaatcgt
```

-continued

```
cgtcagcctggaacacgacagccccgagcgctggggcggcgaagtcgccctggccgatggctccagctactacct cgaaccctctcggcaccgccgaaactgccgatcaccctgcgcgccaaacgggccggcgagggctgaacgatggc gcccagcaacggacgggctccgctgccggctcacctggccctgcgcatcgccctggcggcgcgcgagctgaacgg cgtggataccgggcaactgctgcgcaccctgctcagcgtcaccggcgagccgatcaccgaagcgcggctggccag gctgcgcctaaaccgcctgcgcaaccgcctgctgagcagcgtcgacgggccaccgccggtgctcagcgagcggca attgcagcgtgcgctcggcctgctcaaggggcgtggcgtgcgaatgcccgaggaaccgttgccggccatcgagcc ctatcgcgaaggcgagttgccggattcgatccgcatcgcctgcacctccgacggcggcgagcgcctggacggcag cttcggcagctgcgcgcgctttctcgtctaccagatctcgccgagcgccagccgcctgatcgacctgcgcgagcc ggggccggccgcgccccacgaggatcgccatgcccgccgcgccgaactgctgcacgactgccagctgctctacac cctgagcatcggcgggccggcggcggccaaggtgattcgcgtcggcacccacccggtcaaggtcatgcggccgat cccggcccgcgagatcgtcgaggaactgcaacaggtactggccagtgcgccgccgccctggctggccaaggctat gggcagcgagccggcaccccgcgtttccatgtctgaaaaagaggacaccccatgatcagtcagacccagctcgac gcggtcatccgccaggccgagaacggcccgctgaacgaggcgctgctcgccaggctgcgcagcgagcaccctggt atccacttcacctgttgcatggacgacgacgtggtggtcaacgccaagccggttgccgagcggccgggggttcaac gtctatctggtcaactccagccagcactgctcggtgctgagcaacgacctggacgccgcctcgggcatcgtcctg gccgaagtcatcgccgattagagagcgcccatgcagaacgacggtagcgaggacattatcccctggcggactgc cgcgattgcagctttcgcggcgacctgctgcccagcggccgctgcacgccgggcgaccgctgcgtagcgatccac agcggccggcagatcgaccgtttcttccggcagaatccgcagctggccgtacactacctggccgatccgttctgg gagcggcgcgccatcgccgtgcgctacgccccggtggaggcgctgctgtcgatgatccacgacgtcgacgaggcg gtgcgtcgtgccgtcgcctaccgcctgccgcgcgagcgcctgggcgaactcatgcgcgaccggatcgggaagta cgcatcaccgtcgccgaccgcctgccggccgagcagctggaacggatggctgccgacccggattacctagtgcgc gcctacgtggtccagcgcatcgccccagggcggctgttccgcttcatccgcgacgaggaccgccaggtgcgcaag ttcgtcgcccagcgtctgcctgaggaaagcctcggactgatggtcaccgaccccgaaccggaagtccgccgcctg gttgccgcgcgcctgcatggccaggacgtgctggaaatgctccacgaccccgactggacggtacgcctggccgcc gtggaaaacgccccgctcgaggccctgcgcgagctgaacgaagacgatcccgaagtccaggctgcgatcgcgcaa cggttgggggtaggttgggtggacgcccgacccgagatgatgcttttaggctttggtaggcctgccggcctgcat cgccgcgagggcgcgcctcccacaggtccgcaggctgcttgctgcctttgtgagcccgaccacggggcgatgctt ttcgctagggtgggccgggcggcgttccgcttcagcccaccaatcaagccagcgatcgcgaaggatgctggtggg ctgatgcccaccctacggatccgtaccgcccgacccggcctacggggccactcgccgaatcctttgttgcgaacc cgacatctgggcgcgtttgcgacaattttatttcaatgaaaatcatataaatcaatgagttaattttttggtacag gcattgcactcacctcgttgcgcataaccacgacgaccggagggtgcgatgaaagccaaggacattgccgagctg ctcgacgagcccgcctgcacgcacaacaagaaggagaagtccggctgcgccaagccggcgccgggcgccaccgat ggcggctgcgccttcgacggcgcgcagatcgcgctgctgccgatcgccgatgtggcgcacatcgtccatgggccc atcgcctgcgccggcagttcctgggacaaccgcggcacccgctccagcggcccgcagttgtaccgcatcggcatg accaccgatctctccgagcaggacgtgatcatggggcgcgccgagaagcgcctgttccacgccatccgccaggcg gtggagagctacgcgccgccggcggtgttcgtctacaacacctgcgtgccggcgctgatcggcgacgacctcgac gccgtgtgcaaggccgccagcgagcatttcgccaccccggtggtgccggtggacggcgccggtttctacggtacc aagaacctcggcaaccgcatcgccggcgatgccatggtcaagcacgtgatcggcacccgcgagcccgaccgctg ccggccggcgccgagcgcgccggtattcgcgtgcacgacgtcaacctgatcggtgaatacaacatcgccggcgag ttctggcacgtgctgccgctgctcgacgagctgggcctgcgcgtgctctgcacgctgtcgggcgatgcgcgtttt
```

-continued cgcgaggtgcagaccatgcaccgcgccgaggtgaacatgatggtctgctccaaggccatgctcaatgtcgcgcgc aagctgcaggagcgcttcggcacgccctggttcgagggcagcttctacggcatcaccgacacctcgcaggcgctg cgcgacttcgcccggctgatcggcgacgacgacctcgccgcgcgcaccgaagcgctgatcgcgcgcgaggaagcg aggattcgcgcggcgctggagccctggcgcgaacgcctggccggcaagcgcgtgctgctctacaccggcggggtc aagtcctggtcggtgatctccgcgctgcaggacctgggcatgaaggtggtcgccaccggcaccaagaaatccacc gaggaggacaaggcgcgcatccgcgagctgatgggcgacgacgtcaagatgctcgacgagggcaacccgcgcgcg ttgttgcgcacggtggaggaataccgcgccgacatcctcatcgccggcggtcgcaacatgtacaccgcgctcaag gggcgcatcccctcctcgacatcaaccaggaacgcgaattcggctatgccggctacgacggcatgcgggaactg gtgcgccagctgtgcctgaccctcgagagcccggtgtggccggcggtgcgccagccggcgccgtgggagcggccc gcgtcggccgaggcacaaccccgcacgctggcgaacgcctgaggaggtcgcgatggcacagatcatcaaccgcaa caaggcgctggcggtcagcccgctgaaggccagccagaccatgggtgccgcgctggccttcctcggcctggcgcg cagcatgccgttgctgcacggttcgcagggctgcacggcgttcgccaaggtgttcttcgtccggcacttccgcga gccggtgccgttgcagaccacggcgatggatcaggtcagctcggtgatgggcgccgacgagaacgtggtcgaggc gctgcgcaccatttgcgacaagcagcatccagcggtgatcggcctgctcagcaccgcgctggcggagacccaggg ctgcgacctgcacagcgccgtgcatcagttccgccgcgaatatcccgagtacggcgacgtggccgtggtgtcggt gaacagcccggacttcagcggttgcttcgagagcggtttcgccgccgcgctcaaggcgatgatcgaggcgctggt gcccgagcgccgtgaccaggtcggccagcggccgcgccaggtcaacgtgctgtgcagcgccagcctgacacccgg cgacctggaattcgtcgccgagagcatcgagagcttcggcctgcggccgttgctgatccccgacctgtccggctc gctggacggccatctcgacgaggcggccttcaacccgctgaccaccggcgggctgaccctcgacgagttggccag tgccgggcagagcgccgccaccctggtgatcggccagagcctgaccgccgccgccgatgcgctggccgcccgcag cggcgtaccggaccggcgtttcggcctgctgctgggcctggaggcggtggatgcctggttgatggcgctgagcga gatcagcggcaacccggtgccggagcgctggcagcgccagcgccggcaactgcaggacgccatgctcgatacccca tttcatgctcggcgacgcgcgtctgggcatcgccgccgaccccgacctgctgctcggtttctccaccctggcgcg cggcatgggcgcgcaactggtggccgccgtggtgccggcgcgcgcgccggcgctggccgatgcgccgctggcgcg catccaggtcggtgacctggaggacctggagcaggccgcccgcgacggtggtgcccaactgctgctcggcaacag ccacgcgctggccagcgccgaccgcctgggcattccgctgctgcgcgtgggctttccgcagtacgacctgctggg cggcttccagcgctgctggagcggttaccggccagcgcgcaggcgctgttcgacctggccaacctgctcaccga acaccatcagggtatcgcgccgtatcgctcgatctatgcgcagaagcccgcctccgaccattcgcaatggagcca ctgagccatggccagccccatccgacaactgcaggtactcgacggcgagaacgacggcacgctgctcaaggtggc cttcgcctcgtccgatcggcgcacggtcgaccagcatttcggttcgtcgcggtcgttcgtgttctacggcatcga ccccgagcgggccgagctgcaatcggtggtggaattcggcgagctcgaccaggacggcaacgaggacaagctggc ggccaagctggaactgctcgatggctgcatcgcggtgtactgccgcgcctgcggcgcctcggcggtacgccagct gctggcgatcggcgtgcagccggtcaaggtcagcgaggccgagggcatcgccgaactgatcgaaacgctgcaggc cgagctgcgcgaaggcccttcggcctggctggccaaggcgatccggcgtacccgtggcacgccggaccagcaacg tttcgaggccatggccggcgaggcctgggacgaatagcccgacacccgcaatcgaggacagcgttatgtatgcag aagaacaacaggcggtcgttcgcgacgacgccccggccctgcaggacccggtgatcaagcagatggtggtgcaac tgcgcgccatggacagctacggcacctacgacacctggagcgacgcgcgggtgctcgacccgctggtgctgaccc gcgagcggcgccgcgcgatccccatcgtcggcgatccggacgaggtcaccctgtcgcgggtcaaggccttctaca acgccctggcgcagatgatcgagcgcgagaccgggctgctcgcggtaccggtgatcaacatcacccacgagggct tcggccgcgcgctgatcctggtcggcaagctggtggcgctggacaagaccctgcgcgacgtccatcgcttcggct tcgaatcgctcgaggcgttgtcgctcgacgcgcagaagctgctgggcaaggcgaccgcgctggtcgccgagcacc -continued gtacggtcgccgagttgtaaggggagacgagccgatgaccgaagaggaactcaaggcgttgaagaaggaagtcag ccagaagaagcgcatcgccaccgaatgggcgtcgcagatccacgacctggtcgaggaccggctgctgatcgatta ccggcaattgccggaactggcgacgcaggcacaccaggcctgcctcgactgggccgaggccaacgcccggctgga agcggccggcaacgcctgaccgccaatacagagcgggcccgagcccgccgtatccctaaccgtaggccgccgcca tgccattggcgggcaggagatgacagatggaagcagtgataaccgggcgtacgcgcggtggcgccgaatgggtgc cgcagttcgtcaccgccgtcgatgcgcagaagtgcatcggttgcgggcgttgctacaaggtgtgcccgcgcgacg tgttcgagctggtggagcgctccggcatggtgggcgaggacgacgacctctacgacgaggacgacgagatgatgg tcatggccatcgccgacggcctcgactgcatcggctgcaaggcctgttcggcggtctgcccgaaacaatgccata cccatcaggccctggccggctgaggagctgctgacatgccaagacccgactaccacatcttcctctgcctgcagc gccgcgccgaggggcacccgcgcgcagttgtgctgcgaagggcggcgaagccctgttcgacgccttctcccagg ccctgatccggcgcaacctgatcggccgcatcgccttgaccggcaccggctgcctggggccctgccaggccggcg ccaatgtgctgatctacccgggcgcattgatgtacagctgggtggagccggcggatgtcgacagcatcctcacgc atctgctcgaaggcgagcccttcgccgacaagctcaccccccgcggagctctggtgaggcatgggtgaagtgctgt tgctggagcccgaacgggcgttcttttccgaccgcacgccgacccggctgcgctacctgctgaacagcgcgcgcg gcctcgagcatccggcggcggtcgaagccctgctgctggaggcccggcagcgctggagcgaggagccggacgcgc atgtcggcctgtacaagttctactttctccaggcccgctacgcggaggccgaagccgccgtatgggaagccctgc ggcgggccgcggcctgtgccggcttcagccgcaactaccggcgcctgcaccctgccagcgccgactggcagacac gccgcggtgccacgcggttgtacctgttcagcctcaaggcgctgggcgtgatccgcctgcgccgtggcaaggtgg acaacgcgcggcgggtgctggagaagctgctggagctcgatccgggcaacgagatcggcggcgaggcgttcctgc agatcgcccgcgccttcgaggaggaaaactgatggcggcatcgttcgaagcacgcctgcaggcggcgcggccgct gttcggcgaaatccagcgcgcgctgcaggattgcctgcagcgttcggccatccgcctgcaactgcccgacgagcg tgaaccgtcgcgcagcgaagtgcgggtcgacccgttcgatcgcagcgaatgcttctacagcgaatggcgcagcgc ccagggcgatttcctcggcagcatgcagatcaacggcgacggtcaggtctatgccgagttcgacgtgctgctgaa gcacccgcacgagccggcctggctggtggaggcggtcgccgcctgggggttggccgggggcgctgaaaagcgagtt gcgcctgctgccggcgctcgatcatgaatgagctctacgactggctgctggccagcgccgcgcaggcgcggaccg tcgaacatctgtgcctgggggttgaactggacactggccgaagtcgacggcaaccagggcttcgccttcagcccgc gccaggtgccgcgcacgctcggctggtcgggcacactcgccggccagggcaacgccgcgctgctgccctggctgc tgtcgtggaacagcgccgaagccgcggtcggcctggccgtgctcaatgccagcgtgaacacggcggcgggctgcc agcgcgaggcgcaggcactgcgcacgcaggcaccggggcatctgcaggtgttcgcacatttccgtccacggctgg cgggccagcgggtcgtggtgatcggccattatcccggcctcgaacggctctggcaggaccagccctaccagtgcc tggagcgccagcagcaggagggcgacctgcccgattgcgccgccgagtacctgctgcccgaggccgactgggtgt tcgtcagcgcgagcagcatcgccaacaagaccttgccgcgcctgctcgagctgtcgcgccaggcccaggtggtgc tgatggggccgagcctgccctggctggacggttggcggcgcttcggcgtggactacctggccggggttcgcgtgc tcgacccggacggcgtgcggcgggtgattgccgagggtggcggtacgcggctgttcgccgggccggtggagtatg ccttgatggcgctcgggaaatgatggggtctcacggccggctgggctggcggatgctgatctgtcacaagcaccc ggtcagcgcgcgcctgcatttcctcgtgccgcagcgcggcggggtggtcttgccgcagccccttccggccctcgc ggtattcgccgaaccgccgatgcagggcgatctgctggtccatcctgcgggcgctctgcgcagcctgcagcgcga cctggggatcgagaaaccgctggagctggtggccgattaccgggtcggcctcgaagtgtcgggcggggttctgcc ggtattcctcgccgcactggacgggcacgatcggtgccgggcggccatcggaacccactggatcgaactgacgca gagcatcggcatgccctggctggaccgcgaactgctcaggcgggcctatgaagtgctgatcgggtgaagcgtagg -continued

```
cgcgtggatcgggcggtcgcctagcctgaatttccagacatatggacgccacccatcctactgcaccgaaaagca tcgccccgagggcgggccccccacaaaagcagccagcagcaccgagcccccgtgggcgcgcctcgcggtgatg caggccggtaggcctgccaaagactgaaaagcatcgccccgagggcgggcctcccacaaaagcagccagcagcac cgagcccccgtgggcgcgctctcgcggcgatgcaggccggtaggcctgccaaagactgaaaagcatcgccccggg gtcgggcctccacaaagcagtcccgtagggtgggccgggtggcgttccgcttcagcccacccattccaggcaatg ggcgtcatcgaagtgggctgaagcccaccctgctgctgcgtgccgaaatgtaacctcgtgacggatgcgcggacc gatggctgacgtgttggcgctcagccacctcccgcacctcaggcgcgcagcagcgccttggccatcttcggcgac agctgggcttcgctgaactgtggctcgttcggcggatagagcaggtcctcgatgatgctgtagccgtgttccttg ccgagggcgatcacgtcgcggaccttttcacaggccttgagttttcgccgagcgccgggtcgttcagggcttgg ttcgagaaggcttggatttccttgatggacatagggttctctctgttgcgatgactggaaccagcgccgaacggc tggcgaggcatgccatagcaacatcgatgcctgagatcattccattgaatatcaatggcttatgaggttttgacg agctgccgattgtcgtattggcgacaatcggacaacagccgggctcaacccagcagggccacggccttgatctgt gcccacagcggcagcccgggagcgatgcccaactggtcggccgagcggcgagtgatgcgcgccagcagcggcgtg ccgccggcatccaggcgcaccagcacgtgggccggggtatctgccgcggccagcgcttcgactcgcgccggcagc aggttggtgatgctgctgccctcggcacgggtcagcgccaggctgacgtcgcgggcatgcacgcgaaagcgcagg cgctggccgagcgcttccggccgctgcgccaccagtacctcgccgccggggaaggtcaggcgggtcagatggtag gcgtcgtcgtgttcggccacgtgggattcgaccaccacgccggcgtcctcgccgagggcggtgggcaggtccagt cgtgccagggtttcgcgcaggccgccggcggctaccgcccggccctggtcgagcaacaccacgtgatcggccagc cgcgccacttcgtccggcgaatggctgacgtagagcagcgggatgtcgagttcgtcgtgcaggcgttccagatag ggcaggatttcgttcttgcgcttgaggtccagcgccgccagcggttcgtccatcagcagcaggcgcgggctggtg agcagggcgcgggcgatgccgacgcgctggcgctcacccccggacagcgttcccggcaggcgctccagcaggtgg tcgatacccagcaggttcaccacatggtcccagtccacccggcgctgggcggccttgacccgacgcaggccgtat tcgaggttgcgccgtgccgtgaggtgcgggaacaggctggcttcctggaatacataacccagggcgcgcgcgtgc gtcgggacgaacagcccgcgcgcactgtcctgccagcgttcgccgttgacttccaggtacgcctcgccggcgcgc tccaggccggcgacgcagcgcaggcaggtggtcttgcccgagcccgaatggccgaacagcgccgtcacgccgcgg ccaggcagggcgaggtcgacgtccagttcgaagccgggccaggtcaggcggaagcgggcgtggatctgcccggcg gttggtgagtcgttcatgcacgagtcccttcaattgaggccggacttgaaacggcggctggagtacagcgccagc agcacgcagaaggagaacgccagcatgccgccggccagccagtgggcctgggcgtactccatggcctcgacgtgg tcgaagatctgtaccgagaccgtgcgggtgacaccggggatgttgccgccgatcatcaacaccacgccgaactcg ccgacggtatgggcgaagccgaggatcgaggcggtgacgaagcccggccgcgccagcggcagtaccacgctgaag aaggtgtcccagggactggcgcgcagggtggcggctacttccagcgggcgctcaccgatggcttcgaaggcgttc tgcaggggttgcacgacgaagggcatggagtaaagcaccgagcccaccaccagaccggcgaaggtaaagggcagc agaccgaggccgaggctctgggtcagctggccaaccaggccgttagggcccatggcggtgagcagatagaagccc agcacggtcggcggcaacaccagtggcagtgccaccactgcgccgaccggccccttgagcggcgaatgagtacgc gccagccaccatgccagcggcgtgccgatcagcaacagcagtgcggtggtgaggctggccagcttgaaggtcagc cagatagctgcgaaatcgacgctgtcgagcatcatcgcggttcagtccagctcatagccgtaggcgcgaatcagc gcggcggcggtatcgcccctgaggtagtcgagcagcgcctgtgccgccgggttgccctcgccatggcgaagcagc agggcgtcctggcggatcgccgcgtgctggtcggccggcaccacccaggccgagccgcgggcgatgcggccgtcc tcggtcacctgggacagcgcgacgaagcccagctcggcattgccgctggcgacgaactggtgggcctgggcaatg ttctcgccctgcacgaagcgtggctgcagccgttcgcgcaggcccaggcggtctaaggtttccagtgccgcggcg ccgtagggggcggttttgggattggccagggccaggtgacggaagtcgccgtcggcgaggatgcgcccctgcgga
```

-continued

```
tcgacataaccctcgcgcgccgaccacagcaccaggctgccgatggcataggtgaagcggctaccggagacgccg gaaccctcgtcctcgagtcgtgccggtgtgctgtcgtcggccgccagcaggatgtcgaagggcgcgccattgttg atttgcgcgtagaacttgccggtggcgccgaaggccagcacggcgcggtggccggtgtcgcgggcgaaggcggcg gcgattttctgcattggcgcggtgaagttggccgccacgaccgccacctgcacgtcgtcggcgatggcggttagtggc aggcagagcagcagggcggcgcagaaacggcggacagaatgcatggcgactcctttcaatcgacggcgatgatga cgtgggatgccttgatcagcgcggtgcagggctggcccagggccaggccgagctcttcggcgctctcgttggtga tcacggcgctgagggtgcggttgcccggcagcagcagcttgacctcgcagttcaccgcgccggcatcagcgcgc tgatggtgccggtgaggcgattgcgggcgctgatcttcacgtcaggatcgggcgagagcagcacgaagctggcct tgatcagcgccatggcggtattgctgggcgccaactgcagttcgtcgatgctgtcgttggtcagcgtggcgctga tgcacaggcctgcgccgatgtccaggcgcaggctgccgttgacggcccccttgtcgacggcggtgatacggccgc ggaattgattgcgtgcgctggtcttcatggcgatggccctcagcagccggtcgatgtcgtcgaagccttcgatgc cctcggcgacctgggcgagaaagcgctcgtattcggcctgcatgcgccgccatacgtggagcatctcgcggccga agtcggtcaggcgcgtgccgccgccctgggcgccgccggcagagcagatcaccaacggccgctcggacaggttgt tcatggcatccactgcatcccaggcggccttgtagctcagcttgatggccttggcggcgcggctgatggaaccgg tggcctcgatctgctccagcaggtcgatgcgcttgccgcccagatagcctttctcgccccggttgaaccagagct ggccgtcgatgcgcaggggtaggtccgcttcgttcatgtcgtttcctcgggctccggctctgggcctggagcaag caagaatgcatccaggtctgtgttttcaaataaatccatgaaaatcaaaaagttaatgctttcatggaggcccccg tgagctgtctggaagatgacattgtgtgatgcgctatatcgttttgtatatagcgctacagaggtattccggccc gcccgaggaaccgcggcctggtgtgtcgcaaagccgacattgcgcccatgcgtaccgttcgcgacagcgggaag gtcgtgcgatgaatctatatgtatttgaaaaataattgttttttcagcttggcaaggctgggcatgggcgttgcag aagtacctgtgccgggtggccagatcgccgccacagccgaggagacatgccgatgattaccctgactgaaagcgc caagagtgcgattaaccgcttcatcagcaacgccgacaaacccaccgccggcttgcgcatccgcgtcgagggcgg cggctgtgcgggcgctgaagtacagcctgaagctggaagagcaaggcctcgacggggaccagcaggtcgactgcgg cgccttcaccgtgctgatcgacgacgccagcgcaccgctgctcgacggcgtgaccatggacttcgtcgacagcat ggaaggcagcggcttcaccttcgtcaacccgaacgccagcagcggttgcagctgcggcaagtccttcgcctgcta agcgccattcgaggcggccggccacgaccggccacccagcattcaccgggagatcagccgtcatgtgggattatt cggaaaaggtcaaagaacacttctacaacccgaagaacgccggcgccgtggccgaggccaatgccgtcggtgacg tcggctcgctgagctgcggcgatgccctgcggctgtcgctgaaggtcgatccggacaccgacgtgattctcgacg ccggcttccagaccttcggctgcggctcggcaatcgcatcgagctcggcgctgaccgagatgatcaaggggctga ccgtcgacgaggcgctgaagatcagcaaccaggacatcgccgacttcctcgacggcctgccgccggagaagatgc actgttcggtgatgggtcgcgaggccttgcaggcggcggtggccaactaccgcggcgaaaccctcgaggacgacc acgaggaaggcgcgctggtgtgcaagtgcttcgccatcgacgaggtgatggtgcgcgagaccatccgcgccaacc ggctctccagcgtcgaggacgtgaccaactacaccaaggccggcggcggttgctcgtcctgccacgaaggcatcg agcggttgctggtcgaggaactggccgcgcgcggcgagatcttcgttccggccggtaccggcgccaaggcggcga agaaggccaaggcgccgctggtgaccctggaaaccccgccggcggctccgcaggcggcgcccaccgcgccgcgca tgaccaccctgcagcgcatccgccgcatcgaacgcgtgctcgaatcgatccgcccgaccctgcagcgcgaccacg gcgacgtcgagctgctggatgtcgagggcaagaacatctacgtcaagctgaccgcgcctgcaccggctgccaga tggccagcatgacgttgtccggcatccagcagcggctgatcgaggaactcggcgagttcgtcaaggtggtcccgg tcagctccccggcccacagcgcgatggcggaggtgtgagatgagcggcatctatctcgacaacaacgcgaccacc cgtgtcgatgacgaagtggtgcaggccatgctgccgttcttcaccgagcagttcggcaaccccctcgtcgatgcac
```

-continued

```
agcttcggcaaccaagtcggcatggcgctgaagaaggcgcggcagagcgtgcagcggctgctcggtgccgagtac gactcggaaatcgtgttcacctcctgcggcaccgaggccgattccaccgcgatcctctcggcgctcaaggcccag cccgagcgcaagacgatcatcaccacggtggtcgagcaccggcgatcctcagcctgtgcgactacctggccgag gacggctacaccgtgcacaagctcaaggtggacaagaagggccgcctggatctggacgagtacgccgcgctgctc gacgacgacgtggccatcgtctcggtgatgtgggccaacaacgagaccggcacgctgttccggtggagcagatg gcgcagatggccgacgatgccggggtcatgttccatagcgatgcggtgcaggcggtcggcaaggtgccgatgaac ctcaagggcagcgccatccacatgctctcgctgtccggccacaagctgcatgcgcccaagggcgtcggggtgctc tacctgcgccgcggcacgcgcttccggccgttgctgcgcggtggccaccaggagcgcgggcgccgcgccggcacc gagaacgcggcctcgatcatcggcctgggggtcgccgccgagcgcgcgctggccttcatggaacacgagaacacc gaggtccgccgcctgcgcgacaagctcgaggccggcattctcgccgcgtgccctacgccttcgtcaccggcgat ccgggcaatcgcctgccgaacaccgccaacatcgccttcgaatacatcgagggcgaggccatcctgctgctgctg aacaaggtcggcatcgccgcctccagcggttcggcatgcacctctgggtcgcttgagccgtcccacgttatgcgt gcgatggacattccctatacgcggcccacggcagcgtgcgcttctcgctgtcgcgctacaccaccgaggagcag atcgactacgtgatccgcgaggtgccgccgatcatcgcccagttgcgcaagctgtcgccctactggagtggcaac ggcccggccgaggcagtgggcgactcgttcgaaccggtctacgcctgaccgccgcttgaccgcggcccccatcgcc gaggaggttcagcatgtctatcgtgatcgacgacaccaccctgcgtgacggcgaacagagcgccggggtcgcctt cagcgccgaggagaagctcgccatcgcccgtgctctggcacagctcggcgtgccggagctggagatcggcattcc cagcatgggcgaggaggagtgcgaggtgatgcgcgccatcgccgggctggccctgccggtgcggcttctggcctg gtgccggttgtgcgacgctgacctgctggccgccggcggcaccggcgtcggcatggtcgacctgtcgctaccggt ctcggacctgatgctgcagcacaagcttggccgcgaccgcgactgggcgttgcgcgaggccgcgcgactggtggg cgctgcgcgcgacgccggcctggaggtgtgcctgggctgcgaggacgcctcgcgcgccgatccggagttcatcgt ccgcgtggcggaagtcgcccaggccgccggtgcgcgacggctgcgcttcgccgatacggtgggagtaatggagcc attcgcgatgcacgcgcgcttccgctttctcgccgagcgcctggatctggagctggaagtgcacgcccacgacga cttcggcctggccacagccaacaccctggcagccgtgcgcggaggtgccacgcatatcaacaccacggtcaacgg cctcggcgagcgcgccggtaatgccgcgctggaggaatgcgcgctggcgctcaagcacctccacggcatcgactg cggtatcgacgtgcgcggcattccctcgatctcggcgctggtggagcaggcctccgggcgccaggtggcctggca gaagagcgtggtcggcgccggggtgttcacccacgaggcgggtatccatgtcgacgggctgctcaagcaccggcg caactacgaggggctcaaccccgacgagctcgggcgcagccacagcctggtgctgggcaagcattccggcgcgca catggttgagctgagctaccgcgagctgggtatcgagctgcagcagtggcagagccgcgcgctgctcggctgcat ccgccgttttccacgcagaccaagcgcagtcctcagagcgccgacctgcagggtttctaccagcagctgtgcga acagggcctggccctggccggaggtgccgcatgagcctgtaccgagaatgccgcgacgacgtccgttgcgtgttc cagcgcgaccccgcggcgcgctccacgctggaggtgctgaccacctatccgggcgtgcacgcaatcatgctctac cgcttcgcgcatcgcctgtggcgacgcgagtggcgctatgccgcgcgtctgttgagtttcgccggacggctgctg agcaacgtcgatatccaccccggcgcccgcatcggtgcgcgcttcttcattgaccatggcgctggggtggtgatc ggcgaaaccgccgagatcggcgacgacgtcaccctctatcacggtgtgaccctgggcggaaccagctggcgcaag ggcaagcgccacccgaccctgggcgacggcgtgctggtcggcgccggggcgaagatcctcgggccgatcagcatc ggtgctaatgcccgggttggcgccaactcagtggtggtgcagaacgtgccggacgggtgcacggtggtcggtatc cccggcaaggtggtgcgcctgcgcgaggccggccggcccaacgtgtatggcatcgatctcgaccattacctgatt cccgacccggtgggcaaggccatcgcctgtctgctggagcgcctggacaacctggaaaggcaggtcgagcagggc ggcctggtcgccgccggcagccagcagcggcgctaccaggaatgccagccggacaacagcctgtgtgaaaacgat tgtccggccatggccgggcgctgacggagcacgcccatggacctgcagaatttcgacggcgccggcctgtatttc
```

-continued

```
gacgagccgcgccagccgcgcgtcgcggcgctgctggacgaggcgtcggcgcagtacgccaccggcactgcggag
cagccgctgctggcggcgcaggcgctggcgccgggcgatctcagcgtgctggtcgggctctatcgcttctacttc
taccagcatcgtcatgccgatgccctggccatcgccgcgcaggtcctgcaggtggtcgcgccgcgcctggggctg
ccctgtgactggcgtgcgctcgataccgactgcctggcacgcgtggcgcccggcgccatcggcctgctgcgtttt
catctgctggcgctcaagggcgccggttacctgagcctgcgcctgggcctgttcggcgagggcaaggcgatgctg
agcaaggtcgccgagctcgatgcggacaatcgcctcggcgcgcgcctgctgctcgatgtttttggcggccaacagc
gccgccattttcacctttccccctgctgccaccgtggagacacgcccatgagcgaacaagccgccgaaccgaacc
tggacgggcccttggacgaggcgctggaagagctggtatcggccgaggatttcctgaacttcttcggcgtgccct
tcgtgccgtcggtggtgcaggtcaaccgcctgcacatcatgcagcgctatcacgactacctgtgtcaggccggcg
atatcgagcacctgcaggatgccgtgcggtacgcggtgtatcgcaagctgctggtacgtgcctacgaggatttcg
tcgcctccgatgcgcagaccgaaaaggtcttcaaggtcttccacatgcacgagccgcagacgaccttcgtgccca
tcgatcaactgctgggctgaccccgcgggaggtgagcgccatgagtctgccgctctacgaatatggccaggccgtc
aggctgatccgcaacgtacgcaacgacggcacctaccccggcaaggacaccggcgccctgctgatgcgccgcggc
gcggtggttgcgtctacgacgtcggcacctacctgcaggatcagctgatctaccgcgtgcatttcctcgatcag
ggctgcacggtgggctgccgcgaggaggagctgattcccgcgtcggacccttggatacccaacctgttcgagttc
cgcgaccaggtggtcgccaccccgcagcctggccgtgcgcggcgaggtggtggtggagcagggccgcaccggcagc
atcgagaaggtgctgcgcgacctgcccggcggcatccagtaccacgtctatttcggcgacggccgggtgcttcag
gtgcccgagacgagcctggcctgggccgacgcgcaggcgggagacgagcatgagcattgatctggtcatcggcaa
ggatgcccgctaccagctgctgaaggtcgcccacgagcgtttcggctgtgccccggccgccctcagttcgcaaca
gcgtgaacaggccgagcgcatcatcggtcgccagctgcagctggagaacgccgtgctgcacagcgccgaggcctg
cggtgtggtgatcccggacgagcaggtcgccgatgcctgggccgagatcgccgcccgctacgaggacccgctcgc
gctgcacaaggcgctagacgacagtggtctggacgaagccggcctgcgccagctgctggcccgcgaactcaaggt
cgaaacggtgctgcagcgtgtctgcgccgggctgccggaaatcaccgatacagatgtcagcctgtactacttcaa
tcatccggagcgcttcgtgcggcccgccacgcgactggcgcgacagatcctgattaccgtcaacgaggatttccc
ggaaaacagccggaccagcgcttggcgccgcatcaacctgatcgccgagcgcctgctgcgcaagccgcagcgctt
cgccgagcaggcgctcaagcattccgagtgccccttcggcgatggagggcggaagcctcggcctgatacgccccgg
cgtgctctatccgcagctggaagcctgcctgttcgccttgcgcgcaggcgagatcggcccggtggtggagacgcc
actgggctttcacctgctgttctgcgaggagatccatccggcgggccatttgtcgctgcaggaggtcttgccgca
cctgcgcgagaagctccgcgcccgtcaatacgagcggcaccagcgcgcatggctggccggtttgctgcagtccgc
cccaacctcaccggagtcgctgccatgactgataccgacaagccctgctgttcgttctgcggcgcggaaaaatca
ccgacgtacccttgatcgcgggtaacgaaggccggatctgcgaggcctgcgtcaagctggcccaccaggtggtg
accagctgggggcagcggcgccaggcccagcaactggcgccgcaactgctcacgccggcggcctacatgcagcat
ctggacgagtcggtgatcggccaggacgaggccaaggaaaccctggcggtggcggtctacaaccactacctgcgc
ctgctcaactgcacccgcgagccggtctgccaactgggcggaacggtcgagctggagaagtccaacatcctcatg
gccggcccttcgggcaccggcaagaccctgctggtgcgcaccctggcgcgcatcctcggcgtgcccttcgcctcg
gctgatgccaccaccctgacccaggccggctacgtcggcgacgacgtcgacagcatcatcgcccgcctgctggaa
gccgccggtggcgatgtgcagaaggcgcaatggggcatcgtctatatcgacgaggtggacaagctggcacgcgt
ggcggggcggcacggcggtgcgcgacatctccggcgaaggcgtgcagcaggcgctgctcaagctggtcgagggt
agcgaggtgcgcatcggcaaggggggccggcgtggcgaacacggcgaggagcaggtggtggatacgcgcaacatc
ctgttcatcgccggtggcgcctttccgggcctggaaaccctggtcggcagccgtgtgcatccgcgtggcagcgcg
```

-continued atcggcttccatgcgcggccgcagcagcaggcaccgtcgatcaacgagctgctggcggcgctgctgccggacgac
ctccatgagttcgggctgatcccccgagttcatcggtcgcttcccgatcatcaccttcctccgcgagttggaccac
gcgacgctgctgcgcatcctcagcgaaccgcgcaatgcgctggtcaagcagtaccagcaactgttcgcctaccag
ggcgtgaagctggagttcagcgaggcggcgctcggccacatagccgaccaggcgctgctgcgccgcaccggcgcg
cgcgggctgcgcgcggtcatggagagcgcgctgcagcgcaccatgttcgagatgccggcgcagccgcagctgcgc
agttgcctgctcgacctcgacgaggagggccgcgaactggtggtgctcaggcagttcgacgagtatgccgaagcg
caacctgccgacagccgggcggccgcggcgtcctggcagcgttccctgctggtggtggatggctagtgtcgcatt
gccgacagcggcatgccgctgtcggcggccggtttgtgtggtttgcgacaggtaatgttcatgaaaaggctttgt
tttcattggcttataagaatccagcggctggcgtgtttcctgctatgagtcttttgccgagtgggtatgtgggcc
cgcggtgtttcattcatccaaacagcaatgaggtggcgtgatggccaggatcggacttttcttcggcagcaacac
gggcaagacgcgcaaggtcgccaagatgatcaagaagcgcttcgacgacgacaccctggctgatccgctcaacgt
caaccgcacgagcgccgcagacttcgccggctattcgcacctgatcctcggcacgccgaccctgggcgagggctt
gctgccggggctgagcgccgattgcgagaacgaaagctgggaggaattcctgccgcagatcgagggctggatttt
caccggcaagaccgtggccatcttcggcctcggcgatcaggtcggctacgccgacgagtttctcgatgcgatggg
cgaactgcacgaattcttcagcgagcgcggcgccaccatggtcggcgagtggccgaccacgggctacgaattcac
ccactccgaagcggtggtggacggcaagttcgtcgggctggcgctggacttggacaaccagagcaacctcaccga
ggagcggctgggcgcctggttgcgacagatcgctccggccttcgaactgccgctgtgaccatgcgttgagcttcg
ctgcacgcccggccccgacctacgcctcgtaatccgtaggttgggttgatacgcgcagcatcgaagcccaacgcg
ctccgaagcgcagctcggcggcgatctgtgcgaaccgttgCccggcggccgtgGGCGGAGTAGCGTGATCGCGAA
CCGAGGAAGGAGATTCGCC (SEQ ID NO. 6)

GGCGTATCACGAGGCCCTTTCGTCTTCACCTCGAGAAAATTTATCAAAAAGAGTGTTGACTTGTGAGCGGATAAC
AATGATACTTAGATTCAATTGTGAGCGGATAACAATTTCACACATCTAGAGCTAATCTTCTCGTACTCATGACGC
AAGTAATGAACACGATTAACATCGCTAAGAACGACTTCTCTGACATCGAACTGGCTGCTATCCCGTTCAACACTC
TGGCTGACCATTACGGTGAGCGTTTAGCTCGCGAACAGTTGGCCCTTGAGCATGAGTCTTACGAGATGGGTGAAG
CACGCTTCCGCAAGATGTTTGAGCGTCAACTTAAAGCTGGTGAGGTTGCGGATAACGCTGCCGCCAAGCCTCTCA
TCACTACCCTACTCCCTAAGATGATTGCACGCATCAACGACTGGTTTGAGGAAGTGAAAGCTAAGCGCGGCAAGC
GCCCGACAGCCTTCCAGTTCCTGCAAGAAATCAAGCCGGAAGCCGTAGCGTACATCACCATTAAGACCACTCTGG
CTTGCCTAACCAGTGCTGACAATACAACCGTTCAGGCTGTAGCAAGCGCAATCGGTCGGGCCATTGAGGACGAGG
CTCGCTTCGGTCGTATCCGTGACCTTGAAGCTAAGCACTTCAAGAAAAACGTTGAGGAACAACTCAACAAGCGCG
TAGGGCACGTCTACAAGAAAGCATTTATGCAAGTTGTCGAGGCTGACATGCTCTCTAAGGGTCTACTCGGTGGCG
AGGCGTGGTCTTCGTGGCATAAGGAAGACTCTATTCATGTAGGAGTACGCTGCATCGAGATGCTCATTGAGTCAA
CCGGAATGGTTAGCTTACACCGCCAAAATGCTGGCGTAGTAGGTCAAGACTCTGAGACTATCGAACTCGCACCTG
AATACGCTGAGGCTATCGCAACCCGTGCAGGTGCGCTGGCTGGCATCTCTCCGATGTTCCAACCTTGCGTAGTTC
CTCCTAAGCCGTGGACTGGCATTACTGGTGGTGGCTATTGGGCTAACGGTCGTCGTCCTCTGGCGCTGGTGCGTA
CTCACAGTAAGAAAGCACTGATGCGCTACGAAGACGTTTACATGCCTGAGGTGTACAAAGCGATTAACATTGCGC
AAAACACCGCATGGAAAATCAACAAGAAAGTCCTAGCGGTCGCCAACGTAATCACCAAGTGGAAGCATTGTCCGG
TCGAGGACATCCCTGCGATTGAGCGTGAAGAACTCCCGATGAAACCGGAAGACATCGACATGAATCCTGAGGCTC
TCACCGCGTGGAAACGTGCTGCCGCTGCTGTGTACCGCAAGGACAAGGCTCGCAAGTCTCGCCGTATCAGCCTTG
AGTTCATGCTTGAGCAAGCCAATAAGTTTGCTAACCATAAGGCCATCTGGTTCCCTTACAACATGGACTGGCGCG
GTCGTGTTTACGCTGTGTCAATGTTCAACCCGCAAGGTAACGATATGACCAAAGGACTGCTTACGCTGGCGAAAG

-continued

```
GTAAACCAATCGGTAAGGAAGGTTACTACTGGCTGAAAATCCACGGTGCAAACTGTGCGGGTGTCGACAAGGTTC
CGTTCCCTGAGCGCATCAAGTTCATTGAGGAAAACCACGAGAACATCATGGCTTGCGCTAAGTCTCCACTGGAGA
ACACTTGGTGGGCTGAGCAAGATTCTCCGTTCTGCTTCCTTGCGTTCTGCTTTGAGTACGCTGGGGTACAGCACC
ACGGCCTGAGCTATAACTGCTCCCTTCCGCTGGCGTTTGACGGGTCTTGCTCTGGCATCCAGCACTTCTCCGCGA
TGCTCCGAGATGAGGTAGGTGGTCGCGCGGTTAACTTGCTTCCTAGTGAAACCGTTCAGGACATCTACGGGATTG
TTGCTAAGAAAGTCAACGAGATTCTACAAGCAGACGCAATCAATGGGACCGATAACGAAGTAGTTACCGTGACCG
ATGAGAACACTGGTGAAATCTCTGAGAAAGTCAAGCTGGGCACTAAGGCACTGGCTGGTCAATGGCTGGCTTACG
GTGTTACTCGCAGTGTGACTAAGAGTTCAGTCATGACGCTGGCTTACGGGTCCAAAGAGTTCGGCTTCCGTCAAC
AAGTGCTGGAAGATACCATTCAGCCAGCTATTGATTCCGGCAAGGGTCTGATGTTCACTCAGCCGAATCAGGCTG
CTGGATACATGGCTAAGCTGATTTGGGAATCTGTGAGCGTGACGGTGGTAGCTGCGGTTGAAGCAATGAACTGGC
TTAAGTCTGCTGCTAAGCTGCTGGCTGCTGAGGTCAAAGATAAGAAGACTGGAGAGATTCTTCGCAAGCGTTGCG
CTGTGCATTGGGTAACTCCTGATGGTTTCCCTGTGTGGCAGGAATACAAGAAGCCTATTCAGACGCGCTTGAACC
TGATGTTCCTCGGTCAGTTCCGCTTACAGCCTACCATTAACACCAACAAAGATAGCGAGATTGATGCACACAAAC
AGGAGTCTGGTATCGCTCCTAACTTTGTACACAGCCAAGACGCTAGCCACCTTCGTAAGACTGTAGTGTGGGCAC
ACGAGAAGTACCGAATCGAATCTTTTGCACTGATTCACGACTCCTTCGGTACGATTCCGGCTGACGCTGCGAACC
TGTTCAAAGCACTGCGCGAAACTATCGTTGACACATATGAGTCTTGTGATGTACTGGCTGATTTCTACGACCAGT
TCGCTGACCAGTTGCACGAGTCTCAATTGGACAAAATGCCAGCACTTCCGGCTAAAGGTAACTTGAACCTCCGTG
ACATCTTAGAGTCGGACTTCGCGTTCGCGTAAcagatctcatcaccatcaccatcactaagcttaattagctgag
cttggactcctgttgatagatccagtaatgacctcagaactccatctggatttgttcagaacgctcggttgccgc
cgggcgttttttattggtgagaatccaagctagcttggcgagatccttgcagcacatccccctttcgccagctgg
cgtaatagcgaagaggcccgcaccgatcgcaggccaaccagataagtgaaatctagttccaaactattttgtcat
ttttaattttcgtattagcttacgacgctacacccagttcccatctattttgtcactcttccctaaataatcctt
aaaaactccatttccacccctcccagttcccaactattttgtccgcccacagcggggcattttcttcctgttat
gtttgggcgctgcattaatgaatcggccaacgcgcggggagaggcggtttgcgtattgggcgctcttccgcttcc
tcgctcactgactcgctgcgctcggtcgttcggctgcggcgagcggtatcagctcactcaacaccacttcaagaa
ctctgtagcaccgcctacatacctcgctctgctaatcctgttaccagccggttgtcagccgttaagtgttcctgt
gtcactcaaaattgctttgagaggctctaagggcttctcagtgcgttacatccctggcttgttgtccacaaccgt
taaaccttaaaagctttaaaagccttatatattcttttttttcttataaaacttaaaaccttagaggctatttaa
gttgctgatttatattaattttattgttcaaacatgagagcttagtacgtgaaacatgagagcttagtacgttag
ccatgagagcttagtacgttagccatgagggtttagttcgttaaacatgagagcttagtacgttaaacttgagag
cttagtacgtgaaacatgagagcttagtacgtactatcaacaggttgaactgcccatgttctttcctgcgttatc
agagcttatcggccagcctcgcagagcaggattcccgttgagcaccgccaggtgcgaataagggacagtgaagaa
ggaacaccgctcgcgggtgggcctacttcacctatcctgcccggctgacgccgttggataccaaggaaagtc
tacacgaacccttggcaaatcctgtatatcgtgcgaaaaggatggatataccgaaaaaatcgctataatgac
cccgaagcagggttatgcagcggaaagtatacctaacatgttctttcctgcgttatcccctgattctgtggata
accgtattaccgcctgcggttgagtaataatggatgccctgcgtaagcgggtgtgggcggacaataaagtctta
aactgaacaaaatagatctaaactatgacaataaagtcttaaactagacagaatagttgtaaactgaaatcagtc
cagttatgctgtgaaaaagcatactggacttttgttatggctaaagcaaactcttcattttctgaagtgcaaatt
gcccgtcgtattaaagaggggcgtgggttcgaggtcgacggtatcgataagctagcttaattagctgagcttgg
aagtacctattccgaagttcctattctctagaaagtataggaacttcagcggaaaaggacaattgtcTCACCTCC
AGGTGGCCCGGCTCCATGCACCGCGACGCAACGCGGGGAGGCAGACAAGGTATAGGGCGGCGCCTACAATCCATG
```

-continued

```
CCAACCCGTTCCATGTGCTCGCCGAGGCGGCATAAATCGCCGTGACGATCAGCGGTCCAGTGATCGAAGTTAGGC
TGGTAAGAGCCGCGAGCGATCCTTGAAGCTGTCCCTGATGGTCGTCATCTACCTGCCTGGACAGCATGGCCTGCA
ACGCGGGCATCCCGATGCCGCCGGAAGCGAGAAGAATCATAATGGGGAAGGCCATCCAGCCTCGCGTCGCGAACG
CCAGCAAGACGTAGCCCAGCGCGTCGGCCGCCATGCCGGCGATAATGGCCTGCTTCTCGCCGAAACGTTTGGTGG
CGGGACCAGTGACGAAGGCTTGAGCGAGGGCGTGCAAGATTCCGAATACCGCAAGCGACAGGCCGATCATCGTCG
CGCTCCAGCGAAAGCGGTCCTCGCCGAAAATGACCCAGAGCGCTGCCGGCACCTGTCCTACGAGTTGCATGATAA
AGAAGACAGTCATAAGTGCGGCCACAATGGTCATGCCCCGCGCCCACCGGAAGGAGCTGACTGGGTTGAAGGCTC
TCAAGGGCATCGGACGGCGCTCTCCCTTATGCGACTCCTGCATTAGGAAGCAGCCCAGTAGTAGGTTGAGGCCGT
TGAGCACCGCCGCCGCAAGGAATGGTGCGTGCAGGGAGATGGCGCCCAACAGTCCCCCGGCCACGGGGCCTGCCA
CCATACCCACGCCGAAACAAGCGCTCATGAGCCCGAAGTGGCGAGCCCGATCTTCCCCATCGGTGATGTCGGCGA
TATAGGCGCCAGCAACCGCACCTGTGGCGCCGGTGATGCCGGCCACGATGCGTCCGGCGTAGAGAATCCACAGGA
CGGGTGTGGTCGCCATGATCGCGTAGTCGATAGTGGCTCCAAGTAGCGAAGCGAGCAGGACTGGGCGGCGGCCAA
AGCGGTCGGACAGTGCTCCGAGAACGGGTGCGCATAGAAATTGCATCAACGCATATAGCGCTAGCAGCACGCCAT
AGTGACTGGCGATGCTGTCGGAATGGACGATATCCCGCAAGAGGCCCGGCAGTACCGGCATaaccaagcctatgc
ctacagcatccagggtgacggtgccgaggatgacgatgagcgcattgttagatttcatacacggtgcctgactgc
gttagcaatttaactgtgataaactaccgcattacagtttatcgatgataagctgtcaagaagttcctattccga
agttcctattctctagaaagtataggaacttctgcatttacgttgacaccatAATAAAAAAGCCCCCGAATGAT
CTTCCGGGGCtcactgcccgctttccagtcgggaaacctgtcgtgccagctgcattaatgaatcggccaacgcg
cggggagaggcggtttgcgtattgggcgccagggtggttttcttttcaccagtgagactggcaacagctgattg
cccttcaccgcctggccctgagagagttgcagcaagcggtccacgctggtttgcccagcaggcgaaaatcctgt
ttgatggtggttaacggcgggatataacatgagctatcttcggtatcgtcgtatcccactaccgagatatccgca
ccaacgcgcagcccggactcggtaatggcgcgcattgcgcccagcgccatctgatcgttggcaaccagcatcgca
gtgggaacgatgccctcattcagcatttgcatggtttgttgaaaaccggacatggcactccagtcgccttcccgt
tccgctatcggctgaatttgattgcgagtgagatatttatgccagccagccagacgcagacgcgccgagacagaa
cttaatgggcccgctaacagcgcgatttgctggtgacccaatgcgaccagatgctccacgcccagtcgcgtaccg
tcctcatgggagtaaataatactgttgatgggtgtctggtcagagacatcaagaaataacgccggaacattagtg
caggcagcttccacagcaatggcatcctggtcatccagcggatagttaatgatcagcccactgacgcgttgcgcg
agaagattgtgcaccgccgctttacaggcttcgacgccgcttcgttctaccatcgacaccaccacgctggcaccc
agttgatcggcgcgagatttaatcgccgcgacaatttgcgacggcgcgtgcagggccagactggaggtggcaacg
ccaatcagcaacgactgtttgcccgccagttgttgtgccacgcggttgggaatgtaattcagctccaccatcgcc
gcttccacttttccccgcgttttcgcagaaacgtggctggcctggttcaccacgcgggaaacggtcatataagag
acaccggcatactctgcgacatcgtataacgttactggtttcacattcaccaccctgaattgactctcttccggg
cgctatcatgccataccgcgaaaggttttgcaccattcgatggtgtcaacgtaaatgcatgccgcttcgccttcg
cgcgcgaattgcaggtaccatttatcagggttattgtctcatgagcggatacatatttgaatgtatttagaaaaa
taaacaaataggggttccgcgcacatttccccgaaaagtgccacctgacgtctaagaaaccattattatcatgac
attaacctataaaaata
```

The modified bacteria described herein are capable of colonizing a host plant. In certain cases, the modified bacteria can be applied to the plant, by foliar application, foliar sprays, stem injections, soil drenches, immersion, root dipping, seed coating or encapsulation using known techniques.

Successful colonization can be confirmed by detecting the presence of the bacterial population within the plant. For example, after applying the bacteria to the seeds, high titers of the bacteria can be detected in the roots and shoots of the plants that germinate from the seeds. In addition, significant quantities of the bacteria can be detected in the rhizosphere of the plants. Therefore, in one embodiment, the endophytic microbe population is disposed in an amount effective to colonize the plant. Colonization of the plant can be detected, for example, by detecting the presence of the endophytic microbe inside the plant. This can be accomplished by measuring the viability of the microbe after surface sterilization of the seed or the plant: endophytic colonization results in an internal localization of the microbe, rendering it resistant to conditions of surface sterilization.

In some cases, the modified bacteria is mixed with an agriculturally suitable or compatible carrier. The carrier can be a solid carrier or liquid carrier. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the modified bacteria of the present invention. Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or plant growth medium. Other agricultural carriers that may be used include fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant parts, sugar cane bagasse, hulls or stalks from grain processing, ground plant material or wood from building site refuse, sawdust or small fibers from recycling of paper, fabric, or wood. Other suitable formulations will be known to those skilled in the art.

In one embodiment, the formulation can comprise a tackifier or adherent. Such agents are useful for combining the modified bacteria with carriers that can contain other compounds (e.g., control agents that are not biologic), to yield a coating composition. Such compositions help create coatings around the plant or seed to maintain contact between the microbe and other agents with the plant or plant part. In one embodiment, adherents are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision).

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the modified bacteria used, and should promote the ability of the microbial population to survive application on the seeds and to survive desiccation. Examples of suitable desiccants include one or more of trehalose, sucrose, glycerol, and methylene glycol. Other suitable desiccants include, but are not limited to, non reducing sugars and sugar alcohols (e.g., mannitol or sorbitol).

The formulations may also include one or more agents such as a fungicide, an antibacterial agent, an herbicide, a nematicide, an insecticide, a plant growth regulator, a rodenticide, and a nutrient. Such agents are ideally compatible with the agricultural seed or seedling onto which the formulation is applied (e.g., it should not be deleterious to the growth or health of the plant).

When the formulation is a liquid solution or suspension, the modified bacteria can be mixed or suspended in aqueous solutions. Suitable liquid diluents or carriers include aqueous solutions, petroleum distillates, or other liquid carriers.

A formulation that is a solid composition can be prepared by dispersing the modified bacteria in or on an appropriately divided solid carrier, such as peat, wheat, bran, vermiculite, clay, talc, bentonite, diatomaceous earth, fuller's earth, or pasteurized soil. When such formulations are used as wettable powders, biologically compatible dispersing agents such as nonionic, anionic, amphoteric, or cationic dispersing and emulsifying agents can be used.

Solid carriers useful in aspects of the invention include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

The modified bacteria herein can be combined with one or more of the agents described herein to yield a formulation suitable for combining with a plant, a seed or seedling. The modified bacteria can be obtained from growth in culture, for example, using a synthetic growth medium. In addition, the microbe can be cultured on solid media, for example on petri dishes, scraped off and suspended into the preparation. Microbes at different growth phases can be used. For example, microbes at lag phase, early-log phase, mid-log phase, late-log phase, stationary phase, early death phase, or death phase can be used.

In some embodiments the invention also includes containers or equipment with the modified bacteria, with or without the plants, seeds or seedlings. For instance, the invention may include a bag comprising at least 1,000 seeds having modified bacteria. The bag further comprises a label describing the seeds and/or said modified bacteria.

The population of seeds may be packaged in a bag or container suitable for commercial sale. Such a bag contains a unit weight or count of the seeds comprising the modified bacteria as described herein, and further comprises a label. In one embodiment, the bag or container contains at least 1,000 seeds, for example, at least 5,000 seeds, at least 10,000 seeds, at least 20,000 seeds, at least 30,000 seeds, at least 50,000 seeds, at least 70,000 seeds, at least 80,000 seeds, at least 90,000 seeds or more. In another embodiment, the bag or container can comprise a discrete weight of seeds, for example, at least 1 lb, at least 2 lbs, at least 5 lbs, at least 10 lbs, at least 30 lbs, at least 50 lbs, at least 70 lbs or more. The bag or container comprises a label describing the seeds and/or said modified bacteria. The label can contain additional information, for example, the information selected from the group consisting of: net weight, lot number, geographic origin of the seeds, test date, germination rate, inert matter content, and the amount of noxious weeds, if any. Suitable containers or packages include those traditionally used in plant seed commercialization.

A substantially uniform population of seeds comprising the modified bacteria is provided in other aspects of the invention. In some embodiments, at least 10%, for example, at least 20%, at least 30%, at least 40%, at least 50%, at least 60%, at least 70%, at least 75%, at least 80%, at least 90%, at least 95% or more of the seeds in the population, contains the modified bacteria in an amount effective to colonize a plant. In other cases, at least 10%, for example, at least 20%, at least 30%, at least 40%, at least 50%, at least 60%, at least 70%, at least 75%, at least 80%, at least 90%, at least 95% or more of the seeds in the population, contains at least 100 CFU on its surface, for example, at least 200 CFU, at least 300 CFU, at least 1,000 CFU, at least 3,000 CFU, at least 10,000 CFU, at least 30,000 CFU, at least 100,000 CFU, at least 300,000 CFU, or at least 1,000,000 CFU per seed or more.

Alternatively a substantially uniform population of plants is provided. The population comprises at least 100 plants, for example, at least 300 plants, at least 1,000 plants, at least 3,000 plants, at least 10,000 plants, at least 30,000 plants, at least 100,000 plants or more. The plants are grown from the seeds comprising the modified bacteria as described herein. The increased uniformity of the plants can be measured in a number of different ways.

In some embodiments, there is an increased uniformity with respect to the modified bacteria within the plant population. For example, in one embodiment, a substantial portion of the population of plants, for example at least 10%, at least 20%, at least 30%, at least 40%, at least 50%, at least 60%, at least 70%, at least 75%, at least 80%, at least 90%, at least 95% or more of the seeds or plants in a population, contains a threshold number of the modified bacteria. The threshold number can be at least 100 CFU, for example at least 300 CFU, at least 1,000 CFU, at least 3,000 CFU, at least 10,000 CFU, at least 30,000 CFU, at least 100,000 CFU or more, in the plant or a part of the plant. Alternatively, in a substantial portion of the population of plants, for example, in at least 1%, at least 10%, at least 20%, at least 30%, at least 40%, at least 50%, at least 60%, at least 70%, at least 75%, at least 80%, at least 90%, at least 95% or more of the plants in the population, the modified bacteria that is provided to the seed or seedling represents at least 10%, least 20%, at least 30%, at least 40%, at least 50%, at least 60%, at least 70%, at least 80%, at least 90%, at least 95%, at least 99%, or 100% of the total microbe population in the plant/seed.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1: Nitrogen Fixation in *Salmonella* Using Refactored Nif Clusters

Methodology
Nitrogenase Activity Assay in Bacteria.

Acetylene reduction assay was used to measure nitrogenase activity of bacteria in free-living conditions. Cultures were initiated by inoculating a single colony into 1 mL of LB medium with appropriate antibiotics in a 15 mL culture tube. Cultures grown with shaking at 250 rpm at 37° C. for 12 h were diluted 100-fold in 1 mL of minimal medium plus 17.1 mM $NH_4Ac$ with appropriate antibiotics in 96-well deep well plates. The plates were incubated with shaking at 900 rpm at 30° C. for 20 h. Cultures were diluted an $OD_{600}$ of 0.5 in 2 mL of nitrogen-free minimal medium supplemented with appropriate antibiotics and inducers in 10 mL glass vials with PTFE-silicone septa screw caps (Supelco Analytical, Bellefonte, Pa., cat. #SU860103). Headspace in the bottles was replaced with 100% argon gas using a vacuum manifold equipped with a copper catalyst oxygen trap. Acetylene freshly generated from $CaC_2$ in a Burris bottle was injected to 10% (vol/vol) into each culture vial to begin the reaction. Cultures were allowed to grow for 20 h at 30° C. with shaking at 250 rpm, followed by quenching via the addition of 0.3 mL of 4 M NaOH to each vial. Ethylene production was analyzed by gas chromatography on an Agilent 7890A GC system (Agilent Technologies, Inc. Santa Clara, Calif. USA) equipped with a PAL headspace autosampler and flame ionization detector as follows. 0.25 mL headspace preincubated to 35° C. for 30 s was injected and separated for 5 min on a GS-CarbonPLOT column (0.32 mm×30 m, 3 micron; Agilent) at 60° C. and a He flow rate of 1.8 ml/min. Detection occurred in a FID heated to 300° C. with a gas flow of 35 ml/min $H_2$ and 400 ml/min air. Acetylene and ethylene were detected at 3.0 min and 3.7 min after injection, respectively. Ethylene production was quantified by integrating the 3.7 min peak using Agilent GC/MSD ChemStation Software.

Seed Sterilization, Germination and Inoculation of Bacteria.

For surface-sterilization, *Zea mays* B73 seeds (U.S. National Plant Germplasm System, IA) first were washed with 70% ethanol and immersed in 2% sodium hypochlorite solution (25% commercial bleach) for 15 min with shaking at 50 rpm and subsequently washed three times with sterile water. Surface-sterilized seeds were placed on 1% Bacto agar plate supplemented with 1 μM of gibberellic acid (Sigma-Aldrich, MO) and incubated under dark at room temperature up to 6 days before germination. A regular weight germination paper (Ancor Paper Co., Mn) soaked in 10 mL of sterile water was placed on the bottom of nitrogen-free Fahräeus agar plate. The germinated seeds were transplanted at the top of the germination paper in Fahräeus agar plate (4 seedling/plate). After establishing rooting system for 2 days, maize roots were flooded with 50 mL of bacteria ($OD_{600}$=1) resuspended in sterile water and incubated at room temperature. Bacteria were removed by pipetting after 1 h of incubation. The plant growth was continued under 24 h constant light at 26° C. for additional two weeks before the assays.

Internal Colonization Assay

Two weeks post-inoculation, only plant roots were retained by removing leave and seeds from the seedling using a razor blade. To determine internal colonization, each root was immersed in 20 mL of 1.6% sodium hypochlorite solution (20% commercial bleach) in 50 mL falcon tube and vortexed vigorously for 1 min followed by four times washes with 25 mL of sterile water. The surface sterilized roots were vortexed in 5 mL of PBS for 1 min following the last wash and subsequently plated on LB agar plate to quantify residual bacteria. The sterilized roots were crushed using a mortar and pestle in 5 mL of PBS for 5 min and the extracts were serially diluted in PBS and plated on LB agar plates with or without a selective marker to determine the presence of bacteria and the plasmid stability. The plates were incubated at 37° C. for 24 h before analyzing colony forming unit (CFU).

Nitrogenase Activity Assay in Plants

Acetylene reduction assay was used to measure nitrogenase activity of maize seedlings. Two weeks post-inoculation of bacteria, the intact seedlings were transferred into 30 mL volume anaerobic culture tubes (Chemglass Life Sciences, NJ) containing 2 mL of nitrogen-free Fahräeus medium sealed with a rubber stopper without headspace replacement. For the maize seedlings inoculated with the bacteria strain carrying the refactored cluster, 25 mL of 0.5 M IPTG was applied on seedling roots grown 13 days after inoculation of bacteria, after which the seedlings were incubated under constant light for 12 h before transfer into anaerobic culture tubes containing 2 mL of nitrogen-free Fahräeus medium with 10 mM IPTG. Acetylene freshly generated from $CaC_2$ in a Burris bottle was injected to 7% (vol/vol) into each culture tube to start the reaction. The reaction was continued under a light regimen of 18 h of light and 6 h of dark at 28° C. up to 4 days. Ethylene production was quantified by gas chromatography. 0.5 mL of headspace was sampled and analyzed in a manner identical to that described above.

Results

Transfer of nif Clusters into Salmonella Strains.

Transfer of native and refactored nif clusters of Klebsiella was proven to be functional in K. oxytoca M5al and E. coli such as K12 MG1655. However, it hasn't been shown that heterologous expression of nif clusters would be active in other enteric bacteria that can colonize into crop cereals. We have collected pathogenic Salmonella strains that can infect various hosts ranging from humans to plants. We transferred native and refactored nif clusters into diverse Salmonella strains to test nitrogen fixation in a free living condition. Also, together with the refactored cluster, the controller plasmid encoding a sensor and circuit that drives the expression of the entire nif cluster in response to IPTG was introduced into *Salmonella* strains.

Particularly, *S. typhi* strains containing the native or refactored nif cluster showed higher nitrogenase activity among diverse *Salmonella* strains. *Salmonella dublin, newport* and *pomona* only exhibited nitrogenase activity from the native nif cluster to a lesser extent than those of the nitrogen fixing *S. typhi* strains (FIG. 1).

Internal Colonization of *Zea mays* B73 Roots by *S. typhi*

To determine whether a *Salmonella* strain can be a bacterial endophyte in maize plants, we inoculated bacteria onto the roots of *Zea mays* B73 that is an important commercial crop variety. *S. typhi* ATCC 14028 showing one of the highest nitrogenase activity by heterologous nif expression was selected for internal colonization assay. 14 days post-inoculation, internal colonization by *S. typhi* ATCC 14028 was analyzed using the roots of plant seedlings. No CFU of *S. typhi* ATCC 14028 was detected after surface sterilization of the roots. To assess internally colonized bacteria cells, the surface sterilized roots of each plant seedling were crushed in PBS and plated on LB plates. We detected endophytic colonization of ~$10^6$ CFU/plant by *S. typhi* ATCC 14028 from the crushed root extracts, but no CFU by *E. coli* MG1655 in the same setting (FIG. 2). This shows that *S. typhi* ATCC 14028 can colonize *Zea mays* B73 internally.

Nitrogenase Activity in Maize Plants 14 days post-inoculation, we analyzed nitrogenase activity from the plant seedlings infected with the genetically modified *S. typhi* ATCC 14028 strains by acetylene reduction assay. More than 30 plants from each group were analyzed. 18% and 51% of the plants inoculated with *S. typhi* ATCC 14028 carrying the native nif cluster and the refactored nif cluster, respectively, displayed increased ethylene production compared to those plants inoculated with *S. typhi* ATCC 14028 expressing no nif cluster (FIG. 3). The refactored nif cluster as compared to the native nif cluster resulted in less variation in acetylene reduction in plants. This suggests that the expression of refactored nif cluster is more consistent in our setting conferred by the synthetic controller system that regulates the expression of the refactored nif cluster by an externally added inducer than that of the native nif cluster whose regulation is still under the control of complex native biological signals.

Improvement of Stability of Genetic Systems

Plasmid-based engineering of the clusters and controllers relies on plasmid stability during cell division. Such selective pressure for plasmid stability as antibiotic use can be easily applied and maintained in an in vitro setup. However, plasmids are cured from the host bacteria over time without selective antibiotic pressure in an in vivo setup.

In order to increase stability of the genetic system in bacteria, two engineering strategies were used. First, we introduced a controller that encodes an IPTG inducible T7 RNA polymerase and a selective marker into a target genome using the mini-Tn7 system [Choi, K. H., (2005). A Tn7-based broad-range bacterial cloning and expression system. Nature methods, 2(6), 443-448.]. It has been demonstrated that the transposition with the mini-Tn7 system is broad-host range and site-specific. Genome integration occurs at the Tn7 attachment site (attTn7) located downstream of the essential gene glmS. *Salmonella* contains a single glmS gene that ensures a single-copy insertion of an introduced genetic system. A new controller plasmid pR6K-T7RW designed for genome integration consists of a T7 RNA polymerase and a selection marker flanked by two Tn7 ends (Tn7L and Tn7R). To minimize interference by transcriptional read-through from the upstream glmS expression, a constitutive promoter-driven selection marker and a sensor protein lad are oriented opposite to the glmS. A T7 RNA polymerase read-through was blocked by a terminator between the device and the genome. We transformed a controller plasmid pR6K-T7RW and a helper plasmid pTNS3 encoding the TnsABCD transposase into *Salmonella* ATCC14028. The insertion site of a controller device was verified by PCR. We identified that the device is integrated 25 bp downstream of the glmS stop codon in *Salmonella*. We tested plasmid stability based on a selective marker in the internally colonized *Salmonella* strains containing either a genome-based controller or a plasmid-based controller two weeks after inoculation of germinated maize seeds. There was no marker loss from the genome-based system, whereas only about 20% of strains from the plasmid-based system were retained on the plates supplemented with antibiotics, indicating that the controller device on the *Salmonella* genome was stable without selective pressure over two weeks in the plant seedlings (FIG. 4 A).

The nif clusters were constructed on a broad-host range plasmid pBBR1 such that the optimal expression levels of the nif genes in diverse contexts can be rapidly accessed by swapping genetic parts of the clusters on a plasmid. To keep the versatility and engineerablity of a plasmid-based nif system, we sought to explore an alternative to genome-based engineering while ensuring the stability of the nif clusters on the plasmid. The partitioning system encoded by the two par operons (parCBA and parDE) contributes to stable maintenance of a plasmid RK2 [Easter, C. L., Schwab, H., & Helinski, D. R. (1998). Role of the parCBA operon of the broad-host-range plasmid RK2 in stable plasmid maintenance. Journal of bacteriology, 180(22), 6023-6030.]. However, the transferability of the function of the RK2 par system has not been tested on other types of plasmids. We integrated the RK2 par system into the nif plasmids built upon a plasmid pBBR1 and analyzed plasmid stability in the *Salmonella* strain from the colonized roots. The nif plasmid stability without the par system decreased to 4% in the absence of a selective pressure after 14 days of inoculation into the plants. On the other hand, adding the par system on the nif plasmids resulted in plasmid stability of 96% under the identical conditions, which suggesting the RK2 par system works as a module to improve the stability of other plasmid types (FIG. 4 B). These engineering efforts can be modular standards as a means to provide the stability of complex multigene systems in the bacteria that are supposed to be released into the environment.

REFERENCES

1. Tilman, D., Balzer, C., Hill, J. & Befort, B. L. Global food demand and the sustainable intensification of agriculture. *PNAS* 108, 20260-20264 (2011).
2. Mueller, N. D. et al. Closing yield gaps through nutrient and water management. *Nature* 490, 254-257 (2012).
3. Haapalainen, M., van Gestel, K., Pirhonen, M. & Taira, S. Soluble plant cell signals induce the expression of the type III secretion system of *Pseudomonas syringae* and upregulate the production of pilus protein HrpA. *Mol. Plant Microbe Interact.* 22, 282-290 (2009).
4. Holden, N., Pritchard, L. & Toth, I. Colonization outwith the colon: plants as an alternative environmental reservoir for human pathogenic enterobacteria. *FEMS Microbiol. Rev.* 33, 689-703 (2009).
5. Plotnikova, J. M., Rahme, L. G. & Ausubel, F. M. Pathogenesis of the human opportunistic pathogen *Pseudomonas aeruginosa* PA14 in *Arabidopsis*. *Plant Physiol.* 124, 1766-1774 (2000).
6. Brandl, M. T., Cox, C. E. & Teplitski, M. *Salmonella* interactions with plants and their associated microbiota. *Phytopathology* 103, 316-325 (2013).
7. Kutter, S., Hartmann, A. & Schmid, M. Colonization of barley (*Hordeum vulgare*) with *Salmonella enterica* and *Listeria* spp. *FEMS Microbiol. Ecol.* 56, 262-271 (2006).
8. Temme, K., Zhao, D. & Voigt, C. A. Refactoring the nitrogen fixation gene cluster from *Klebsiella oxytoca*. *PNAS* 109, 7085-7090 (2012).
9. Smanski, M. J. et al. Functional optimization of gene clusters by combinatorial design and assembly. *Nat Biotech* 32, 1241-1249 (2014).
10. Chan, L. Y., Kosuri, S. & Endy, D. Refactoring bacteriophage T7. *Mol Syst Biol* 1, 2005.0018 (2005).
11. Jaschke, P. R., Lieberman, E. K., Rodriguez, J., Sierra, A. & Endy, D. A fully decompressed synthetic bacteriophage øX174 genome assembled and archived in yeast. *Virology* 434, 278-284 (2012).
12. Wang, X. et al. Using Synthetic Biology to Distinguish and Overcome Regulatory and Functional Barriers Related to Nitrogen Fixation. *PLoS ONE* 8, e68677 (2013).
13. Widmaier, D. M. et al. Engineering the *Salmonella* type III secretion system to export spider silk monomers. *Mol. Syst. Biol.* 5, 309 (2009).

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A method for providing fixed nitrogen from atmospheric nitrogen to a cereal plant, or to soil where a cereal plant or seed is growing or is to be planted, comprising delivering genetically engineered bacteria having a refactored exogenous nif cluster to a cereal plant, or to soil where a cereal plant or seed is growing or is to be planted, wherein the genetically engineered bacteria comprise transgenic bacteria, wherein the genetically engineered bacteria comprise bacteria of a species which does not natively contain a nif cluster, wherein the genetically engineered bacteria become established in the cereal plant and provide the cereal plant with fixed nitrogen, wherein the refactored exogenous nif cluster comprises at least one of: codon- optimized nif cluster genes; operons under the control of synthetic parts; operons separated by spacer parts; and a controller.

2. The method of claim 1, wherein the genetically engineered bacteria are gamma-proteobacteria.

3. The method of claim 1, wherein the refactored exogenous_nif cluster is a *Klebsiella* nif cluster, a *Pseudomonas stutzi* nif cluster, or a *Paenibacillus* nif cluster.

4. The method of claim 1, wherein the cereal plant is selected from wheat, rye, barley, triticale, oats, millet, sorghum, teff, fonio, buckwheat, quinoa, corn and rice.

5. The method of claim 1, wherein the genetically engineered bacteria further comprise an exogenous gene encoding a plant growth-stimulating peptide.

6. The method of claim 5, wherein secretion of the plant growth-stimulating peptide from the genetically engineered bacteria is regulated by a type 3 secretion system (T3SS).

7. The method of claim 5, wherein the plant growth stimulating peptide is directly delivered into root or stem tissues.

8. The method of claim 1, wherein the genetically engineered bacteria comprise a system for stable plasmid maintenance.

9. The method of claim 1, wherein the controller is a nucleic acid encoding an IPTG inducible T7 RNA polymerase.

10. The method of claim 8, wherein the system for stable plasmid maintenance is a partitioning system encoded by the two par operons (parCBA and parDE).

11. The method of claim 1, wherein the genetically engineered bacteria comprise a partitioning system, wherein the partitioning system is an RK2 par system.

12. The method of claim 1, wherein the refactored exogenous nif cluster does not comprise an internal regulator.

13. The method of claim 12, wherein at least one of the operons comprises a synthetic regulatory element selected from the group consisting of: a nucleotide sequence that increases or decreases transcription or translation rate, stability, or mobility of a transcription or translation product; a ribozyme; an enhancer sequence; a response element; a protein recognition site; a protein binding sequence; a 5' untranslated region; a 3' untranslated region; a transcription terminator sequence; and a polyadenylation sequence.

14. The method of claim 1, wherein the refactored exogenous nif cluster is from an organism of a different species than the genetically engineered bacteria.

15. The method of claim 1, wherein the genetically engineered bacteria are endophytes.

* * * * *